US009403839B2

(12) United States Patent
Hadida-Ruah et al.

(10) Patent No.: US 9,403,839 B2
(45) Date of Patent: Aug. 2, 2016

(54) PYRAN-SPIROCYCLIC PIPERIDINE AMIDES AS MODULATORS OF ION CHANNELS

(71) Applicant: Vertex Pharmaceuticals Incorporated, Boston, MA (US)

(72) Inventors: Sara Sabina Hadida-Ruah, La Jolla, CA (US); Vijayalaksmi Arumugam, San Marcos, CA (US); Michael Paul Deninno, San Diego, CA (US); Bryan A. Frieman, La Jolla, CA (US); Edward Adam Kallel, Escondido, CA (US); Mark Thomas Miller, San Diego, CA (US); Johnny Uy, San Diego, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 14/372,353

(22) PCT Filed: Jan. 15, 2013

(86) PCT No.: PCT/US2013/021535

§ 371 (c)(1),
(2) Date: Jul. 15, 2014

(87) PCT Pub. No.: WO2013/109521

PCT Pub. Date: Jul. 25, 2013

(65) Prior Publication Data

US 2015/0005304 A1 Jan. 1, 2015

Related U.S. Application Data

(60) Provisional application No. 61/586,875, filed on Jan. 16, 2012.

(51) Int. Cl.
*C07D 491/107* (2006.01)

(52) U.S. Cl.
CPC .................................. *C07D 491/107* (2013.01)

(58) Field of Classification Search
CPC .................................................. C07D 491/107
USPC ........................... 546/16; 544/230; 514/235.5
See application file for complete search history.

(56) References Cited

FOREIGN PATENT DOCUMENTS

| | | |
|---|---|---|
| WO | WO 2010/002483 | 1/2010 |
| WO | WO 2012/125613 | 9/2012 |

OTHER PUBLICATIONS

Dorwald F. A. Side Reactions in Organic Synthesis, 2005, Wiley: VCH, Weinheim p. IX of Preface.*
Hong C. Shen et al, Discovery of spirocyclic secondary amine -derived tertiaryl ureas as highly potent, selective bioavailable soluble epoxide hydrolase inhibitors, 2009.*
International Search Report dated Mar. 14, 2013, prepared in International Application No. PCT/US2013/021535.
International Preliminary Report on Patentability dated Jul. 22, 2014, prepared in International Application No. PCT/US2013/021535.

* cited by examiner

*Primary Examiner* — Rita Desai
(74) *Attorney, Agent, or Firm* — Brinks Gilson & Lione

(57) ABSTRACT

The invention relates to pyran spirocyclic piperidine amide compounds useful as inhibitors of ion channels. The invention also provides pharmaceutically acceptable compositions comprising the compounds of the invention and methods of using the compositions in the treatment of various disorders.

23 Claims, No Drawings

PYRAN-SPIROCYCLIC PIPERIDINE AMIDES AS MODULATORS OF ION CHANNELS

CROSS-REFERENCE TO RELATED APPLICATIONS

This application is a National Stage application of International Application No. PCT/US2013/021535, filed Jan. 15, 2013. The International application claims the benefit of U.S. Provisional Patent Application No. 61/586,875, filed Jan. 16, 2012, the entire contents of which are hereby incorporated herein by reference.

TECHNICAL FIELD OF THE INVENTION

The invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Pain is a protective mechanism that allows healthy animals to avoid tissue damage and to prevent further damage to injured tissue. Nonetheless there are many conditions where pain persists beyond its usefulness, or where patients would benefit from inhibition of pain. Voltage-gated sodium channels are believed to play a critical role in pain signaling. This belief is based on the known roles of these channels in normal physiology, pathological states arising from mutations in sodium channel genes, preclinical work in animal models of disease, and the clinical usefulness of known sodium channel modulating agents (Cummins, T. R., Sheets, P. L., and Waxman, S. G., The roles of sodium channels in nociception: Implications for mechanisms of pain. *Pain* 131 (3), 243 (2007); England, S., Voltage-gated sodium channels: the search for subtype-selective analgesics. *Expert Opin Investig Drugs* 17 (12), 1849 (2008); Krafte, D. S, and Bannon, A. W., Sodium channels and nociception: recent concepts and therapeutic opportunities. *Curr Opin Pharmacol* 8 (1), 50 (2008)).

Voltage-gated sodium channels (NaV's) are key biological mediators of electrical signaling. NaV's are the primary mediators of the rapid upstroke of the action potential of many excitable cell types (e.g. neurons, skeletal myocytes, cardiac myocytes), and thus are critical for the initiation of signaling in those cells (Hille, Bertil, *Ion Channels of Excitable Membranes*, Third ed. (Sinauer Associates, Inc., Sunderland, Mass., 2001)). Because of the role NaV's play in the initiation and propagation of neuronal signals, antagonists that reduce NaV currents can prevent or reduce neural signaling. Thus NaV channels are considered likely targets in pathologic states where reduced excitability is predicted to alleviate the clinical symptoms, such as pain, epilepsy, and some cardiac arrhythmias (Chahine, M., Chatelier, A., Babich, O., and Krupp, J. J., Voltage-gated sodium channels in neurological disorders. *CNS Neurol Disord Drug Targets* 7 (2), 144 (2008)).

The NaV's form a subfamily of the voltage-gated ion channel super-family and comprises 9 isoforms, designated NaV 1.1-NaV 1.9. The tissue localizations of the nine isoforms vary greatly. NaV 1.4 is the primary sodium channel of skeletal muscle, and NaV 1.5 is primary sodium channel of cardiac myocytes. NaV's 1.7, 1.8 and 1.9 are primarily localized to the peripheral nervous system, while NaV's 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol Rev* 57 (4), 397 (2005)).

NaV channels have been identified as the primary target for some clinically useful pharmaceutical agents that reduce pain (Cummins, T. R., Sheets, P. L., and Waxman, S. G., The roles of sodium channels in nociception: Implications for mechanisms of pain. *Pain* 131 (3), 243 (2007)). The local anesthetic drugs such as lidocaine block pain by inhibiting NaV channels. These compounds provide excellent local pain reduction but suffer the drawback of abolishing normal acute pain and sensory inputs. Systemic administration of these compounds results in dose limiting side effects that are generally ascribed to block of neural channels in the CNS (nausea, sedation, confusion, ataxia). Cardiac side effects can also occur, and indeed these compounds are also used as class 1 anti-arrhythmics, presumably due to block of NaV1.5 channels in the heart. Other compounds that have proven effective at reducing pain have also been suggested to act by sodium channel blockade including carbamazepine, lamotragine, and tricyclic antidepressants (Soderpalm, B., Anticonvulsants: aspects of their mechanisms of action. *Eur J Pain* 6 Suppl A, 3 (2002); Wang, G. K., Mitchell, J., and Wang, S. Y., Block of persistent late Na+ currents by antidepressant sertraline and paroxetine. *J Membr Biol* 222 (2), 79 (2008)). These compounds are likewise dose limited by adverse effects similar to those seen with the local anesthetics. Antagonists that specifically block only the isoform(s) critical for nocioception are expected to have increased efficacy since the reduction of adverse effects caused by block of off-target channels should enable higher dosing and thus more complete block of target channels isoforms.

Four NaV isoforms, NaV 1.3, 1.7, 1.8, and 1.9, have been specifically indicated as likely pain targets. NaV 1.3 is normally found in the pain sensing neurons of the dorsal root ganglia (DRG) only early in development and is lost soon after birth both in humans and in rodents. Nonetheless, nerve damaging injuries have been found to result in a return of the NaV 1.3 channels to DRG neurons and this may contribute to the abnormal pain signaling in various chronic pain conditions resulting from nerve damage (neuropathic pain). These data have led to the suggestion that pharmaceutical block of NaV 1.3 could be an effective treatment for neuropathic pain. In opposition to this idea, global genetic knockout of NaV 1.3 in mice does not prevent the development of allodynia in mouse models of neuropathic pain (Nassar, M. A. et al., Nerve injury induces robust allodynia and ectopic discharges in NaV 1.3 null mutant mice. *Mol Pain* 2, 33 (2006)). It remains unknown whether compensatory changes in other channels allow for normal neuropathic pain in NaV 1.3 knockout mice, though it has been reported that knockout of NaV 1.1 results in drastic upregulation of NaV 1.3. The converse effect in NaV 1.3 knockouts might explain these results.

NaV 1.7, 1.8, and 1.9 are highly expressed in DRG neurons, including the neurons whose axons make up the C-fibers and Aδ nerve fibers that are believed to carry most pain signals from the nocioceptive terminals to the central nervous system. Like NaV 1.3, NaV 1.7 expression increases after nerve injury and may contribute to neuropathic pain states. The localization of NaV 1.7, 1.8, and 1.9 in nocioceptors led to the hypothesis that reducing the sodium currents through these channels might alleviate pain. Indeed, specific interventions that reduce the levels of these channels have proven effective in animal models of pain.

Specific reduction of NaV 1.7 in rodents by multiple different techniques has resulted in the reduction of observable pain behaviors in model animals. Injection of a viral antisense NaV 1.7 cDNA construct greatly reduces normal pain responses due to inflammation or mechanical injury (Yeomans, D. C. et al., Decrease in inflammatory hyperalgesia by herpes vector-mediated knockdown of NaV 1.7 sodium channels in primary afferents. *Hum Gene Ther* 16 (2), 271 (2005)). Likewise, a genetic knockout of NaV 1.7 in a subset of nociceptor neurons reduced acute and inflammatory pain in mouse models (Nassar, M. A. et al., Nociceptor-specific gene deletion reveals a major role for NaV 1.7 (PN1) in acute and inflammatory pain. *Proc Natl Acad Sci USA* 101 (34), 12706 (2004)). Global knockouts of NaV 1.7 in mice lead to animals that die on the first day after birth. These mice fail to feed and this is the presumed cause of death.

Treatments that specifically reduce NaV 1.8 channels in rodent models effectively reduce pain sensitivity. Knockdown of NaV 1.8 in rats by intrathecal injection of antisense oligodeoxynucleotides reduces neuropathic pain behaviors, while leaving acute pain sensation intact (Lai, J. et al., Inhibition of neuropathic pain by decreased expression of the tetrodotoxin-resistant sodium channel, NaV1.8. Pain 95 (1-2), 143 (2002); Porreca, F. et al., A comparison of the potential role of the tetrodotoxin-insensitive sodium channels, PN3/SNS and NaN/SNS2, in rat models of chronic pain. *Proc Natl Acad Sci USA* 96 (14), 7640 (1999)). Global genetic knockout of NaV 1.8 in mice or specific destruction of NaV 1.8 expressing neurons greatly reduces perception of acute mechanical, inflammatory, and visceral pain (Akopian, A. N. et al., The tetrodotoxin-resistant sodium channel SNS has a specialized function in pain pathways. *Nat Neurosci* 2 (6), 541 (1999); Abrahamsen, B. et al., The cell and molecular basis of mechanical, cold, and inflammatory pain. *Science* 321 (5889), 702 (2008); Laird, J. M., Souslova, V., Wood, J. N., and Cervero, F., Deficits in visceral pain and referred hyperalgesia in NaV 1.8 (SNS/PN3)-null mice. *J Neurosci* 22 (19), 8352 (2002)). In contrast to the antisense experiments in rats, genetic knockout mice appear to develop neuropathic pain behaviors normally after nerve injury (Lai, J. et al., Inhibition of neuropathic pain by decreased expression of the tetrodotoxin-resistant sodium channel, NaV1.8. *Pain* 95 (1-2), 143 (2002); Akopian, A. N. et al., The tetrodotoxin-resistant sodium channel SNS has a specialized function in pain pathways. *Nat Neurosci* 2 (6), 541 (1999); Abrahamsen, B. et al., The cell and molecular basis of mechanical, cold, and inflammatory pain. *Science* 321 (5889), 702 (2008); Laird, J. M., Souslova, V., Wood, J. N., and Cervero, F., Deficits in visceral pain and referred hyperalgesia in NaV 1.8 (SNS/PN3)-null mice. *J Neurosci* 22 (19), 8352 (2002)).

NaV 1.9 global knock out mice have decreased sensitivity to inflammation induced pain, despite normal acute, and neuropathic pain behaviors (Amaya, F. et al., The voltage-gated sodium channel Na(v)1.9 is an effector of peripheral inflammatory pain hypersensitivity. *J Neurosci* 26 (50), 12852 (2006); Priest, B. T. et al., Contribution of the tetrodotoxin-resistant voltage-gated sodium channel NaV 1.9 to sensory transmission and nociceptive behavior. *Proc Natl Acad Sci USA* 102 (26), 9382 (2005)). Spinal knockdown of NaV 1.9 had no apparent effect on pain behavior in rats (Porreca, F. et al., A comparison of the potential role of the tetrodotoxin-insensitive sodium channels, PN3/SNS and NaN/SNS2, in rat models of chronic pain. *Proc Natl Acad Sci USA* 96 (14), 7640 (1999)).

The understanding of the role of NaV channels in human physiology and pathology has been greatly advanced by the discovery and analysis of naturally occurring human mutations. NaV 1.1 and NaV 1.2 mutations result in various forms of epilepsy (Fujiwara, T., Clinical spectrum of mutations in SCN1A gene: severe myoclonic epilepsy in infancy and related epilepsies. Epilepsy Res 70 Suppl 1, S223 (2006); George, A. L., Jr., Inherited disorders of voltage-gated sodium channels. J Clin Invest 115 (8), 1990 (2005); Misra, S, N., Kahlig, K. M., and George, A. L., Jr., Impaired NaV1.2 function and reduced cell surface expression in benign familial neonatal-infantile seizures. *Epilepsia* 49 (9), 1535 (2008)). Mutations of the NaV 1.4 cause muscular disorders like paramyotonia congenital (Vicart, S., Sternberg, D., Fontaine, B., and Meola, G., Human skeletal muscle sodium channelopathies. *Neurol Sci* 26 (4), 194 (2005)). NaV 1.5 mutations result in cardiac abnormalities like Brugada Syndrome and long QT syndrome (Bennett, P. B., Yazawa, K., Makita, N., and George, A. L., Jr., Molecular mechanism for an inherited cardiac arrhythmia. Nature 376 (6542), 683 (1995); Darbar, D. et al., Cardiac sodium channel (SCN5A) variants associated with atrial fibrillation. Circulation 117 (15), 1927 (2008); Wang, Q. et al., SCN5A mutations associated with an inherited cardiac arrhythmia, long QT syndrome. *Cell* 80 (5), 805 (1995)).

Recent discoveries have demonstrated that mutations in the gene that encodes the NaV 1.7 channel (SCN9A) can cause both enhanced and reduced pain syndromes. Work by Waxman's group and others have identified at least 15 mutations that result in enhanced current through NaV 1.7 and are linked to dominant congenital pain syndromes. Mutations that lower the threshold for NaV 1.7 activation cause inherited erythromelalgia (IEM). IEM patients exhibit abnormal burning pain in their extremities. Mutations that interfere with the normal inactivation properties of NaV 1.7 lead to prolonged sodium currents and cause paroxysmal extreme pain disorder (PEPD). PEPD patients exhibit periocular, perimandibular, and rectal pain symptoms that progresses throughout life (Drenth, J. P. et al., SCN9A mutations define primary erythermalgia as a neuropathic disorder of voltage gated sodium channels. J Invest Dermatol 124 (6), 1333 (2005); Estacion, M. et al., NaV 1.7 gain-of-function mutations as a continuum: A1632E displays physiological changes associated with erythromelalgia and paroxysmal extreme pain disorder mutations and produces symptoms of both disorders. *J Neurosci* 28 (43), 11079 (2008)).

NaV 1.7 null mutations in human patients were recently described by several groups (Ahmad, S. et al., A stop codon mutation in SCN9A causes lack of pain sensation. *Hum Mol Genet.* 16 (17), 2114 (2007); Cox, J. J. et al., An SCN9A channelopathy causes congenital inability to experience pain. *Nature* 444 (7121), 894 (2006); Goldberg, Y. P. et al., Loss-of-function mutations in the NaV 1.7 gene underlie congenital indifference to pain in multiple human populations. *Clin Genet.* 71 (4), 311 (2007)). In all cases patients exhibit congenital indifference to pain. These patients report no pain under any circumstances. Many of these patients suffer dire injuries early in childhood since they do not have the protective, normal pain that helps to prevent tissue damage and develop appropriate protective behaviors. Aside from the striking loss of pain sensation and reduced or absent of smell (Goldberg, Y. P. et al., Loss-of-function mutations in the NaV 1.7 gene underlie congenital indifference to pain in multiple human populations. *Clin Genet.* 71 (4), 311 (2007)), these patients appear completely normal. Despite the normally high expression of NaV 1.7 in sympathetic neurons (Toledo-Aral, J. J. et al., Identification of PN1, a predominant voltage-dependent sodium channel expressed principally in peripheral neurons. *Proc Natl Acad Sci USA* 94 (4), 1527 (1997)) and adrenal chromafin cells (Klugbauer, N., Lacinova, L., Flockerzi, V., and Hofmann, F., Structure and functional expression of a new member of the tetrodotoxin-sensitive voltage-activated sodium channel family from human neuroendocrine cells. EMBO J. 14 (6), 1084 (1995)), these NaV 1.7-null patients show no sign of neuroendocrine or sympathetic nervous dysfunction.

The gain of NaV 1.7 function mutations that cause pain, coupled with the loss of NaV 1.7 function mutations that abolish pain, provide strong evidence that NaV 1.7 plays an important role in human pain signaling. The relative good health of NaV 1.7-null patients indicates that ablation of NaV 1.7 is well tolerated in these patients.

Unfortunately, the efficacy of currently used sodium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the general formula I:

I

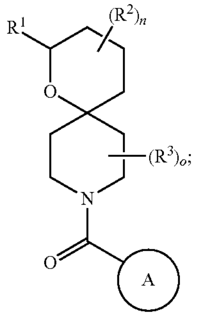

or a pharmaceutically acceptable salt thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

In one aspect, the invention provides compounds of formula I:

I

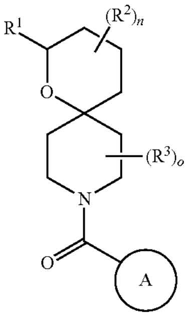

or a pharmaceutically acceptable salt thereof, wherein, independently for each occurrence:

$R^1$ is H, C1-C6 alkyl, C1-C6 fluoroalkyl, C3-C8 cycloalkyl, $CF_3$, optionally substituted heterocycloalkyl, aryl, heteroaryl, or a straight chain, branched, or cyclic (C1-C8)-$R^9$ wherein up to two $CH_2$ units may be replaced with O, CO, S, SO, $SO_2$, N, $CF_2$, or $NR^8$;

$R^2$ is C1-C6 alkyl, deuterated C1-C6 alkyl, C1-C6 alkoxy, C1-C6 fluoroalkyl, $CF_3$, $CHF_2$, or a straight chain, branched, or cyclic (C1-C8)-$R^9$ wherein up to two $CH_2$ units may be replaced with O, CO, S, SO, $SO_2$, N, $CF_2$, or $NR^8$;

$R^3$ is C1-C6 alkyl or halo;

$R^8$ is H, C1-C6 alkyl, C3-C8 cycloalkyl, $CF_3$, or a straight chain, branched, or cyclic (C1-C8)-$R^9$ wherein up to two $CH_2$ units may be replaced with O, CO, S, SO, $SO_2$, N, $CF_2$, or NR, or 2 $R^8$ taken together with the atoms to which they are attached form a ring;

$R^9$ is H, $CF_3$, $CHF_2$, $CH_2F$, $CO_2R$, halo, OH, optionally substituted aryl, heteroaryl, C3-C8 cycloalkyl, heterocycloalkyl, $N(R)_2$, NRCOR, $CON(R)_2$, CN, or $SO_2R$;

R is H, C1-C6 alkyl, optionally substituted aryl, heteroaryl, C3-C8 cycloalkyl, or heterocycloalkyl;

ring A is an optionally substituted aryl, heteroaryl or heterocyclic;

n is an integer from 0 to 4 inclusive; and o is an integer from 0 to 4 inclusive.

For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

As described herein, compounds of the invention can optionally be substituted with one or more substituents, such as are illustrated generally above, or as exemplified by particular classes, subclasses, and species of the invention. The phrase "optionally substituted" is used interchangeably with the phrase "substituted or unsubstituted." As described herein, the variables $R^1$-$R^9$ in formula I encompass specific groups, such as, for example, alkyl and aryl. Unless otherwise noted, each of the specific groups for the variables $R^1$-$R^8$ can be optionally substituted with one or more substituents of halo, cyano, oxoalkoxy, hydroxy, amino, nitro, aryl, haloalkyl, and alkyl. For instance, an alkyl group can be optionally substituted with one or more of halo, cyano, oxoalkoxy, hydroxy, amino, nitro, aryl, haloalkyl, and alkyl. As an additional example, an aryl group can be optionally substituted with one or more of halo, cyano, alkoxy, hydroxy, nitro, haloalkyl, and alkyl. As one of ordinary skill in the art will recognize, combinations of substituents envisioned by this invention are those combinations that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "up to", as used herein, refers to zero or any integer number that is equal or less than the number following the phrase. For example, "up to 3" means any one of 0, 1, 2, and 3. The term "aliphatic", "aliphatic group" or "alkyl" as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups. The term "cycloaliphatic" or "cycloalkyl" mean a monocyclic hydrocarbon, bicyclic, or tricyclic hydrocarbon that is completely saturated or that contains one or more units of unsaturation, but which is not aromatic and has a single point of attachment to the rest of the molecule. In some embodiments, "cycloaliphatic" refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members.

The term "electron withdrawing group", as used herein means an atom or a group that is electronegative relative to hydrogen. See, e.g., "Advanced Organic Chemistry: Reactions, Mechanisms, and Structure," Jerry March, $4^{th}$ Ed., John Wiley & Sons (1992), e.g., pp. 14-16, 18-19, etc. Exemplary such substituents include halo such as Cl, Br, or F, CN, COOH, $CF_3$, etc.

Unless otherwise specified, the term "heterocycle", "heterocyclyl", "heterocycloaliphatic", "heterocycloalkyl" or "heterocyclic" as used herein means non-aromatic, monocyclic, bicyclic, or tricyclic ring systems in which one or more ring atoms in one or more ring members is an independently selected heteroatom. Heterocyclic ring can be saturated or can contain one or more unsaturated bonds. In some embodiments, the "heterocycle", "heterocyclyl", "heterocycloaliphatic", "heterocycloalkyl" or "heterocyclic" group has three to fourteen ring members in which one or more ring members is a heteroatom independently selected from oxygen, sulfur, nitrogen, or phosphorus, and each ring in the ring system contains 3 to 7 ring members.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation but is not aromatic.

The term "alkoxy", or "thioalkyl", as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl", "aralkoxy", or "aryloxyalkyl", refers to monocyclic, bicyclic, and tricyclic ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring". The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "alkylidene chain" refers to a straight or branched carbon chain that may be fully saturated or have one or more units of unsaturation and has two points of attachment to the rest of the molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Thus, included within the scope of the invention are tautomers of compounds of formula I.

Additionally, unless otherwise stated, structures depicted herein are also meant to include compounds that differ only in the presence of one or more isotopically enriched atoms. For example, compounds of formula I, wherein one or more hydrogen atoms are replaced by deuterium or tritium, or one or more carbon atoms are replaced by a $^{13}C$- or $^{14}C$-enriched carbon are within the scope of this invention. Such compounds are useful, for example, as analytical tools, probes in biological assays, or sodium channel blockers with improved therapeutic profile.

In the formulas and drawings, a line transversing a ring and bonded to an R group such as in

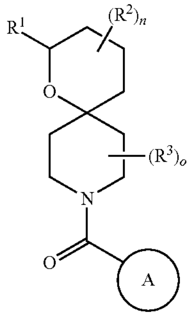

means that the R group can be bonded to any carbon, or if applicable, heteroatom such as N, of that ring as valency allows.

Within a definition of a term as, for example, $R^1$, $R^2$, $R^3$, $R^4$, $R^5$, or $R^6$ when a $CH_2$ unit or, interchangeably, methylene unit may be replaced by O, CO, S, SO, $SO_2$ or $NR^8$, it is meant to include any $CH_2$ unit, including a $CH_2$ within a terminal methyl group. For example, —$CH_2CH_2CH_2SH$ is within the definition of C1-C6 alkyl wherein up to two $CH_2$ units may be replaced by S because the $CH_2$ unit of the terminal methyl group has been replaced by S.

In another embodiment, the invention features a compound of formula I and the attendant definitions, wherein $R^1$ is optionally substituted C3-C8 cycloalkyl, aryl, heteroaryl, or C1-C6 alkyl. In another embodiment, $R^1$ is optionally substituted phenyl, pyridyl, thiazole, or pyrazole, $CH_2CH_3$,

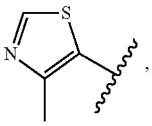, 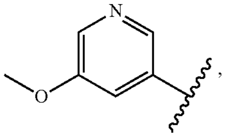, 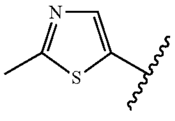,

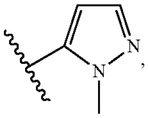, 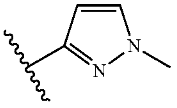, 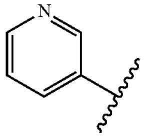,

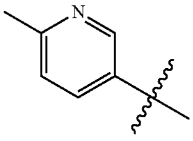, 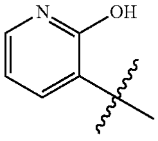,

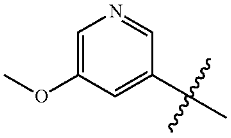, 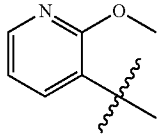, 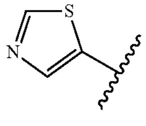,

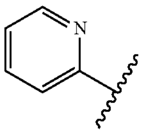, 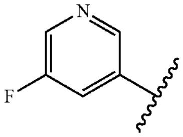, 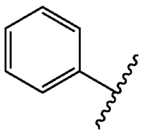,

-continued

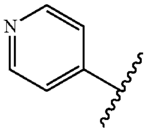, 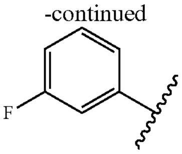, 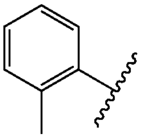,

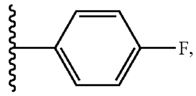, 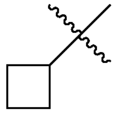, or 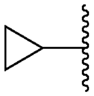.

In another embodiment, the invention features a compound of formula I and the attendant definitions, wherein $R^2$ is C1-C6 alkyl, C1-C6 fluoroalkyl, $CF_3$, C1-C6 alkoxy, or a straight chain, branched, or cyclic (C1-C8)-$R^9$ wherein up to two $CH_2$ units may be replaced with O, CO, S, SO, $SO_2$, N, or $NR^8$. In another embodiment, $R^2$ is $CH_2CH_3$, $OCH_3$, $OCH_2CH_3$, $OCH_2CH_2CH_3$, $OCH_2CH_2F$, $OCH_2CH_2OCH_3$, $OCH_2Ph$,

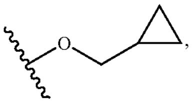 [SMILES: *OCC1CC1], or $OCH(CH_3)_2$.

In another embodiment, the invention features a compound of formula I and the attendant definitions, wherein n is 1 or 2. In another embodiment, n is 1. In another embodiment, o is 0 or 1. In another embodiment, o is 0.

In another embodiment, the invention features a compound of formula I and the attendant definitions, wherein $R^1$ and $R^2$ are cis to each other. In another embodiment, $R^1$ and $R^2$ are trans to each other.

In another embodiment, the invention features a compound of formula I and the attendant definitions, wherein A is

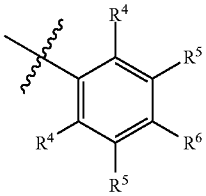

wherein:

$R^4$ is H, C1-C6 alkyl, C1-C6 alkoxy, C3-C8 cycloalkyl, halo, CN, $OR^8$, $SO_2R^8$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$;

$R^5$ is H, C1-C6 alkyl, C1-C6 alkoxy, C3-C8 cycloalkyl, halo, CN, $OR^8$, $SO_2R^8$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$;

$R^6$ is H, C1-C6 alkyl, C1-C6 alkoxy, C3-C8 cycloalkyl, halo, CN, $OR^8$, $SO_2R^8$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$; or two occurrences of $R^4$ and $R^5$, or $R^5$ and $R^6$ together with the carbons to which they are attached form an optionally substituted ring comprising up to 2 heteroatoms.

In another embodiment, $R^4$ is H, C1-C6 alkyl, C1-C6 alkoxy, heterocycloalkyl, halo, $CHF_2$, $CF_3$, $OCHF_2$, or a straight chain, branched, or cyclic (C1-C8)-$R^9$ wherein up to three $CH_2$ units may be replaced with O, CO, S, SO, $SO_2$, N, $CF_2$, or $NR^8$. In another embodiment, $R^4$ is H, $CH_3$, $OCH_3$, $OCH_2CH_3$, F, Cl, $OCHF_2$, $CHF_2$, $CF_3$, $CH_2OCH_3$, $OCH(CH_3)_2$, $CH_2OCH_3$, or

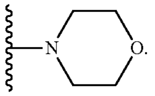

In another embodiment, $R^5$ is H, C1-C6 alkyl, C1-C6 alkoxy, halo, $CF_3$, CN, $OCHF_2$, or a straight chain, branched, or cyclic (C1-C8)-$R^9$ wherein up to three $CH_2$ units may be replaced with O, CO, S, SO, $SO_2$, N, or $NR^8$. In another embodiment, $R^5$ is H, $CH_3$, $OCH_3$, $OCH(CH_3)_2$, F, Cl, $CF_3$, CN, or $CH_2OH$.

In another embodiment, $R^6$ is H, C1-C6 alkyl, C1-C6 alkoxy, C3-C8 cycloalkyl, halo, $CF_3$, $SO_2R^8$, $SO_2N(R^8)_2$, $R^9$, or a straight chain, branched, or cyclic (C1-C8)-$R^9$, wherein up to three $CH_2$ units may be replaced with O, S, SO, $SO_2$, N, or $NR^8$. In another embodiment, $R^6$ is H, F, Cl, $CH_3$, $CF_3$, $CH_2CH_3$, $OCH_3$, $OCH_2CF_3$, $OCH_2CH_3$, $OCH_2CH_2CH_3$, $OCH_2CH_2CH(CH_3)_2$, OtBu, tBu, $OCH(CH_3)_2$, $OCH_2CH(CH_3)_2$, $OCH(CH_3)CH_2CH_3$, $CH(OH)CH(CH_3)_2$, $C(OH)(CH_3)CH_2CH_3$, $OCH_2C(CH_3)_2OH$, $C(CH_3)_2OH$, $CH_2C(CH_3)_2OH$ $OCH_2CH_2OCH_3$, $OCH_2CH_2OH$, $OCH_2CH_2CH_2OH$, $SO_2CH_3$, $SO_2CF_3$, $SO_2CH(CH_3)_2$, $SO_2CH_2CH_3$, $CH_2OCH_2CF_3$, $CH_2OCH_2CH_2CF_3$, $OCHF_2$, $OCH_2CF(CH_3)_2$,

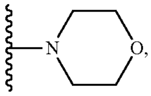, 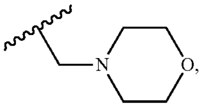, 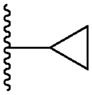,

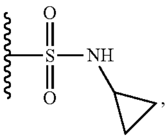, 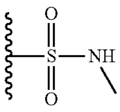, 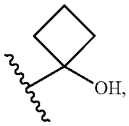

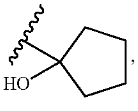, 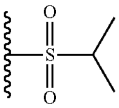, 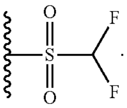.

In another embodiment,

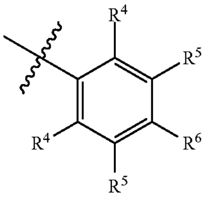

is selected from:

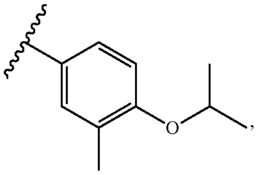, 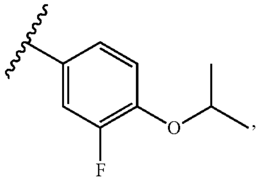,

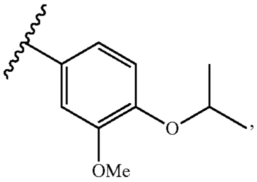, 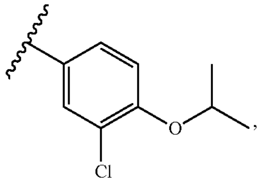,

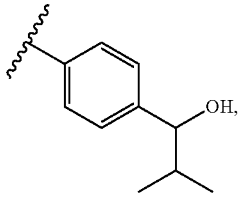 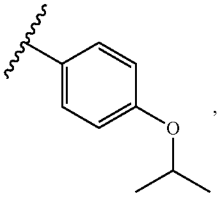,

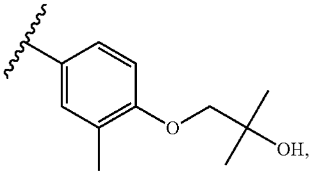

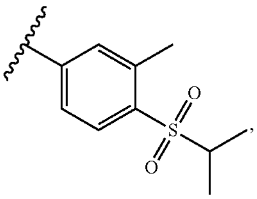, 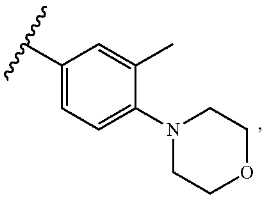,

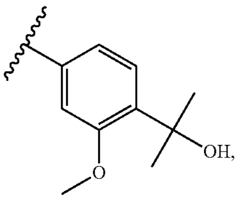 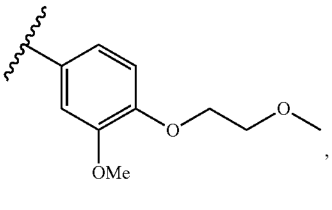,

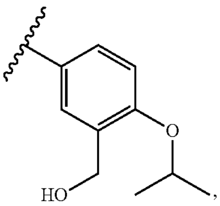, 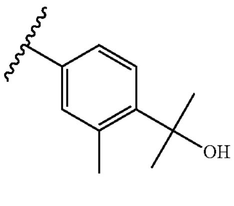,

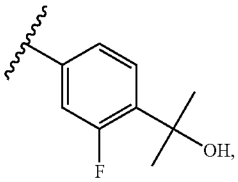 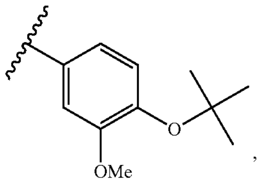,

-continued
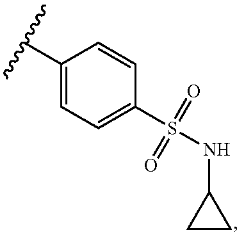
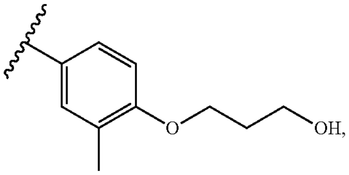
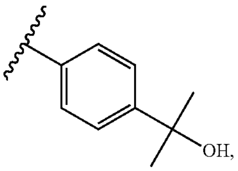
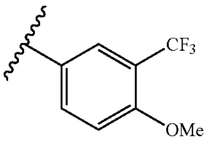
,
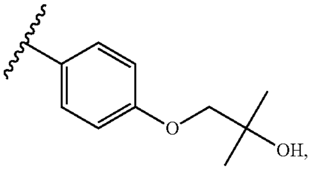
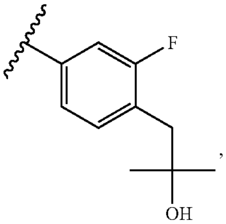
,
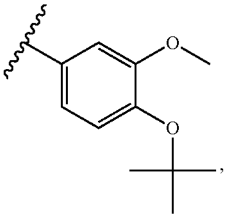
,
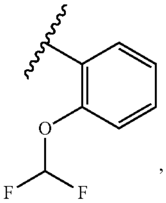
,
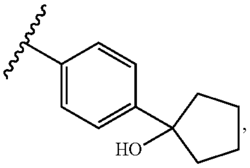
,
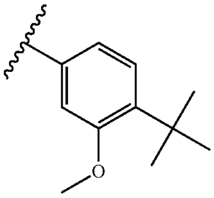
,
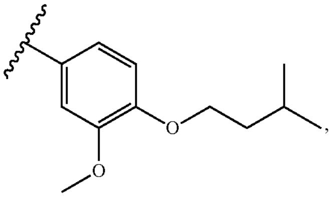
,
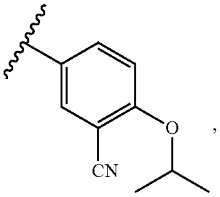
,
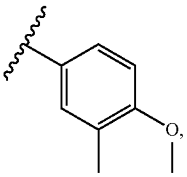
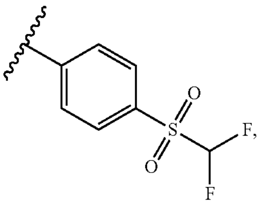
-continued
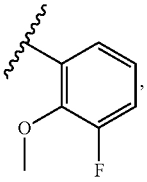
,
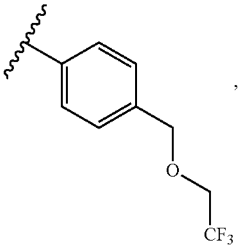
,
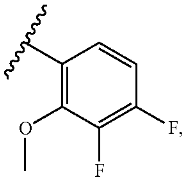
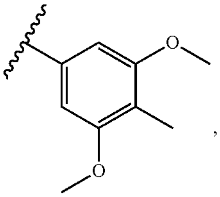
,
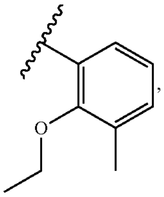
,
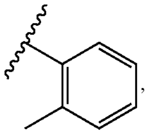
,
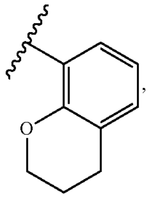
,
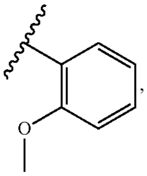
,
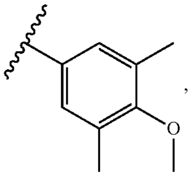
,
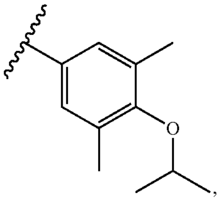
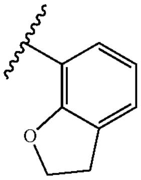
,
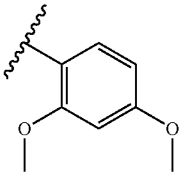
,
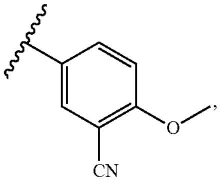
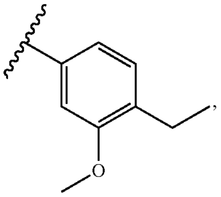
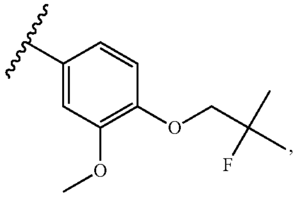
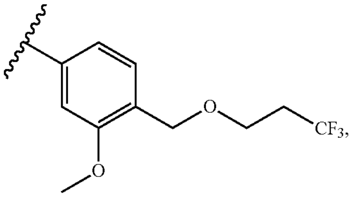

-continued
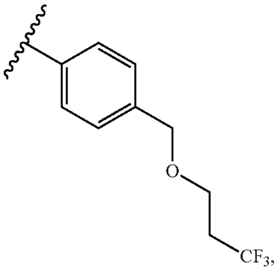
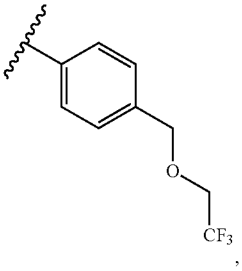
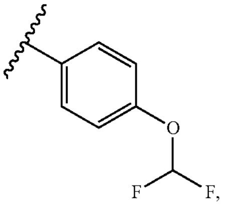
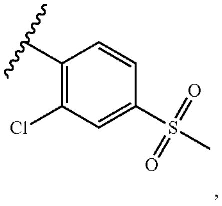
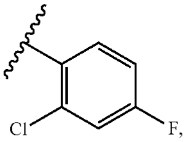
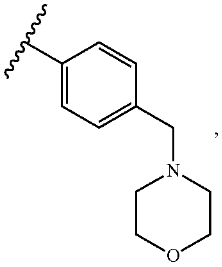
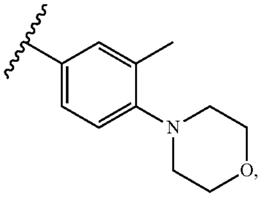
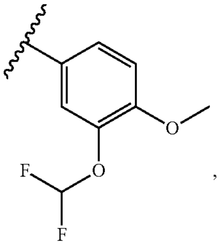
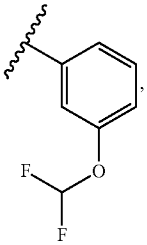
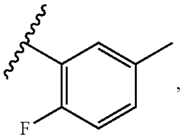
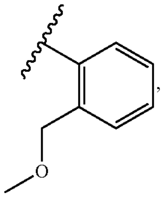
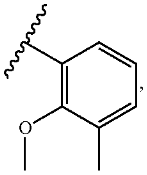
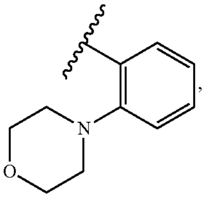
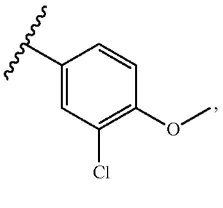
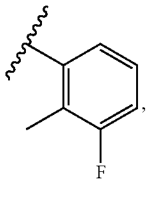
-continued
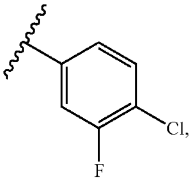
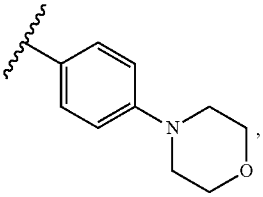
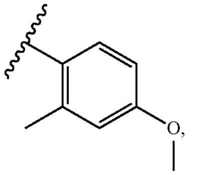
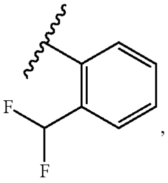
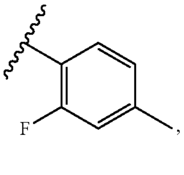
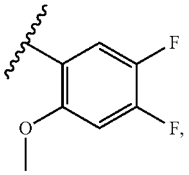
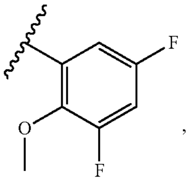
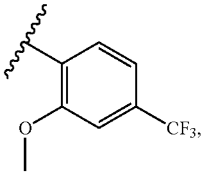
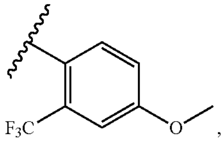
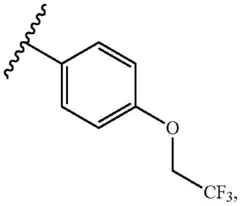
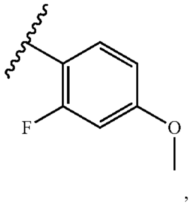
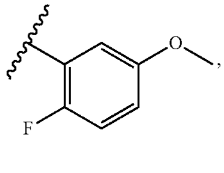
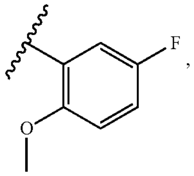
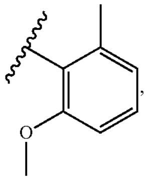
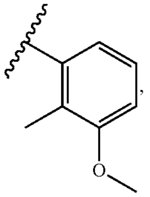
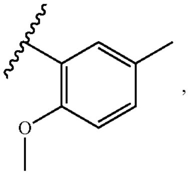
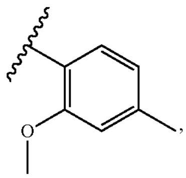
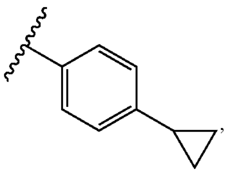
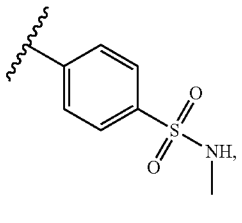
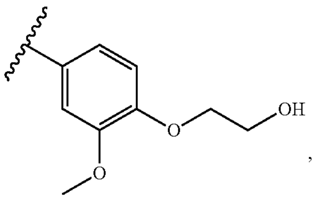

-continued

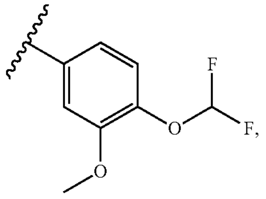

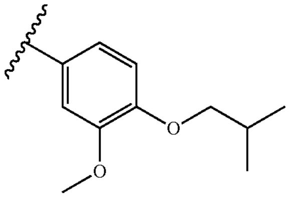

,

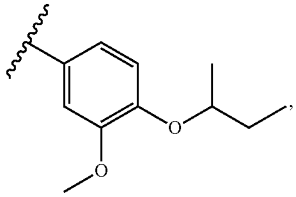

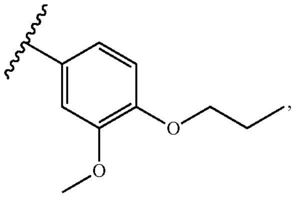

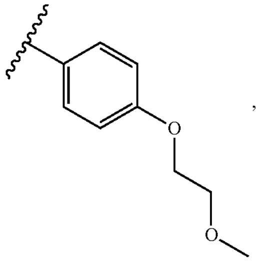

,

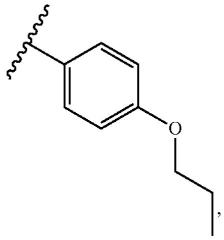

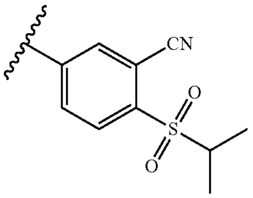

,

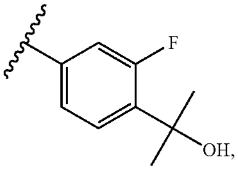

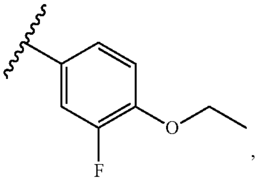

,

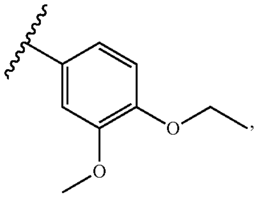

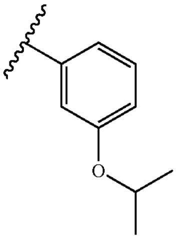

,

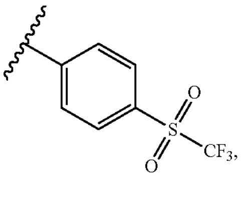

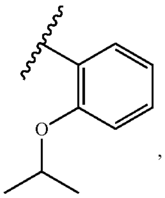

,

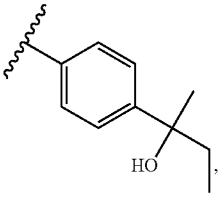

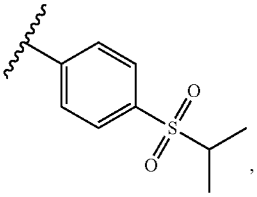

,

-continued

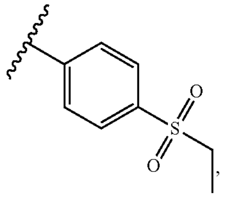

, or

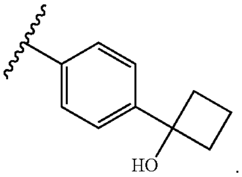

.

In another embodiment, the invention features a compound of formula I and the attendant definitions, wherein A is heteroaryl or heterocyclic. In another embodiment, A is a monocyclic heteroaryl comprising 1 to 3 heteroatoms independently selected from N, O, or S. In another embodiment, A is a bicyclic heteroaryl comprising from 1 to 3 heteroatoms independently selected from N, O, or S.

In another embodiment, A is

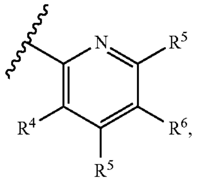

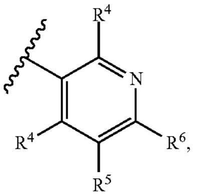

or

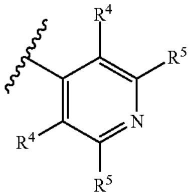

wherein:

$R^4$ is H, C1-C6 alkyl, C3-C8 cycloalkyl, C1-C6 alkoxy, C1-C6 fluoroalkoxy, halo, CN, OH, $OR^8$, $N(R^8)_2$, $SO_2R^8$, $SO_2N(R^8)_2$, $CHF_2$, $CF_3$, $R^9$, heterocycloalkyl, or a straight chain, branched, or cyclic (C1-C8)-$R^9$ wherein up to three $CH_2$ units may be replaced with O, CO, S, SO, $SO_2$, N, $CF_2$, or $NR^8$;

$R^5$ is H, C1-C6 alkyl, C3-C8 cycloalkyl, C1-C6 alkoxy, C1-C6 fluoroalkoxy, halo, CN, OH, $OR^8$, $N(R^8)_2$, $SO_2R^8$, $SO_2N(R^8)_2$, $CHF_2$, $CF_3$, $R^9$, heterocycloalkyl, or a straight chain, branched, or cyclic (C1-C8)-$R^9$ wherein up to three $CH_2$ units may be replaced with O, CO, S, SO, $SO_2$, N, $CF_2$, or $NR^8$;

$R^6$ is H, C1-C6 alkyl, C3-C8 cycloalkyl, C1-C6 alkoxy, C1-C6 fluoroalkoxy, halo, CN, OH, $OR^8$, $N(R^8)_2$, $SO_2R^8$, $SO_2N(R^8)_2$, $CHF_2$, $CF_3$, $R^9$, heterocycloalkyl, or a straight chain, branched, or cyclic (C1-C8)-$R^9$ wherein up to three $CH_2$ units may be replaced with O, CO, S, SO, $SO_2$, N, $CF_2$, or $NR^8$; or two occurrences of $R^4$ and $R^5$, or $R^5$ and $R^6$ together with the carbons to which they are attached form an optionally substituted ring comprising up to 2 heteroatoms.

In another embodiment, $R^4$ is H, C1-C6 alkoxy, C1-C6 fluoroalkoxy, heterocycloalkyl, or $N(R^8)_2$. In another embodiment, $R^4$ is H, $OCH_3$, $OCH_2CH_3$, $OCH_2CF_3$, $N(CH_3)_2$, $NH(CH_2CH(CH_3)_2)$, or

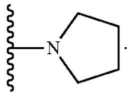.

In another embodiment, $R^5$ is H, C1-C6 alkyl, or C1-C6 alkoxy, halo, heterocycloalkyl, or $N(R^8)_2$. In another embodiment, $R^5$ is H, $CH_3$, $OCH_3$, Cl, tBu, $N(CH_3)_2$, or

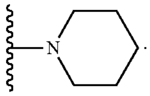.

In another embodiment, $R^6$ is H, CN, C1-C6 alkoxy, C1-C6 fluoroalkoxy, $CF_3$, or heterocycloalkyl. In another embodiment, $R^6$ is H, CN, $OCH_3$, $OCH_2CH_3$, $OCH(CH_3)_2$, $CF_3$, $OCH_2CF_3$,

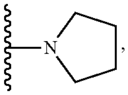, 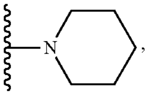 [SMILES: *N1CCCCC1], or 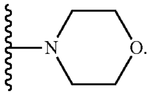.

In another embodiment, A is selected from the following:

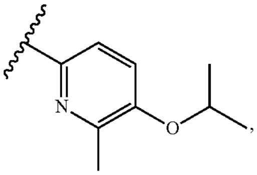, 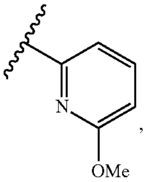,

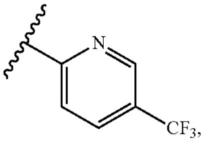, 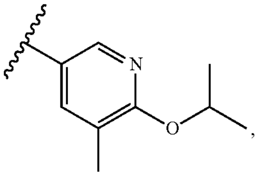,

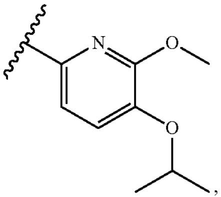, 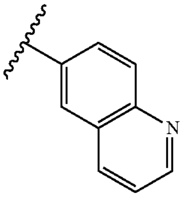,

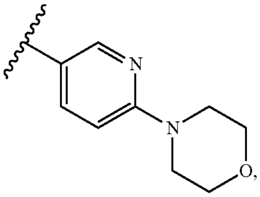, 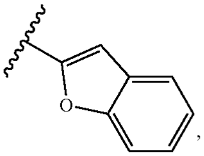,

-continued

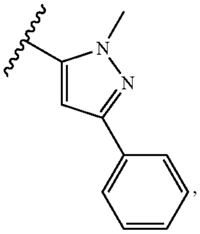, 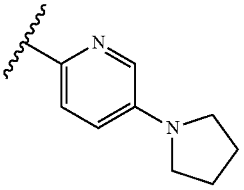,

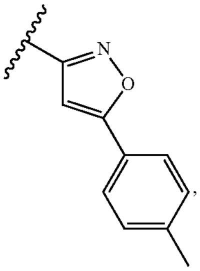, 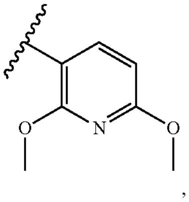,

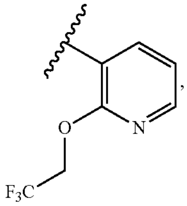, 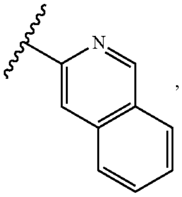,

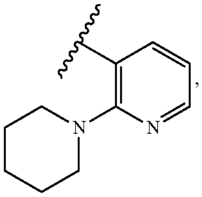, 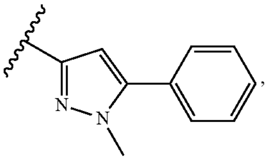,

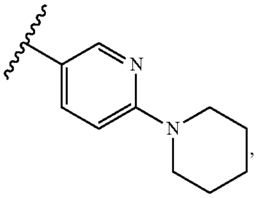, 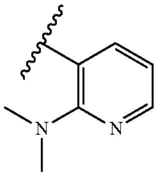,

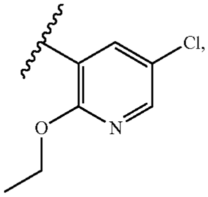, 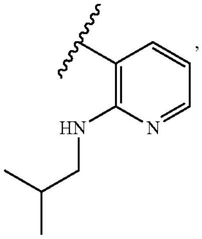,

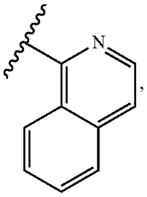, 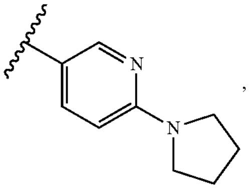,

-continued

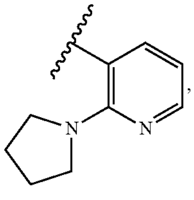,
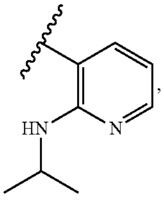,
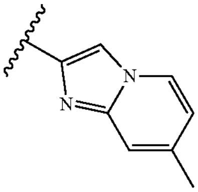,
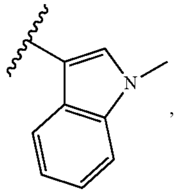,
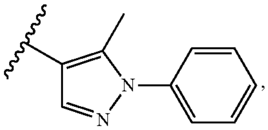,
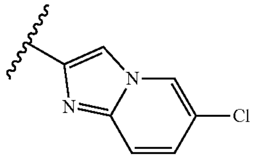,
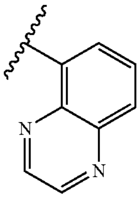,
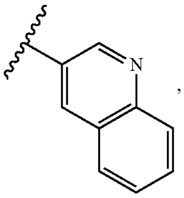,
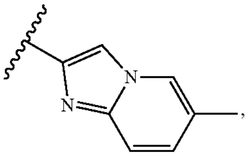,
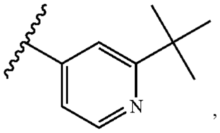,
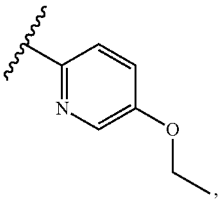,
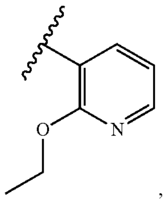,
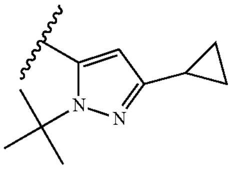,
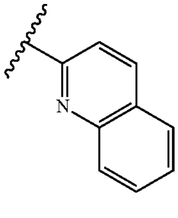,
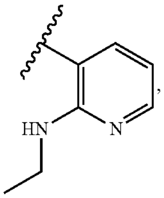,
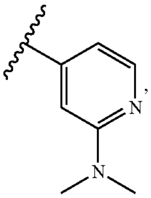,
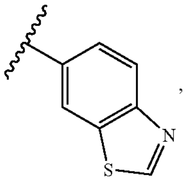, -continued

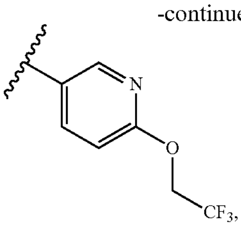
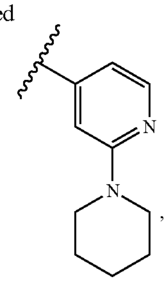,
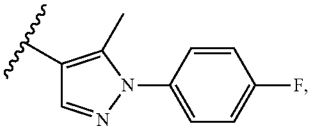
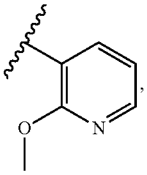,
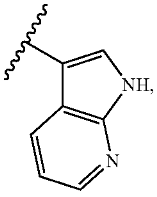
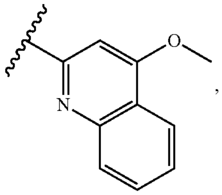,
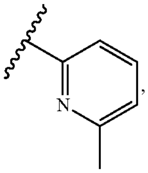,
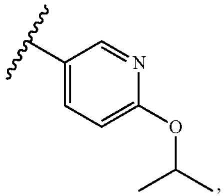 or
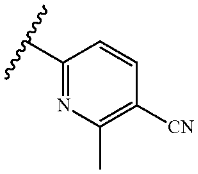.

In another embodiment, the invention features a compound of formula IA:

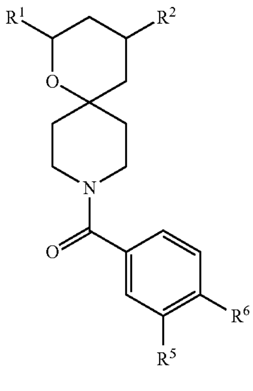
IA wherein:

$R^1$ is an aryl or heteroaryl;

$R^2$ is C1-C6 alkoxy or C1-C6 fluoroalkoxy;

$R^5$ is H, C1-C6 alkyl, C1-C6 alkoxy, C3-C8 cycloalkyl, halo, CN, $OR^8$, $SO_2R^8$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$;

$R^6$ is H, C1-C6 alkyl, C1-C6 alkoxy, C3-C8 cycloalkyl, halo, CN, $OR^8$, $SO_2R^8$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$; and $R^8$ is H, C1-C6 alkyl, C3-C8 cycloalkyl, $CF_3$, or a straight chain, branched, or cyclic (C1-C8)-$R^9$ wherein up to two $CH_2$ units may be replaced with O, CO, S, SO, $SO_2$, N, $CF_2$, or NR, or 2 $R^8$ taken together with the atoms to which they are attached form a ring.

In another embodiment, the invention features a compound of formula IA and the attendant definitions, wherein $R^1$ is selected from phenyl thiazole, pyridine, or pyrazole. In another embodiment, $R^1$ is

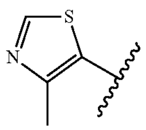, 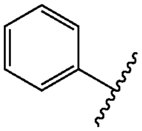, 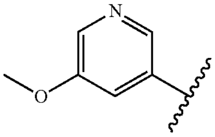,
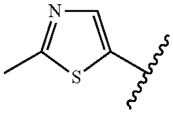, 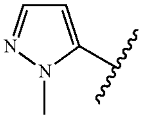, 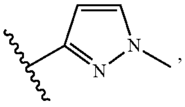,
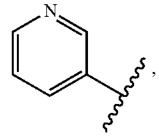, 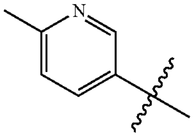, 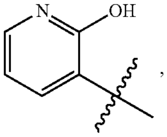,
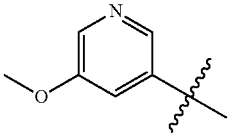, 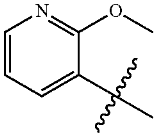, 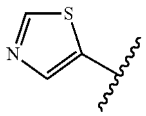,
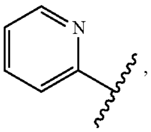, 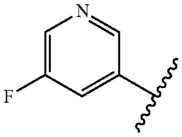, 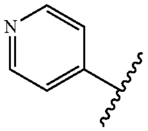,
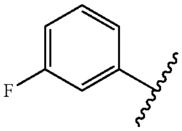, 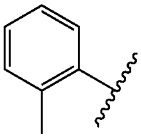, 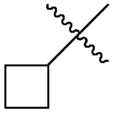, or
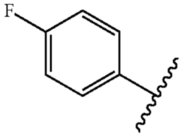.

In another embodiment, the invention features a compound of formula IA and the attendant definitions, wherein $R^2$ is C1-C6 alkoxy. In another embodiment, $R^2$ is selected from $OCH_3$, $OCH_2CH_3$, $OCH_2CH_2CH_3$, $OCH_2CH_2F$, $OCH_2CH_2OCH_3$,

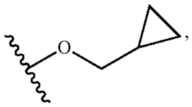 [SMILES: *OCC1CC1], or $OCH(CH_3)_2$.

In another embodiment, the invention features a compound of formula IA and the attendant definitions, wherein $R^5$ is selected from H, C1-C6 alkyl, C1-C6 fluoroalkyl, C1-C6 alkoxy, C1-C6 fluoroalkoxy, halo, or a straight chain, branched, or cyclic (C1-C8)-$R^9$ wherein up to three $CH_2$ units may be replaced with O, CO, S, SO, $SO_2$, N, $CF_2$, or $NR^8$. In another embodiment, $R^5$ is H, $CH_3$, $OCH_3$, $CF_3$, $OCHF_2$, F, Cl, CN, or $CH_2OH$.

In another embodiment, the invention features a compound of formula IA and the attendant definitions, wherein $R^6$ is H, C1-C6 alkyl, C1-C6 fluoroalkyl, C1-C6 alkoxy, C1-C6 fluoroalkoxy, halo, heterocycloalkyl, or a straight chain, branched, or cyclic (C1-C8)-$R^9$ wherein up to three $CH_2$ units may be replaced with O, CO, S, SO, $SO_2$, N, $CF_2$, or $NR^8$. In another embodiment, $R^6$ is H, Cl $CH_2CH_3$, tBu, OtBu, $OCH_3$, $OCH(CH_3)_2$, $OCH_2CH_2(CH_3)_2$, $OCH_2CH_3$, $OCH_2CH_2CH_3$, $OCH_2CH_2CH(CH_3)_2$, $OCH_2CF(CH_3)_2$, $CH_2OCH_2CH_2CF_3$, $OCH_2CH_2OH$, $CH_2CH_2CH_2OH$, $OCHF_2$, $OCH_2CH_2OCH_3$, $OCH(CH_3)CH_2CH_3$, $OCH_2C(CH_3)_2OH$, $C(CH_3)_2OH$, $CH_2C(CH_3)_2OH$,

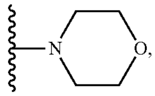, or 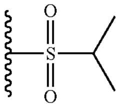.

In another embodiment, the

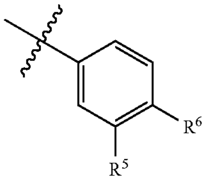

moiety is selected from:

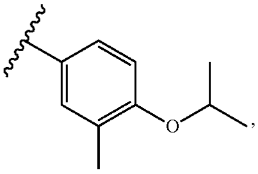, 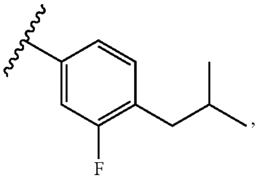,
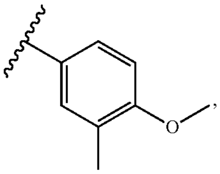, 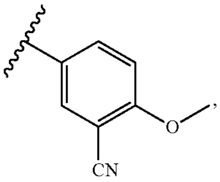,
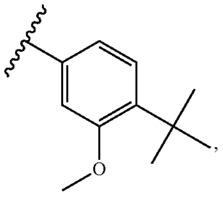, 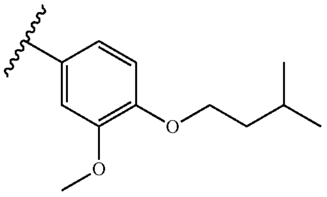,

-continued
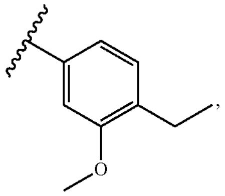
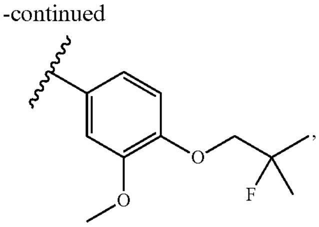
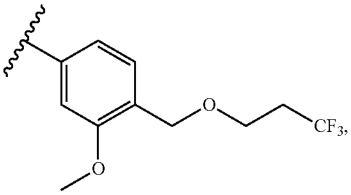
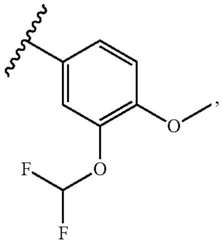
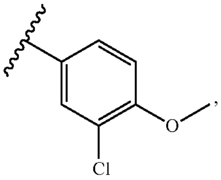
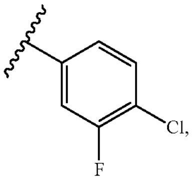
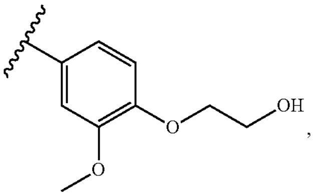
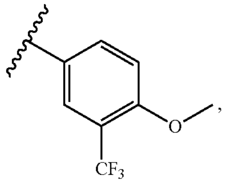
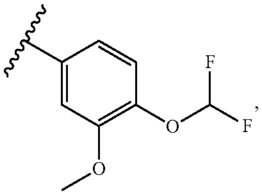
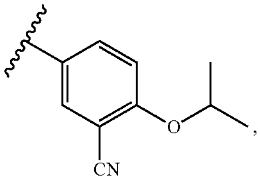
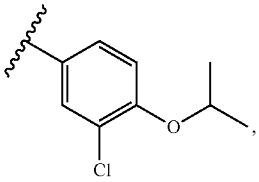
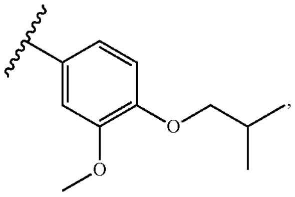
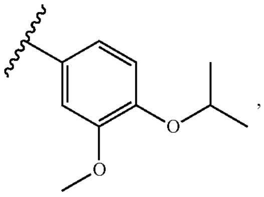
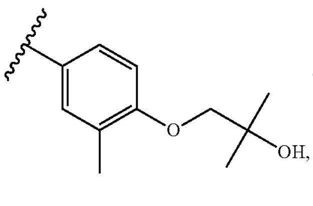
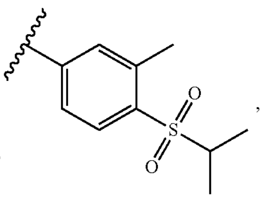
-continued
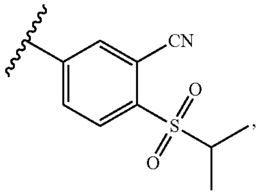
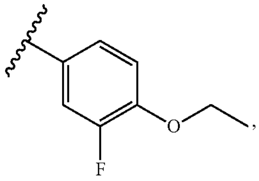
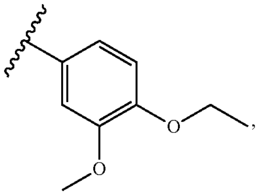
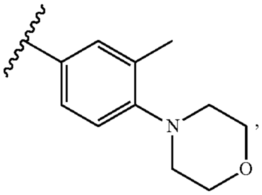
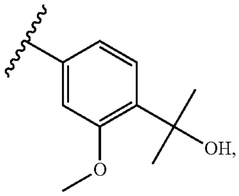
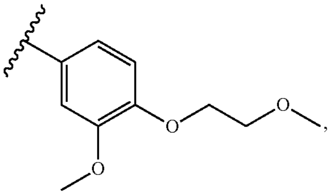
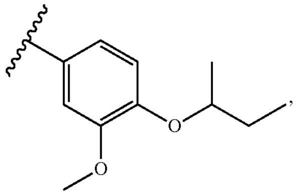
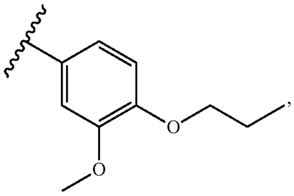
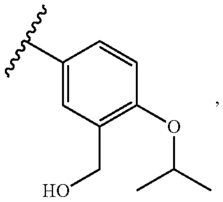
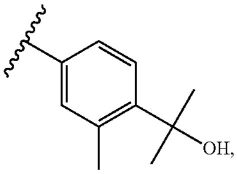
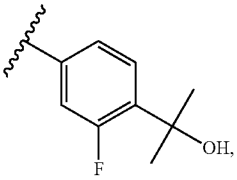
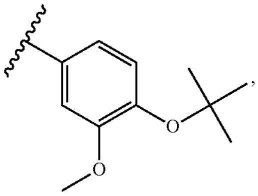
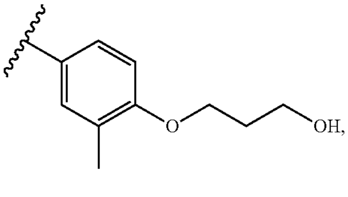
or -continued
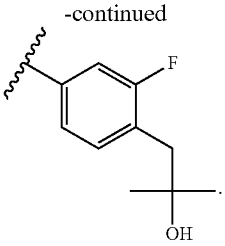
In another embodiment, the invention features a compound of formula I and the attendant definitions, wherein the compound is selected from the following table:
1 cis
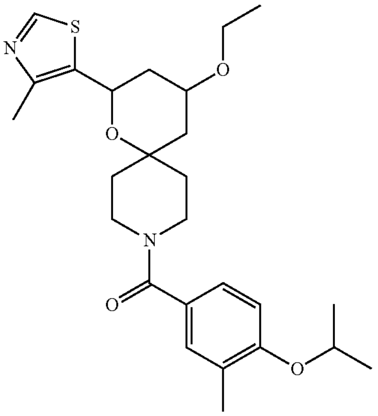
2 cis
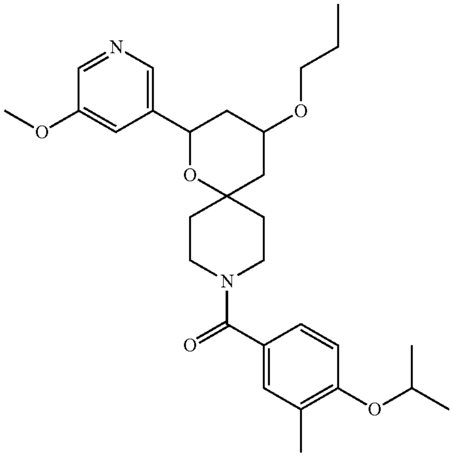
3 cis
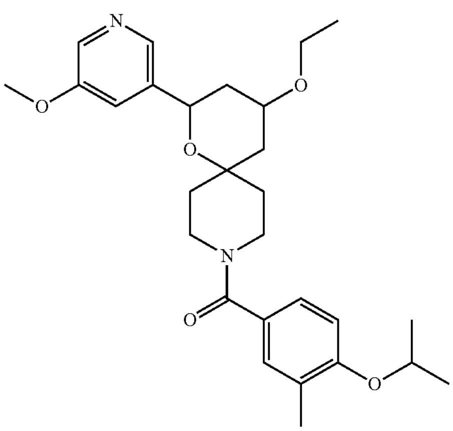
-continued
4 cis
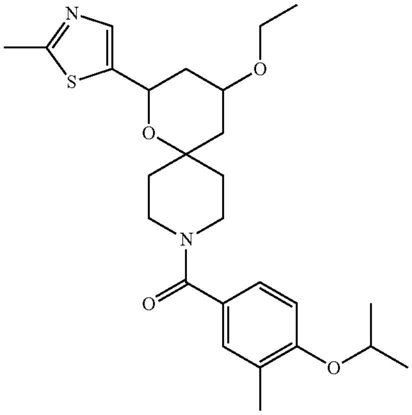
5 cis
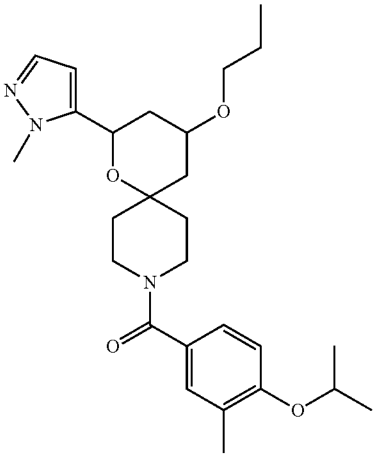
6 cis
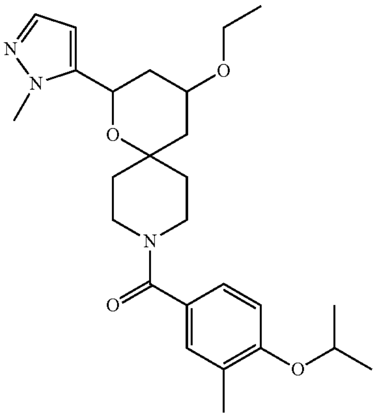

-continued
7 cis
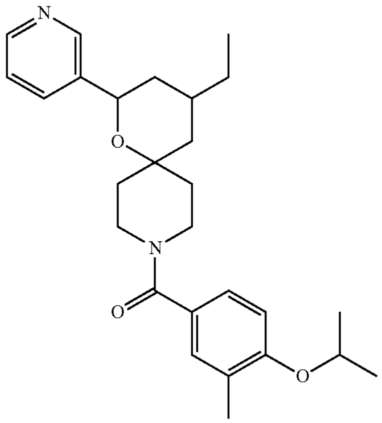
8 cis
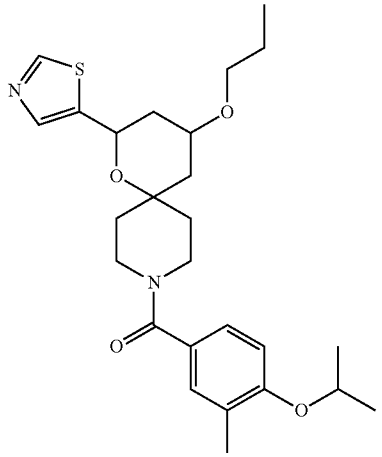
9 cis
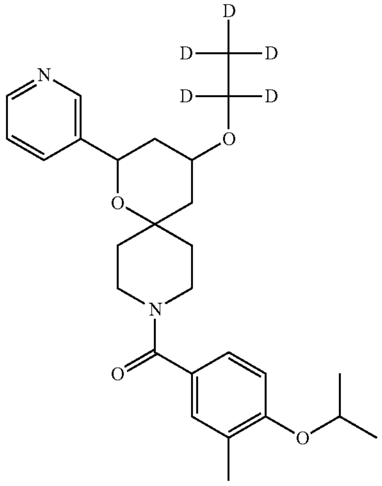
-continued
10 cis
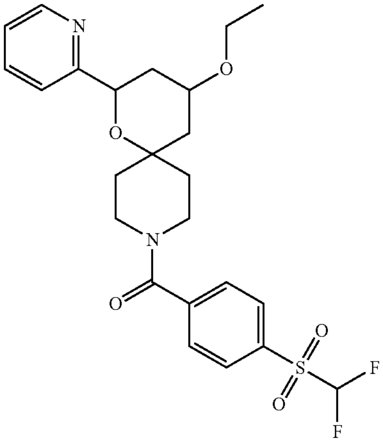
11 cis
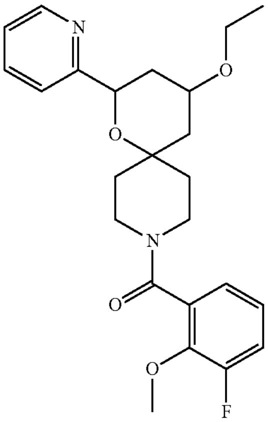
12 cis
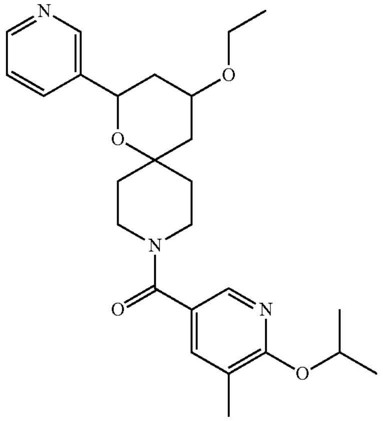

-continued
13 cis
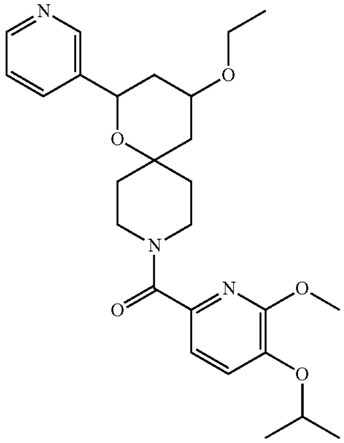
14 cis
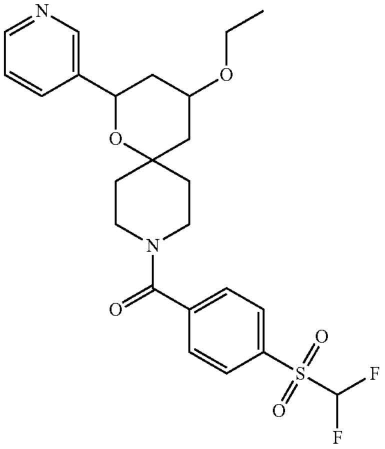
15 cis
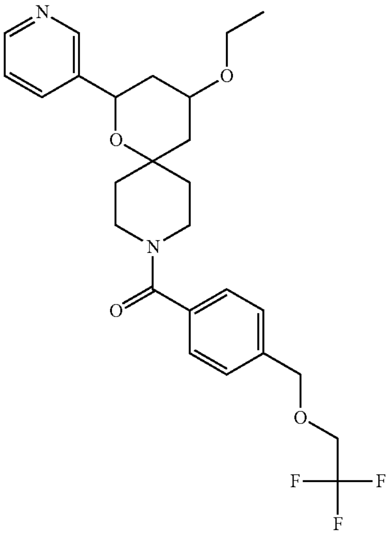
-continued
16 cis
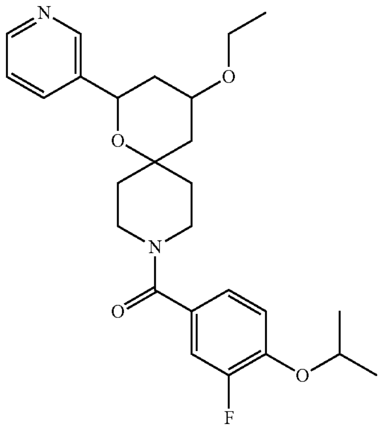
17 cis
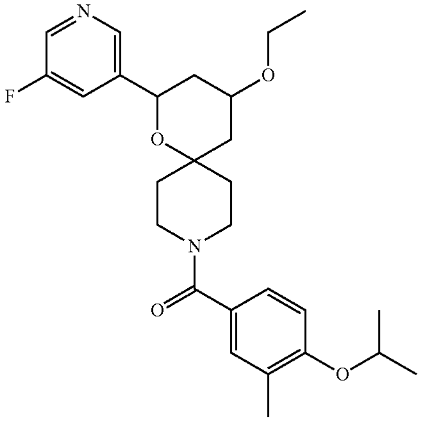
18 cis
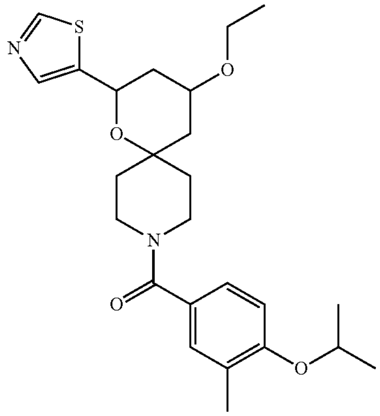

-continued
19 cis
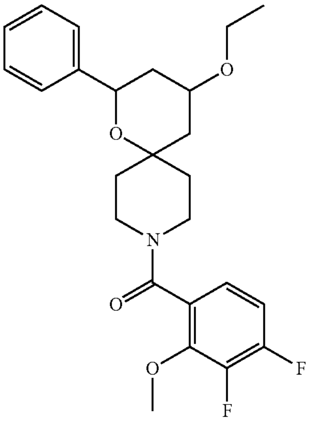
20 cis
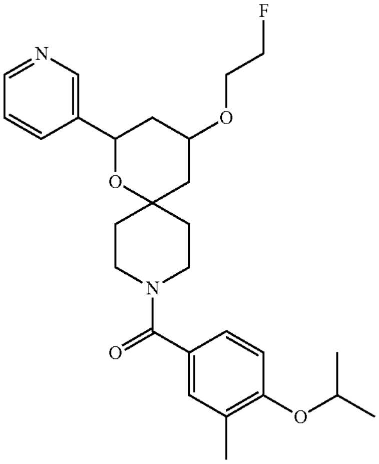
21 cis
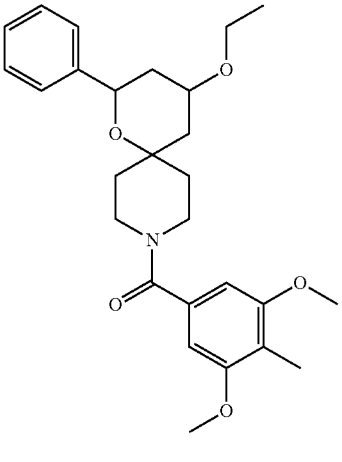
-continued
22 cis
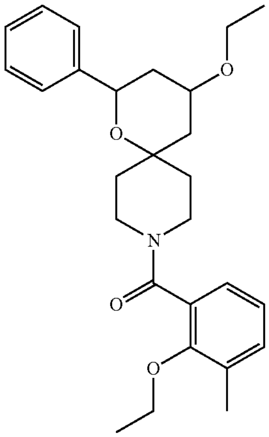
23 cis
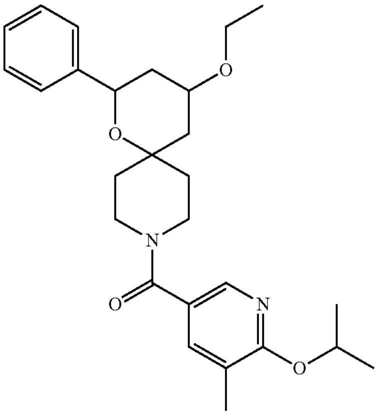
24 cis
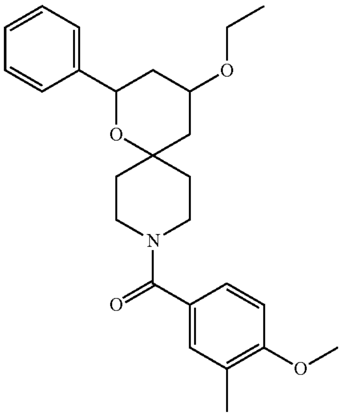
25 cis
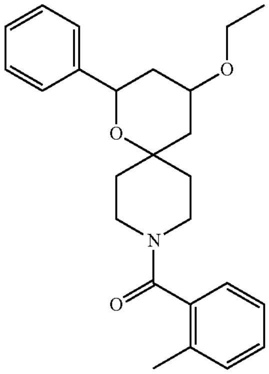

-continued
26 cis
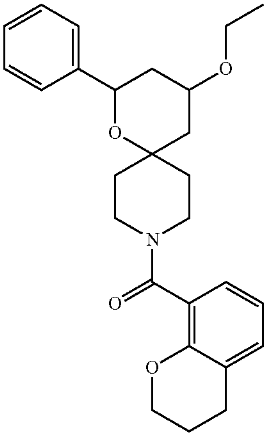
27 cis
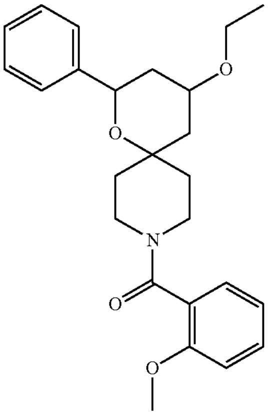
28 cis
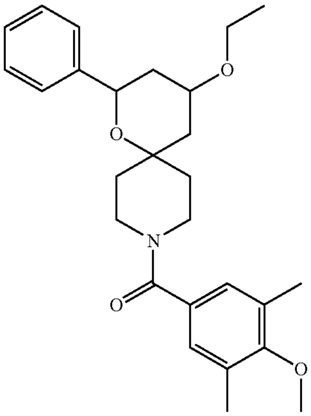
-continued
29 cis
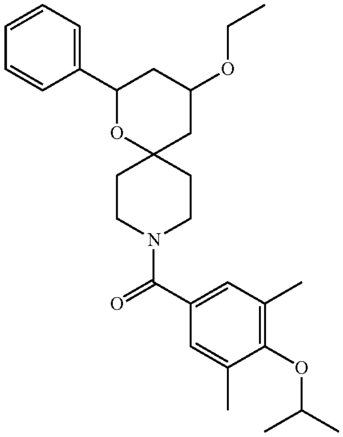
30 cis
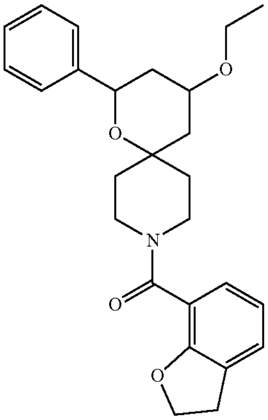
31 cis
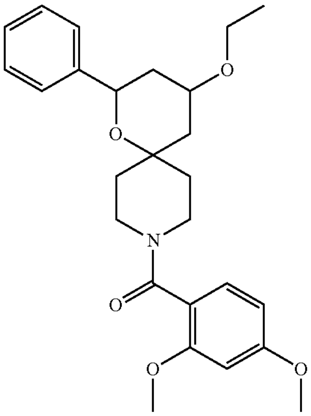

-continued
32 cis
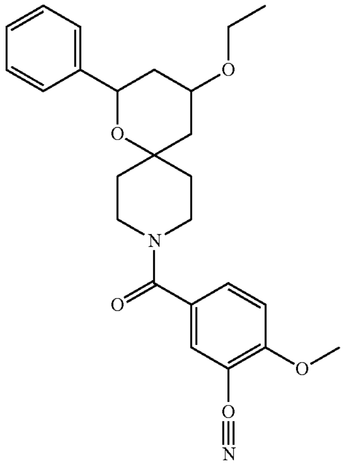
33 cis
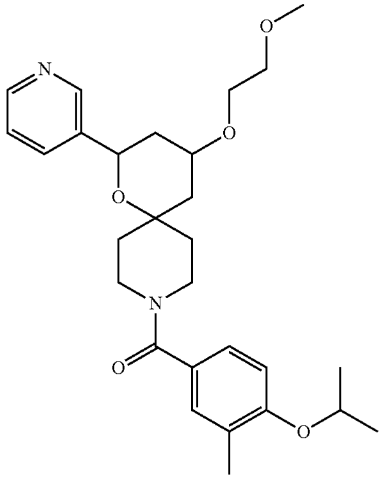
34 cis
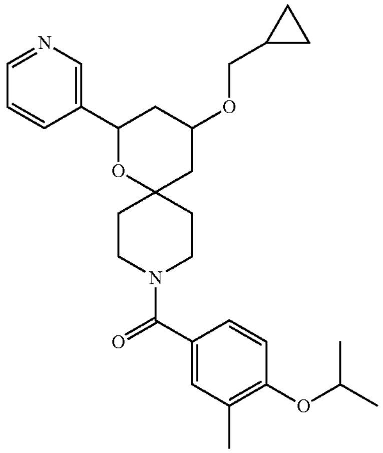
-continued
35 cis
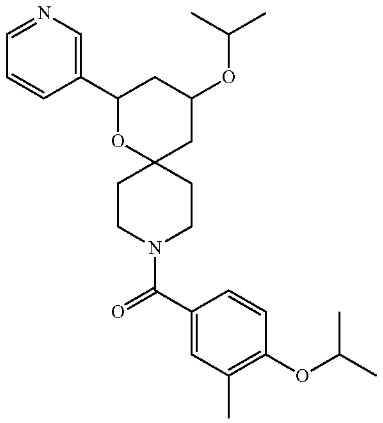
36 cis
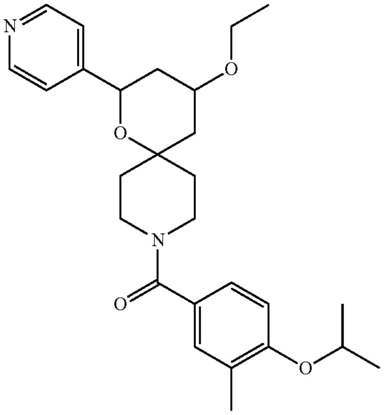
37 cis
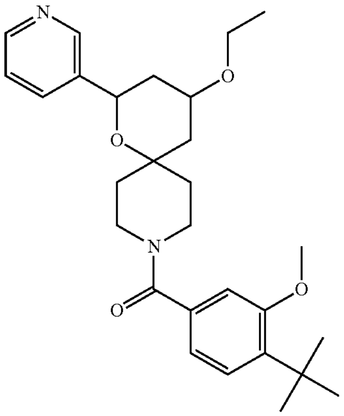

-continued
38 cis
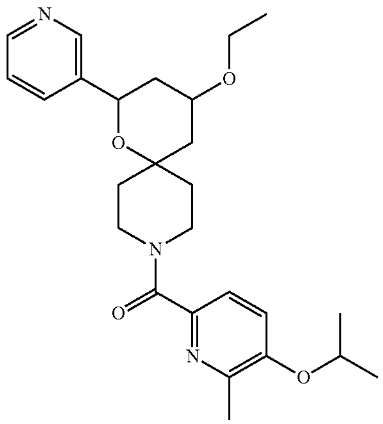
39 cis
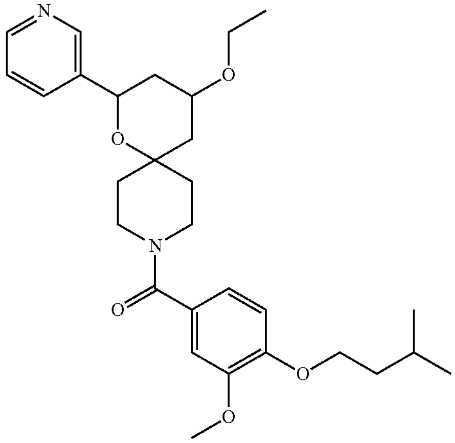
40 cis
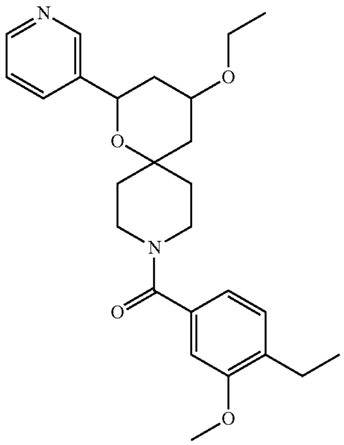
-continued
41 cis
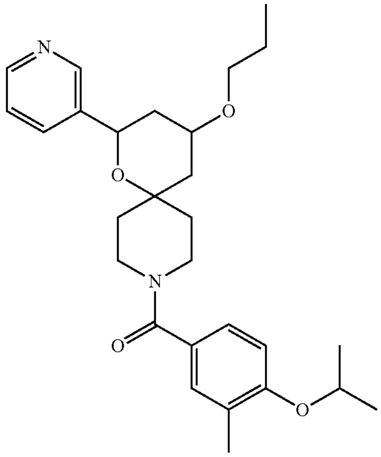
42 cis
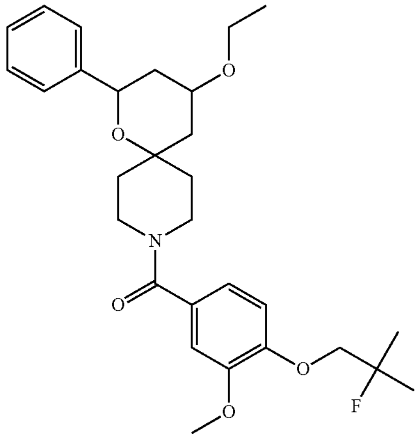
43 cis
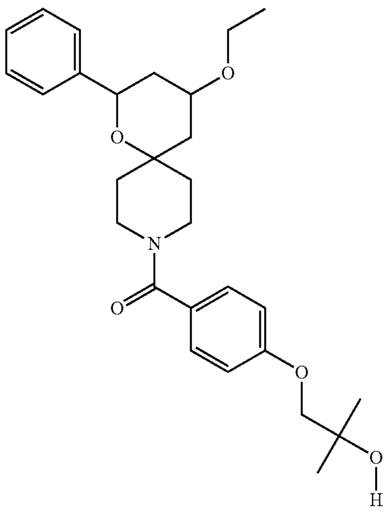

-continued
44 cis
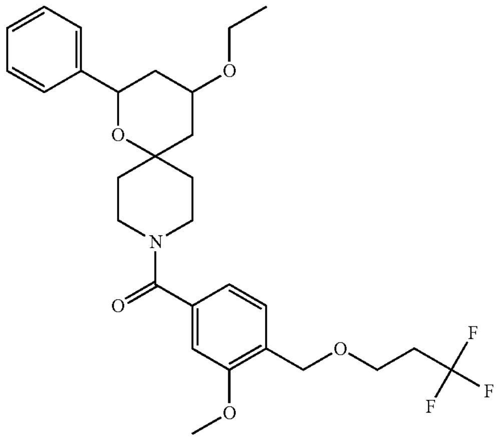
45 cis
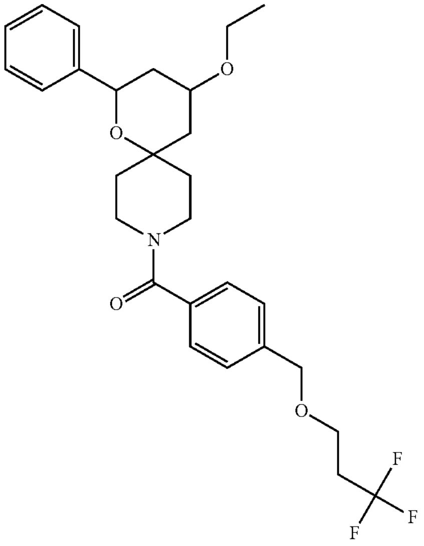
46 cis
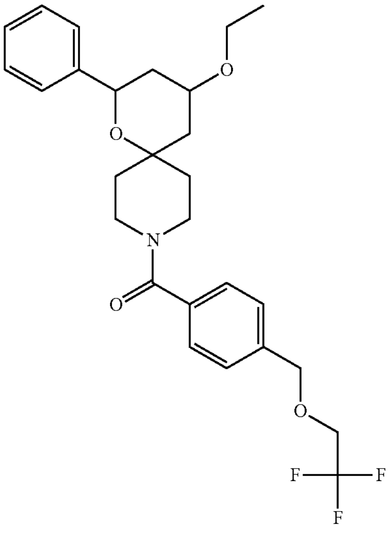
-continued
47 cis
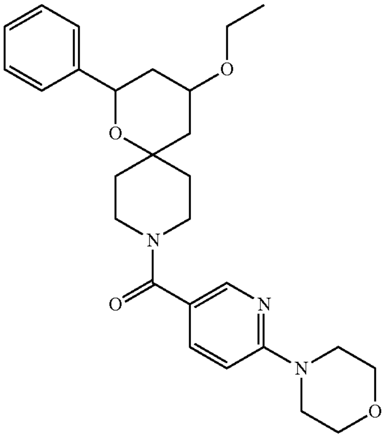
48 cis
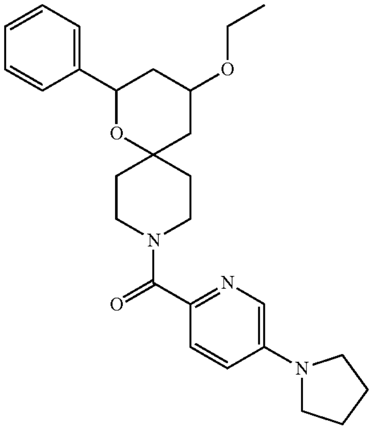
49 cis
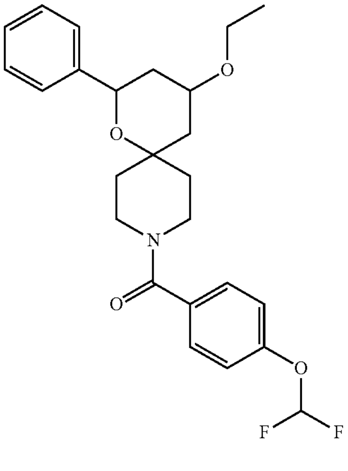

50 cis
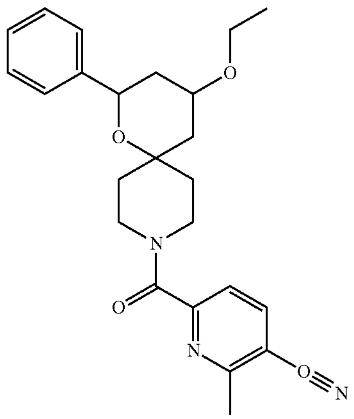
51 cis
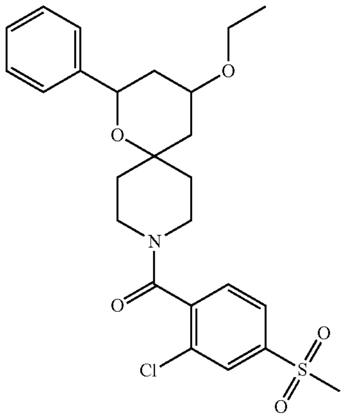
52 cis
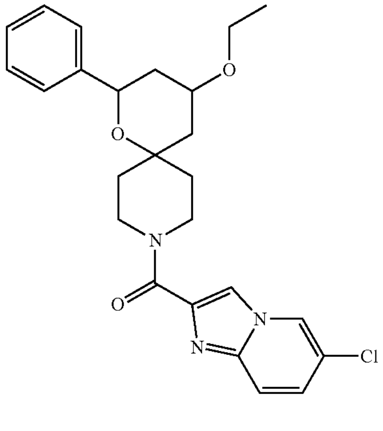
53 cis
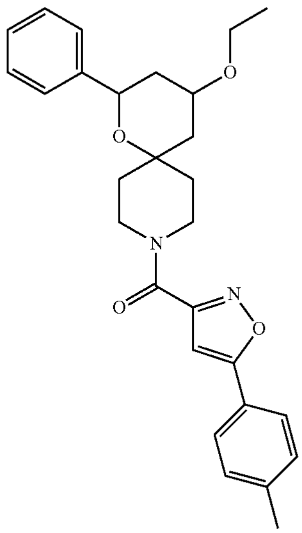
54 cis
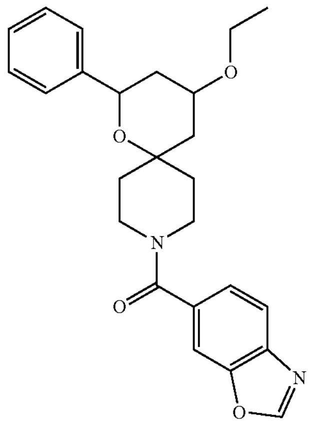
55 cis
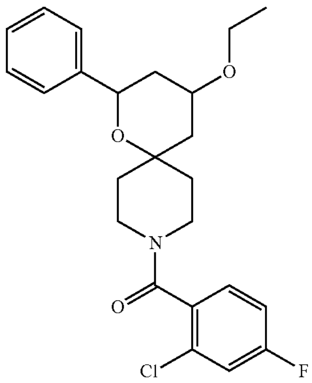

-continued
56 cis
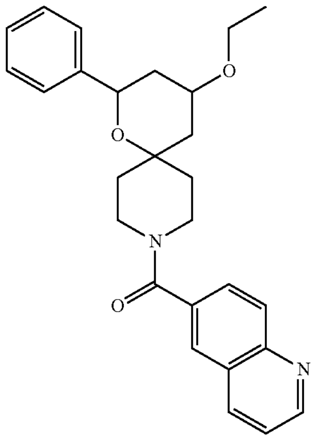
57 cis
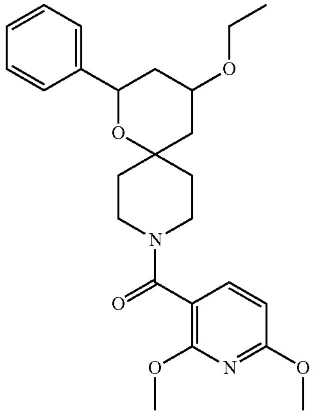
58 cis
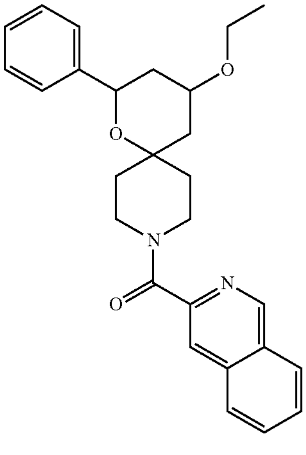
-continued
59 cis
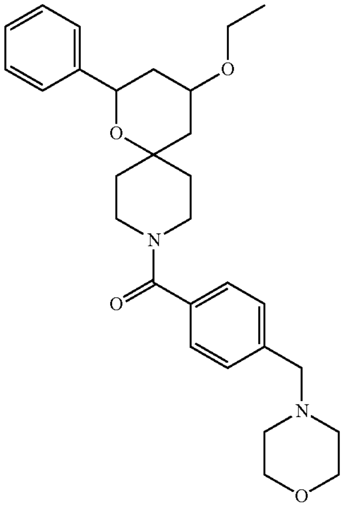
60 cis
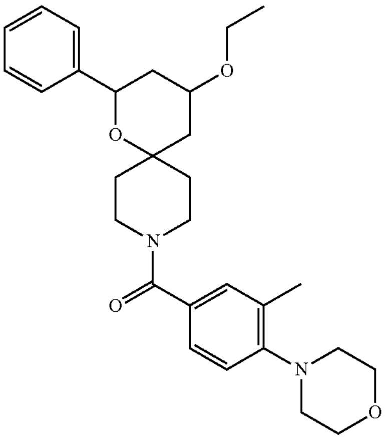
61 cis
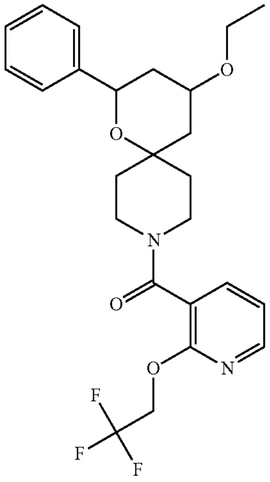

-continued
62 cis
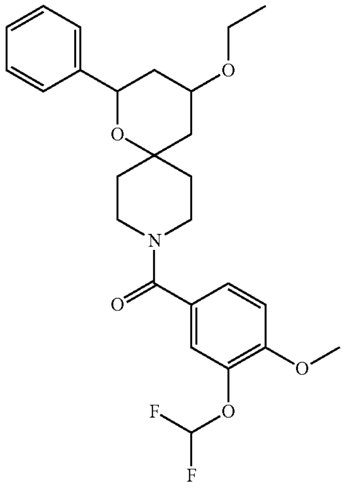
63 cis
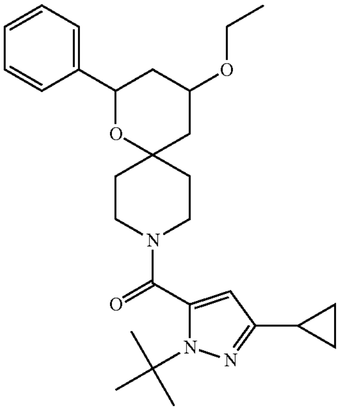
64 cis
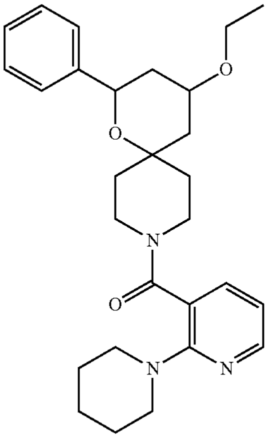
-continued
65 cis
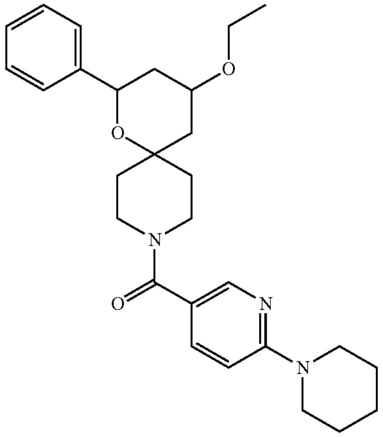
66 cis
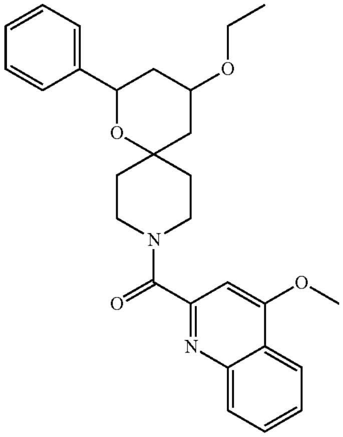
67 cis
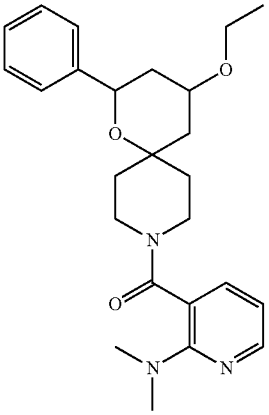

-continued
68 cis
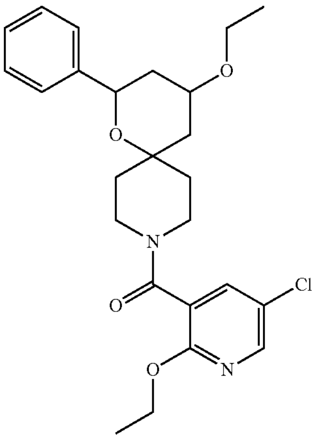
69 cis
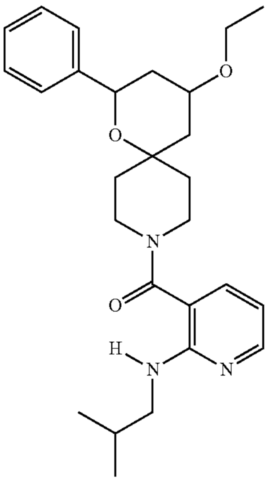
70 cis
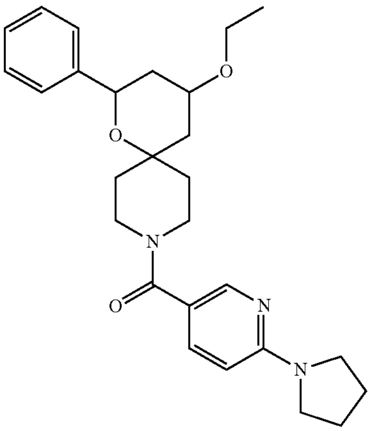
-continued
71 cis
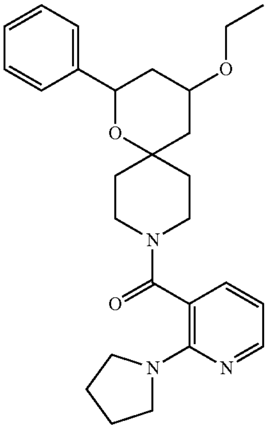
72 cis
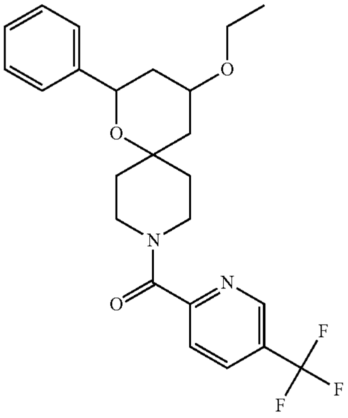
73 cis
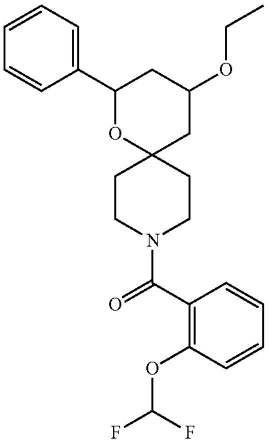

-continued
74 cis
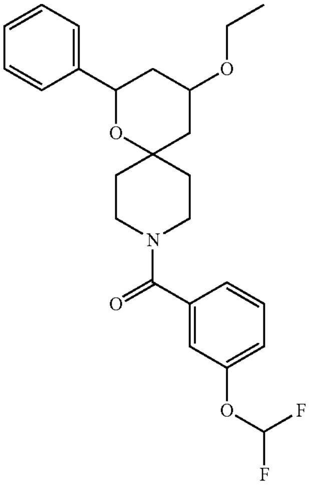
75 cis
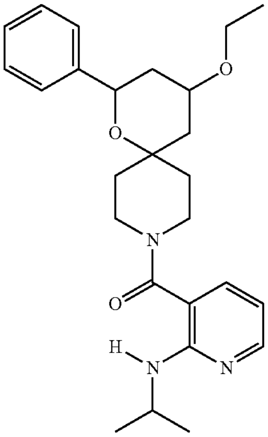
76 cis
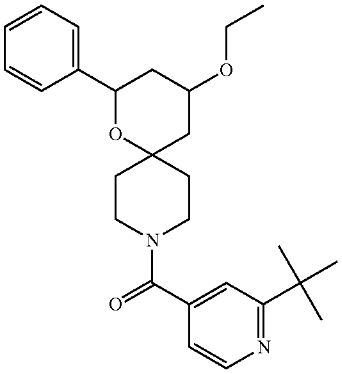
-continued
77 cis
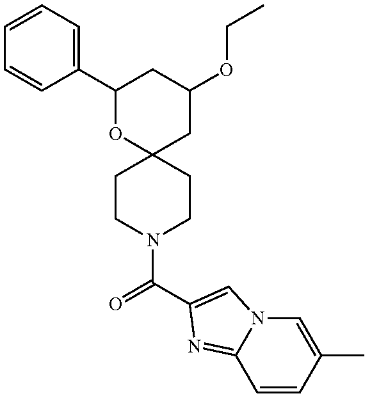
78 cis
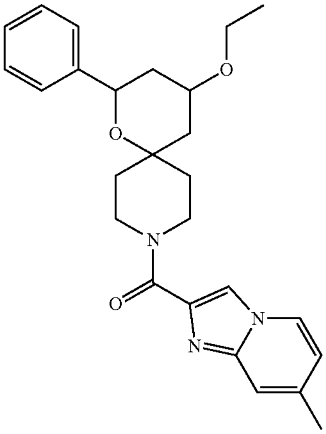
79 cis
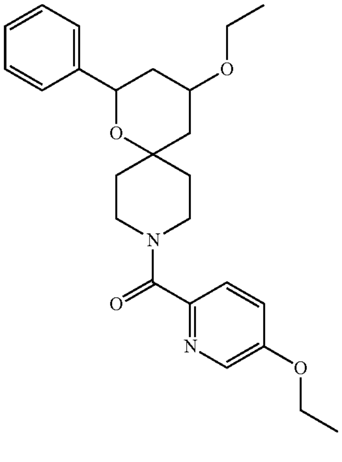

80 cis
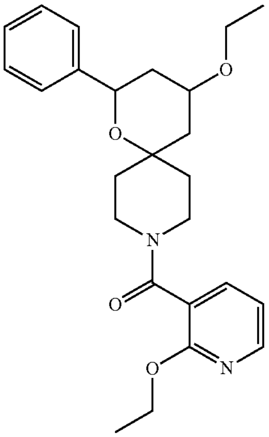
81 cis
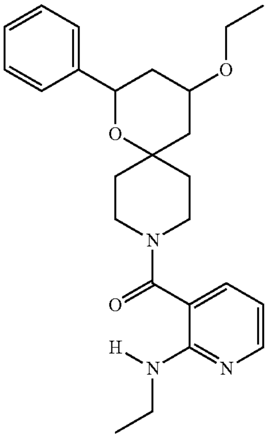
82 cis
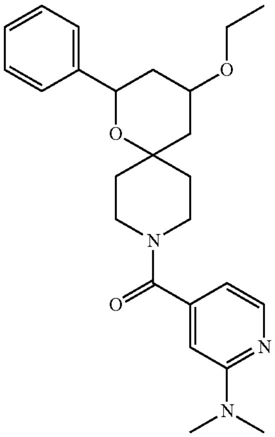
83 cis
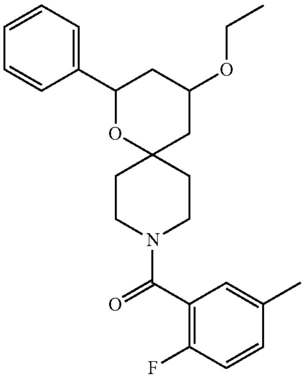
84 cis
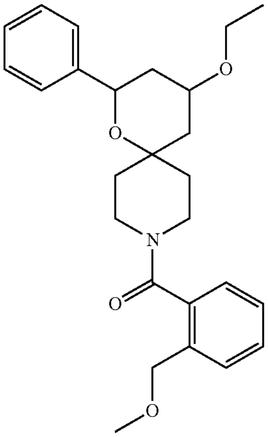
85 cis
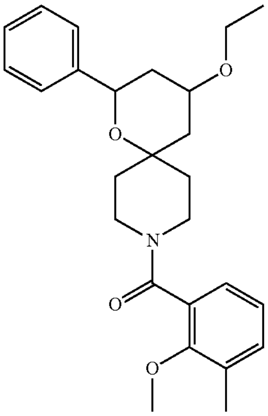

-continued
86 cis
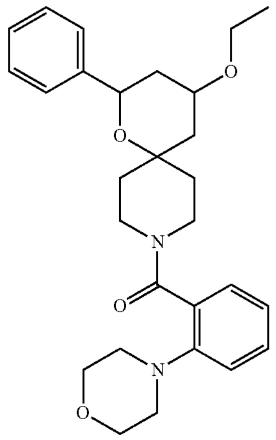
87 cis
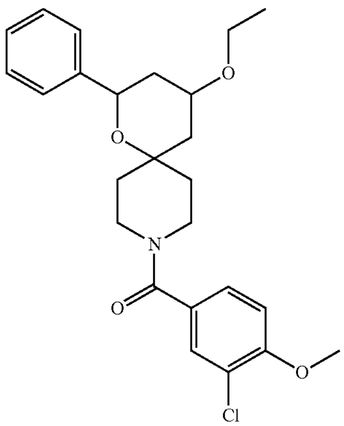
88 cis
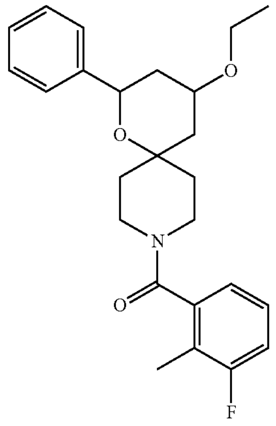
-continued
89 cis
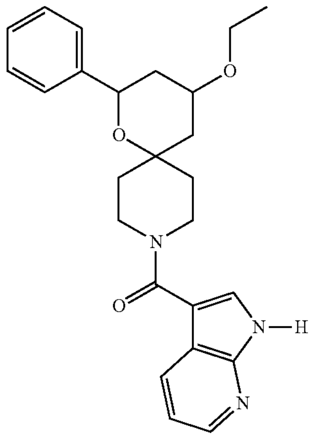
90 cis
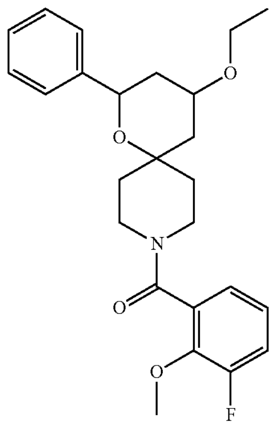
91 cis
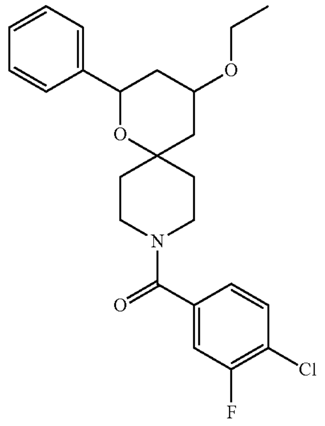

-continued
92 cis
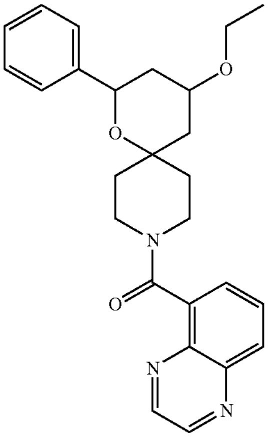
93 cis
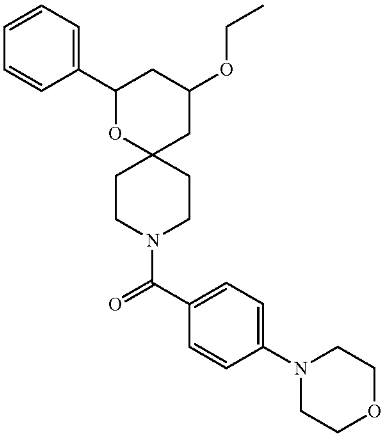
94 cis
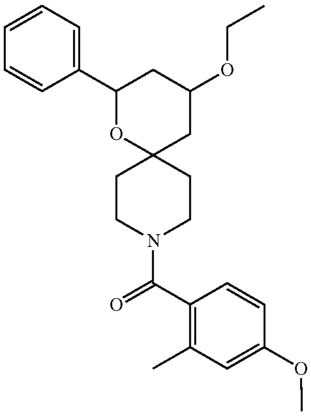
-continued
95 cis
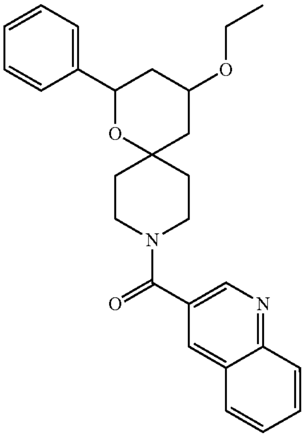
96 cis
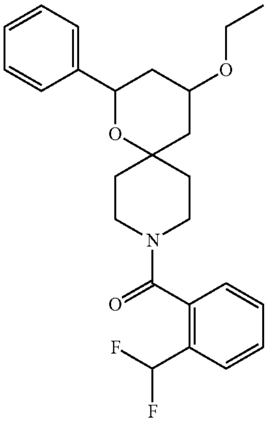
97 cis
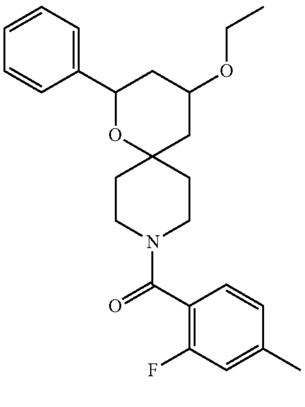

-continued
98 cis
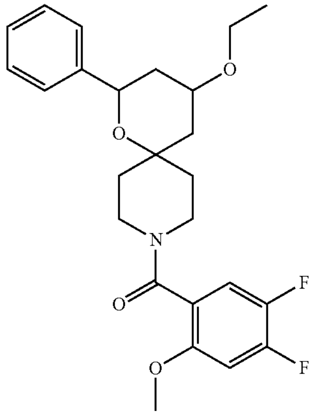
99 cis
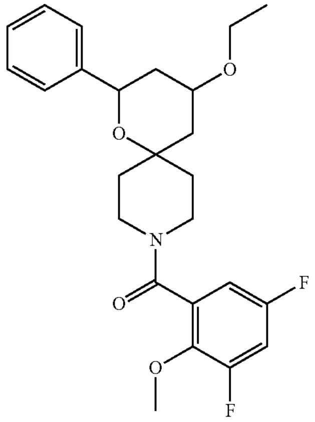
100 cis
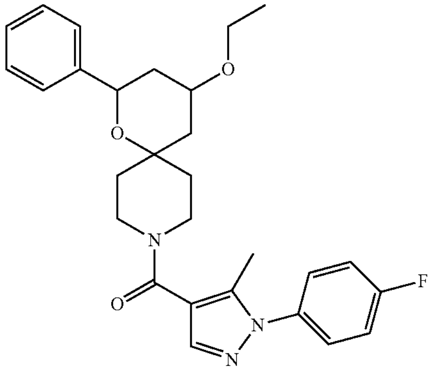
101 cis
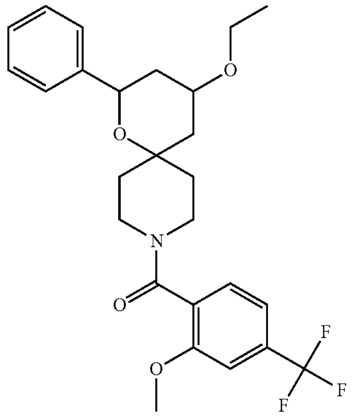
-continued
102 cis
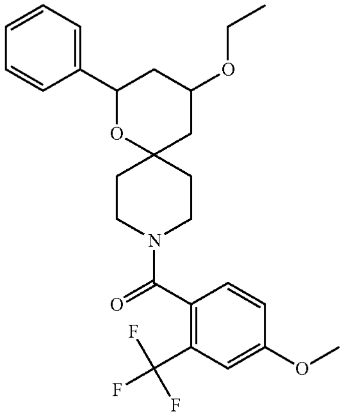
103 cis
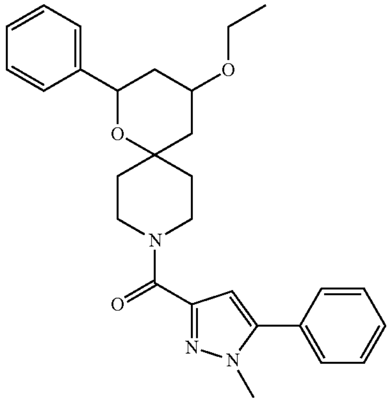
104 cis
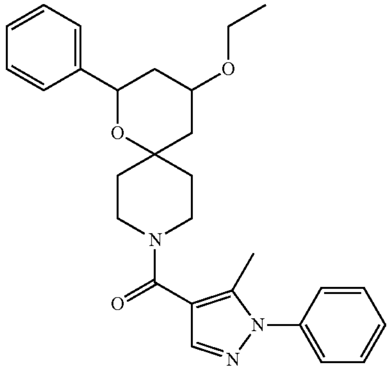

-continued
105 cis
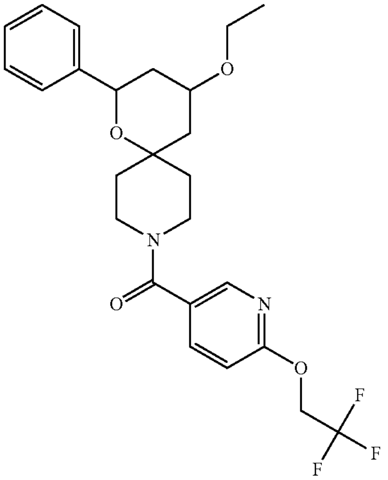
106 cis
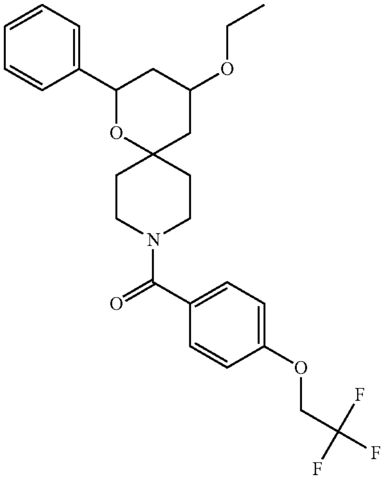
107 cis
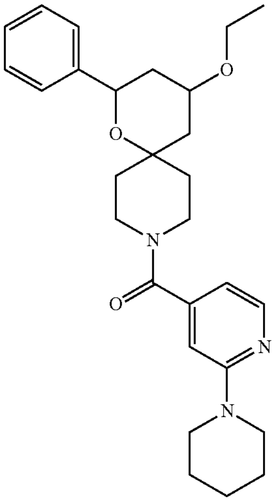
-continued
108 cis
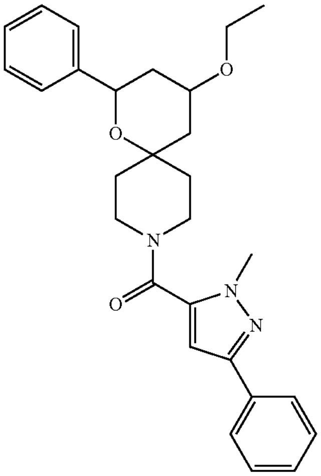
109 cis
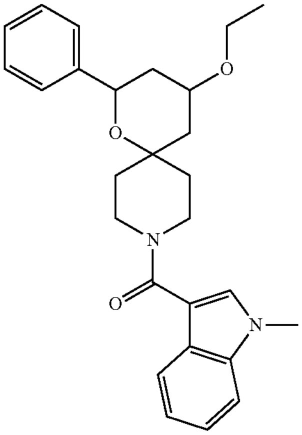
110 cis
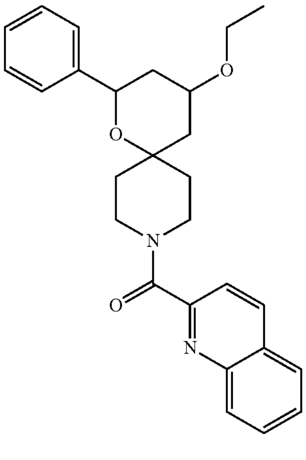

-continued
111 cis
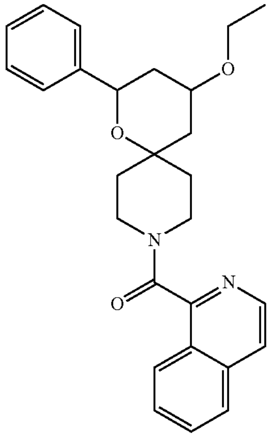
112 cis
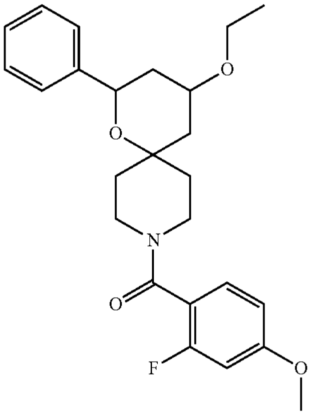
113 cis
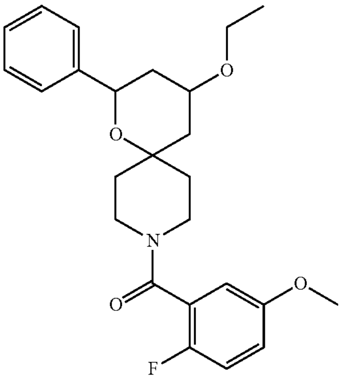
114 cis
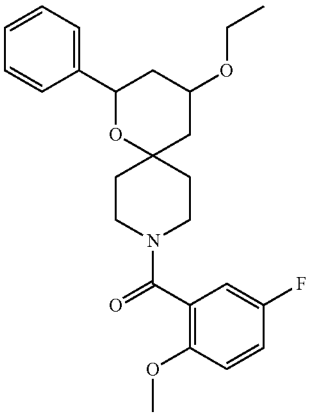
-continued
115 cis
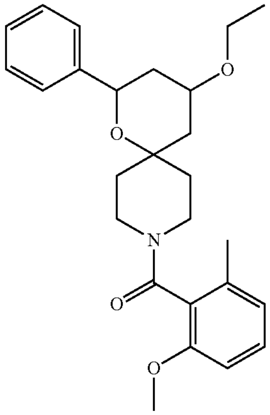
116 cis
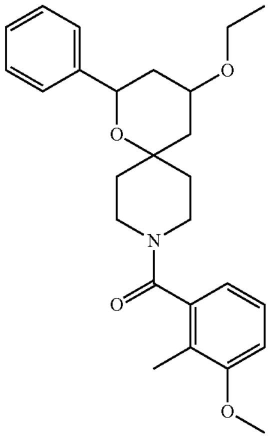
117 cis
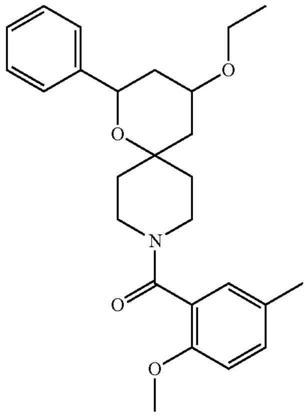

-continued
118 cis
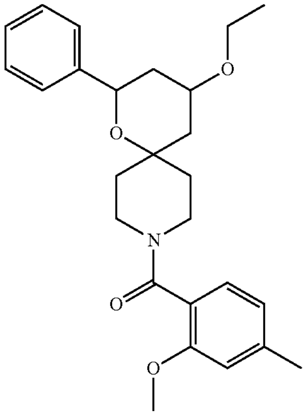
119 cis
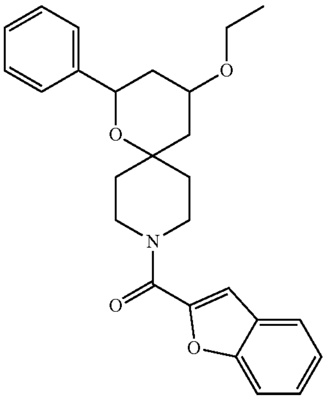
120 cis
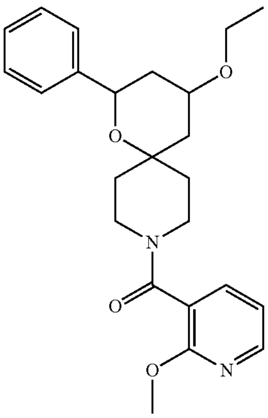
-continued
121 cis
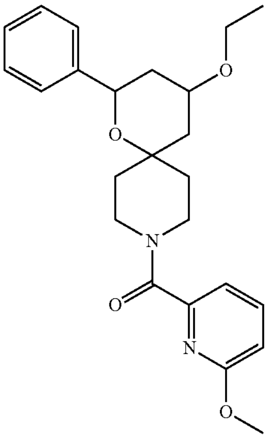
122 cis
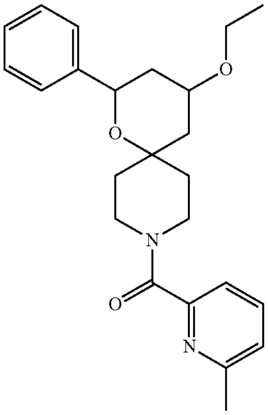
123 cis
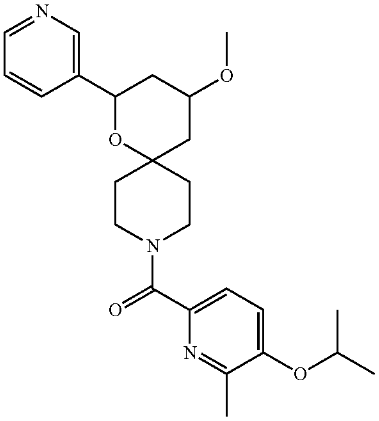

-continued
124 cis
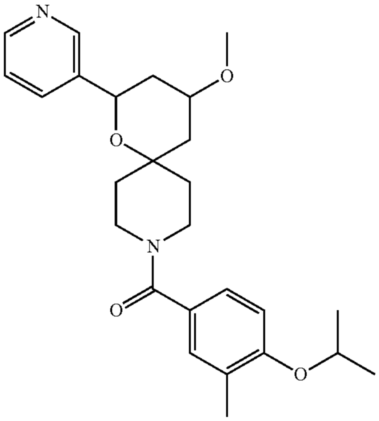
125 cis
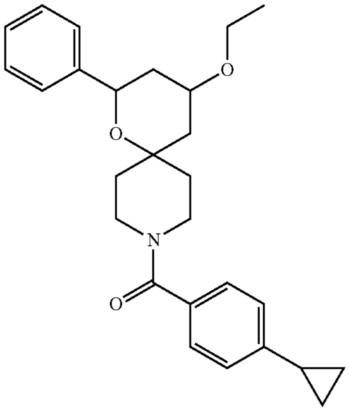
126 cis
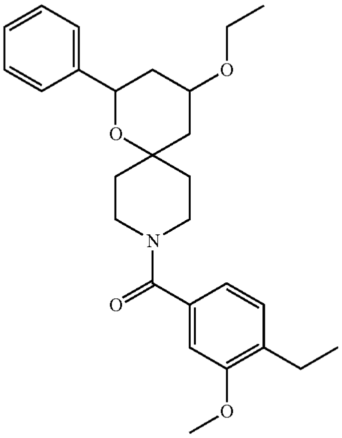
-continued
127 cis
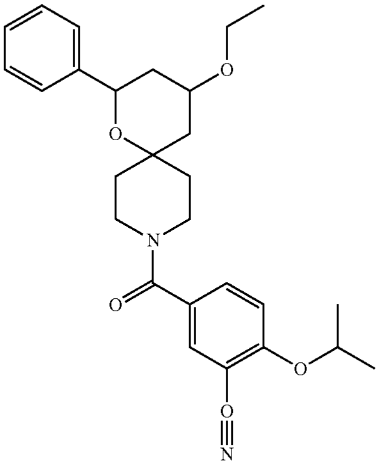
128 cis
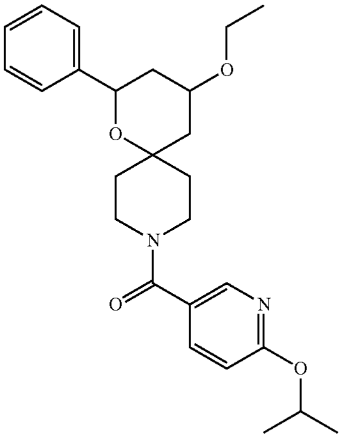
129 cis
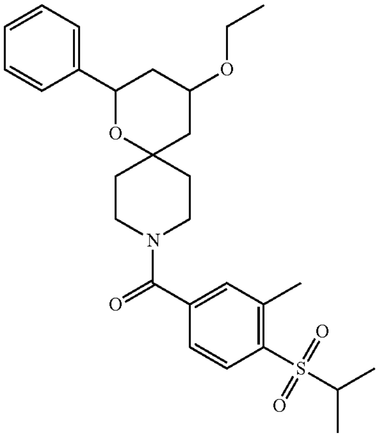

-continued
130 cis
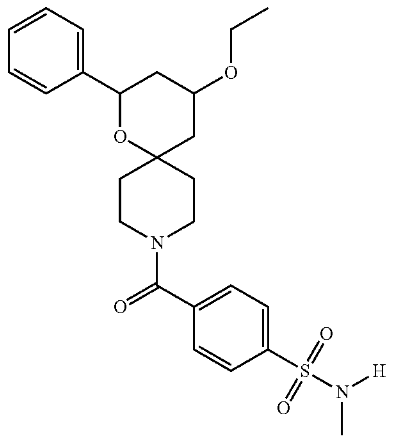
131 cis
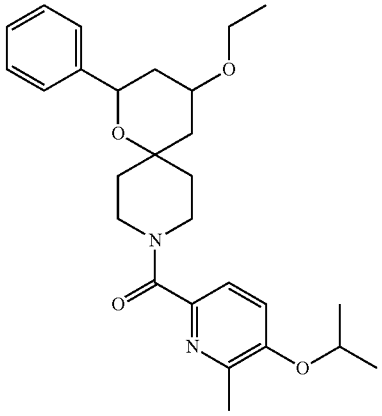
132 cis
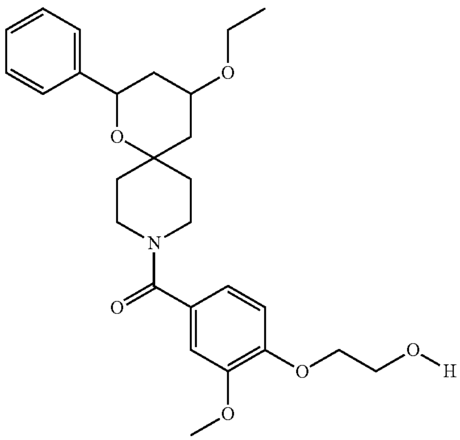
-continued
133 cis
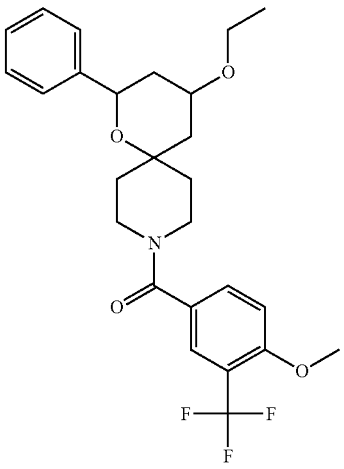
134 cis
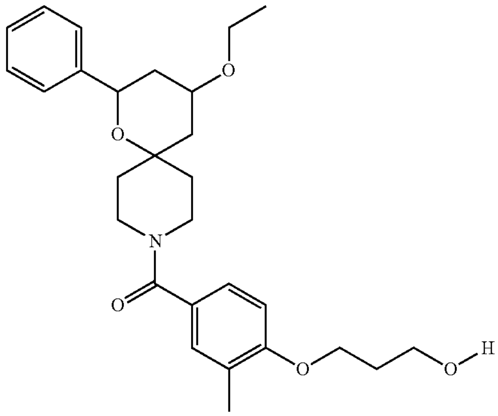
135 cis
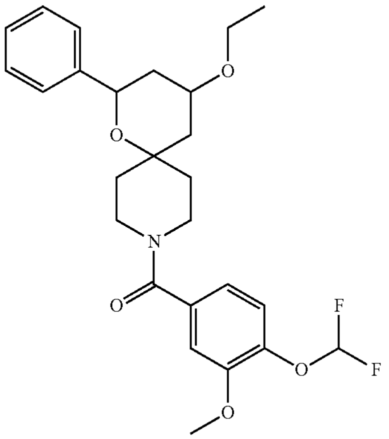

136 cis
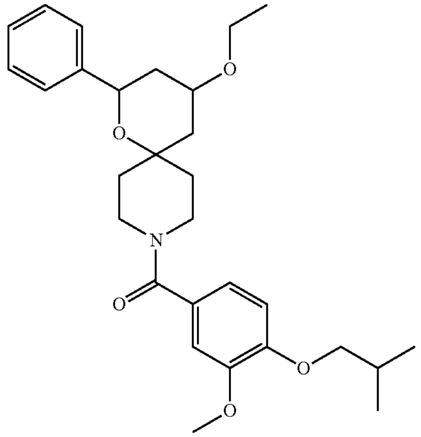
137 cis
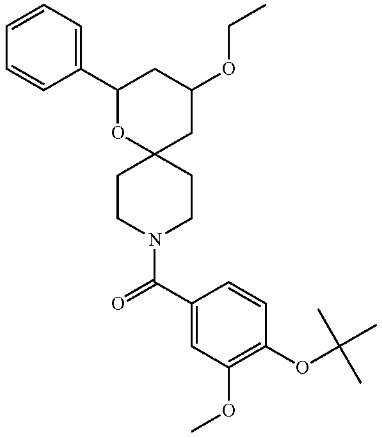
138 cis
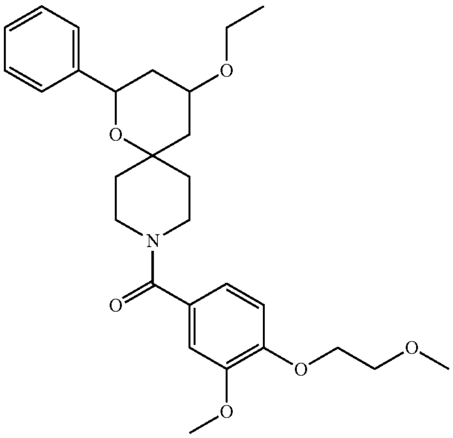
139 cis
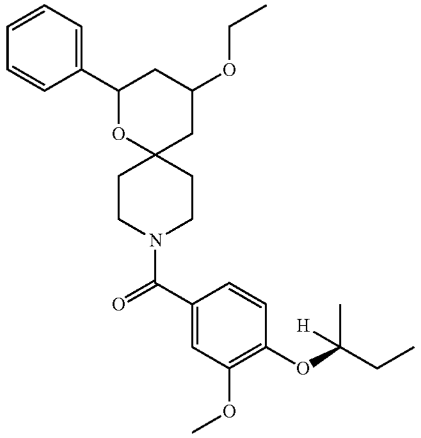
140 cis
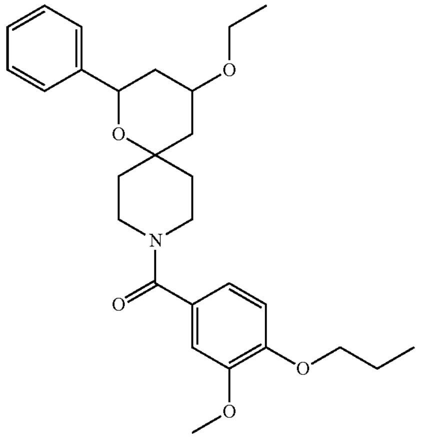
141 cis
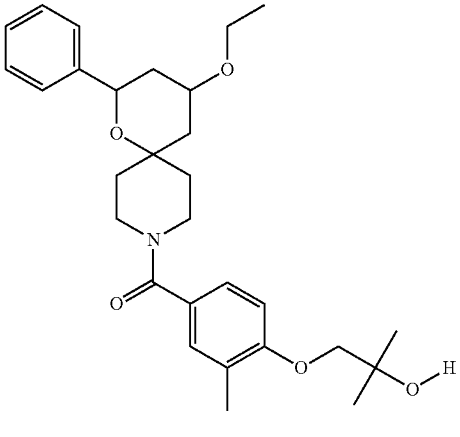

-continued
142 cis
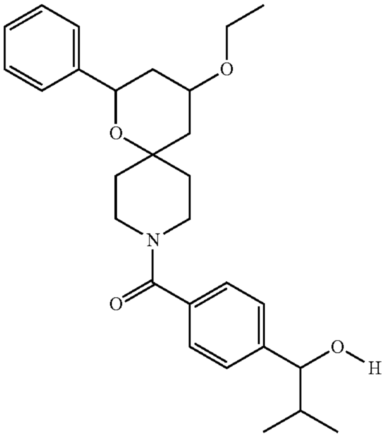
143 cis
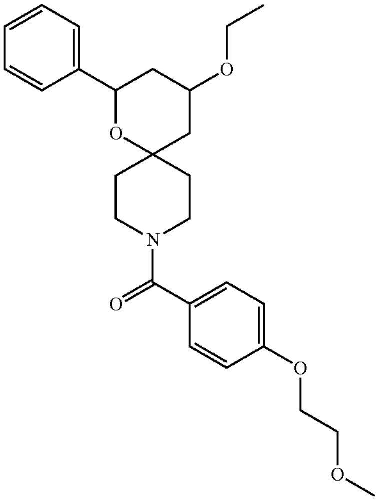
144 cis
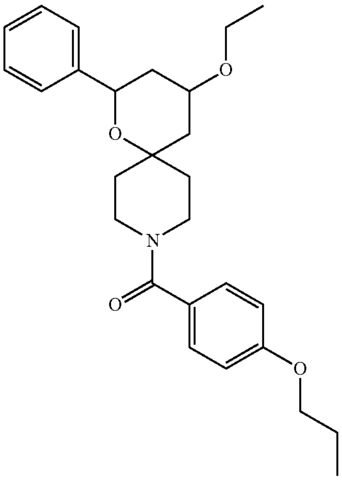
-continued
145 cis
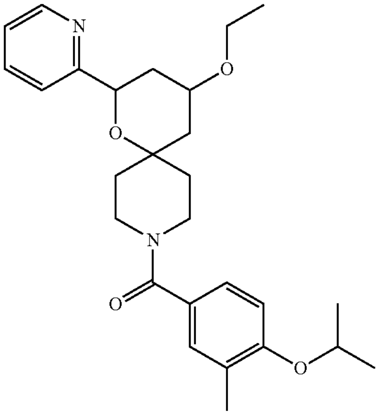
146 cis
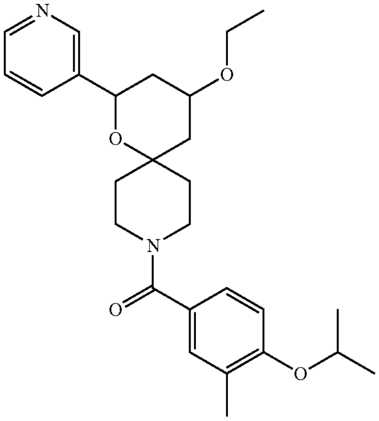
147 trans
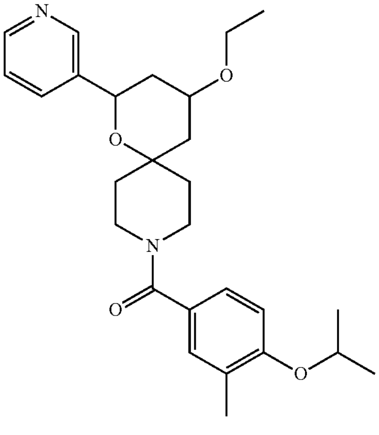

-continued
148 trans
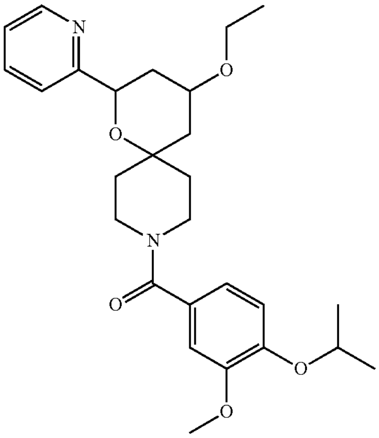
149 cis
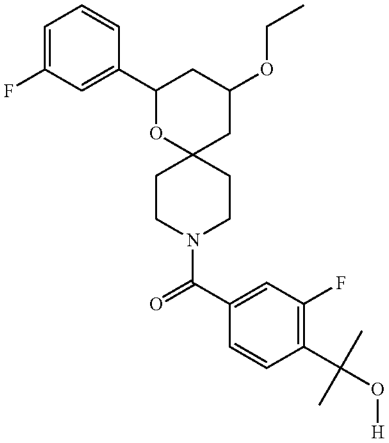
150 cis
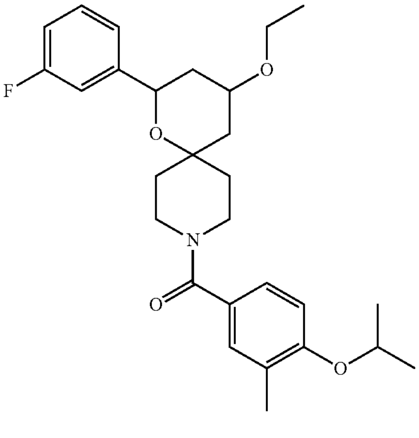
-continued
151 cis
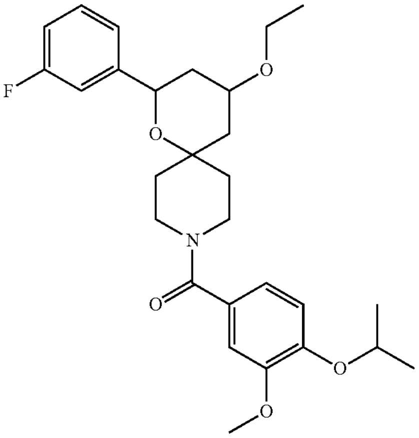
152 trans
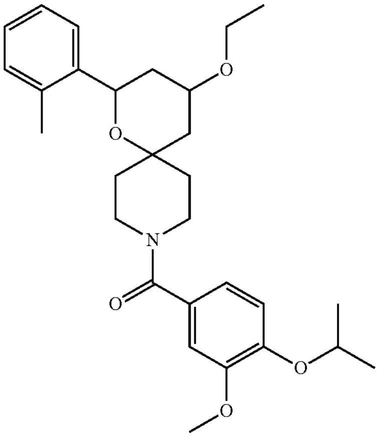
153 cis
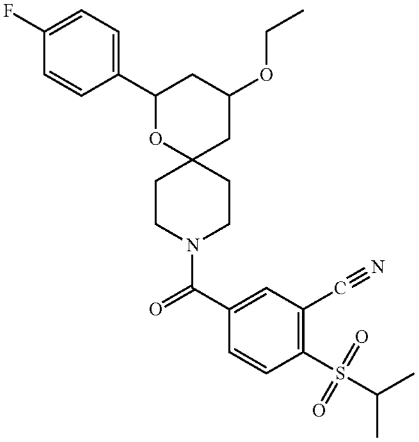

-continued
154 cis
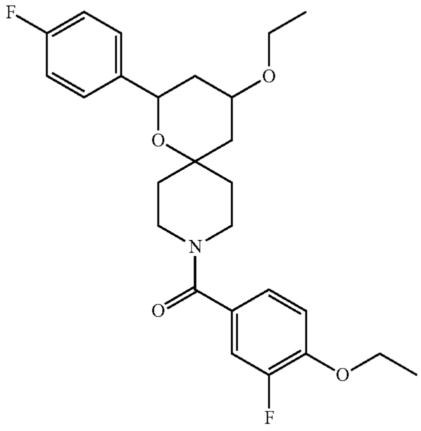
155 cis
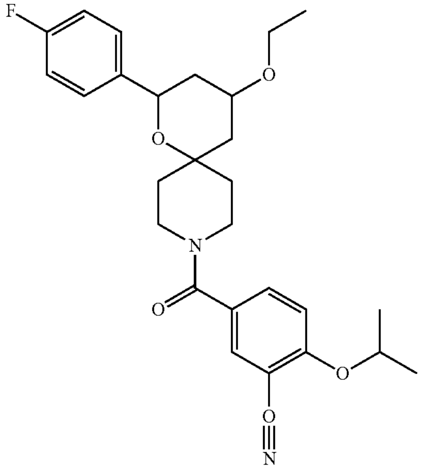
156 cis
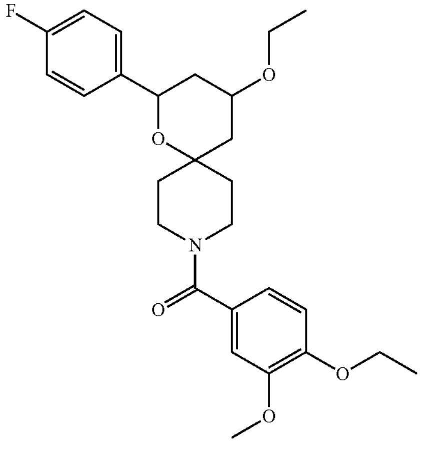
-continued
157 cis
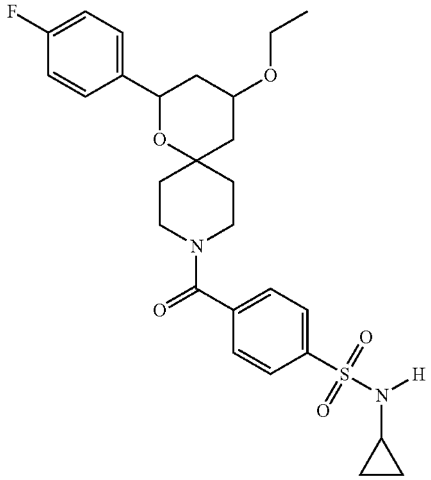
158 cis
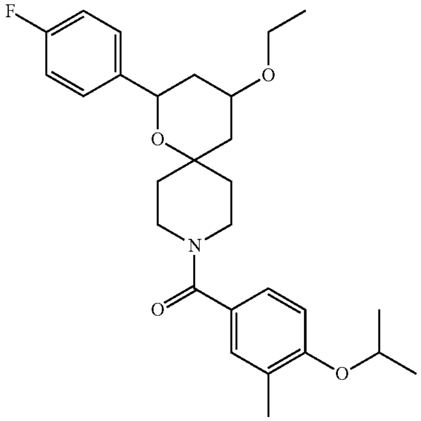
159 cis
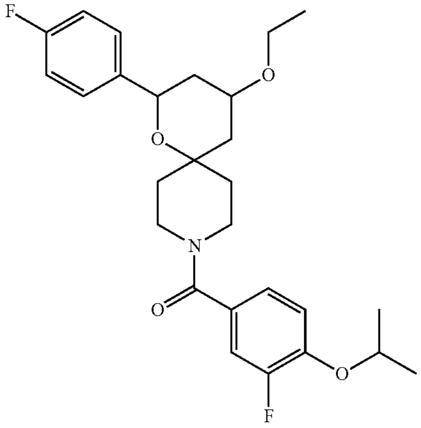

-continued
160 cis
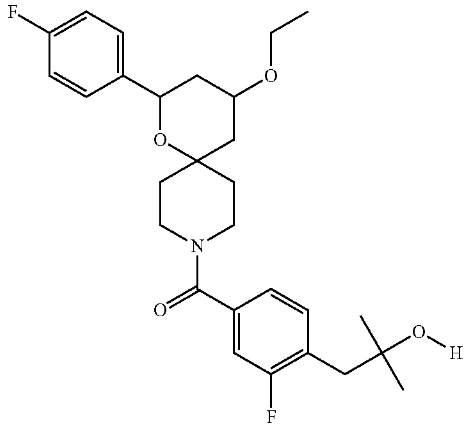
161 cis
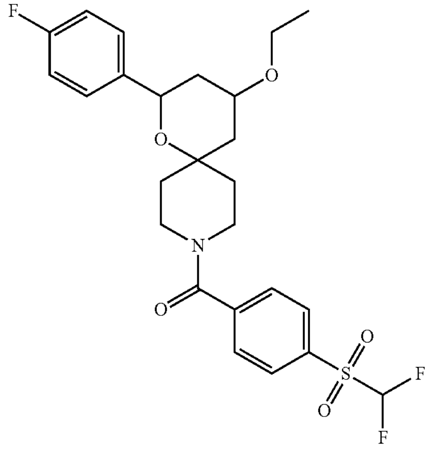
162 cis
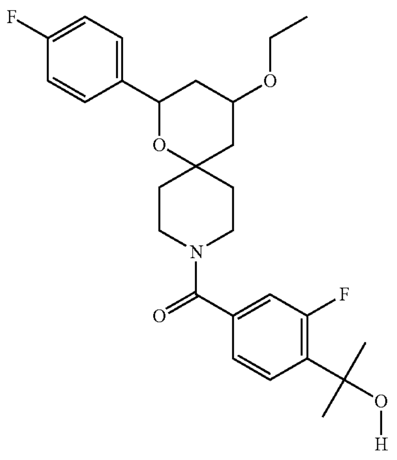
-continued
163 cis
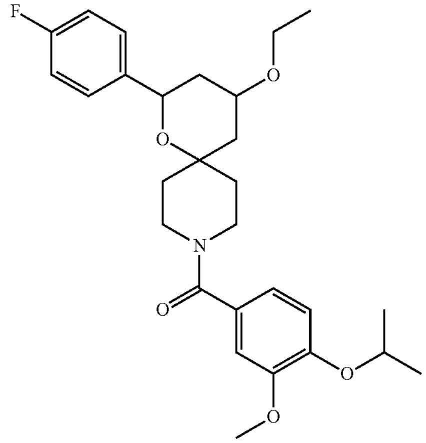
164 trans
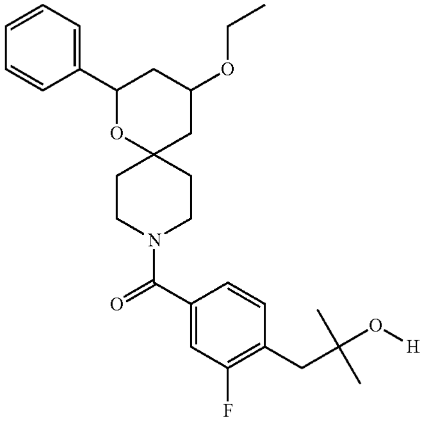
165 trans
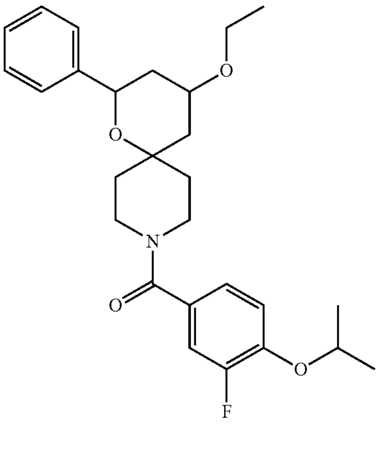

-continued
166 trans
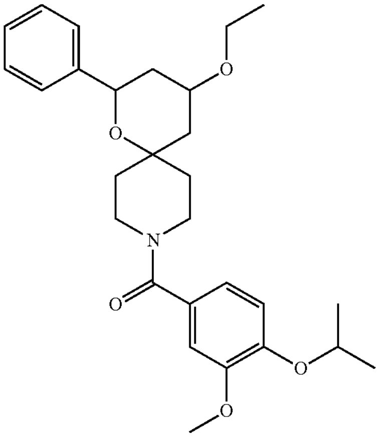
167 cis
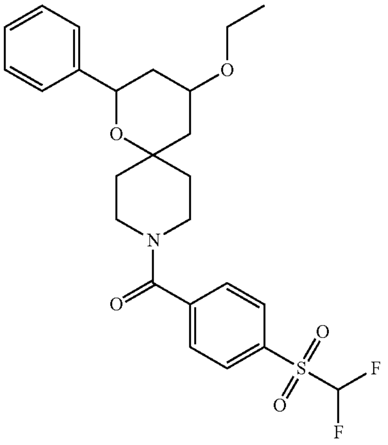
168 cis
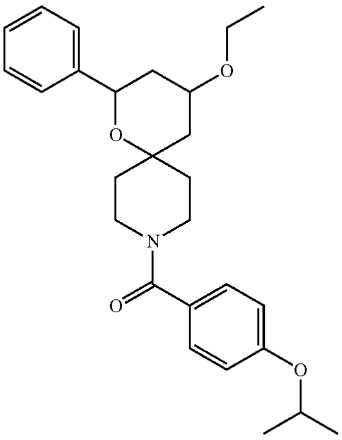
-continued
169 cis
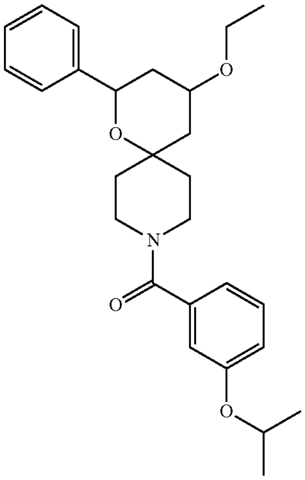
170 cis
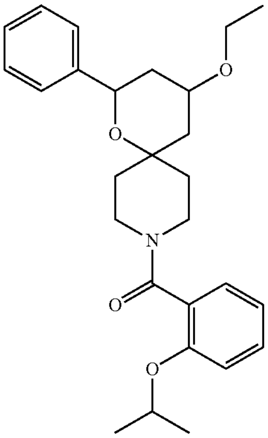
171 cis
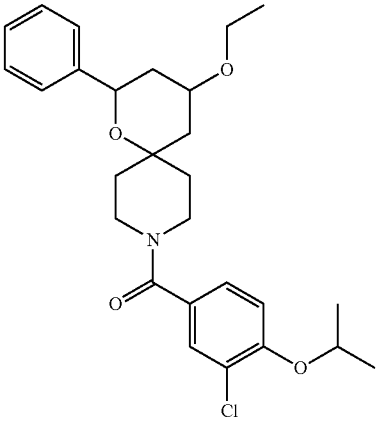

-continued
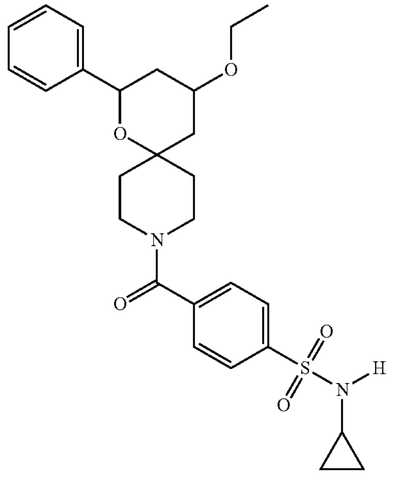
172 cis
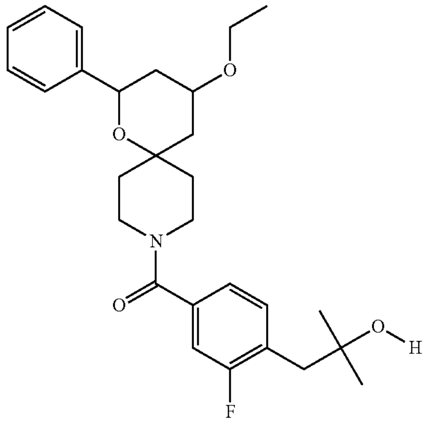
173 cis
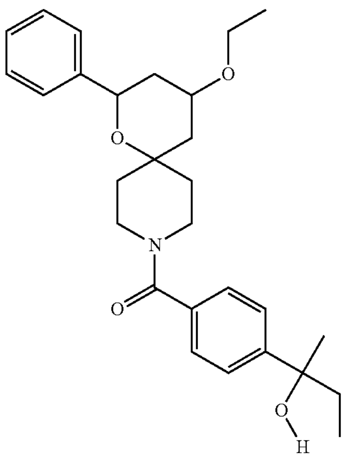
174 cis
-continued
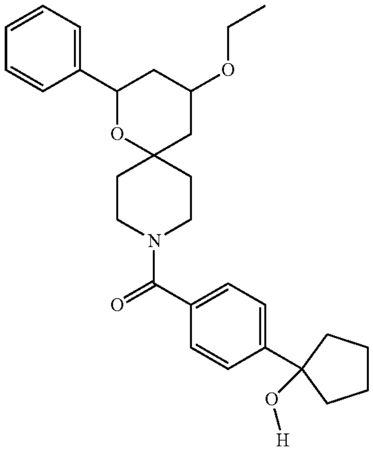
175 cis
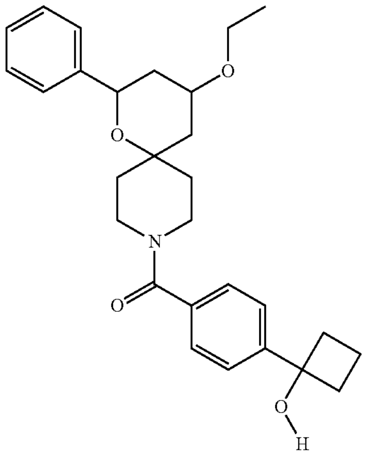
176 cis
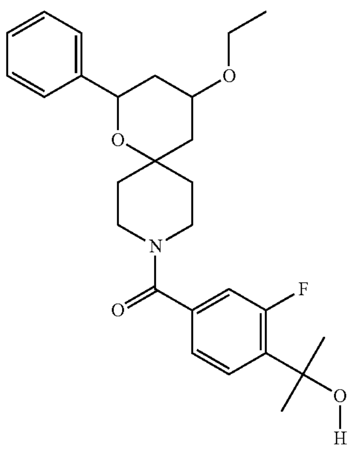
177 cis -continued
178 cis
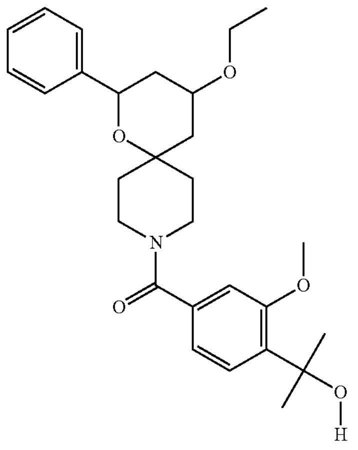
179 cis
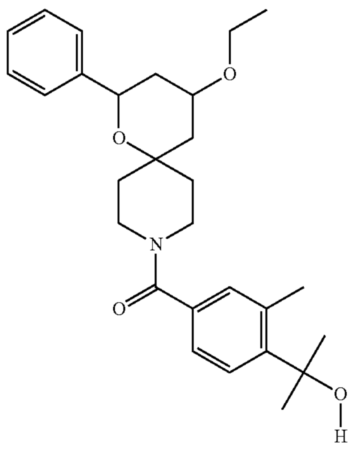
180 cis
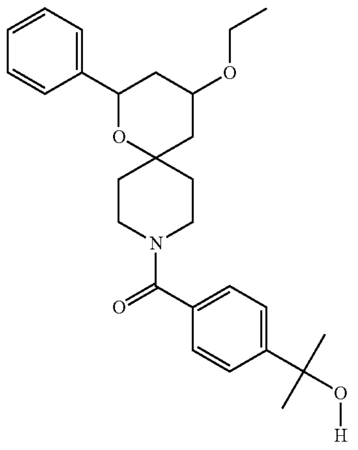
-continued
181 cis
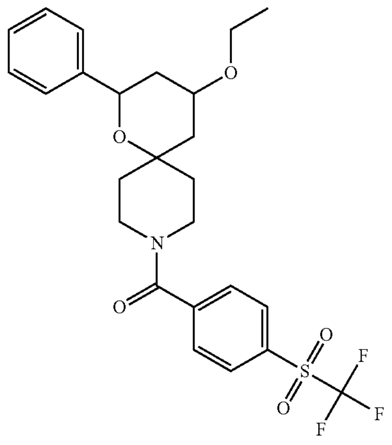
182 cis
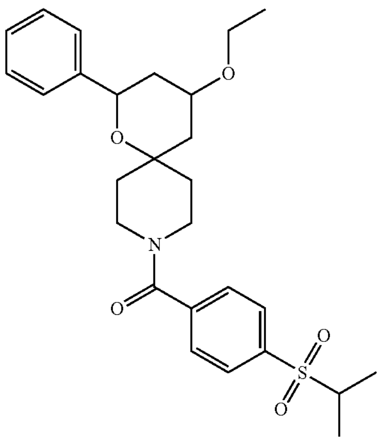
183 cis
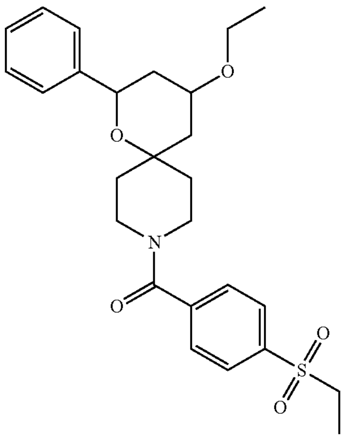

-continued
184 cis
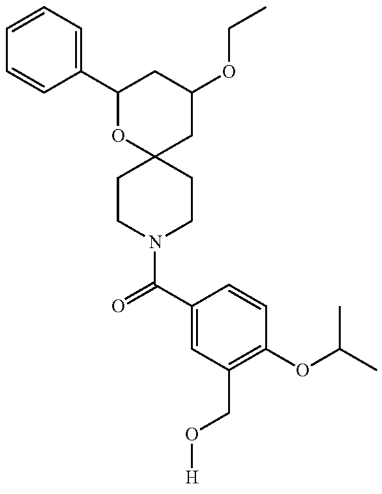
185 cis
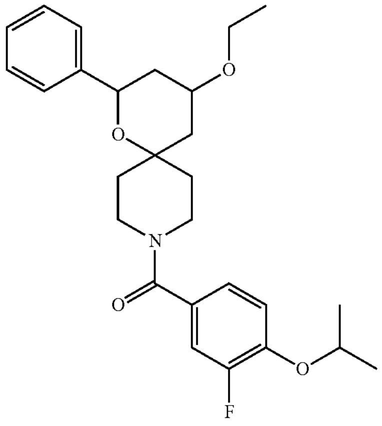
186 cis
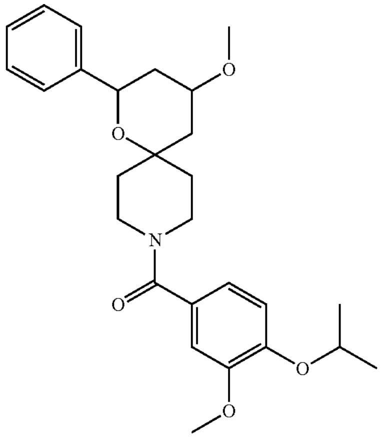
-continued
187 cis
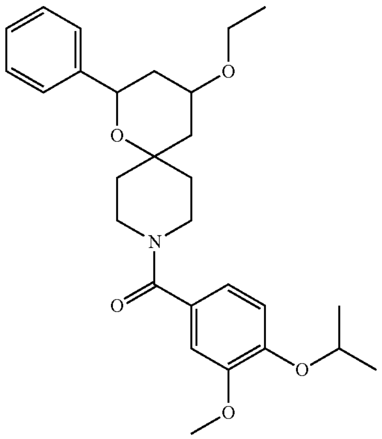
188 cis
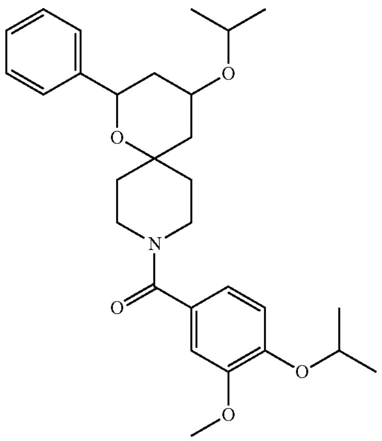
189 cis
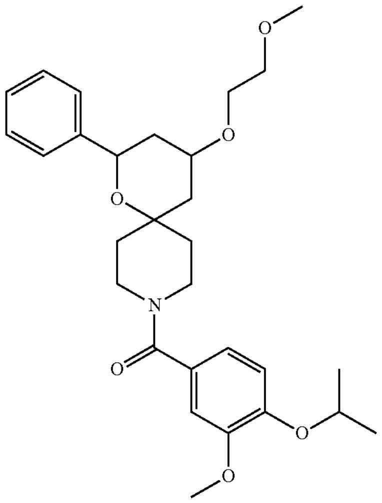

-continued

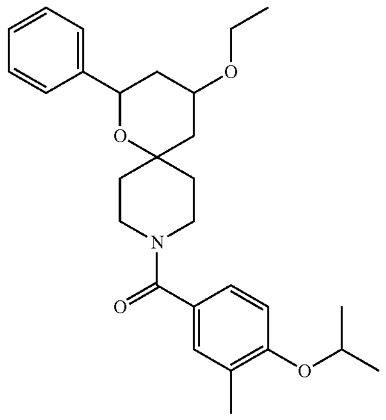

190 cis

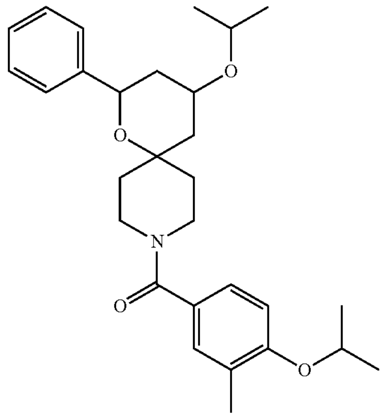

191 cis

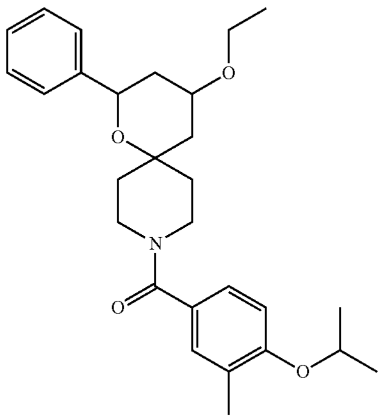

192 trans

-continued

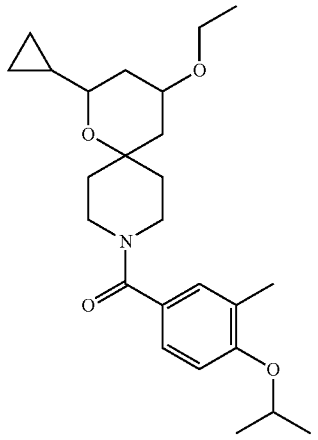

193 cis

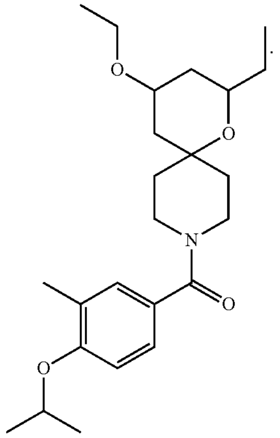

194 cis

In another aspect, the invention features a pharmaceutical composition comprising a compound of the invention and a pharmaceutically acceptable carrier.

In another aspect, the invention features a method of inhibiting a voltage-gated sodium ion channel in a patient or a biological sample comprising administering to the patient, or contacting the biological sample, with a compound or composition of the invention. In another embodiment, the voltage-gated sodium ion channel is NaV 1.7.

In another aspect, the invention features a method of treating or lessening the severity in a subject of acute, chronic, neuropathic, or inflammatory pain, arthritis, migraine, cluster headaches, trigeminal neuralgia, herpatic neuralgia, general neuralgias, epilepsy or epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, stroke, cerebral ischemia, traumatic brain injury, amyotrophic lateral sclerosis, stress- or exercise induced angina, palpitations, hypertension, migraine, or abormal gastro-intestinal motility, comprising administering an effective amount of a compound or composition of the invention.

In another embodiment, the method is used for treating or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, abdominal pain; pancreatic; IBS pain; chronic and acute headache pain; migraine; tension headache, including, cluster headaches; chronic and acute neuropathic pain, post-herpatic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, abdominal pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn and trauma pain; acute intermittent pain, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); prostatitis; complex regional pain syndrome (CRPS), type I and type II; widespread pain, paroxysmal extreme pain, pruritis, tinnitis, or angina-induced pain.

The compounds of the invention may be prepared readily using the following methods. Illustrated below in Scheme 1 through Scheme 8 are methods for preparing the compounds of the invention.

Scheme 1

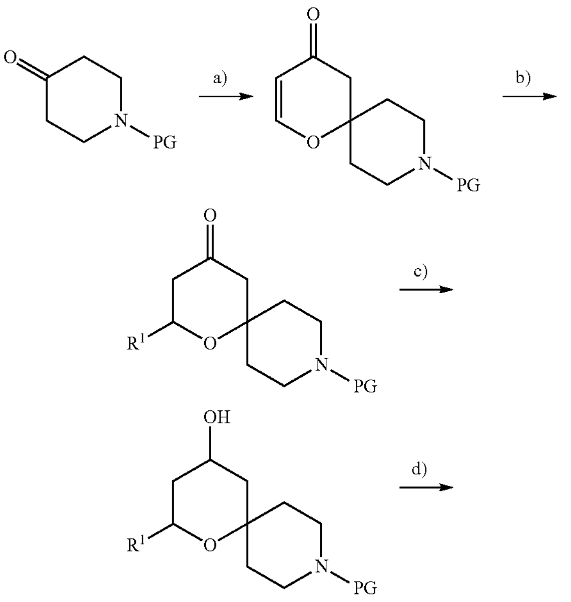

-continued

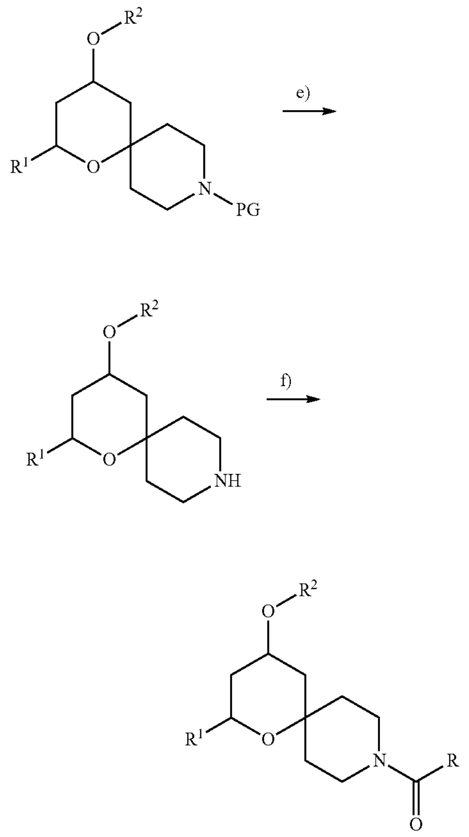

PG = protecting group (Boc, $CO_2Bn$), LG = leaving group (Cl, Br, I, OMs, OTs). a) 1) (1E)-3-[tert-butyl(dimethyl)silyl]oxy-N,N-dimethyl-buta-1,3-dien-1-amine, 2-butanol; 2) AcCl, $Et_2O$; b) $R^1$—MgBr, CuI, HMPA, TMSCl, tetrahydrofuran; c) $NaBH_4$, $CeCl_3$, MeOH; d) $R^2$—LG, NaH, DMF; e) PG = Boc: TFA, $CH_2Cl_2$; f) R—$CO_2H$, coupling agent (HATU, EDCI), base ($Et_3N$, $Et_2NiPr$), solvent (DMF, $CH_2Cl_2$).

Scheme 2

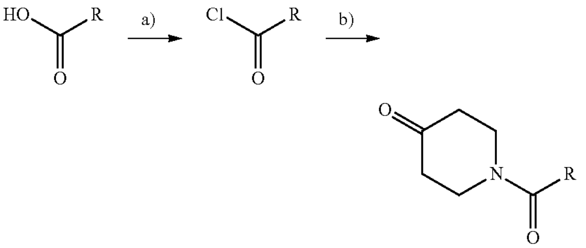

a) $SOCl_2$, $CH_2Cl_2$; b) piperidin-4-one, NaOH, toluene.

Scheme 3

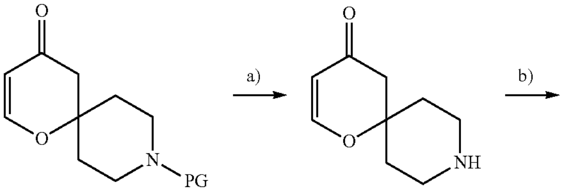

-continued
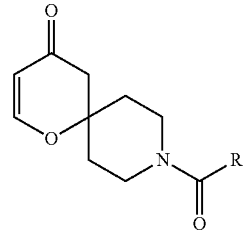
a) PG = Boc: TFA, $CH_2Cl_2$; b) $Et_3N$, RCOCl, $CH_2Cl_2$.
Scheme 4
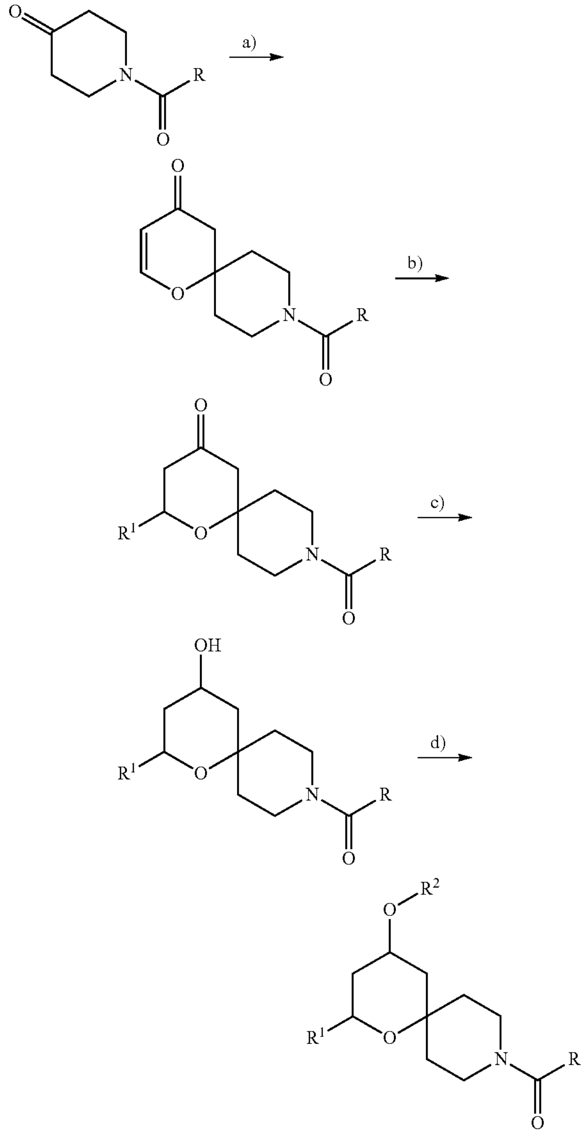
a) 1) (1E)-3-[tert-butyl(dimethyl)silyl]oxy-N,N-dimethyl-buta-1,3-dien-1-amine, 2-butanol; 2) AcCl, $Et_2O$; b) $R^1$-MgBr, CuI, HMPA, TMSCl, THF; c) $NaBH_4$, $CeCl_3$, MeOH; d) $R^2$-LG, NaH, DMF.
Scheme 5
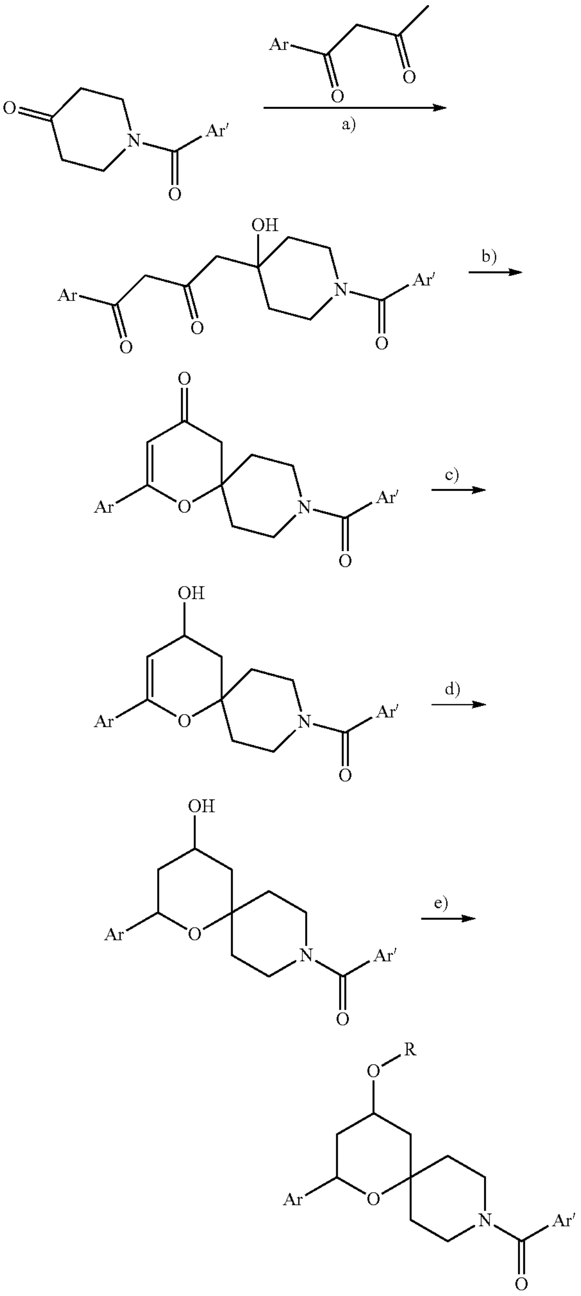
a) LDA, THF, -78° C.-rt; b) PPTS, $CH_2Cl_2$, microwave, 120° C.; c) NaBH, MeOH, rt; d) $H_2$, Pd/C, MeOH; e) RX, NaH, DMF.
Scheme 6
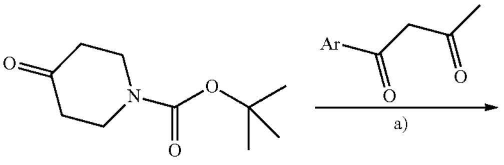

-continued
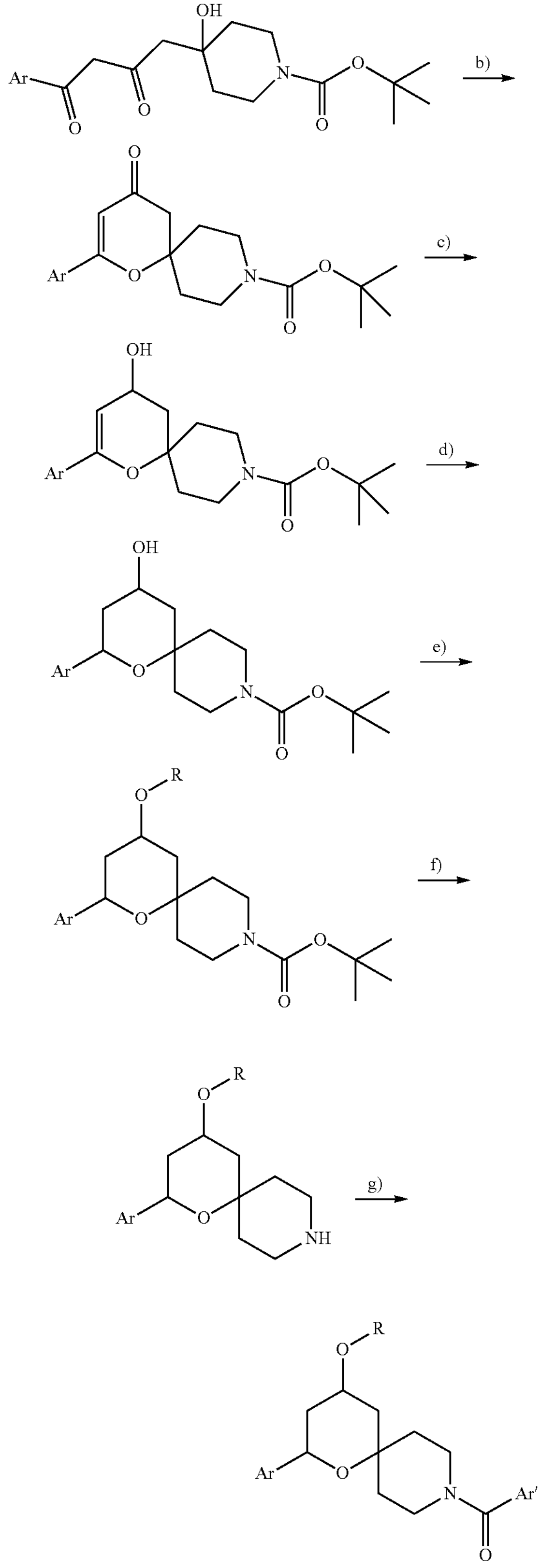
a) LDA, THF, -78° C.-rt; b) PPTS, $CH_2Cl_2$, microwave, 120° C.; c) NaBH, MeOH, rt; d) $H_2$, Pd/C, MeOH; e) RX, NaH, DMF; f) TFA, $CH_2Cl_2$, rt; g) ArCOCl, $NEt_3$, $CH_2Cl_2$ or ArCOOH, EDCl, DIEA, $CH_2Cl_2$, rt or ArCOOH, DIEA, HATU, DMF, rt.
Scheme 7
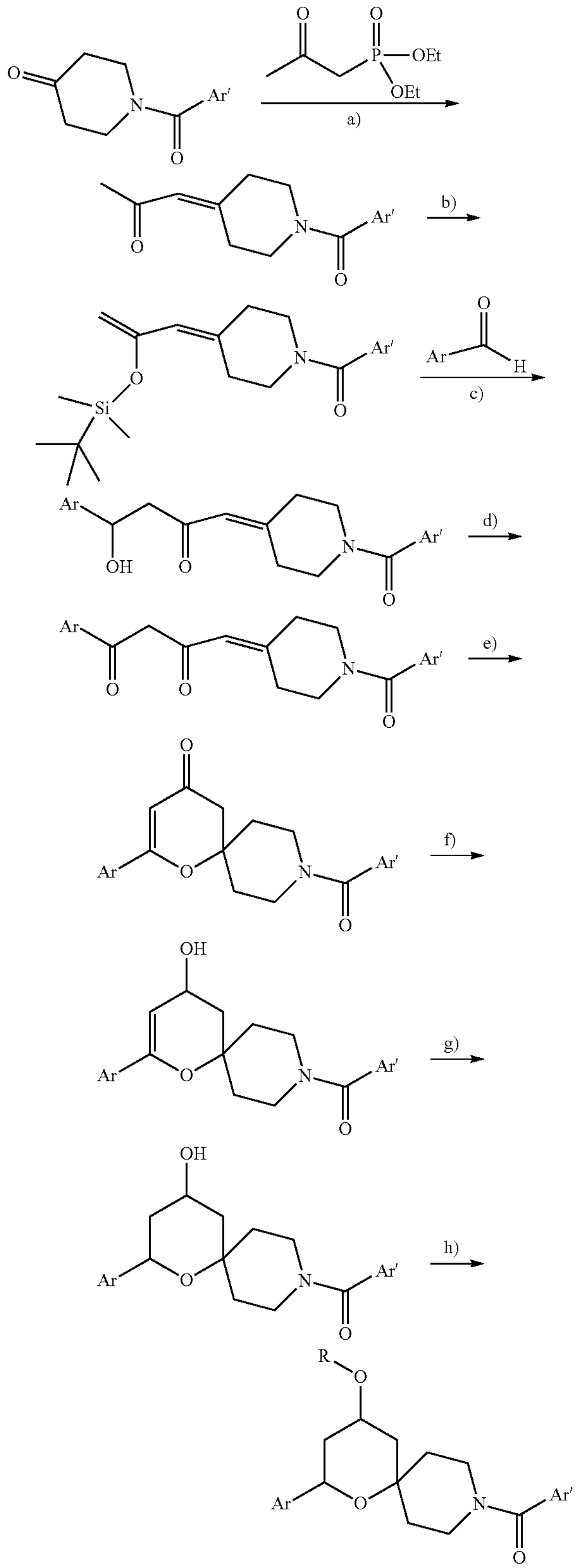
a) NaH, THF, rt; b) TBSOTf, TEA, $CH_2Cl_2$, 0° C; c) $BF_3$•$OEt_2$, $CH_2Cl_2$, -78° C.; d) Dess-Martin Periodinance, $CH_2Cl_2$, 0° C.; e) HOAc, reflux; f) $NaBH_4$, MeOH, rt; g) $H_2$, Pd/C, MeOH, rt; h) RX, NaH, DMF, rt.

Scheme 8

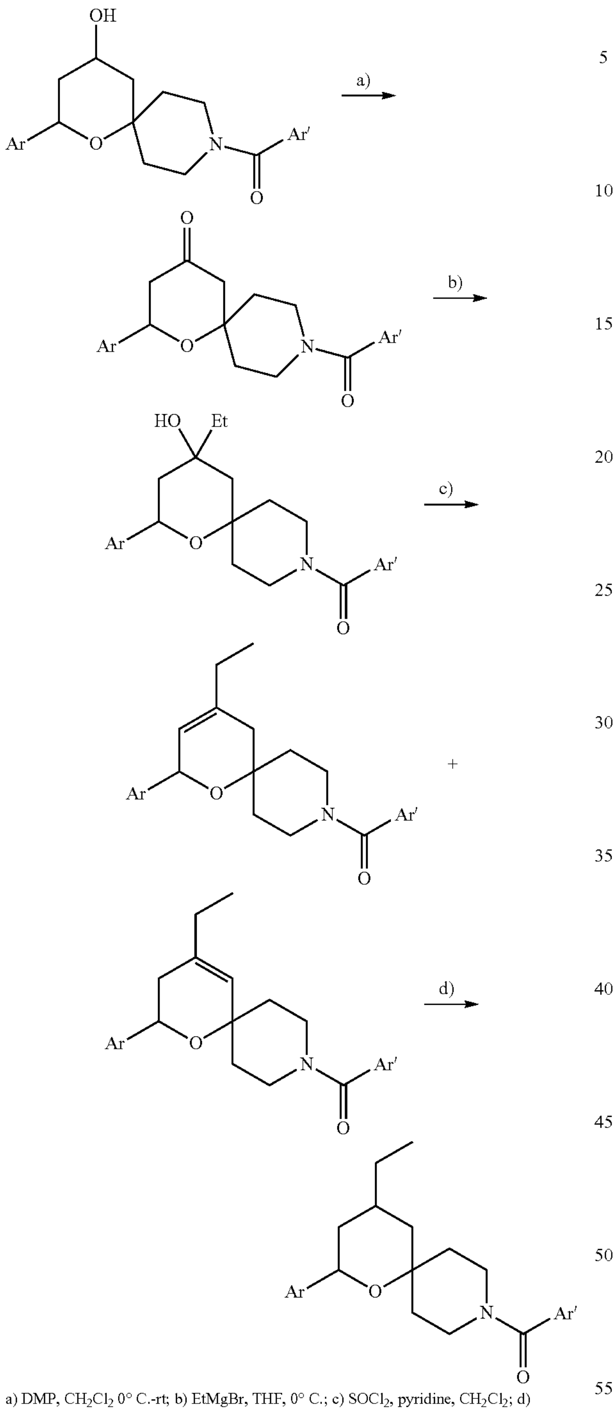

a) DMP, $CH_2Cl_2$ 0° C.-rt; b) EtMgBr, THF, 0° C.; c) $SOCl_2$, pyridine, $CH_2Cl_2$; d) $H_2$, Pd/C, EtOH, rt.

Uses, Formulation and Administration

Pharmaceutically Acceptable Compositions

As discussed above, the invention provides compounds that are inhibitors of voltage-gated sodium ion channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of invention can exist in free form for treatment, or where appropriate, as a pharmaceutically acceptable derivative thereof. According to the invention, a pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof.

In certain embodiments, a method of treatment or lessening the severity of stroke, cerebral ischemia, traumatic brain injury, amyotrophic lateral sclerosis, stress- or exercise induced angina, palpitations, hypertension, migraine, or abormal gastro-intestinal motility is provided comprising administering an effective amount of a compound, or a pharmaceutically acceptable composition comprising a compound to a subject in need thereof.

In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitis or cancer pain is provided comprising administering an effective amount of a compound or a pharmaceutically acceptable composition to a subject in need thereof.

In certain embodiments, a method for the treatment or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic and acute headache pain; migraine; tension headache, including, cluster headaches; chronic and acute neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis; complex regional pain syndrome (CRPS), type I and type II; angina-induced pain is provided, comprising administering an effective amount of a compound or a pharmaceutically acceptable composition to a subject in need thereof.

In certain embodiments of the invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain.

The compounds and compositions, according to the method of the invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the invention will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts. The term "subject" or "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels. In one embodiment, the compounds and compositions of the invention are inhibitors of one or more of NaV1.1, NaV1.2, NaV1.3, NaV1.4, NaV1.5, NaV1.6, NaV1.7, NaV1.8, or NaV1.9, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease, condition, or disorder. When activation or hyperactivity of NaV1.1, NaV1.2, NaV1.3, NaV1.4, NaV1.5, NaV1.6, NaV1.7, NaV1.8, or NaV1.9 is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, or NaV1.9 may be assayed according to methods described generally in the Examples herein, or according to methods available to one of ordinary skill in the art.

In certain exemplary embodiments, compounds of the invention are useful as inhibitors of NaV1.7 and/or NaV1.8.

It will also be appreciated that the compounds and pharmaceutically acceptable compositions of the invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butabital, mephobarbital, metharbital, methohexital, pentobarbital, phenobartital, secobarbital, talbutal, theamylal or thiopental;

(4) a benzodiazepine having a sedative action, e.g. chlordiazepoxide, clorazepate, diazepam, flurazepam, lorazepam, oxazepam, temazepam or triazolam;

(5) an H1 antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphrenadine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(R), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

(10) a tricyclic antidepressant, e.g. desipramine, imipramine, amitriptyline or nortriptyline;

(11) an anticonvulsant, e.g. carbamazepine, lamotrigine, topiratmate or valproate;

(12) a tachykinin (NK) antagonist, particularly an NK-3, NK-2 or NK-I antagonist, e.g. ([alpha]R,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion(R) or sarizotan;

(17) a vanilloid receptor agonist (e.g. resinferatoxin) or antagonist (e.g. capsazepine);

(18) a beta-adrenergic such as propranolol;

(19) a local anaesthetic such as mexiletine;

(20) a corticosteroid such as dexamethasone;

(21) a 5-HT receptor agonist or antagonist, particularly a 5-HT1 B/I D agonist such as eletriptan, sumatriptan, naratriptan, zolmitriptan or rizatriptan;

(22) a 5-HT2A receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol(R);

(25) a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7//-pyrazolo[4,3-<i]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-<i] pvrimidm-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(26) an alpha-2-delta ligand such as gabapentin, pregabalin, 3-methyl gabapentin, (1[alpha],3[alpha],5[alpha])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl) bicyclo[3.2.0]hept-6-yl]acetic acid, 3-(1-aminomethyl-cyclohexylmethyl)-4H-[1,2,4]oxadiazol-5-one, C-[1-(IH-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(27) a cannabinoid;

(28) metabotropic glutamate subtype 1 receptor (mGluRl) antagonist;

(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(30) a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan(R)), especially a selective noradrenaline reuptake inhibitor such as reboxetine, in particular (S,S)-reboxetine;

(31) a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

(32) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S, 5Z)-2-amino-2-methyl-7-[(1-iminoethyl)amino]-5-heptenoic acid, 2-[[(1R,3S)-3-amino-4-hydroxy-1-(5-thiazolyl)-butylJthioJ-S-chloro-5-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R, 3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl] phenyl]thiophene-2-carboxamidine, or guanidinoethyldisulfide;

(33) an acetylcholinesterase inhibitor such as donepezil;

(34) a prostaglandin E2 subtype 4 (EP4) antagonist such as 7V-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(15)-1-({[5-chloro-2-(3-fluorophenoxy) pyridin-3-yl]carbonyl}amino)ethyl]benzoic acid;

(35) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870,

(36) a 5-lipoxygenase inhibitor, such as zileuton, 6-[(3-fluoro-5-[4-methoxy-3,4,5,6-tetrahydro-2H-pyran-4-yl]) phenoxy-methyl]-1-methyl-2-quinolone (ZD-2138), or 2,3, 5-trimethyl-6-(3-pyridylmethyl),1,4-benzoquinone (CV-6504);

(37) a sodium channel blocker, such as lidocaine;

(38) a 5-HT3 antagonist, such as ondansetron; and the pharmaceutically acceptable salts and solvates thereof.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound of the invention as described generally above, and in classes and subclasses herein, and a carrier suitable for coating said implantable device. In still another aspect, the invention includes an implantable device coated with a composition comprising a compound of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, or NaV1.9, activity in a biological sample or a subject, which method comprises administering to the subject, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, or NaV1.9, activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

EXAMPLES

General Methods. $^{1}H$ NMR (400 MHz or 300 MHz) and $^{13}C$ NMR (100 MHz) spectra were obtained as solutions in deuterioacetonitrile ($CD_3CN$), chloroform-d ($CDCl_3$), deuteromethanol (MeOD-d4), or dimethyl sulfoxide-$D_6$ (DMSO). Mass spectra (MS) were obtained using an Applied Biosystems API EX LC/MS system equipped with a Phenomenex 50×4.60 mm luna-5μ C18 column. The LC/MS eluting system was 1-99% or 10-99% acetonitrile in $H_2O$ with 0.035% v/v trifluoroacetic acid, 0.035% v/v formic acid, 5 mM HCl or 5 mM ammonium formate using a 3 or 15 minute linear gradient and a flow rate of 12 mL/minute. Silica gel chromatography was performed using silica gel-60 with a particle size of 230-400 mesh. Pyridine, dichloromethane ($CH_2Cl_2$), tetrahydrofuran (THF), dimethylformamide (DMF), acetonitrile (ACN), methanol (MeOH), and 1,4-dioxane were from Aldrich Sure-Seal bottles kept under dry nitrogen. All reactions were stirred magnetically unless otherwise noted.

[cis-8-ethoxy-10-(4-fluorophenyl)-11-oxa-3-azaspiro[5.5]undecan-3-yl]-[3-fluoro-4-(1-hydroxy-1-methyl-ethyl)phenyl]methanone Step 1: tert-butyl 8-oxo-11-oxa-3-azaspiro[5.5]undec-9-ene-3-carboxylate

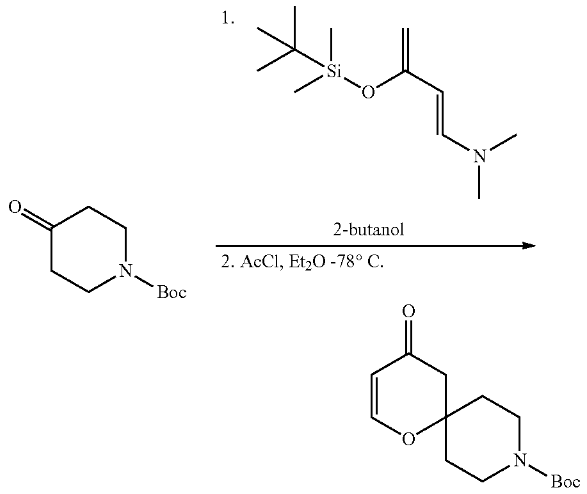

tert-Butyl 4-oxopiperidine-1-carboxylate (19.3 g, 96.7 mmol) was placed into an oven-dried flask. 2-Butanol (140 mL) was added. The light yellow solution was purged with argon for 2 min. (1E)-3-[tert-butyl(dimethyl)silyl]oxy-N,N-dimethyl-buta-1,3-dien-1-amine (20.0 g, 87.9 mmol) was added dropwise at room temperature (water bath) under argon gas. The solution turned dark brown. The mixture was stirred at room temperature for 3 hours. Solvent was removed under vacuum Anhydrous diethyl ether (100 mL) was added and removed under vacuum. The residue was dissolved in anhydrous diethyl ether (300 mL) and cooled to −78° C. Acetyl chloride (7.50 mL, 106 mmol) was added dropwise. The mixture was stirred at −78° C. for 15 minutes. The reaction was quenched with saturated sodium bicarbonate (100 mL). Water was added. The mixture was extracted with diethyl ether (3×). The combined organic layers were washed with brine, dried over sodium sulfate, filtered and concentrated. The crude dark red oil were purified by column chromatography (20-30% ethyl acetate-Hex) to provide 17.5 grams of yellow-orange oil. It was taken up in hexanes (40 mL) at 60° C. and seeded with crystalline material. Immediately, white crystalline solids were observed. The mixture was allowed to stir while slowly cooling to room temperature overnight. Crystalline solids were collected by vacuum filtration and rinsed with hexane to provide tert-butyl 8-oxo-11-oxa-3-azaspiro[5.5]undec-9-ene-3-carboxylate (12.09 g) as a pale yellow crystalline powder. $^1$H NMR (400 MHz, $CDCl_3$) δ 7.26 (d, J=6.1 Hz, 1H), 5.42 (d, J=6.1 Hz, 1H), 3.86 (d, J=12.5 Hz, 2H), 3.24-3.08 (m, 2H), 2.52 (s, 2H), 2.12-2.02 (m, 2H), 1.60-1.49 (m, 2H), 1.46 (s, 9H). ESI-MS m/z calc. 267.15, found 268.5 $(M+1)^+$; Retention time: 1.13 minutes (3 minute run).

The following compound was prepared using the procedure reported above:

| Product | Precursor |
|---|---|
| benzyl 8-oxo-11-oxa-3-azaspiro[5.5]undec-9-ene-3-carboxylate | benzyl 4-oxopiperidine-1-carboxylate |

Step 2: tert-butyl 10-(4-fluorophenyl)-8-oxo-11-oxa-3-azaspiro[5.5]undecane-3-carboxylate

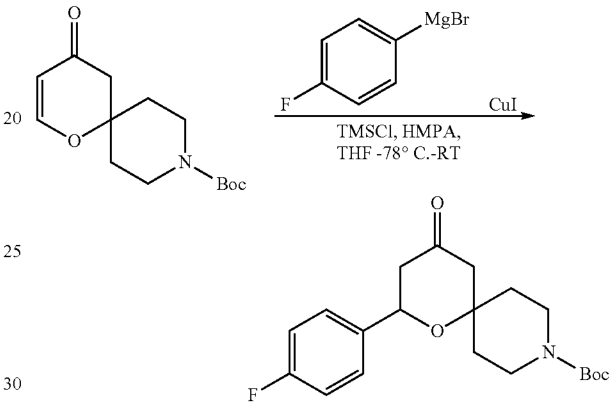

To an oven-dried flask under argon gas was added copper iodide (1.28 g, 6.73 mmol) followed by anhydrous THF (125 mL). The suspension was cooled to −78° C. prior to the dropwise addition of (4-fluorophenyl)magnesium bromide (33.7 mL of 2 M in diethyl ether, 67.3 mmol). The resulting mixture was stirred at −78° C. for 20 minutes. HMPA (23.4 mL, 135 mmol) was added, and the reaction mixture was allowed to further stir at −78° C. for 30 minutes. In a separate flask, TMSCl (17.1 mL, 135 mmol) was slowly added to a solution of tert-butyl 8-oxo-11-oxa-3-azaspiro[5.5]undec-9-ene-3-carboxylate (3.00 g, 11.2 mmol) in THF (10 mL). This solution was then slowly transferred to the reaction mixture at −78° C. The resulting thick opaque white mixture was then allowed to slowly warm to room temperature and stirred overnight. To the obtained grey reaction mixture was added a saturated ammonium chloride (75 mL). The mixture was allowed to stir at room temperature for 5 minutes, and volatiles were removed under reduced pressure. To the remaining ⅓ volume was mixed with ethyl acetate (100 mL) and water (25 mL). The aqueous layer was further extracted with ethyl acetate (2×50 mL). Organic layers were combined, dried over sodium sulfate, filtered and concentrated under reduced pressure. The obtained yellow oil was purified by column chromatography (20-40% ethyl acetate/hexane) to provide tert-butyl 10-(4-fluorophenyl)-8-oxo-11-oxa-3-azaspiro[5.5]undecane-3-carboxylate (3.81 g). $^1$H NMR (400 MHz, $CDCl_3$) δ 7.41-7.33 (m, 2H), 7.11-7.03 (m, 2H), 4.83 (dd, J=11.2, 3.1 Hz, 1H), 3.87-3.72 (m, 2H), 3.32 (ddd, J=13.4, 11.5, 3.3 Hz, 1H), 3.09-2.98 (m, 1H), 2.61 (ddd, J=14.0, 3.1, 1.7 Hz, 1H), 2.57-2.47 (m, 2H), 2.39 (dd, J=13.9, 1.8 Hz, 1H), 2.02-1.95 (m, 1H), 1.85 (ddd, J=13.4, 5.8, 3.2 Hz, 1H), 1.68 (ddd, J=13.4, 11.5, 4.8 Hz, 1H), 1.54-1.47 (m, 1H), 1.45 (d, J=6.0 Hz, 9H). ESI-MS m/z calc. 363.18, found 364.0 $(M+1)^+$; Retention time: 1.81 minutes (3 minute run).

The following compounds were prepared using the procedure reported above:

| Grignard Reagent | Product |
|---|---|
| phenylmagnesium bromide | tert-butyl 8-oxo-10-phenyl-11-oxa-3-azaspiro[5.5]undecane-3-carboxylate |
| (3-fluorophenyl)magnesium bromide | tert-butyl 10-(3-fluorophenyl)-8-oxo-11-oxa-3-azaspiro[5.5]undecane-3-carboxylate |
| vinylmagnesium bromide | benzyl 8-oxo-10-vinyl-11-oxa-3-azaspiro[5.5]undecane-3-carboxylate |

Step 3: cis and trans tert-butyl 10-(4-fluorophenyl)-8-hydroxy-11-oxa-3-azaspiro[5.5]undecane-3-carboxylate

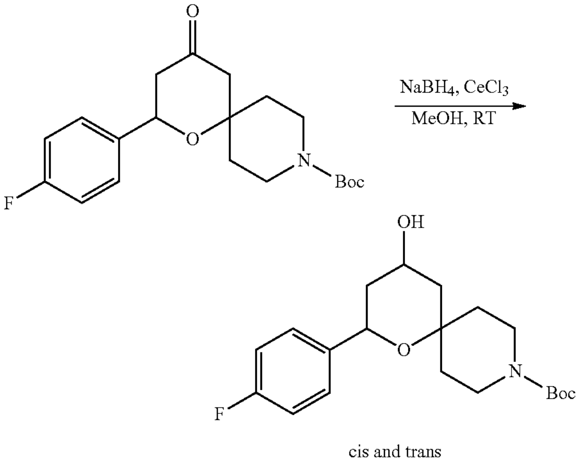

To a solution of tert-butyl 10-(4-fluorophenyl)-8-oxo-11-oxa-3-azaspiro[5.5]undecane-3-carboxylate (2.00 g, 5.50 mmol) in MeOH (50 mL) was added cerium trichloride (1.49 g, 6.05 mmol). The mixture was stirred for 5 minutes prior to the addition of sodium borohydride (250 mg, 6.60 mmol). The reaction mixture was allowed to stir at room temperature for 1 hour. Saturated ammonium chloride (50 mL) was added to quench the reaction. It was stirred for 5 minutes, and extracted with ethyl acetate (3×75 mL). The organic layer was dried over sodium sulfate, filtered and concentrated under reduced pressure. The crude product was purified by column chromatography (20-40% ethyl acetate/hexane) to provide tert-butyl cis-(4-fluorophenyl)-8-hydroxy-11-oxa-3-azaspiro[5.5]undecane-3-carboxylate (749 mg) and tert-butyl trans-10-(4-fluorophenyl)-8-hydroxy-11-oxa-3-azaspiro [5.5]undecane-3-carboxylate (644 mg). Cis-isomer: $^1$H NMR (400 MHz, $CDCl_3$) δ 7.39-7.33 (m, 2H), 7.03 (ddd, J=8.8, 5.8, 2.5 Hz, 2H), 4.94 (d, J=11.5 Hz, 1H), 4.37 (dd, J=6.1, 3.0 Hz, 1H), 3.76 (d, J=13.9 Hz, 2H), 3.27 (ddd, J=13.2, 10.2, 4.9 Hz, 1H), 3.10-2.98 (m, 1H), 2.69 (d, J=15.7 Hz, 1H), 1.96-1.89 (m, 1H), 1.71 (ddd, J=11.9, 11.0, 2.9 Hz, 2H), 1.64-1.55 (m, 4H), 1.55-1.48 (m, 1H), 1.44 (s, 9H). ESI-MS m/z calc. 365.20, found 366.3 $(M+1)^+$; Retention time: 1.54 minutes (3 minute run). trans-isomer: $^1$H NMR (400 MHz, $CDCl_3$) δ 7.38-7.31 (m, 2H), 7.03 (ddd, J=10.7, 5.9, 2.5 Hz, 2H), 4.58-4.50 (m, 1H), 4.13 (ddd, J=11.3, 6.8, 4.6 Hz, 1H), 3.82-3.72 (m, 2H), 3.26 (ddd, J=13.3, 10.4, 4.6 Hz, 1H), 3.07-2.96 (m, 1H), 2.23 (ddd, J=10.3, 4.4, 2.2 Hz, 1H), 2.12 (d, J=14.7 Hz, 1H), 1.96 (ddd, J=12.5, 4.6, 1.8 Hz, 1H), 1.70-1.58 (m, 2H), 1.55 (s, 1H), 1.49-1.43 (m, 9H), 1.43-1.27 (m, 2H). ESI-MS m/z calc. 365.20, found 366.5 $(M+1)^+$. Retention time: 1.63 minutes (3 minute run).

The following compounds were prepared using the procedure reported above:

| Product | Ketone |
|---|---|
| tert-butyl cis-8-hydroxy-10-phenyl-11-oxa-3-azaspiro[5.5]undecane-3-carboxylate | tert-butyl 8-oxo-10-phenyl-11-oxa-3-azaspiro[5.5]undecane-3-carboxylate |
| tert-butyl cis-10-(3-fluorophenyl)-8-hydroxy-11-oxa-3-aza-spiro[5.5]undecane-3-carboxylate | tert-butyl 10-(3-fluorophenyl)-8-oxo-11-oxa-3-aza-spiro[5.5]undecane-3-carboxylate |

Step 4: cis-tert-butyl-8-ethoxy-10-(4-fluorophenyl)-11-oxa-3-azaspiro[5.5]undecane-3-carboxylate

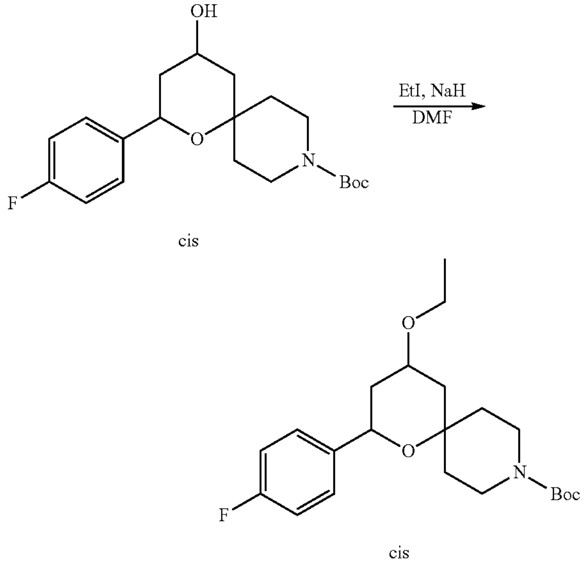

To a solution of tert-butyl cis-(4-fluorophenyl)-8-hydroxy-11-oxa-3-azaspiro[5.5]undecane-3-carboxylate (749 mg) in DMF (15 mL) was added sodium hydride (410 mg, 10.3 mmol) (60 wt % in mineral oil). The mixture was stirred at room temperature for 20 minutes prior to the addition of iodoethane (5 eq.). The mixture was then stirred overnight at room temperature. The reaction mixture was diluted with ethyl acetate (100 mL) and washed with water (1×75 mL). The aqueous layer was extracted with additional ethyl acetate (2×75 mL). All organic layers were combined, dried over sodium sulfate, filtered and concentrated under reduced pressure. Purification was performed by column chromatography (10-20% ethyl acetate/hexane) to provide tert-butyl cis-8-ethoxy-10-(4-fluorophenyl)-11-oxa-3-azaspiro[5.5]undecane-3-carboxylate (510 mg). $^1$H NMR (400 MHz, $CDCl_3$) δ 7.37-7.31 (m, 2H), 7.03 (ddd, J=10.8, 5.9, 2.5 Hz, 2H), 4.52 (dd, J=11.8, 1.7 Hz, 1H), 3.76 (tt, J=11.1, 4.3 Hz, 3H), 3.62-3.47 (m, 2H), 3.26 (ddd, J=13.3, 10.6, 4.3 Hz, 1H), 3.08-2.98 (m, 1H), 2.28 (ddt, J=12.3, 4.0, 1.9 Hz, 1H), 2.13 (d, J=13.3 Hz, 1H), 1.97 (ddd, J=12.6, 4.4, 1.8 Hz, 1H), 1.63 (dd, J=10.6, 4.5 Hz, 2H), 1.50 (s, 9H), 1.50-1.29 (m, 3H), 1.20 (t, J=7.0 Hz, 3H). ESI-MS m/z calc. 393.23, found 394.4 $(M+1)^+$; Retention time: 2.03 minutes (3 minute run).

The following compounds were prepared using the procedure reported above:

| Product | Alcohol Precursor |
|---|---|
| tert-butyl cis-8-ethoxy-10-phenyl-11-oxa-3-azaspiro[5.5]undecane-3-carboxylate | tert-butyl cis-8-hydroxy-10-phenyl-11-oxa-3-azaspiro[5.5]undecane-3-carboxylate |
| tert-butyl cis-8-ethoxy-10-(3-fluorophenyl)-11-oxa-3-azaspiro[5.5]undecane-3-carboxylate | tert-butyl cis-10-(3-fluorophenyl)-8-hydroxy-11-oxa-3-azaspiro[5.5]undecane-3-carboxylate |

Step 5: cis-8-ethoxy-10-(4-fluorophenyl)-11-oxa-3-azaspiro[5.5]undecane

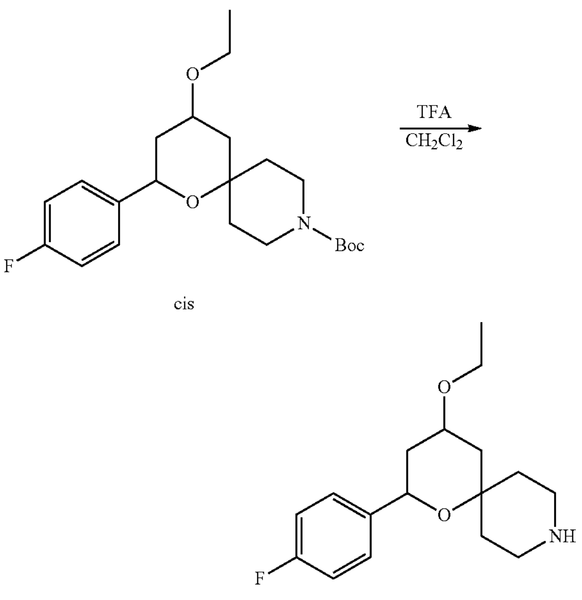

cis cis

To a solution of tert-butyl cis-8-ethoxy-10-(4-fluorophenyl)-11-oxa-3-azaspiro[5.5]undecane-3-carboxylate (510 mg, 1.30 mmol) in $CH_2Cl_2$ (1 mL) was added a 1:1 solution of trifluoroacetic acid (1 mL) in $CH_2Cl_2$ (1 mL). After 1 hour, the reaction mixture was diluted with aqueous 1 N NaOH (50 mL) and extracted with ethyl acetate (2×50 mL). The organic layers were combined, dried over sodium sulfate, filtered and concentrated under reduced pressure to provide cis-8-ethoxy-10-(4-fluorophenyl)-11-oxa-3-azaspiro[5.5]undecane (520 mg). $^1H$ NMR (400 MHz, $CDCl_3$) δ 7.46-7.31 (m, 2H), 7.10-6.98 (m, 2H), 4.54 (d, J=11.8 Hz, 1H), 3.76 (ddd, J=15.7, 11.3, 4.4 Hz, 1H), 3.66-3.46 (m, 2H), 3.09 (dt, J=13.9, 7.0 Hz, 1H), 2.99-2.76 (m, 3H), 2.69-2.21 (m, 2H), 2.17-2.00 (m, 2H), 1.79-1.64 (m, 1H), 1.64-1.49 (m, 1H), 1.50-1.24 (m, 2H), 1.24-1.12 (m, 3H). ESI-MS m/z calc. 293.18, found 294.5 $(M+1)^+$; Retention time: 0.97 minutes (3 minute run).

The following compounds were prepared using the procedure reported above:

| Product | Precursor |
|---|---|
| cis-8-ethoxy-10-phenyl-11-oxa-3-azaspiro[5.5]undecane | tert-butyl cis-8-ethoxy-10-phenyl-11-oxa-3-azaspiro[5.5]undecane-3-carboxylate |
| cis-8-ethoxy-10-(3-fluorophenyl)-11-oxa-3-azaspiro[5.5]undecane | tert-butyl cis-8-ethoxy-10-(3-fluorophenyl)-11-oxa-3-azaspiro[5.5]undecane-3-carboxylate |

Step 6: [cis-8-ethoxy-10-(4-fluorophenyl)-11-oxa-3-azaspiro[5.5]undecan-3-yl]-[H3-fluoro-4-(1-hydroxy-1-methyl-ethyl)phenyl]methanone

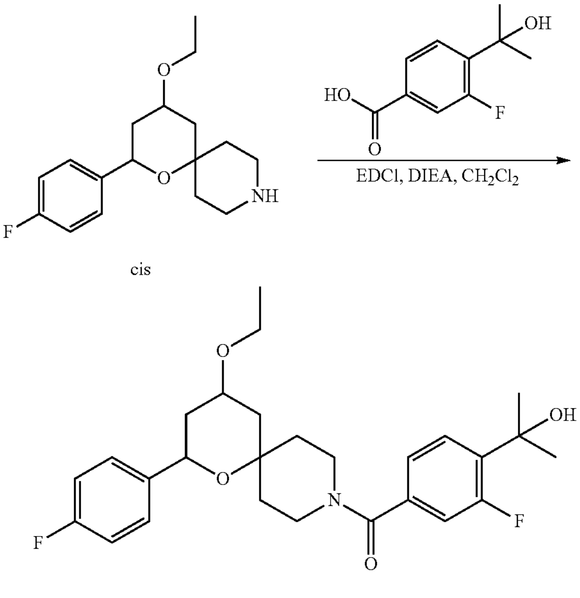

cis cis

To a solution of cis-8-ethoxy-10-(4-fluorophenyl)-11-oxa-3-azaspiro[5.5]undecane (75 mg, 0.26 mmol) and 3-fluoro-4-(1-hydroxy-1-methyl-ethyl)benzoic acid (56 mg, 0.28 mmol) in $CH_2Cl_2$ (1 mL) was added EDCI (54 mg, 0.28 mmol). Diisopropylethylamine (134 μL, 0.767 mmol) was added last. The reaction mixture was allowed to stir at room temperature for 1 hour. The reaction mixture was purified by column chromatography (0-50% EtOAc-Hex) to provide [cis-8-ethoxy-10-(4-fluorophenyl)-11-oxa-3-azaspiro[5.5]undecan-3-yl]-[3-fluoro-4-(1-hydroxy-1-methyl-ethyl)phenyl]methanone (28.3 mg). $^1H$ NMR (400 MHz, $CDCl_3$) δ 7.60 (t, J=8.1 Hz, 1H), 7.34 (dd, J=8.5, 5.4 Hz, 2H), 7.14 (dd, J=8.0, 1.6 Hz, 1H), 7.11-7.00 (m, 3H), 4.60-4.30 (m, 2H), 3.77 (br s, 1H), 3.65-3.05 (m, 6H), 2.27 (br s, 2H), 2.23-2.07 (m, 1H), 1.64 (s, 6H), 1.62-1.30 (m, 5H), 1.22 (dd, J=16.6, 9.6 Hz, 3H). ESI-MS m/z calc. 473.24, found 474.5 $(M+1)^+$; Retention time: 1.63 minutes (3 minute run).

The following compounds were prepared using the procedure reported above:

| Product | Amine | Carboxylic acid |
|---|---|---|
| (3-chloro-4-isopropoxy-phenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 3-chloro-4-isopropoxy-benzoic acid |

-continued

| Product | Amine | Carboxylic acid |
|---|---|---|
| N-cyclopropyl-4-[cis-8-ethoxy-10-phenyl-11-oxa-3-azaspiro[5.5]undecane-3-carbonyl]benzenesulfonamide | cis-8-ethoxy-10-phenyl-11-oxa-3-azaspiro[5.5]undecane | 4-(cyclopropylsulfamoyl) benzoic acid |
| [cis-8-ethoxy-10-phenyl-11-oxa-3-azaspiro[5.5]undecan-3-yl]-[3-fluoro-4-(2-hydroxy-2-methyl-propyl)phenyl]-methanone | cis-8-ethoxy-10-phenyl-11-oxa-3-azaspiro[5.5]undecane | 3-fluoro-4-(2-hydroxy-2-methyl-propyl)benzoic acid |
| [cis-8-ethoxy-10-phenyl-11-oxa-3-azaspiro[5.5]undecan-3-yl]-[4-(1-hydroxy-1-methyl-propyl)phenyl]-methanone | cis-8-ethoxy-10-phenyl-11-oxa-3-azaspiro[5.5]undecane | 4-(1-hydroxy-1-methyl-propyl)benzoic acid |
| [cis-8-ethoxy-10-phenyl-11-oxa-3-azaspiro[5.5]undecan-3-yl]-[4-(1-hydroxycyclopentyl)phenyl]-methanone | cis-8-ethoxy-10-phenyl-11-oxa-3-azaspiro[5.5]undecane | 4-(1-hydroxycyclopentyl) benzoic acid |
| [cis-8-ethoxy-10-phenyl-11-oxa-3-azaspiro[5.5]undecan-3-yl]-[4-(1-hydroxycyclobutyl)phenyl]-methanone | cis-8-ethoxy-10-phenyl-11-oxa-3-azaspiro[5.5]undecane | 4-(1-hydroxycyclobutyl) benzoic acid |
| [cis-8-ethoxy-10-phenyl-11-oxa-3-azaspiro[5.5]undecan-3-yl]-[3-fluoro-4-(1-hydroxy-1-methyl-ethyl)phenyl]-methanone | cis-8-ethoxy-10-phenyl-11-oxa-3-azaspiro[5.5]undecane | 3-fluoro-4-(1-hydroxy-1-methyl-ethyl)benzoic acid |
| [cis-8-ethoxy-10-phenyl-11-oxa-3-azaspiro[5.5]undecan-3-yl]-[4-(1-hydroxy-1-methyl-ethyl)-3-methoxy-phenyl]-methanone | cis-8-ethoxy-10-phenyl-11-oxa-3-azaspiro[5.5]undecane | 4-(1-hydroxy-1-methyl-ethyl)-3-methoxy-benzoic acid |
| [cis-8-ethoxy-10-phenyl-11-oxa-3-azaspiro[5.5]undecan-3-yl]-[4-(1-hydroxy-1-methyl-ethyl)-3-methyl-phenyl]-methanone | cis-8-ethoxy-10-phenyl-11-oxa-3-azaspiro[5.5]undecane | 4-(1-hydroxy-1-methyl-ethyl)-3-methyl-benzoic acid |
| [cis-8-ethoxy-10-phenyl-11-oxa-3-azaspiro[5.5]undecan-3-yl]-[4-(1-hydroxy-1-methyl-ethyl)phenyl]-methanone | cis-8-ethoxy-10-phenyl-11-oxa-3-azaspiro[5.5]undecane | 4-(1-hydroxy-1-methyl-ethyl)benzoic acid |
| [cis-8-ethoxy-10-phenyl-11-oxa-3-azaspiro[5.5]undecan-3-yl]-[4-(trifluoromethylsulfonyl)phenyl]-methanone | cis-8-ethoxy-10-phenyl-11-oxa-3-azaspiro[5.5]undecane | 4-(trifluoromethylsulfonyl) benzoic acid |
| [cis-8-ethoxy-10-phenyl-11-oxa-3-azaspiro[5.5]undecan-3-yl]-(4-isopropylsulfonylphenyl)-methanone | cis-8-ethoxy-10-phenyl-11-oxa-3-azaspiro[5.5]undecane | 4-isopropylsulfonylbenzoic acid |
| [cis-8-ethoxy-10-phenyl-11-oxa-3-azaspiro[5.5]undecan-3-yl]-(4-ethylsulfonylphenyl)-methanone | cis-8-ethoxy-10-phenyl-11-oxa-3-azaspiro[5.5]undecane | 4-ethylsulfonylbenzoic acid |
| [cis-8-ethoxy-10-phenyl-11-oxa-3-azaspiro[5.5]undecan-3-yl]-[3-(hydroxymethyl)-4-isopropoxy-phenyl]-methanone | cis-8-ethoxy-10-phenyl-11-oxa-3-azaspiro[5.5]undecane | 3-(hydroxymethyl)-4-isopropoxy-benzoic acid |
| [cis-8-ethoxy-10-phenyl-11-oxa-3-azaspiro[5.5]undecan-3-yl]-(3-fluoro-4-isopropoxy-phenyl)-methanone | cis-8-ethoxy-10-phenyl-11-oxa-3-azaspiro[5.5]undecane | 3-fluoro-4-isopropoxy-benzoic acid |
| [cis-8-ethoxy-10-phenyl-11-oxa-3-azaspiro[5.5]undecan-3-yl]-(2-isopropoxyphenyl)-methanone | cis-8-ethoxy-10-phenyl-11-oxa-3-azaspiro[5.5]undecane | 2-isopropoxybenzoic acid |
| [cis-8-ethoxy-10-phenyl-11-oxa-3-azaspiro[5.5]undecan-3-yl]-(3-isopropoxyphenyl)-methanone | cis-8-ethoxy-10-phenyl-11-oxa-3-azaspiro[5.5]undecane | 3-isopropoxybenzoic acid |
| [cis-8-ethoxy-10-phenyl-11-oxa-3-azaspiro[5.5]undecan-3-yl]-(4-isopropoxyphenyl)-methanone | cis-8-ethoxy-10-phenyl-11-oxa-3-azaspiro[5.5]undecane | 4-isopropoxybenzoic acid |
| [4-(difluoromethylsulfonyl)phenyl]-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 4-(difluoromethylsulfonyl) benzoic acid |
| [trans-8-ethoxy-10-phenyl-11-oxa-3-azaspiro[5.5]undecan-3-yl]-(4-isopropoxy-3-methoxy-phenyl)-methanone | (trans-8-ethoxy-10-phenyl-11-oxa-3-azaspiro[5.5]undecane | 4-isopropoxy-3-methoxy-benzoic acid |
| [trans-8-ethoxy-10-phenyl-11-oxa-3-azaspiro[5.5]undecan-3-yl]-(3-fluoro-4-isopropoxy-phenyl)-methanone | trans-8-ethoxy-10-phenyl-11-oxa-3-azaspiro[5.5]undecane | 3-fluoro-4-isopropoxy-benzoic acid |

-continued

| Product | Amine | Carboxylic acid |
|---|---|---|
| [trans-8-ethoxy-10-phenyl-11-oxa-3-azaspiro[5.5]undecan-3-yl]-[3-fluoro-4-(2-hydroxy-2-methyl-propyl)phenyl]-methanone | trans-8-ethoxy-10-phenyl-11-oxa-3-azaspiro[5.5]undecane | 3-fluoro-4-(2-hydroxy-2-methyl-propyl)benzoic acid |
| [cis-8-ethoxy-10-(4-fluorophenyl)-11-oxa-3-azaspiro[5.5]undecan-3-yl]-(4-isopropoxy-3-methoxy-phenyl)-methanone | cis-8-ethoxy-10-(4-fluorophenyl)-11-oxa-3-azaspiro[5.5]undecane | 4-isopropoxy-3-methoxy-benzoic acid |
| [4-(difluoromethylsulfonyl)phenyl]-[cis-8-ethoxy-10-(4-fluorophenyl)-11-oxa-3-azaspiro[5.5]undecan-3-yl]-methanone | cis-8-ethoxy-10-(4-fluorophenyl)-11-oxa-3-azaspiro[5.5]undecane | 4-(difluoromethylsulfonyl) benzoic acid |
| [cis-8-ethoxy-10-(4-fluorophenyl)-11-oxa-3-azaspiro[5.5]undecan-3-yl]-[3-fluoro-4-(2-hydroxy-2-methyl-propyl)phenyl]-methanone | cis-8-ethoxy-10-(4-fluorophenyl)-11-oxa-3-azaspiro[5.5]undecane | 3-fluoro-4-(2-hydroxy-2-methyl-propyl)benzoic acid |
| [cis-8-ethoxy-10-(4-fluorophenyl)-11-oxa-3-azaspiro[5.5]undecan-3-yl]-(3-fluoro-4-isopropoxy-phenyl)-methanone | cis-8-ethoxy-10-(4-fluorophenyl)-11-oxa-3-azaspiro[5.5]undecane | 3-fluoro-4-isopropoxy-benzoic acid |
| [cis-8-ethoxy-10-(4-fluorophenyl)-11-oxa-3-azaspiro[5.5]undecan-3-yl]-(4-isopropoxy-3-methyl-phenyl)-methanone | cis-8-ethoxy-10-(4-fluorophenyl)-11-oxa-3-azaspiro[5.5]undecane | 4-isopropoxy-3-methyl-benzoic acid |
| N-cyclopropyl-4-[cis-8-ethoxy-10-(4-fluorophenyl)-11-oxa-3-azaspiro[5.5]undecane-3-carbonyl]benzenesulfonamide | cis-8-ethoxy-10-(4-fluorophenyl)-11-oxa-3-azaspiro[5.5]undecane | 4-(cyclopropylsulfamoyl) benzoic acid |
| [cis-8-ethoxy-10-(4-fluorophenyl)-11-oxa-3-azaspiro[5.5]undecan-3-yl]-(4-ethoxy-3-methoxy-phenyl)-methanone | cis-8-ethoxy-10-(4-fluorophenyl)-11-oxa-3-azaspiro[5.5]undecane | 4-ethoxy-3-methoxy-benzoic acid |
| 5-[cis-8-ethoxy-10-(4-fluorophenyl)-11-oxa-3-azaspiro[5.5]undecane-3-carbonyl]-2-isopropoxy-benzonitrile | cis-8-ethoxy-10-(4-fluorophenyl)-11-oxa-3-azaspiro[5.5]undecane | 3-cyano-4-isopropoxy-benzoic acid |
| (4-ethoxy-3-fluoro-phenyl)-[cis-8-ethoxy-10-(4-fluorophenyl)-11-oxa-3-azaspiro[5.5]undecan-3-yl]-methanone | cis-8-ethoxy-10-(4-fluorophenyl)-11-oxa-3-azaspiro[5.5]undecane | 4-ethoxy-3-fluoro-benzoic acid |
| 5-[cis-8-ethoxy-10-(4-fluorophenyl)-11-oxa-3-azaspiro[5.5]undecane-3-carbonyl]-2-isopropylsulfonyl-benzonitrile | cis-8-ethoxy-10-(4-fluorophenyl)-11-oxa-3-azaspiro[5.5]undecane | 3-cyano-4-isopropylsulfonyl-benzoic acid |
| [cis-8-ethoxy-10-(3-fluorophenyl)-11-oxa-3-azaspiro[5.5]undecan-3-yl]-(4-isopropoxy-3-methoxy-phenyl)-methanone | cis-8-ethoxy-10-(3-fluorophenyl)-11-oxa-3-azaspiro[5.5]undecane | 4-isopropoxy-3-methoxy-benzoic acid |
| [cis-8-ethoxy-10-(3-fluorophenyl)-11-oxa-3-azaspiro[5.5]undecan-3-yl]-(4-isopropoxy-3-methyl-phenyl)-methanone | cis-8-ethoxy-10-(3-fluorophenyl)-11-oxa-3-azaspiro[5.5]undecane | 4-isopropoxy-3-methyl-benzoic acid |
| [cis-8-ethoxy-10-(3-fluorophenyl)-11-oxa-3-azaspiro[5.5]undecan-3-yl]-[3-fluoro-4-(1-hydroxy-1-methyl-ethyl)phenyl]-methanone | cis-8-ethoxy-10-(3-fluorophenyl)-11-oxa-3-azaspiro[5.5]undecane | 3-fluoro-4-(1-hydroxy-1-methyl-ethyl)benzoic acid |
| [cis-8-ethoxy-10-phenyl-11-oxa-3-azaspiro[5.5]undecan-3-yl]-(4-propoxyphenyl)-methanone | cis-8-ethoxy-10-phenyl-11-oxa-3-azaspiro[5.5]undecane | 4-propoxybenzoic acid |
| [cis-8-ethoxy-10-phenyl-11-oxa-3-azaspiro[5.5]undecan-3-yl]-[4-(2-methoxyethoxy)phenyl]-methanone | cis-8-ethoxy-10-phenyl-11-oxa-3-azaspiro[5.5]undecane | 4-(2-methoxyethoxy) benzoic acid |

-continued

| Product | Amine | Carboxylic acid |
|---|---|---|
| [cis-8-ethoxy-10-phenyl-11-oxa-3-azaspiro[5.5]undecan-3-yl]-[4-(1-hydroxy-2-methyl-propyl)phenyl]-methanone | cis-8-ethoxy-10-phenyl-11-oxa-3-azaspiro[5.5]undecane | 4-(1-hydroxy-2-methyl-propyl)benzoic acid |
| [cis-8-ethoxy-10-phenyl-11-oxa-3-azaspiro[5.5]undecan-3-yl]-[4-(2-hydroxy-2-methyl-propoxy)-3-methyl-phenyl]-methanone | cis-8-ethoxy-10-phenyl-11-oxa-3-azaspiro[5.5]undecane | 4-(2-hydroxy-2-methyl-propoxy)-3-methyl-benzoic acid |
| [cis-8-ethoxy-10-phenyl-11-oxa-3-azaspiro[5.5]undecan-3-yl]-(3-methoxy-4-propoxy-phenyl)-methanone | cis-8-ethoxy-10-phenyl-11-oxa-3-azaspiro[5.5]undecane | 3-methoxy-4-propoxy-benzoic acid |
| [cis-8-ethoxy-10-phenyl-11-oxa-3-azaspiro[5.5]undecan-3-yl]-[3-methoxy-4-[(1S)-1-methylpropoxy]phenyl]-methanone | cis-8-ethoxy-10-phenyl-11-oxa-3-azaspiro[5.5]undecane | 3-methoxy-4-[(1S)-1-methylpropoxy]benzoic acid |
| [cis-8-ethoxy-10-phenyl-11-oxa-3-azaspiro[5.5]undecan-3-yl]-[3-methoxy-4-(2-methoxyethoxy)phenyl]-methanone | cis-8-ethoxy-10-phenyl-11-oxa-3-azaspiro[5.5]undecane | 3-methoxy-4-(2-methoxyethoxy)benzoic acid |
| (4-tert-butoxy-3-methoxy-phenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 4-tert-butoxy-3-methoxy-benzoic acid |
| [cis-8-ethoxy-10-phenyl-11-oxa-3-azaspiro[5.5]undecan-3-yl]-(4-isobutoxy-3-methoxy-phenyl)-methanone | cis-8-ethoxy-10-phenyl-11-oxa-3-azaspiro[5.5]undecane | 4-isobutoxy-3-methoxy-benzoic acid |
| [4-(difluoromethoxy)-3-methoxy-phenyl]-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 4-(difluoromethoxy)-3-methoxy-benzoic acid |
| [cis-8-ethoxy-10-phenyl-11-oxa-3-azaspiro[5.5]undecan-3-yl]-[4-(3-hydroxypropoxy)-3-methyl-phenyl]-methanone | cis-8-ethoxy-10-phenyl-11-oxa-3-azaspiro[5.5]undecane | 4-(3-hydroxypropoxy)-3-methyl-benzoic acid |
| [cis-8-ethoxy-10-phenyl-11-oxa-3-azaspiro[5.5]undecan-3-yl]-[4-methoxy-3-(trifluoromethyl)phenyl]-methanone | cis-8-ethoxy-10-phenyl-11-oxa-3-azaspiro[5.5]undecane | 4-methoxy-3-(trifluoromethyl)benzoic acid |
| [cis-8-ethoxy-10-phenyl-11-oxa-3-azaspiro[5.5]undecan-3-yl]-[4-(2-hydroxyethoxy)-3-methoxy-phenyl]-methanone | cis-8-ethoxy-10-phenyl-11-oxa-3-azaspiro[5.5]undecane | 4-(2-hydroxyethoxy)-3-methoxy-benzoic acid |
| [cis-8-ethoxy-10-phenyl-11-oxa-3-azaspiro[5.5]undecan-3-yl]-(5-isopropoxy-6-methyl-2-pyridyl)-methanone | cis-8-ethoxy-10-phenyl-11-oxa-3-azaspiro[5.5]undecane | 5-isopropoxy-6-methyl-pyridine-2-carboxylic acid |
| 4-[cis-8-ethoxy-10-phenyl-11-oxa-3-azaspiro[5.5]undecane-3-carbonyl]-N-methyl-benzenesulfonamide | cis-8-ethoxy-10-phenyl-11-oxa-3-azaspiro[5.5]undecane | 4-(methylsulfamoyl)benzoic acid |
| [cis-8-ethoxy-10-phenyl-11-oxa-3-azaspiro[5.5]undecan-3-yl]-(4-isopropylsulfonyl-3-methyl-phenyl)-methanone | cis-8-ethoxy-10-phenyl-11-oxa-3-azaspiro[5.5]undecane | 4-isopropylsulfonyl-3-methyl-benzoic acid |
| [cis-8-ethoxy-10-phenyl-11-oxa-3-azaspiro[5.5]undecan-3-yl]-(6-isopropoxy-3-pyridyl)-methanone | cis-8-ethoxy-10-phenyl-11-oxa-3-azaspiro[5.5]undecane | 6-isopropoxypyridine-3-carboxylic acid |
| 5-[cis-8-ethoxy-10-phenyl-11-oxa-3-azaspiro[5.5]undecane-3-carbonyl]-2-isopropoxy-benzonitrile | cis-8-ethoxy-10-phenyl-11-oxa-3-azaspiro[5.5]undecane | 3-cyano-4-isopropoxy-benzoic acid |
| [cis-8-ethoxy-10-phenyl-11-oxa-3-azaspiro[5.5]undecan-3-yl]-(4-ethyl-3-methoxy-phenyl)-methanone | cis-8-ethoxy-10-phenyl-11-oxa-3-azaspiro[5.5]undecane | 4-ethyl-3-methoxy-benzoic acid |
| (4-cyclopropylphenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 4-cyclopropylbenzoic acid |

-continued

| Product | Amine | Carboxylic acid |
|---|---|---|
| [cis-8-ethoxy-10-phenyl-11-oxa-3-azaspiro[5.5]undecan-3-yl]-(6-methyl-2-pyridyl)-methanone | cis-8-ethoxy-10-phenyl-11-oxa-3-azaspiro[5.5]undecane | 6-methylpyridine-2-carboxylic acid |
| [cis-8-ethoxy-10-phenyl-11-oxa-3-azaspiro[5.5]undecan-3-yl]-(6-methoxy-2-pyridyl)-methanone | cis-8-ethoxy-10-phenyl-11-oxa-3-azaspiro[5.5]undecane | 6-methoxypyridine-2-carboxylic acid |
| [cis-8-ethoxy-10-phenyl-11-oxa-3-azaspiro[5.5]undecan-3-yl]-(2-methoxy-3-pyridyl)-methanone | cis-8-ethoxy-10-phenyl-11-oxa-3-azaspiro[5.5]undecane | 2-methoxypyridine-3-carboxylic acid |
| benzofuran-2-yl-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | benzofuran-2-carboxylic acid |
| [cis-8-ethoxy-10-phenyl-11-oxa-3-azaspiro[5.5]undecan-3-yl]-(2-methoxy-4-methyl-phenyl)-methanone | cis-8-ethoxy-10-phenyl-11-oxa-3-azaspiro[5.5]undecane | 2-methoxy-4-methyl-benzoic acid |
| [cis-8-ethoxy-10-phenyl-11-oxa-3-azaspiro[5.5]undecan-3-yl]-(2-methoxy-5-methyl-phenyl)-methanone | cis-8-ethoxy-10-phenyl-11-oxa-3-azaspiro[5.5]undecane | 2-methoxy-5-methyl-benzoic acid |
| [cis-8-ethoxy-10-phenyl-11-oxa-3-azaspiro[5.5]undecan-3-yl]-(3-methoxy-2-methyl-phenyl)-methanone | cis-8-ethoxy-10-phenyl-11-oxa-3-azaspiro[5.5]undecane | 3-methoxy-2-methyl-benzoic acid |
| [cis-8-ethoxy-10-phenyl-11-oxa-3-azaspiro[5.5]undecan-3-yl]-(2-methoxy-6-methyl-phenyl)-methanone | cis-8-ethoxy-10-phenyl-11-oxa-3-azaspiro[5.5]undecane | 2-methoxy-6-methyl-benzoic acid |
| [cis-8-ethoxy-10-phenyl-11-oxa-3-azaspiro[5.5]undecan-3-yl]-(5-fluoro-2-methoxy-phenyl)-methanone | cis-8-ethoxy-10-phenyl-11-oxa-3-azaspiro[5.5]undecane | 5-fluoro-2-methoxy-benzoic acid |
| [cis-8-ethoxy-10-phenyl-11-oxa-3-azaspiro[5.5]undecan-3-yl]-(2-fluoro-5-methoxy-phenyl)-methanone | cis-8-ethoxy-10-phenyl-11-oxa-3-azaspiro[5.5]undecane | 2-fluoro-5-methoxy-benzoic acid |
| [cis-8-ethoxy-10-phenyl-11-oxa-3-azaspiro[5.5]undecan-3-yl]-(2-fluoro-4-methoxy-phenyl)-methanone | cis-8-ethoxy-10-phenyl-11-oxa-3-azaspiro[5.5]undecane | 2-fluoro-4-methoxy-benzoic acid |
| [cis-8-ethoxy-10-phenyl-11-oxa-3-azaspiro[5.5]undecan-3-yl]-(1-isoquinolyl)-methanone | cis-8-ethoxy-10-phenyl-11-oxa-3-azaspiro[5.5]undecane | isoquinoline-1-carboxylic acid |
| [cis-8-ethoxy-10-phenyl-11-oxa-3-azaspiro[5.5]undecan-3-yl]-(2-quinolyl)-methanone | cis-8-ethoxy-10-phenyl-11-oxa-3-azaspiro[5.5]undecane | quinoline-2-carboxylic acid |
| [cis-8-ethoxy-10-phenyl-11-oxa-3-azaspiro[5.5]undecan-3-yl]-(1-methylindol-3-yl)-methanone | cis-8-ethoxy-10-phenyl-11-oxa-3-azaspiro[5.5]undecane | 1-methylindole-3-carboxylic acid |
| [cis-8-ethoxy-10-phenyl-11-oxa-3-azaspiro[5.5]undecan-3-yl]-(2-methyl-5-phenyl-pyrazol-3-yl)-methanone | cis-8-ethoxy-10-phenyl-11-oxa-3-azaspiro[5.5]undecane | 2-methyl-5-phenyl-pyrazole-3-carboxylic acid |
| [cis-8-ethoxy-10-phenyl-11-oxa-3-azaspiro[5.5]undecan-3-yl]-[2-(1-piperidyl)-4-pyridyl]-methanone | cis-8-ethoxy-10-phenyl-11-oxa-3-azaspiro[5.5]undecane | 2-(1-piperidyl)pyridine-4-carboxylic acid |
| [cis-8-ethoxy-10-phenyl-11-oxa-3-azaspiro[5.5]undecan-3-yl]-[4-(2,2,2-trifluoroethoxy)phenyl]-methanone | cis-8-ethoxy-10-phenyl-11-oxa-3-azaspiro[5.5]undecane | 4-(2,2,2-trifluoroethoxy)benzoic acid |
| [cis-8-ethoxy-10-phenyl-11-oxa-3-azaspiro[5.5]undecan-3-yl]-[6-(2,2,2-trifluoroethoxy)-3-pyridyl]-methanone | cis-8-ethoxy-10-phenyl-11-oxa-3-azaspiro[5.5]undecane | 6-(2,2,2-trifluoroethoxy)pyridine-3-carboxylic acid |
| [cis-8-ethoxy-10-phenyl-11-oxa-3-azaspiro[5.5]undecan-3-yl]-(5-methyl-1-phenyl-pyrazol-4-yl)-methanone | cis-8-ethoxy-10-phenyl-11-oxa-3-azaspiro[5.5]undecane | 5-methyl-1-phenyl-pyrazole-4-carboxylic acid |
| [cis-8-ethoxy-10-phenyl-11-oxa-3-azaspiro[5.5]undecan-3-yl]-(1-methyl-5-phenyl-pyrazol-3-yl)-methanone | cis-8-ethoxy-10-phenyl-11-oxa-3-azaspiro[5.5]undecane | 1-methyl-5-phenyl-pyrazole-3-carboxylic acid |

-continued

| Product | Amine | Carboxylic acid |
|---|---|---|
| [cis-8-ethoxy-10-phenyl-11-oxa-3-azaspiro[5.5]undecan-3-yl]-[4-methoxy-2-(trifluoromethyl)phenyl]-methanone | cis-8-ethoxy-10-phenyl-11-oxa-3-azaspiro[5.5]undecane | 4-methoxy-2-(trifluoromethyl)benzoic acid |
| [cis-8-ethoxy-10-phenyl-11-oxa-3-azaspiro[5.5]undecan-3-yl]-[2-methoxy-4-(trifluoromethyl)phenyl]-methanone | cis-8-ethoxy-10-phenyl-11-oxa-3-azaspiro[5.5]undecane | 2-methoxy-4-(trifluoromethyl)benzoic acid |
| [cis-8-ethoxy-10-phenyl-11-oxa-3-azaspiro[5.5]undecan-3-yl]-[1-(4-fluorophenyl)-5-methyl-pyrazol-4-yl]-methanone | cis-8-ethoxy-10-phenyl-11-oxa-3-azaspiro[5.5]undecane | 1-(4-fluorophenyl)-5-methyl-pyrazole-4-carboxylic acid |
| (3,5-difluoro-2-methoxy-phenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 3,5-difluoro-2-methoxy-benzoic acid |
| (4,5-difluoro-2-methoxy-phenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 4,5-difluoro-2-methoxy-benzoic acid |
| [cis-8-ethoxy-10-phenyl-11-oxa-3-azaspiro[5.5]undecan-3-yl]-(2-fluoro-4-methyl-phenyl)-methanone | cis-8-ethoxy-10-phenyl-11-oxa-3-azaspiro[5.5]undecane | 2-fluoro-4-methyl-benzoic acid |
| [2-(difluoromethyl)phenyl]-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2-(difluoromethyl)benzoic acid |
| [cis-8-ethoxy-10-phenyl-11-oxa-3-azaspiro[5.5]undecan-3-yl]-(3-quinolyl)-methanone | cis-8-ethoxy-10-phenyl-11-oxa-3-azaspiro[5.5]undecane | quinoline-3-carboxylic acid |
| [cis-8-ethoxy-10-phenyl-11-oxa-3-azaspiro[5.5]undecan-3-yl]-(4-methoxy-2-methyl-phenyl)-methanone | cis-8-ethoxy-10-phenyl-11-oxa-3-azaspiro[5.5]undecane | 4-methoxy-2-methyl-benzoic acid |
| [cis-8-ethoxy-10-phenyl-11-oxa-3-azaspiro[5.5]undecan-3-yl]-(4-morpholinophenyl)-methanone | cis-8-ethoxy-10-phenyl-11-oxa-3-azaspiro[5.5]undecane | 4-morpholinobenzoic acid |
| [cis-8-ethoxy-10-phenyl-11-oxa-3-azaspiro[5.5]undecan-3-yl]-quinoxalin-5-yl--methanone | cis-8-ethoxy-10-phenyl-11-oxa-3-azaspiro[5.5]undecane | quinoxaline-5-carboxylic acid |
| (4-chloro-3-fluoro-phenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 4-chloro-3-fluoro-benzoic acid |
| [cis-8-ethoxy-10-phenyl-11-oxa-3-azaspiro[5.5]undecan-3-yl]-(3-fluoro-2-methoxy-phenyl)-methanone | cis-8-ethoxy-10-phenyl-11-oxa-3-azaspiro[5.5]undecane | 3-fluoro-2-methoxy-benzoic acid |
| [cis-8-ethoxy-10-phenyl-11-oxa-3-azaspiro[5.5]undecan-3-yl]-(1H-pyrrolo[2,3-b]pyridin-3-yl)-methanone | cis-8-ethoxy-10-phenyl-11-oxa-3-azaspiro[5.5]undecane | 1H-pyrrolo[2,3-b]pyridine-3-carboxylic acid |
| [cis-8-ethoxy-10-phenyl-11-oxa-3-azaspiro[5.5]undecan-3-yl]-(3-fluoro-2-methyl-phenyl)-methanone | cis-8-ethoxy-10-phenyl-11-oxa-3-azaspiro[5.5]undecane | 3-fluoro-2-methyl-benzoic acid |
| (3-chloro-4-methoxy-phenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 3-chloro-4-methoxy-benzoic acid |
| [cis-8-ethoxy-10-phenyl-11-oxa-3-azaspiro[5.5]undecan-3-yl]-(2-morpholinophenyl)-methanone | cis-8-ethoxy-10-phenyl-11-oxa-3-azaspiro[5.5]undecane | 2-morpholinobenzoic acid |
| [cis-8-ethoxy-10-phenyl-11-oxa-3-azaspiro[5.5]undecan-3-yl]-(2-methoxy-3-methyl-phenyl)-methanone | cis-8-ethoxy-10-phenyl-11-oxa-3-azaspiro[5.5]undecane | 2-methoxy-3-methyl-benzoic acid |
| [cis-8-ethoxy-10-phenyl-11-oxa-3-azaspiro[5.5]undecan-3-yl]-[2-(methoxymethyl)phenyl]-methanone | cis-8-ethoxy-10-phenyl-11-oxa-3-azaspiro[5.5]undecane | 2-(methoxymethyl) benzoic acid |

-continued

| Product | Amine | Carboxylic acid |
|---|---|---|
| [cis-8-ethoxy-10-phenyl-11-oxa-3-azaspiro[5.5]undecan-3-yl]-(2-fluoro-5-methyl-phenyl)-methanone | cis-8-ethoxy-10-phenyl-11-oxa-3-azaspiro[5.5]undecane | 2-fluoro-5-methyl-benzoic acid |
| [2-(dimethylamino)-4-pyridyl]-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2-(dimethylamino) pyridine-4-carboxylic acid |
| [cis-8-ethoxy-10-phenyl-11-oxa-3-azaspiro[5.5]undecan-3-yl]-[2-(ethylamino)-3-pyridyl]-methanone | cis-8-ethoxy-10-phenyl-11-oxa-3-azaspiro[5.5]undecane | 2-(ethylamino)pyridine-3-carboxylic acid |
| [cis-8-ethoxy-10-phenyl-11-oxa-3-azaspiro[5.5]undecan-3-yl]-(2-ethoxy-3-pyridyl)-methanone | cis-8-ethoxy-10-phenyl-11-oxa-3-azaspiro[5.5]undecane | 2-ethoxypyridine-3-carboxylic acid |
| [cis-8-ethoxy-10-phenyl-11-oxa-3-azaspiro[5.5]undecan-3-yl]-(5-ethoxy-2-pyridyl)-methanone | cis-8-ethoxy-10-phenyl-11-oxa-3-azaspiro[5.5]undecane | 5-ethoxypyridine-2-carboxylic acid |
| [cis-8-ethoxy-10-phenyl-11-oxa-3-azaspiro[5.5]undecan-3-yl]-(7-methylimidazo[1,2-a]pyridin-2-yl)-methanone | cis-8-ethoxy-10-phenyl-11-oxa-3-azaspiro[5.5]undecane | 7-methylimidazo[1,2-a]pyridine-2-carboxylic acid |
| [cis-8-ethoxy-10-phenyl-11-oxa-3-azaspiro[5.5]undecan-3-yl]-(6-methylimidazo[1,2-a]pyridin-2-yl)-methanone | cis-8-ethoxy-10-phenyl-11-oxa-3-azaspiro[5.5]undecane | 6-methylimidazo[1,2-a]pyridine-2-carboxylic acid |
| (2-tert-butyl-4-pyridyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2-tert-butylpyridine-4-carboxylic acid |
| [cis-8-ethoxy-10-phenyl-11-oxa-3-azaspiro[5.5]undecan-3-yl]-[2-(isopropylamino)-3-pyridyl]-methanone | cis-8-ethoxy-10-phenyl-11-oxa-3-azaspiro[5.5]undecane | 2-(isopropylamino) pyridine-3-carboxylic acid |
| [3-(difluoromethoxy)phenyl]-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 3-(difluoromethoxy) benzoic acid |
| [2-(difluoromethoxy)phenyl]-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2-(difluoromethoxy) benzoic acid |
| [cis-8-ethoxy-10-phenyl-11-oxa-3-azaspiro[5.5]undecan-3-yl]-[5-(trifluoromethyl)-2-pyridyl]-methanone | cis-8-ethoxy-10-phenyl-11-oxa-3-azaspiro[5.5]undecane | 5 -(trifluoromethyl) pyridine-2-carboxylic acid |
| [cis-8-ethoxy-10-phenyl-11-oxa-3-azaspiro[5.5]undecan-3-yl]-(2-pyrrolidin-1-yl-3-pyridyl)-methanone | cis-8-ethoxy-10-phenyl-11-oxa-3-azaspiro[5.5]undecane | 2-pyrrolidin-1-ylpyridine-3-carboxylic acid |
| [cis-8-ethoxy-10-phenyl-11-oxa-3-azaspiro[5.5]undecan-3-yl]-(6-pyrrolidin-1-yl-3-pyridyl)-methanone | cis-8-ethoxy-10-phenyl-11-oxa-3-azaspiro[5.5]undecane | 6-pyrrolidin-1-ylpyridine-3-carboxylic acid |
| [cis-8-ethoxy-10-phenyl-11-oxa-3-azaspiro[5.5]undecan-3-yl]-[2-(isobutylamino)-3-pyridyl]-methanone | cis-8-ethoxy-10-phenyl-11-oxa-3-azaspiro[5.5]undecane | 2-(isobutylamino) pyridine-3-carboxylic acid |
| (5-chloro-2-ethoxy-3-pyridyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 5-chloro-2-ethoxy-pyridine-3-carboxylic acid |
| [2-(dimethylamino)-3-pyridyl]-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2-(dimethylamino) pyridine-3-carboxylic acid |
| [cis-8-ethoxy-10-phenyl-11-oxa-3-azaspiro[5.5]undecan-3-yl]-(4-methoxy-2-quinolyl)-methanone | cis-8-ethoxy-10-phenyl-11-oxa-3-azaspiro[5.5]undecane | 4-methoxyquinoline-2-carboxylic acid |
| [cis-8-ethoxy-10-phenyl-11-oxa-3-azaspiro[5.5]undecan-3-yl]-[6-(1-piperidyl)-3-pyridyl]-methanone | cis-8-ethoxy-10-phenyl-11-oxa-3-azaspiro[5.5]undecane | 6-(1-piperidyl)pyridine-3-carboxylic acid |
| [cis-8-ethoxy-10-phenyl-11-oxa-3-azaspiro[5.5]undecan-3-yl]-[2-(1-piperidyl)-3-pyridyl]-methanone | cis-8-ethoxy-10-phenyl-11-oxa-3-azaspiro[5.5]undecane | 2-(1-piperidyl)pyridine-3-carboxylic acid |

-continued

| Product | Amine | Carboxylic acid |
|---|---|---|
| (2-tert-butyl-5-cyclopropyl-pyrazol-3-yl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2-tert-butyl-5-cyclopropyl-pyrazole-3-carboxylic acid |
| [3-(difluoromethoxy)-4-methoxy-phenyl]-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 3-(difluoromethoxy)-4-methoxy-benzoic acid |
| [cis-8-ethoxy-10-phenyl-11-oxa-3-azaspiro[5.5]undecan-3-yl]-[2-(2,2,2-trifluoroethoxy)-3-pyridyl]-methanone | cis-8-ethoxy-10-phenyl-11-oxa-3-azaspiro[5.5]undecane | 2-(2,2,2-trifluoroethoxy) pyridine-3-carboxylic acid |
| [cis-8-ethoxy-10-phenyl-11-oxa-3-azaspiro[5.5]undecan-3-yl]-(3-methyl-4-morpholino-phenyl)-methanone | cis-8-ethoxy-10-phenyl-11-oxa-3-azaspiro[5.5]undecane | 3-methyl-4-morpholino-benzoic acid |
| [cis-8-ethoxy-10-phenyl-11-oxa-3-azaspiro[5.5]undecan-3-yl]-[4-(morpholinomethyl)phenyl]-methanone | cis-8-ethoxy-10-phenyl-11-oxa-3-azaspiro[5.5]undecane | 4-(morpholinomethyl) benzoic acid |
| [cis-8-ethoxy-10-phenyl-11-oxa-3-azaspiro[5.5]undecan-3-yl]-(3-isoquinolyl)-methanone | cis-8-ethoxy-10-phenyl-11-oxa-3-azaspiro[5.5]undecane | isoquinoline-3-carboxylic acid |
| (2,6-dimethoxy-3-pyridyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2,6-dimethoxypyridine-3-carboxylic acid |
| [cis-8-ethoxy-10-phenyl-11-oxa-3-azaspiro[5.5]undecan-3-yl]-(6-quinolyl)-methanone | cis-8-ethoxy-10-phenyl-11-oxa-3-azaspiro[5.5]undecane | quinoline-6-carboxylic acid |
| (2-chloro-4-fluoro-phenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2-chloro-4-fluoro-benzoic acid |
| 1,3-benzothiazol-6-yl-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 1,3-benzothiazole-6-carboxylic acid |
| [cis-8-ethoxy-10-phenyl-11-oxa-3-azaspiro[5.5]undecan-3-yl]-[5-(p-tolyl)isoxazol-3-yl]-methanone | cis-8-ethoxy-10-phenyl-11-oxa-3-azaspiro[5.5]undecane | 5-(p-tolyl)isoxazole-3-carboxylic acid |
| (6-chloroimidazo[1,2-a]pyridin-2-yl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 6-chloroimidazo[1,2-a]pyridine-2-carboxylic acid |
| (2-chloro-4-methylsulfonyl-phenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2-chloro-4-methylsulfonyl-benzoic acid |
| 6-[cis-8-ethoxy-10-phenyl-11-oxa-3-azaspiro[5.5]undecane-3-carbonyl]-2-methyl-pyridine-3-carbonitrile | cis-8-ethoxy-10-phenyl-11-oxa-3-azaspiro[5.5]undecane | 5-cyano-6-methyl-pyridine-2-carboxylic acid |
| [4-(difluoromethoxy)phenyl]-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 4-(difluoromethoxy) benzoic acid |
| [cis-8-ethoxy-10-phenyl-11-oxa-3-azaspiro[5.5]undecan-3-yl]-(5-pyrrolidin-1-yl-2-pyridyl)-methanone | cis-8-ethoxy-10-phenyl-11-oxa-3-azaspiro[5.5]undecane | 5-pyrrolidin-1-yl-pyridine-2-carboxylic acid |
| [cis-8-ethoxy-10-phenyl-11-oxa-3-azaspiro[5.5]undecan-3-yl]-(6-morpholino-3-pyridyl)-methanone | cis-8-ethoxy-10-phenyl-11-oxa-3-azaspiro[5.5]undecane | 6-morpholinopyridine-3-carboxylic acid |
| [cis-8-ethoxy-10-phenyl-11-oxa-3-azaspiro[5.5]undecan-3-yl]-[4-(2,2,2-trifluoroethoxymethyl)phenyl]-methanone | cis-8-ethoxy-10-phenyl-11-oxa-3-azaspiro[5.5]undecane | 4-(2,2,2-trifluoroethoxymethyl) benzoic acid |

-continued

| Product | Amine | Carboxylic acid |
|---|---|---|
| [cis-8-ethoxy-10-phenyl-11-oxa-3-azaspiro[5.5]undecan-3-yl]-[4-(3,3,3-trifluoropropoxymethyl)phenyl]-methanone | cis-8-ethoxy-10-phenyl-11-oxa-3-azaspiro[5.5]undecane | 4-(3,3,3-trifluoropropoxymethyl) benzoic acid |
| [cis-8-ethoxy-10-phenyl-11-oxa-3-azaspiro[5.5]undecan-3-yl]-[3-methoxy-4-(3,3,3-trifluoropropoxymethyl)phenyl]-methanone | cis-8-ethoxy-10-phenyl-11-oxa-3-azaspiro[5.5]undecane | 3-methoxy-4-(3,3,3-trifluoropropoxymethyl) benzoic acid |
| [cis-8-ethoxy-10-phenyl-11-oxa-3-azaspiro[5.5]undecan-3-yl]-[4-(2-hydroxy-2-methyl-propoxy)phenyl]-methanone | cis-8-ethoxy-10-phenyl-11-oxa-3-azaspiro[5.5]undecane | 4-(2-hydroxy-2-methyl-propoxy)benzoic acid |
| [cis-8-ethoxy-10-phenyl-11-oxa-3-azaspiro[5.5]undecan-3-yl]-[4-(2-fluoro-2-methyl-propoxy)-3-methoxy-phenyl]-methanone | cis-8-ethoxy-10-phenyl-11-oxa-3-azaspiro[5.5]undecane | 4-(2-fluoro-2-methyl-propoxy)-3-methoxy-benzoic acid |
| 5-[cis-8-ethoxy-10-phenyl-11-oxa-3-azaspiro[5.5]undecane-3-carbonyl]-2-methoxy-benzonitrile | cis-8-ethoxy-10-phenyl-11-oxa-3-azaspiro[5.5]undecane | 3-cyano-4-methoxy-benzoic acid |
| (2,4-dimethoxyphenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2,4-dimethoxybenzoic acid |
| 2,3-dihydrobenzofuran-7-yl-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2,3-dihydrobenzofuran-7-carboxylic acid |
| [cis-8-ethoxy-10-phenyl-11-oxa-3-azaspiro[5.5]undecan-3-yl]-(4-isopropoxy-3,5-dimethyl-phenyl)-methanone | cis-8-ethoxy-10-phenyl-11-oxa-3-azaspiro[5.5]undecane | 4-isopropoxy-3,5-dimethyl-benzoic acid |
| [cis-8-ethoxy-10-phenyl-11-oxa-3-azaspiro[5.5]undecan-3-yl]-(4-methoxy-3,5-dimethyl-phenyl)-methanone | cis-8-ethoxy-10-phenyl-11-oxa-3-azaspiro[5.5]undecane | 4-methoxy-3,5-dimethyl-benzoic acid |
| [cis-8-ethoxy-10-phenyl-11-oxa-3-azaspiro[5.5]undecan-3-yl]-(2-methoxyphenyl)-methanone | cis-8-ethoxy-10-phenyl-11-oxa-3-azaspiro[5.5]undecane | 2-methoxybenzoic acid |
| chroman-8-yl-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | chromane-8-carboxylic acid |
| [cis-8-ethoxy-10-phenyl-11-oxa-3-azaspiro[5.5]undecan-3-yl]-(o-tolyl)-methanone | cis-8-ethoxy-10-phenyl-11-oxa-3-azaspiro[5.5]undecane | 2-methylbenzoic acid |
| [cis-8-ethoxy-10-phenyl-11-oxa-3-azaspiro[5.5]undecan-3-yl]-(4-methoxy-3-methyl-phenyl)-methanone | cis-8-ethoxy-10-phenyl-11-oxa-3-azaspiro[5.5]undecane | 4-methoxy-3-methyl-benzoic acid |
| [cis-8-ethoxy-10-phenyl-11-oxa-3-azaspiro[5.5]undecan-3-yl]-(6-isopropoxy-5 -methyl-3-pyridyl)-methanone | cis-8-ethoxy-10-phenyl-11-oxa-3-azaspiro[5.5]undecane | 6-isopropoxy-5-methyl-pyridine-3-carboxylic acid |
| (2-ethoxy-3-methyl-phenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 2-ethoxy-3-methyl-benzoic acid |
| (3,5-dimethoxy-4-methyl-phenyl)-[cis-8-ethoxy-10-phenyl-11-oxa-3-azaspiro[5.5]undecan-3-yl]-methanone | cis-8-ethoxy-10-phenyl-11-oxa-3-azaspiro[5.5]undecane | 3,5-dimethoxy-4-methyl-benzoic acid |

1-(4-isopropoxy-3-methoxy-benzoyl)piperidin-4-one

Step 1: 4-isopropoxy-3-methoxy-benzoyl chloride

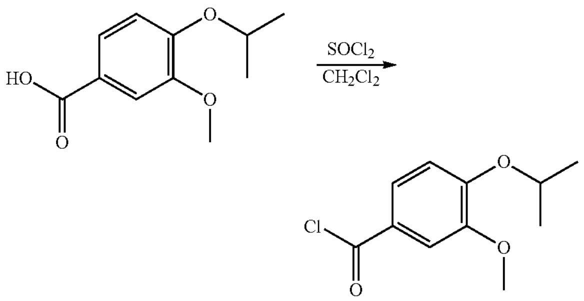

To a stirring solution of 4-isopropoxy-3-methoxy-benzoic acid (40.0 g, 190.3 mmol) in anhydrous dichloromethane (400 mL) at room temperature was slowly added thionyl chloride (27.8 mL, 381 mmol). The reaction was then transferred from a room temperature water bath to an oil bath that was then warmed to 30° C. The solution was allowed to stir overnight at 30° C. The reaction mixture was allowed to cool to room temperature prior to the addition of additional thionyl chloride (10.0 mL, 137 mmol). The reaction was allowed to stir at 40° C. for 3 hours. After completion, the reaction mixture was concentrated under reduced pressure, azeotrophing with toluene to provide 4-isopropoxy-3-methoxy-benzoyl chloride (44.3 g) as a yellow oil. The product was used in the next step without further purification.

The following compound was prepared using the procedure reported above:

| Product | Carboxylic acid |
|---|---|
| 4-isopropoxy-3-methyl-benzoyl chloride | 4-isopropoxy-3-methyl-benzoic acid |

Step 2:
1-(4-isopropoxy-3-methoxy-benzoyl)piperidin-4-one

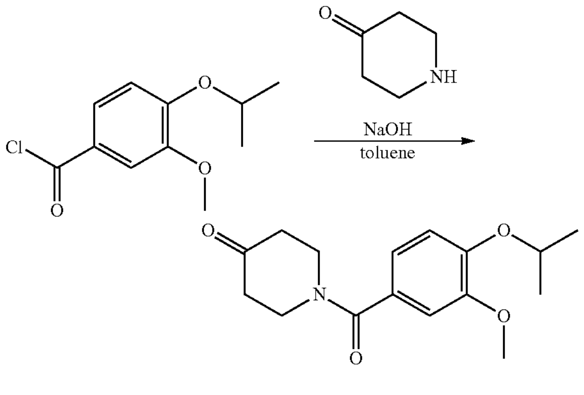

Piperidin-4-one hydrochloride hydrate (29.2 g, 190 mmol) was dissolved in an aqueous solution of sodium hydroxide (95 mL of 2.0 M, 190 mmol). The resulting clear solution was then stirred under nitrogen in an ice water bath. 4-isopropoxy-3-methoxy-benzoyl chloride (43.5 g, 190 mmol) was dissolved in toluene (90 mL) to provide a final volume of 100 mL. This solution was added dropwise in 2 mL portions followed by addition of 1 mL of an aqueous sodium hydroxide (48 mL of 4.0 M, 192 mmol) solution. This process was repeated until both reagents were completely added. When complete, the reaction mixture was allowed to stir at 0° C. for an additional 30 minutes. To the mixture was added $CH_2Cl_2$ (250 mL) followed by water (200 mL). The mixture was mixed well in a separatory funnel, and the aqueous layer was further extracted with $CH_2Cl_2$ (2×100 mL). Organic layers were combined, dried over sodium sulfate, filtered and concentrated under reduced pressure to provide a dark brown oil. Purification was performed by column chromatography to provide 1-(4-isopropoxy-3-methoxy-benzoyl)piperidin-4-one (16.56 g) as a clear light brown oil that crystallized to a slightly tan white solid upon standing. $^1H$ NMR (400 MHz, $CDCl_3$) δ 7.06 (d, J=1.9 Hz, 1H), 7.02 (dd, J=8.2, 2.0 Hz, 1H), 6.90 (d, J=8.3 Hz, 1H), 4.59 (dt, J=12.2, 6.1 Hz, 1H), 3.90-3.88 (br s, 4H), 3.88 (s, 3H), 2.51 (s, 4H), 1.40 (d, J=6.1 Hz, 6H). ESI-MS m/z calc. 291.15, found 292.0 $(M+1)^+$; Retention time: 0.94 minutes (3 minute run).

The following compound was prepared using the procedure reported above:

| Product | Acid chloride |
|---|---|
| 1-(4-isopropoxy-3-methyl-benzoyl)piperidin-4-one | 4-isopropoxy-3-methyl-benzoyl chloride |

3-(4-isopropoxy-3-methyl-benzoyl)-11-oxa-3-aza-spiro[5.5]undec-9-en-8-one

Step 1: 11-oxa-3-azaspiro[5.5]undec-9-en-8-one

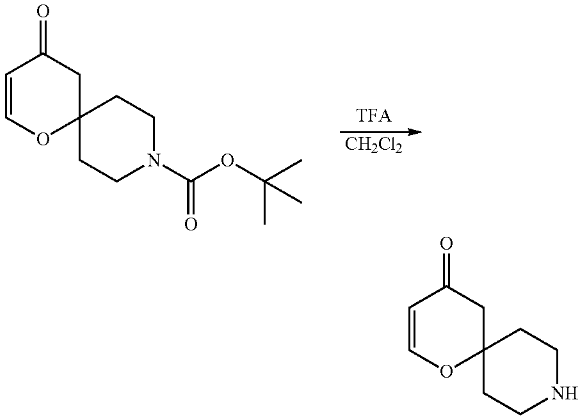

To a solution of tert-butyl 8-oxo-11-oxa-3-azaspiro[5.5]undec-9-ene-3-carboxylate (200 mg, 0.748 mmol) in $CH_2Cl_2$ (2.4 mL) was added TFA (0.6 mL, 7.8 mmol). The mixture was stirred at room temperature for 15 min. Solvent was removed. The crude material was evaporated again from toluene (2×) and dried under high vacuum overnight to provide 11-oxa-3-azaspiro[5.5]undec-9-en-8-one (300 mg). $^1H$ NMR (400 MHz, $CDCl_3$) δ 7.34 (d, J=6.1 Hz, 1H), 5.57 (d, J=6.1 Hz, 1H), 3.45 (d, J=11.7 Hz, 2H), 3.34 (dd, J=24.1, 12.7 Hz, 2H), 2.67 (s, 2H), 2.38 (d, J=14.6 Hz, 2H), 1.98 (td, J=14.8, 4.8 Hz, 2H). ESI-MS m/z calc. 167.09, found 168.2 $(M+1)^+$; Retention time: 0.17 minutes (3 minute run).

Step 2: 3-(4-isopropoxy-3-methyl-benzoyl)-11-oxa-3-azaspiro[5.5]undec-9-en-8-one

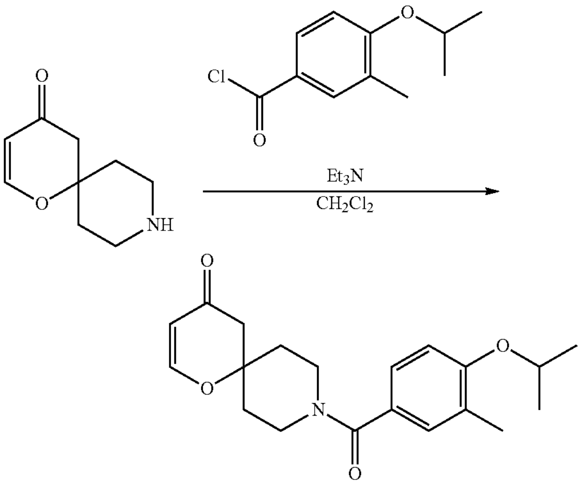

To a solution of 11-oxa-3-azaspiro[5.5]undec-9-en-8-one; 2,2,2-trifluoroacetic acid (2.42 g, 8.6 mmol) in $CH_2Cl_2$ (35 mL) was added triethylamine (10.9 mL, 78.2 mmol) followed by the addition of 4-isopropoxy-3-methyl-benzoyl chloride (1.83 g, 8.60 mmol) in $CH_2Cl_2$ (5 mL) dropwise. The mixture was stirred at room temperature overnight. The mixture was diluted with $CH_2Cl_2$, washed with water, dried over $MgSO_4$, filtered and concentrated to dryness. The crude material was purified by column chromatography (30-50% ethyl acetate-Hex) to provide 3-(4-isopropoxy-3-methyl-benzoyl)-11-oxa-3-azaspiro[5.5]undec-9-en-8-one (2.65 g) as a light yellow solid. $^1$H NMR (400 MHz, $CDCl_3$) δ 7.27 (t, J=4.0 Hz, 1H), 7.25-7.17 (m, 2H), 6.81 (d, J=8.1 Hz, 1H), 5.43 (d, J=6.1 Hz, 1H), 4.56 (dd, J=12.1, 6.0 Hz, 1H), 4.43-3.61 (m, 2H), 3.33 (s, 2H), 2.55 (s, 2H), 2.20 (s, 3H), 2.13 (d, J=13.2 Hz, 2H), 1.61 (s, 2H), 1.35 (d, J=6.0 Hz, 6H). ESI-MS m/z calc. 343.18, found 344.3 $(M+1)^+$; Retention time: 1.50 minutes (3 minute run).

10-ethyl-3-(4-isopropoxy-3-methyl-benzoyl)-11-oxa-3-azaspiro[5.5]undecan-8-one

Step 1:
10-ethyl-1'-oxa-3-azaspiro[5.5]undecan-8-one

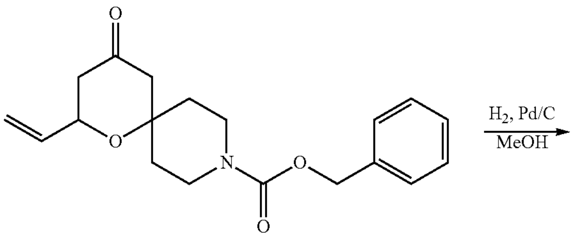

-continued

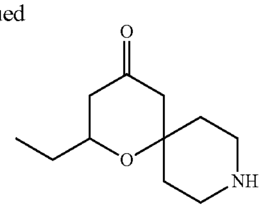

A solution of benzyl 8-oxo-10-vinyl-11-oxa-3-azaspiro[5.5]undecane-3-carboxylate (380 mg, 1.15 mmol) in MeOH (30 mL) was purged with $N_2$ for 2 min. Palladium (10% on carbon) (50 mg, 0.047 mmol) was added. The mixture was hydrogenated at room temperature using hydrogen balloon for 24 h. Catalyst was removed via filtration. The filtrate was concentrated to dryness to provide 10-ethyl-1'-oxa-3-aza-spiro[5.5]undecan-8-one (243 mg) as a light yellow thick oil that was used directly in next step without further purification. ESI-MS m/z calc. 197.14, found 198.2 $(M+1)^+$; Retention time: 0.17 minutes (3 minute run).

Step 2: 10-ethyl-3-(4-isopropoxy-3-methyl-benzoyl)-1'-oxa-3-azaspiro[5.5]undecan-8-one

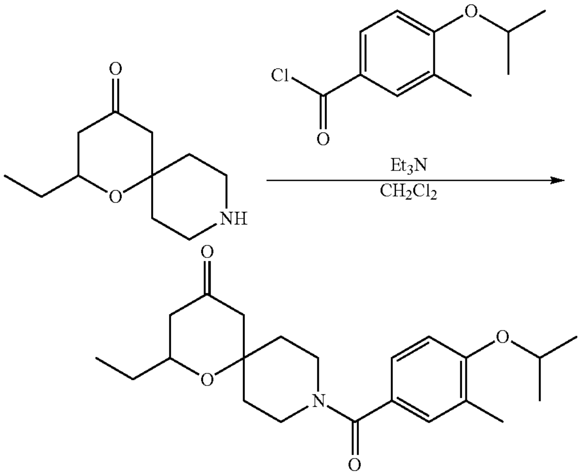

To a solution of 10-ethyl-1'-oxa-3-azaspiro[5.5]undecan-8-one (208 mg, 1.05 mmol) in $CH_2Cl_2$ (5 mL) was added triethylamine (441 µL, 3.16 mmol) followed by the addition of 4-isopropoxy-3-methyl-benzoyl chloride (247 mg, 1.16 mmol) in $CH_2Cl_2$ (1 mL) dropwise. The mixture was stirred at room temperature overnight, diluted with $CH_2Cl_2$, washed with saturated sodium bicarbonate (2×), 10% citric acid (2×), brine, dried over $MgSO_4$, filtered and concentrated to dryness. The crude material was purified by column chromatography (30-40% ethyl acetate-Hexane) to provide 10-ethyl-3-(4-isopropoxy-3-methyl-benzoyl)-11-oxa-3-azaspiro[5.5]undecan-8-one (191 mg). $^1$H NMR (400 MHz, $CDCl_3$) δ 7.23-7.17 (m, 2H), 6.81 (d, J=8.0 Hz, 1H), 4.56 (dt, J=12.1, 6.1 Hz, 1H), 4.12 (d, J=7.1 Hz, 2H), 3.69 (s, 1H), 3.49 (s, 1H), 3.06 (s, 1H), 2.37 (ddd, J=14.0, 10.5, 8.1 Hz, 2H), 2.32-2.23 (m, 2H), 2.20 (d, J=4.3 Hz, 3H), 1.93 (d, J=13.9 Hz, 1H), 1.86-1.54 (m, 5H), 1.34 (d, J=6.0 Hz, 6H), 1.03 (t, J=7.4 Hz, 3H). ESI-MS m/z calc. 373.23, found 374.5 $(M+1)^+$; Retention time: 1.78 minutes (3 minute run).

(4-isopropoxy-3-methoxy-phenyl)-[cis-8-methoxy-10-phenyl-11-oxa-3-azaspiro[5.5]undecan-3-yl] methanone Step 1: 3-(4-isopropoxy-3-methoxy-benzoyl)-11-oxa-3-azaspiro[5.5]undec-9-en-8-one

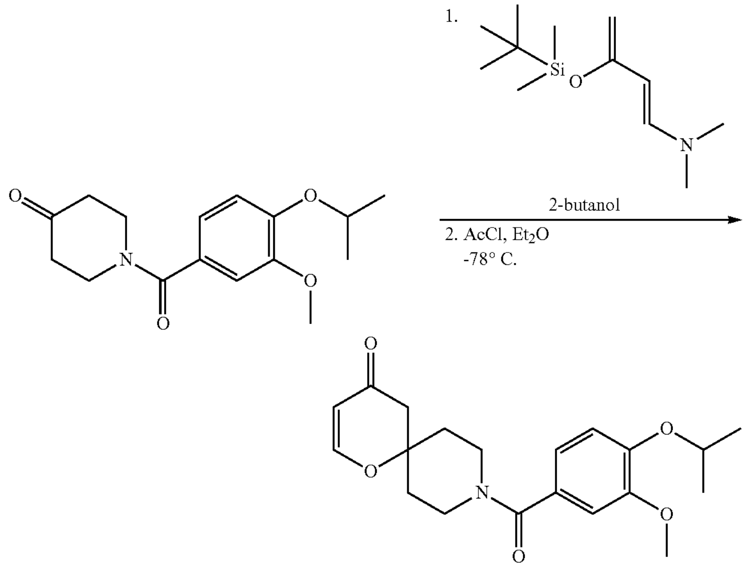

A suspension of 1-(4-isopropoxy-3-methoxy-benzoyl)piperidin-4-one (12.8 g, 44.0 mmol) in 2-butanol (100 mL) was purged with argon gas for 5 minutes. (1E)-3-[tert-butyl(dimethyl)silyl]oxy-N,N-dimethyl-buta-1,3-dien-1-amine (10.0 g, 4.0 mmol) was added dropwise at room temperature under argon gas. The reaction mixture was stirred at room temperature overnight. The mixture turned to a dark brown clear solution. Solvent was removed. The residue was redissolved in THF (200 mL) and cooled to −78° C. Acetyl chloride (3.75 mL, 52.8 mmol) was added dropwise. The mixture was stirred at −78° C. for 30 min. The reaction was quenched with saturated sodium bicarbonate (25 mL). The organic layer was separated. The aqueous layer was extracted with diethyl ether (3×). The combined organic layers were washed with brine, dried over $MgSO_4$, filtered and concentrated. The crude material was purified by column chromatography (40-60% ethyl acetate-Hex) to provide 3-(4-isopropoxy-3-methoxy-benzoyl)-11-oxa-3-azaspiro[5.5]undec-9-en-8-one (8.5 g) as a light yellow thick oil. $^1H$ NMR (400 MHz, $CDCl_3$) δ 7.28 (d, J=6.1 Hz, 1H), 6.99 (d, J=1.9 Hz, 1H), 6.94 (dd, J=8.2, 1.9 Hz, 1H), 6.87 (d, J=8.3 Hz, 1H), 5.44 (d, J=6.1 Hz, 1H), 4.57 (dt, J=12.2, 6.1 Hz, 1H), 4.25-4.00 (m, 2H), 3.87 (s, 3H), 3.34 (s, 2H), 2.56 (s, 2H), 2.15 (d, J=14.1 Hz, 2H), 1.62 (s, 2H), 1.39 (t, J=5.3 Hz, 6H). ESI-MS m/z calc. 359.17, found 360.3 $(M+1)^+$; Retention time: 1.18 minutes (3 minute run).

Step 2: 3-(4-isopropoxy-3-methoxy-benzoyl)-10-phenyl-11-oxa-3-azaspiro[5.5]undecan-8-one

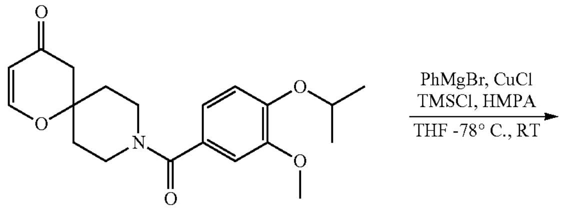

-continued

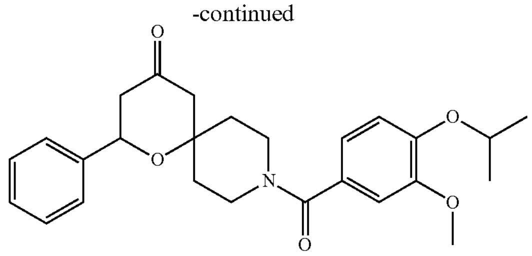

A round bottom flask was heated with a heat-gun under vacuum followed by being flushed with Ar. The process was repeated three times. To the flask, copper iodide (2.32 g, 12.2 mmol) was placed followed by the addition of THF (5 mL). The suspension was purged with argon for 2 minutes and then cooled to −78° C. Phenylmagnesium bromide (122 mL of 1 M, 122 mmol) in THF was added dropwise at −78° C. under argon. The mixture was stirred at −78° C. for 20 minutes. HMPA (44.0 g, 244 mmol) was added. The mixture was stirred at −78° C. for 30 min. TMSCl (26.5 g, 244 mmol) was added to a solution of 3-(4-isopropoxy-3-methoxy-benzoyl)-11-oxa-3-azaspiro[5.5]undec-9-en-8-one (7.30 g, 20.3 mmol) in THF (25 mL). The above solution was added to the reaction mixture dropwise. The mixture was slowly warmed to room temperature and was stirred at room temperature overnight. The reaction was quenched with saturated $NH_4Cl$ solution, repartitioned between ethyl acetate and water. The aqueous layer was extracted with ethyl acetate (2×). The combined organic layers were washed with brine, dried over $MgSO_4$, filtered and concentrated to dryness. The crude material was purified by column chromatography (40-60% ethyl acetate-Hex) to provide 3-(4-isopropoxy-3-methoxy-benzoyl)-10-phenyl-11-oxa-3-azaspiro[5.5]undecan-8-one (6 g). ESI-MS m/z calc. 437.22, found 438.0 $(M+1)^+$; Retention time: 1.69 minutes (3 minute run).

The following compounds were prepared using the procedure reported above:

| Product | Ketone Precursor | Grignard Reagent |
|---|---|---|
| 3-(4-isopropoxy-3-methyl-benzoyl)-10-phenyl-11-oxa-3-azaspiro[5.5]undecan-8-one | 3-(4-isopropoxy-3-methyl-benzoyl)-11-oxa-3-azaspiro[5.5]undec-9-en-8-one | Phenylmagnesium bromide |
| 10-cyclopropyl-3-(4-isopropoxy-3-methyl-benzoyl)-11-oxa-3-azaspiro[5.5]undecan-8-one | 3-(4-isopropoxy-3-methyl-benzoyl)-11-oxa-3-azaspiro[5.5]undec-9-en-8-one | Cyclopropylmagnesium bromide |
| 3-(4-isopropoxy-3-methoxy-benzoyl)-10-(o-tolyl)-11-oxa-3-azaspiro[5.5]undecan-8-one | 3-(4-isopropoxy-3-methoxy-benzoyl)-11-oxa-3-azaspiro[5.5]undec-9-en-8-one | bromo-(o-tolyl)magnesium |

Step 3: cis and trans [8-hydroxy-10-phenyl-11-oxa-3-azaspiro[5.5]undecan-3-yl]-(4-isopropoxy-3-methoxy-phenyl)methanone

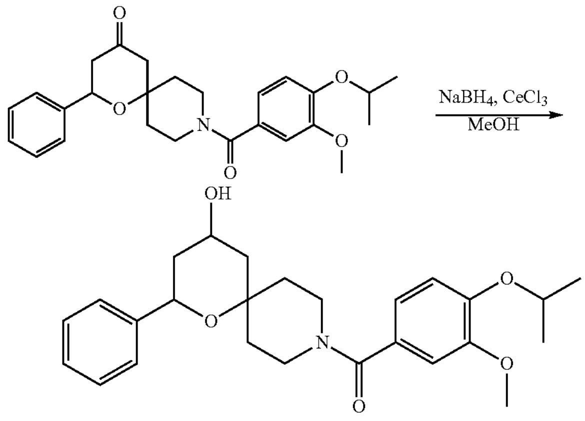

cis and trans

To a solution of 3-(4-isopropoxy-3-methoxy-benzoyl)-10-phenyl-11-oxa-3-azaspiro[5.5]undecan-8-one (4.50 g, 10.3 mmol) in MeOH (110 mL) was added trichlorocerium (2.79 g, 11.3 mmol). The mixture was stirred at room temperature for 5 minutes. Sodium borohydride (467 mg, 12.4 mmol) was added. The mixture was stirred at room temperature for 20 minutes. The reaction was quenched with water and extracted with ethyl acetate (2×). The combined organic layers were washed with brine, dried over $MgSO_4$, filtered and concentrated to dryness. The crude material was purified by column chromatography (40-60% ethyl acetate-Hex) to provide [cis-8-hydroxy-10-phenyl-11-oxa-3-azaspiro[5.5]undecan-3-yl]-(4-isopropoxy-3-methoxy-phenyl)methanone (1.5 g) and [trans-8-hydroxy-10-phenyl-11-oxa-3-azaspiro[5.5]undecan-3-yl]-(4-isopropoxy-3-methoxy-phenyl)methanone (1.3 g). cis-isomer: $^1$H NMR (400 MHz, $CDCl_3$) δ 7.43-7.33 (m, 4H), 7.33-7.27 (m, 1H), 6.96 (d, J=1.6 Hz, 1H), 6.95-6.90 (m, 1H), 6.86 (d, J=8.2 Hz, 1H), 4.65-4.48 (m, 2H), 4.23-4.05 (m, 2H), 3.95-3.75 (m, 1H), 3.85 (s, 3H), 3.49 (s, 1H), 3.20 (s, 1H), 2.25 (dd, J=20.6, 8.4 Hz, 2H), 1.98 (dd, J=12.5, 2.9 Hz, 1H), 1.73 (s, 2H), 1.62-1.40 (m, 3H), 1.37 (t, J=6.0 Hz, 6H). ESI-MS m/z calc. 439.24, found 440.4 $(M+1)^+$; Retention time: 1.49 minutes (3 minute run). trans-isomer $^1$H NMR (400 MHz, $CDCl_3$) δ 7.43-7.38 (m, 2H), 7.39-7.33 (m, 2H), 7.31-7.24 (m, 1H), 6.96 (d, J=1.7 Hz, 1H), 6.92 (dd, J=8.2, 1.8 Hz, 1H), 6.85 (d, J=8.2 Hz, 1H), 4.97 (d, J=11.2 Hz, 1H), 4.55 (dt, J=12.2, 6.1 Hz, 1H), 4.44-4.32 (m, 1H), 4.05-3.75 (m, 2H), 3.85 (s, 3H), 3.49 (s, 1H), 3.24 (s, 1H), 2.77 (dd, J=25.2, 13.7 Hz, 1H), 1.96 (d, J=13.4 Hz, 1H), 1.84-1.70 (m, 2H), 1.70-1.54 (m, 5H), 1.37 (d, J=6.1 Hz, 6H). ESI-MS m/z calc. 439.24, found 440.2 $(M+1)^+$; Retention time: 1.61 minutes (3 minute run).

The following compounds were prepared using the procedure reported above:

| Product | Ketone Precursor |
|---|---|
| [cis-8-hydroxy-10-phenyl-11-oxa-3-azaspiro[5.5]undecan-3-yl]-(4-isopropoxy-3-methyl-phenyl)methanone | 3-(4-isopropoxy-3-methyl-benzoyl)-10-phenyl-11-oxa-3-azaspiro[5.5]undecan-8-one |
| [trans-8-hydroxy-10-phenyl-11-oxa-3-azaspiro[5.5]undecan-3-yl]-(4-isopropoxy-3-methyl-phenyl)methanone | 3-(4-isopropoxy-3-methyl-benzoyl)-10-phenyl-11-oxa-3-azaspiro[5.5]undecan-8-one |
| [cis-10-cyclopropyl-8-hydroxy-11-oxa-3-azaspiro[5.5]undecan-3-yl]-(4-isopropoxy-3-methyl-phenyl)methanone | 10-cyclopropyl-3-(4-isopropoxy-3-methyl-benzoyl)-11-oxa-3-azaspiro[5.5]undecan-8-one |
| [trans-10-cyclopropyl-8-hydroxy-11-oxa-3-azaspiro[5.5]undecan-3-yl]-(4-isopropoxy-3-methyl-phenyl)methanone | 10-cyclopropyl-3-(4-isopropoxy-3-methyl-benzoyl)-11-oxa-3-azaspiro[5.5]undecan-8-one |
| [cis-8-hydroxy-10-(o-tolyl)-11-oxa-3-azaspiro[5.5]undecan-3-yl]-(4-isopropoxy-3-methoxy-phenyl)methanone | 3-(4-isopropoxy-3-methoxy-benzoyl)-10-(o-tolyl)-11-oxa-3-azaspiro[5.5]undecan-8-one |
| [trans-8-hydroxy-10-(o-tolyl)-11-oxa-3-azaspiro[5.5]undecan-3-yl]-(4-isopropoxy-3-methoxy-phenyl)methanone | 3-(4-isopropoxy-3-methoxy-benzoyl)-10-(o-tolyl)-11-oxa-3-azaspiro[5.5]undecan-8-one |

-continued

| Product | Ketone Precursor |
|---|---|
| cis-(10-ethyl-8-hydroxy-11-oxa-3-azaspiro[5.5]undecan-3-yl)-(4-isopropoxy-3-methyl-phenyl)methanone | 10-ethyl-3-(4-isopropoxy-3-methyl-benzoyl)-11-oxa-3-azaspiro[5.5]undecan-8-one |
| trans-(10-ethyl-8-hydroxy-11-oxa-3-azaspiro[5.5]undecan-3-yl)-(4-isopropoxy-3-methyl-phenyl)methanone | 10-ethyl-3-(4-isopropoxy-3-methyl-benzoyl)-11-oxa-3-azaspiro[5.5]undecan-8-one |

Step 4: (4-isopropoxy-3-methoxy-phenyl)-[cis-8-methoxy-10-phenyl-11-oxa-3-azaspiro[5.5]undecan-3-yl]methanone

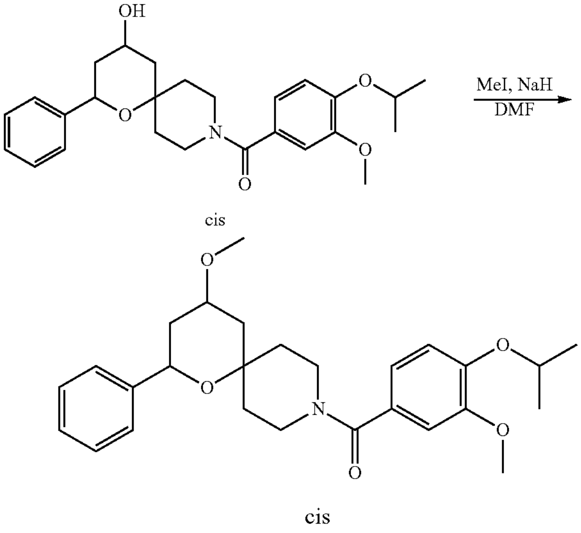

To a solution of [cis-8-hydroxy-10-phenyl-11-oxa-3-aza-spiro[5.5]undecan-3-yl]-(4-isopropoxy-3-methoxy-phenyl) methanone (139 mg, 0.3 mmol) in DMF (4 mL) was added sodium hydride (34 mg, 1.5 mmol). The mixture was stirred at room temperature for 30 minutes. Iodomethane (187 μL, 3.00 mmol) was added. The mixture was stirred at room temperature overnight, then repartitioned between ethyl acetate and water. The aqueous layer was extracted with ethyl acetate (2×). The combined organic layers were washed with water (3×), brine, dried over $MgSO_4$, filtered and concentrated to dryness. The crude material was purified by column chromatography (50-60% ethyl acetate-Hex) to provide (4-isopropoxy-3-methoxy-phenyl)-[cis-8-methoxy-10-phenyl-11-oxa-3-azaspiro[5.5]undecan-3-yl]methanone (102 mg). $^1H$ NMR (400 MHz, $CDCl_3$) δ 7.48-7.33 (m, 4H), 7.33-7.28 (m, 1H), 7.01-6.90 (m, 2H), 6.86 (d, J=8.2 Hz, 1H), 4.66-4.46 (m, 2H), 4.12-3.90 (m, 2H), 3.86 (s, 3H), 3.76-3.61 (m, 1H), 3.48 (s, 1H), 3.37 (d, J=4.5 Hz, 3H), 3.21 (t, J=11.8 Hz, 1H), 2.28 (dd, J=39.8, 13.2 Hz, 2H), 2.00 (dd, J=12.6, 2.7 Hz, 1H), 1.85-1.62 (m, 3H), 1.59-1.44 (m, 1H), 1.42-1.33 (m, 7H). ESI-MS m/z calc. 453.25, found 454.5 $(M+1)^+$; Retention time: 1.65 minutes (3 minute run).

The following compounds were prepared using the procedure reported above:

| Product | Alcohol Precursor | Alkyl halide |
|---|---|---|
| (4-isopropoxy-3-methyl-phenyl)-[cis-8-isopropoxy-10-phenyl-11-oxa-3-azaspiro[5.5]undecan-3-yl]methanone | [cis-8-hydroxy-10-phenyl-11-oxa-3-azaspiro[5.5]undecan-3-yl]-(4-isopropoxy-3-methyl-phenyl)methanone | 2-iodopropane |
| [cis-10-cyclopropyl-8-ethoxy-11-oxa-3-azaspiro[5.5]undecan-3-yl]-(4-isopropoxy-3-methyl-phenyl)methanone | [cis-10-cyclopropyl-8-hydroxy-11-oxa-3-azaspiro[5.5]undecan-3-yl]-(4-isopropoxy-3-methyl-phenyl)methanone | iodoethane |
| [cis-8-ethoxy-10-phenyl-11-oxa-3-azaspiro[5.5]undecan-3-yl]-(4-isopropoxy-3-methyl-phenyl)methanone | [cis-8-hydroxy-10-phenyl-11-oxa-3-azaspiro[5.5]undecan-3-yl]-(4-isopropoxy-3-methyl-phenyl)methanone | iodoethane |
| [trans-8-ethoxy-10-phenyl-11-oxa-3-azaspiro[5.5]undecan-3-yl]-(4-isopropoxy-3-methyl-phenyl)methanone | [trans-8-hydroxy-10-phenyl-11-oxa-3-azaspiro[5.5]undecan-3-yl]-(4-isopropoxy-3-methyl-phenyl)methanone | iodoethane |
| [trans-8-ethoxy-10-(o-tolyl)-11-oxa-3-azaspiro[5.5]undecan-3-yl]-(4-isopropoxy-3-methoxy-phenyl)methanone | [trans-8-hydroxy-10-(o-tolyl)-11-oxa-3-azaspiro[5.5]undecan-3-yl]-(4-isopropoxy-3-methoxy-phenyl)methanone | iodoethane |
| [cis-8-ethoxy-10-phenyl-11-oxa-3-azaspiro[5.5]undecan-3-yl]-(4-isopropoxy-3-methoxy-phenyl)methanone | [cis-8-hydroxy-10-phenyl-11-oxa-3-azaspiro[5.5]undecan-3-yl]-(4-isopropoxy-3-methoxy-phenyl)methanone | iodoethane |
| (4-isopropoxy-3-methoxy-phenyl)-[cis-8-(2- | [cis-8-hydroxy-10-phenyl-11-oxa-3-azaspiro[5.5]undecan- | 1-bromo-2-methoxy-ethane |

-continued

| Product | Alcohol Precursor | Alkyl halide |
|---|---|---|
| methoxyethoxy)-10-phenyl-11-oxa-3-azaspiro[5.5]undecan-3-yl]methanone | 3-yl]-(4-isopropoxy-3-methoxy-phenyl)methanone | |
| (4-isopropoxy-3-methoxy-phenyl)-[cis-8-isopropoxy-10-phenyl-11-oxa-3-azaspiro[5.5]undecan-3-yl]methanone | [cis-8-hydroxy-10-phenyl-11-oxa-3-azaspiro[5.5]undecan-3-yl]-(4-isopropoxy-3-methoxy-phenyl)methanone | 2-iodopropane |
| cis-(8-ethoxy-10-ethyl-11-oxa-3-azaspiro[5.5]undecan-3-yl)-(4-isopropoxy-3-methyl-phenyl)methanone | cis-(10-ethyl-8-hydroxy-11-oxa-3-azaspiro[5.5]undecan-3-yl)-(4-isopropoxy-3-methyl-phenyl)methanone | iodoethane |

cis-4-ethoxy-2-(pyridin-2-yl)-1-oxa-9-azaspiro[5.5]undecan-9-yl)(4-isopropoxy-3-methylphenyl)methanone Step 1: tent-Butyl 4-oxospiro[chromane-2,4'-piperidine]-1'-carboxylate

Step 1: 1-(3-pyridyl)butane-1,3-dione

Method A:

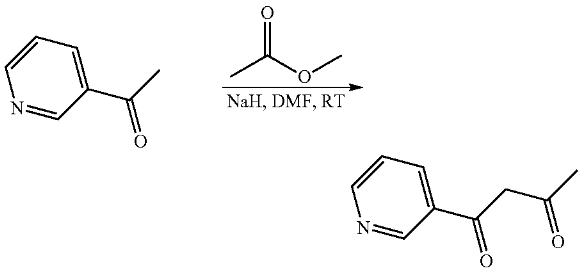

To a solution of 1-(3-pyridyl)ethanone (15.0 g, 124 mmol) in DMF (100 mL) at 0° C. was added sodium hydride (5.9 g, 149 mmol). The reaction mixture was then stirred at room temperature for 10 minutes. After cooling to 0° C., methyl acetate (11.8 mL, 149 mmol) was slowly added dropwise. The reaction mixture was allowed to slowly warm to room temperature and stirred overnight. The reaction mixture was quenched with the addition of saturated ammonium chloride (100 mL) and acidified to pH 5 with the addition of 1 N HCl. The mixture was then extracted with ethyl acetate (2×75 mL). The organic layers were combined, dried over sodium sulfate, filtered and concentrated under reduced pressure. The 16 grams of crude product were filtered through a plug of silica gel. The filtrate was concentrated under reduced pressure. The residue was taken up in a 1:9 solution of ethyl acetate/hexane (300 mL) at 65° C. The resulting solution was slowly allowed to cool to warm temperature while stirring. The precipitate was collected by vacuum filtration to provide 1-(3-pyridyl)butane-1,3-dione (7.7 g) as a yellow solid.

Method B:

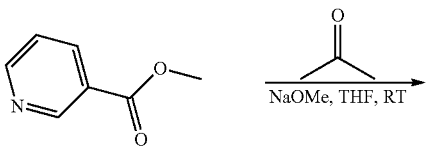

-continued

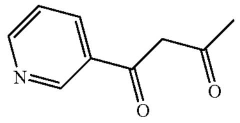

To a solution of methylpyridine-3-carboxylate (20.0 g, 146 mmol) in THF (200 mL) was added acetone (50 mL, 681.0 mmol). Sodium methoxide (32.7 mL of 25% w/w, 146.0 mmol) was added dropwsie at rt under $N_2$. The mixture was stirred at rt for 72 hours, quenched with sat. $NH_4Cl$, acidifed with 1 N HCl to pH-5. The aqueous layer was extracted with EtOAc (3×). The combined organic layers were washed with brine, dried over $MgSO_4$, filtered and concentrated to dryness. The crude material was purified by column chromatography (0-10% EtOAc-Hex) to provide 1-(3-pyridyl)butane-1,3-dione (7 g) as a light yellow crystalline solid. $^1H$ NMR (400 MHz, $CDCl_3$) δ 15.98 (s, 1H), 9.19-8.99 (m, 1H), 8.74 (dd, J=4.8, 1.7 Hz, 1H), 8.34-8.04 (m, 1H), 7.41 (ddd, J=8.0, 4.8, 0.8 Hz, 1H), 6.20 (s, 1H), 2.24 (s, 3H). ESI-MS m/z calc. 163.06, found 164.3 $(M+1)^+$; Retention time: 0.32 minutes (3 min run).

The following compounds were prepared using the procedure reported above:

| Ester | Product |
|---|---|
| 1-(2-pyridyl)ethanone | 1-(2-pyridyl)butane-1,3-dione |
| 1-(4-pyridyl)ethanone | 1-(4-pyridyl)butane-1,3-dione |

Step 2: 4-[4-hydroxy-1-(4-isopropoxy-3-methyl-benzoyl)-4-piperidyl]-1-(3-pyridyl)butane-1,3-dione

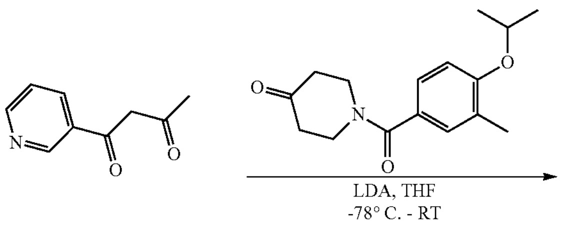

-continued

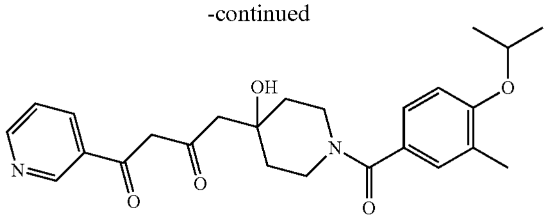

To an oven-dried round bottom flask was added diisopropylamine (6.4 mL, 46 mmol) and THF (125 mL). It was cooled to −78° C., and a solution of nBuLi (18 mL of 2.5 M, 46 mmol) in hexane was added. It was stirred at 0° C. for 30 minutes and again cooled to −78° C. 1-(3-pyridyl)butane-1,3-dione (3.40 g, 21.0 mmol) in a solution of THF (25 mL) was added dropwise. After 30 minutes at −78° C., a solution of 1-(4-isopropoxy-3-methyl-benzoyl)piperidin-4-one (5.74 g, 20.8 mmol) in THF (25 mL) was added dropwise. The reaction mixture was allowed to slowly warm to room temperature and stirred overnight. The reaction mixture was quenched with saturated ammonium chloride (100 mL). Volatiles were removed under reduced pressure to one-third volume. It was extracted with ethyl acetate (2×75 mL). Organic layers were combined, dried over sodium sulfate, filtered and concentrated under reduced pressure. The crude brown oil was purified by column chromatography (100% ethyl acetate) to provide 4-[4-hydroxy-1-(4-isopropoxy-3-methyl-benzoyl)-4-piperidyl]-1-(3-pyridyl)butane-1,3-dione (5.85 g) as a yellow foaming solid. $^1$H NMR (400 MHz, $CDCl_3$) δ 15.81 (s, 1H), 9.08 (d, J=1.9 Hz, 1H), 8.76 (dd, J=4.8, 1.5 Hz, 1H), 8.19 (dd, J=8.0, 1.6 Hz, 1H), 7.49-7.42 (m, 1H), 7.24-7.17 (m, 2H), 6.80 (d, J=8.2 Hz, 1H), 6.20 (s, 1H), 4.55 (m, 1H), 4.51-4.25 (br s, 1H), 3.52-3.26 (m, 4H), 2.68 (s, 2H), 2.20 (s, 3H), 1.75-1.51 (m, 4H), 1.34 (d, J=6.0 Hz, 6H). ESI-MS m/z calc. 438.22, found 439.5 (M+1)$^+$; Retention time: 1.37 minutes (3 min run).

The following compounds were prepared using the procedure reported above:

| Diketone | Ketone | Product |
|---|---|---|
| 1-(2-pyridyl)butane-1,3-dione | 1-(4-isopropoxy-3-methyl-benzoyl)piperidin-4-one | 4-[4-hydroxy-1-(4-isopropoxy-3-methyl-benzoyl)-4-piperidyl]-1-(2-pyridyl)butane-1,3-dione |
| 1-(4-pyridyl)butane-1,3-dione | 1-(4-isopropoxy-3-methyl-benzoyl)piperidin-4-one | 4-[4-hydroxy-1-(4-isopropoxy-3-methyl-benzoyl)-4-piperidyl]-1-(4-pyridyl)butane-1,3-dione |
| 1-(2-pyridyl)butane-1,3-dione | tert-butyl 4-oxopiperidine-1-carboxylate | tert-butyl 4-[2,4-dioxo-4-(2-pyridyl)butyl]-4-hydroxy-piperidine-1-carboxylate |
| 1-(3-pyridyl)butane-1,3-dione | tert-butyl 4-oxopiperidine-1-carboxylate | tert-butyl 4-[2,4-dioxo-4-(3-pyridyl)butyl]-4-hydroxy-piperidine-1-carboxylate |
| 1-(4-pyridyl)butane-1,3-dione | tert-butyl 4-oxopiperidine-1-carboxylate | tert-butyl 4-[2,4-dioxo-4-(4-pyridyl)butyl]-4-hydroxy-piperidine-1-carboxylate |

Step 3: 3-(4-isopropoxy-3-methyl-benzoyl)-10-(3-pyridyl)-11-oxa-3-azaspiro[5.5]undec-9-en-8-one Method A:

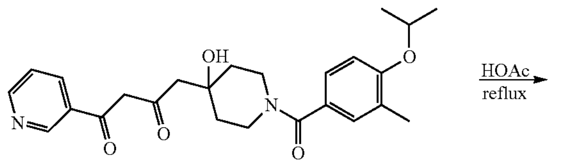

-continued

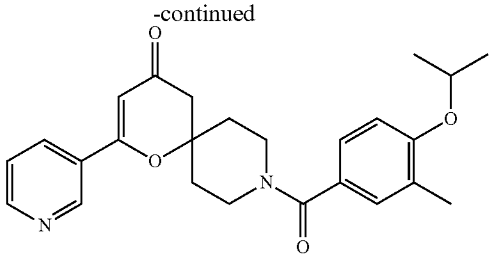

4-[4-hydroxy-1-(4-isopropoxy-3-methyl-benzoyl)-4-piperidyl]-1-(3-pyridyl)butane-1,3-dione (4.5 g, 10.3 mmol) was dissolved in glacial acetic acid (45 mL, 791 mmol) and stirred at reflux for 2 hours. Acetic acid was removed under reduced pressure. The crude residue was purified by column chromatography (40 gram silica gel column, 40-80% ethyl acetate/hexane) to provide 3-(4-isopropoxy-3-methyl-benzoyl)-10-(3-pyridyl)-11-oxa-3-azaspiro[5.5]undec-9-en-8-one (3.75 g) as a yellow sticky foam. $^1$H NMR (400 MHz, $CDCl_3$) δ=9.04 (d, J=1.9, 1H), 8.74 (dd, J=4.8, 1.5, 1H), 8.08-8.02 (m, 1H), 7.44 (dd, J=8.0, 4.9, 1H), 7.26-7.21 (m, 2H), 6.82 (d, J=8.6, 1H), 6.07 (s, 1H), 4.57 (dt, J=12.1, 6.0, 1H), 4.5-3.75 (m, 2H), 3.44 (br s, 2H), 2.65 (s, 2H), 2.23 (br s, 2H), 2.22 (s, 3H), 1.74 (br s, 2H), 1.35 (d, J=6.0, 6H). ESI-MS m/z calc. 420.20, found 420.8 (M+1)$^+$; Retention time: 1.45 minutes (3 min run).

Method B:

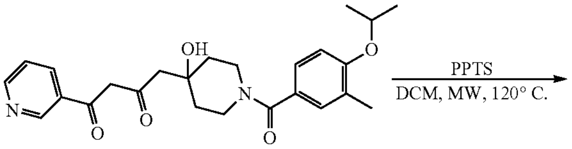

-continued

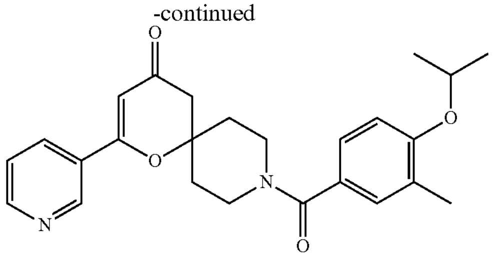

To a solution of 4-[4-hydroxy-1-(4-isopropoxy-3-methyl-benzoyl)-4-piperidyl]-1-(3-pyridyl)butane-1,3-dione (1 mmol) in dichloromethane (5 mL) was added PPTS (251 mg, 1.00 mmol). The mixture was heated in microwave at 120° C. for 45 min. Water was added. The aqueous layer was extracted with dichloromethane (2×). The combined organic layers were washed with brine, dried over $MgSO_4$, filtered and concentrated to dryness. The residue was purified by column chromatography (40-50% ethyl acetate-Hex) to provide 3-(4-isopropoxy-3-methyl-benzoyl)-10-(3-pyridyl)-11-oxa-3-azaspiro[5.5]undec-9-en-8-one.

The following compounds were prepared using the procedure reported above:

| Diketone | Product |
|---|---|
| 4-[4-hydroxy-1-(4-isopropoxy-3-methyl-benzoyl)-4-piperidyl]-1-(2-pyridyl)butane-1,3-dione | 3-(4-isopropoxy-3-methyl-benzoyl)-10-(2-pyridyl)-11-oxa-3-azaspiro[5.5]undec-9-en-8-one. |
| 4-[4-hydroxy-1-(4-isopropoxy-3-methyl-benzoyl)-4-piperidyl]-1-(4-pyridyl)butane-1,3-dione | 3-(4-isopropoxy-3-methyl-benzoyl)-10-(4-pyridyl)-11-oxa-3-azaspiro[5.5]undec-9-en-8-one. |
| tert-butyl 4-[2,4-dioxo-4-(2-pyridyl)butyl]-4-hydroxy-piperidine-1-carboxylate | tert-butyl 8-oxo-10-(2-pyridyl)-11-oxa-3-azaspiro[5.5]undec-9-ene-3-carboxylate |
| tert-butyl 4-[2,4-dioxo-4-(3-pyridyl)butyl]-4-hydroxy-piperidine-1-carboxylate | tert-butyl 8-oxo-10-(3-pyridyl)-11-oxa-3-azaspiro[5.5]undec-9-ene-3-carboxylate |
| tert-butyl 4-[2,4-dioxo-4-(4-pyridyl)butyl]-4-hydroxy-piperidine-1-carboxylate | tert-butyl 8-oxo-10-(4-pyridyl)-11-oxa-3-azaspiro[5.5]undec-9-ene-3-carboxylate |

Step 4: (4-hydroxy-2-(pyridin-3-yl)-1-oxa-9-azaspiro[5.5]undec-2-en-9-yl)(4-isopropoxy-3-methylphenyl)methanone

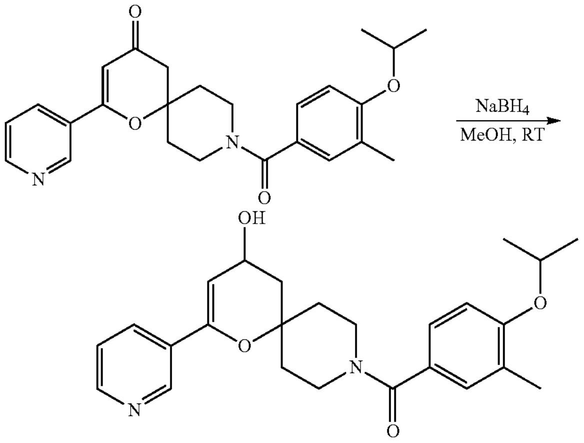

To a solution of 3-(4-isopropoxy-3-methyl-benzoyl)-10-(3-pyridyl)-11-oxa-3-azaspiro[5.5]undec-9-en-8-one (3.65 g, 8.68 mmol) in methanol (35 mL) was slowly added sodium borohydride (328 mg, 8.68 mmol). After 2 hours, saturated ammonium chloride (75 mL) was added. The mixture was allowed to stir for 15 minutes, and the mixture was concentrated to half volume under reduced pressure. The remaining suspension was extracted with ethyl acetate (3×75 mL). Organic layers were combined, dried over sodium sulfate, filtered and concentrated under reduced pressure. The crude product was purified by column chromatography (70-100% ethyl acetate/hexane) to afford (4-hydroxy-2-(pyridin-3-yl)-1-oxa-9-azaspiro[5.5]undec-2-en-9-yl)(4-isopropoxy-3-methylphenyl)methanone (3.32 g). $^1$H NMR (400 MHz, $CDCl_3$) δ 8.90 (d, J=1.8 Hz, 1H), 8.57 (dd, J=4.7, 1.3 Hz, 1H), 7.91 (d, J=8.0 Hz, 1H), 7.31 (dd, J=8.0, 4.8 Hz, 1H), 7.23 (dd, J=13.9, 5.8 Hz, 2H), 6.81 (d, J=8.1 Hz, 1H), 5.56 (d, J=3.5 Hz, 1H), 4.56 (dt, J=12.0, 6.0 Hz, 2H), 4.51-4.22 (m, 1H), 3.82 (br s, 1H), 3.39 (br s, 2H), 2.21 (s, 3H), 2.17-1.55 (m, 6H), 1.34 (d, J=6.0 Hz, 6H). ESI-MS m/z calc. 422.2, found 423 $(M+1)^+$; Retention time: 1.23 minutes (3 min run).

The following compounds were prepared using the procedure reported above:

| Diketone | Product |
|---|---|
| 3-(4-isopropoxy-3-methyl-benzoyl)-10-(2-pyridyl)-11-oxa-3-azaspiro[5.5]undec-9-en-8-one. | [8-hydroxy-10-(2-pyridyl)-11-oxa-3-azaspiro[5.5]undec-9-en-3-yl]-(4-isopropoxy-3-methyl-phenyl)methanone |
| 3-(4-isopropoxy-3-methyl-benzoyl)-10-(4-pyridyl)-11-oxa-3-azaspiro[5.5]undec-9-en-8-one. | [8-hydroxy-10-(4-pyridyl)-11-oxa-3-azaspiro[5.5]undec-9-en-3-yl]-(4-isopropoxy-3-methyl-phenyl)methanone |
| tert-butyl 8-oxo-10-(2-pyridyl)-11-oxa-3-azaspiro[5.5]undec-9-ene-3-carboxylate | tert-butyl 8-hydroxy-10-(2-pyridyl)-11-oxa-3-azaspiro[5.5]undec-9-ene-3-carboxylate |
| tert-butyl 8-oxo-10-(3-pyridyl)-11-oxa-3-azaspiro[5.5]undec-9-ene-3-carboxylate | tert-butyl 8-hydroxy-10-(3-pyridyl)-11-oxa-3-azaspiro[5.5]undec-9-ene-3-carboxylate |
| tert-butyl 8-oxo-10-(4-pyridyl)-11-oxa-3-azaspiro[5.5]undec-9-ene-3-carboxylate | tert-butyl 8-hydroxy-10-(4-pyridyl)-11-oxa-3-azaspiro[5.5]undec-9-ene-3-carboxylate |

Step 5: cis-8-hydroxy-10-(3-pyridyl)-11-oxa-3-azaspiro[5.5]undecan-3-yl]-(4-isopropoxy-3-methyl-phenyl)methanone

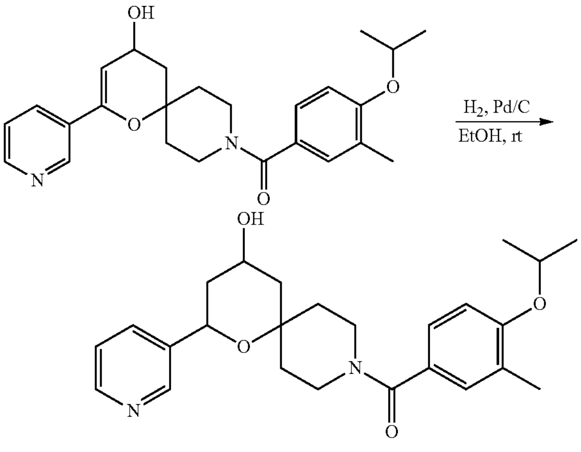

cis

[8-hydroxy-10-(3-pyridyl)-11-oxa-3-azaspiro[5.5]undec-9-en-3-yl]-(4-isopropoxy-3-methyl-phenyl)methanone (1.20 g, 2.84 mmol) was dissolved in ethanol. Under nitrogen, palladium (90.7 mg, 0.09 mmol) (10 wt % on carbon, wet) was added. The reaction system was flushed with hydrogen gas, and the mixture was stirred under a balloon of hydrogen gas overnight. The reaction mixture was filtered through a pad of celite. The concentrated filtrate was purified by column chromatography (70-100% ethyl acetate/hexane) to provide cis-8-hydroxy-10-(3-pyridyl)-11-oxa-3-azaspiro[5.5]undecan-3-yl]-(4-isopropoxy-3-methyl-phenyl)methanone (520 mg) as a white foaming solid. $^1$H NMR (400 MHz, $CDCl_3$) δ 8.65 (s, 1H), 8.57 (d, J=4.2 Hz, 1H), 7.80 (d, J=7.5 Hz, 1H), 7.37 (s, 1H), 7.19 (d, J=8.5 Hz, 2H), 6.80 (d, J=8.1 Hz, 1H), 4.65 (br s, 1H), 4.55 (dt, J=12.1, 6.0 Hz, 1H), 4.40 (br s, 1H), 4.17 (br s, 1H), 3.75-3.01 (m, 3H), 2.27-2.12 (m, 2H), 2.19 (s, 3H), 2.13-1.93 (m, 2H), 1.84-1.39 (m, 4H), 1.34 (d, J=6.0 Hz, 6H). ESI-MS m/z calc. 424.24, found 425.4 $(M+1)^+$; Retention time: 1.13 minutes (3 min run).

The following compounds were prepared using the procedure reported above:

| Diketone | Product |
|---|---|
| [8-hydroxy-10-(2-pyridyl)-11-oxa-3-azaspiro[5.5]undec-9-en-3-yl]-(4-isopropoxy-3-methyl-phenyl)methanone | cis-8-hydroxy-10-(2-pyridyl)-11-oxa-3-azaspiro[5.5]undecan-3-yl]-(4-isopropoxy-3-methyl-phenyl)methanone |
| [8-hydroxy-10-(4-pyridyl)-11-oxa-3-azaspiro[5.5]undec-9-en-3-yl]-(4-isopropoxy-3-methyl-phenyl)methanone | cis-8-hydroxy-10-(4-pyridyl)-11-oxa-3-azaspiro[5.5]undecan-3-yl]-(4-isopropoxy-3-methyl-phenyl)methanone |
| tert-butyl 8-hydroxy-10-(2-pyridyl)-11-oxa-3-azaspiro[5.5]undec-9-ene-3-carboxylate | cis-tert-butyl 4-hydroxy-2-(pyridin-2-yl)-1-oxa-9-azaspiro[5.5]undecane-9-carboxylate |
| tert-butyl 8-hydroxy-10-(3-pyridyl)-11-oxa-3-azaspiro[5.5]undec-9-ene-3-carboxylate | cis-tert-butyl 4-hydroxy-2-(pyridin-3-yl)-1-oxa-9-azaspiro[5.5]undecane-9-carboxylate |
| tert-butyl 8-hydroxy-10-(4-pyridyl)-11-oxa-3-azaspiro[5.5]undec-9-ene-3-carboxylate | cis-tert-butyl 4-hydroxy-2-(pyridin-4-yl)-1-oxa-9-azaspiro[5.5]undecane-9-carboxylate |

Step 6: cis-4-(cyclopropylmethoxy)-2-(pyridin-3-yl)-1-oxa-9-azaspiro[5.5]undecan-9-yl)(4-isopropoxy-3-methylphenyl)methanone.

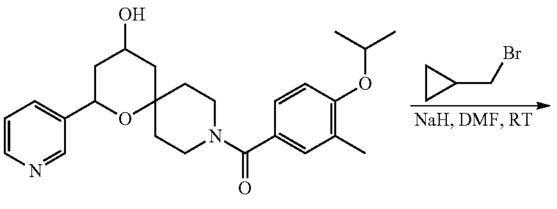

cis

-continued

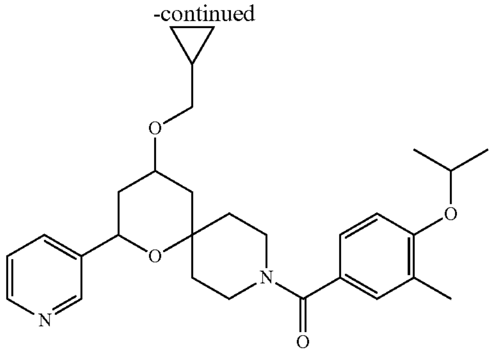

cis

To [cis-8-hydroxy-10-(3-pyridyl)-11-oxa-3-azaspiro[5.5]undecan-3-yl]-(4-isopropoxy-3-methyl-phenyl)methanone (80 mg) in DMF at 0° C. was added sodium hydride (5 eq., 60 wt % in mineral oil). After stirring at room temperature for 5 minutes, the cyclopropylmethyl bromide (5 eq.) was added. The reaction mixture was allowed to stir overnight at room temperature. The reaction mixture was stirred with saturated sodium bicarbonate solution (20 mL). The mixture was repartitioned between water (50 mL) and ethyl acetate (50 mL). The organic layer was dried over sodium sulfate, filtered and concentrated under reduced pressure. The crude material was purified by column chromatography to provide cis-4-(cyclopropylmethoxy)-2-(pyridin-3-yl)-1-oxa-9-azaspiro[5.5]undecan-9-yl)(4-isopropoxy-3-methylphenyl)methanone. $^1$H NMR (400 MHz, $CDCl_3$) δ 8.62 (s, 1H), 8.55 (d, J =3.9 Hz, 1H), 7.74 (d, J=7.8 Hz, 1H), 7.30 (dd, J=7.8, 4.8 Hz, 1H), 7.23-7.11 (m, 2H), 6.80 (d, J=8.2 Hz, 1H), 4.70-4.51 (m, 1H), 4.56 (dq, J=12.1, 6.1 Hz, 1H), 4.37 (br s, 1H), 3.82-3.00 (m, 5H), 3.34 (d, J=6.8 Hz, 1H), 2.40-2.10 (m, 2H), 2.19 (s, 3H), 2.09-1.92 (m, 2H), 1.88-1.39 (m, 4H), 1.42-1.26 (m, 6H), 1.04 (td, J=7.0, 3.5 Hz, 1H), 0.64-0.47 (m, 2H), 0.30-0.12 (m, 2H).

The following compounds were prepared using the procedure reported above:

| Diketone | Alkyl bromide | Product |
|---|---|---|
| cis-8-hydroxy-10-(3-pyridyl)-11-oxa-3-azaspiro[5.5]undecan-3-yl]-(4-isopropoxy-3-methyl-phenyl)methanone | 1-fluoro-2-iodo-ethane | cis-4-(2-fluoroethoxy)-2-(pyridin-3-yl)-1-oxa-9-azaspiro[5.5]undecan-9-yl)(4-isopropoxy-3-methylphenyl)methanone |
| cis-8-hydroxy-10-(3-pyridyl)-11-oxa-3-azaspiro[5.5]undecan-3-yl]-(4-isopropoxy-3-methyl-phenyl)methanone | 1-bromo-2-methoxy-ethane | cis-4-(2-methoxyethoxy)-2-(pyridin-3-yl)-1-oxa-9-azaspiro[5.5]undecan-9-yl)(4-isopropoxy-3-methylphenyl)methanone |
| cis-tert-butyl 4-hydroxy-2-(pyridin-2-yl)-1-oxa-9-azaspiro[5.5]undecane-9-carboxylate | iodoethane | cis-tert-butyl 8-ethoxy-10-(2-pyridyl)-11-oxa-3-azaspiro[5.5]undecane-3-carboxylate |

-continued

| Diketone | Alkyl bromide | Product |
|---|---|---|
| cis-tert-butyl 4-hydroxy-2-(pyridin-3-yl)-1-oxa-9-azaspiro[5.5]undecane-9-carboxylate | iodoethane | cis-tert-butyl 8-ethoxy-10-(3-pyridyl)-11-oxa-3-azaspiro[5.5]undecane-3-carboxylate |
| cis-tert-butyl 4-hydroxy-2-(pyridin-4-yl)-1-oxa-9-azaspiro[5.5]undecane-9-carboxylate | iodoethane | cis-tert-butyl 8-ethoxy-10-(4-pyridyl)-11-oxa-3-azaspiro[5.5]undecane-3-carboxylate |

cis-4-isopropoxy-2-(pyridin-3-yl)-1-oxa-9-azaspiro[5.5]undecan-9-yl)(4-isopropoxy-3-methylphenyl)methanone

Step 1: (4-isopropoxy-3-methyl-phenyl)-[8-isopropoxy-10-(3-pyridyl)-11-oxa-3-azaspiro[5.5]undec-9-en-3-yl]methanone

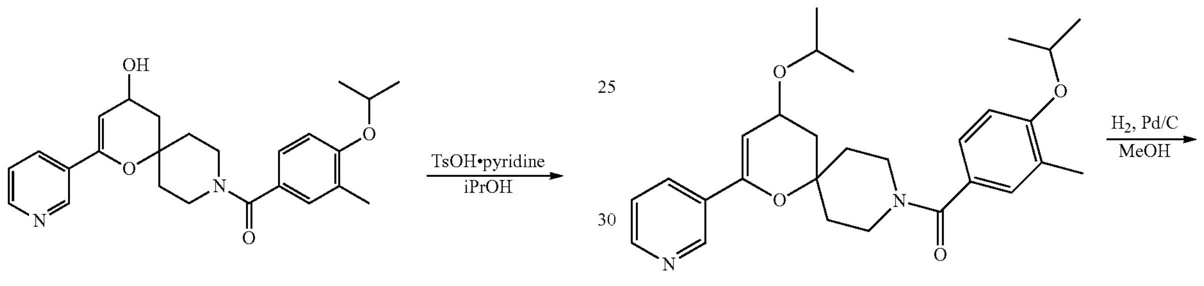

[8-hydroxy-10-(3-pyridyl)-11-oxa-3-azaspiro[5.5]undec-9-en-3-yl]-(4-isopropoxy-3-methyl-phenyl)methanone (300 mg, 0.71 mmol) was dissolved in isopropanol (6.0 mL, 78 mmol). Pyridinium p-toluenesulfonate (178 mg, 0.71 mmol) was added, and the reaction mixture was allowed to stir at 50° C. for 1 hour. The reaction mixture was diluted with water (50 mL) and extracted with ethyl acetate (2×50 mL). The organic layers were combined, dried over sodium sulfate, filtered and concentrated under reduced pressure. The crude product was purified by column chromatography (50-75% ethyl acetate/hexane) to provide (4-isopropoxy-3-methyl-phenyl)-[8-isopropoxy-10-(3-pyridyl)-11-oxa-3-azaspiro[5.5]undec-9-en-3-yl]methanone (173 mg) as a clear oil. $^1$H NMR (400 MHz, $CDCl_3$) δ 8.90 (d, J=1.5 Hz, 1H), 8.55 (d, J=3.6 Hz, 1H), 7.90 (dt, J=8.0, 1.9 Hz, 1H), 7.28 (dd, J=7.6, 4.5 Hz, 1H), 7.26-7.17 (m, 2H), 6.82 (d, J=8.2 Hz, 1H), 5.55 (d, J=3.9 Hz, 1H), 4.71-4.27 (m, 2H), 4.19 (dd, J=9.4, 5.3 Hz, 1H), 3.97-3.59 (m, 2H), 3.39 (br s, 2H), 2.40-2.10 (m, 1H), 2.21 (s, 3H), 2.05-1.84 (m, 3H), 1.83-1.49 (m, 2H), 1.33 (t, J=9.8 Hz, 6H), 1.19 (dd, J =6.1, 2.8 Hz, 6H). ESI-MS m/z calc. 464.27, found 465.5 (M+1)$^+$; Retention time: 1.56 minutes (3 min run).

Step 2: cis-(4-isopropoxy-3-methyl-phenyl)-8-isopropoxy-10-(3-pyridyl)-[1-oxa-3-azaspiro[5.5]undecan-3-yl]methanone

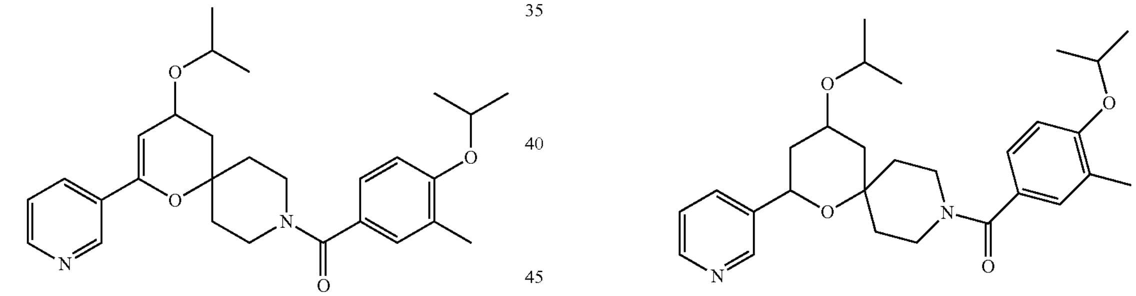

cis

To a solution of (4-isopropoxy-3-methyl-phenyl)[8-isopropoxy-10-(3-pyridyl)-11-oxa-3-azaspiro[5.5]undec-9-en-3-yl]methanone (163 mg, 0.35 mmol) in ethanol (10 mL) under nitrogen was added palladium (37 mg, 0.035 mmol) (10 wt % on carbon, wet). The reaction was purged with hydrogen gas and allowed to stir under a balloon of hydrogen overnight. The reaction mixture was filtered through a pad of celite. The filtrate was concentrated under reduced pressure. The reaction mixture was purified by column chromatography (50-100% ethyl acetate/hexane) to provide (4-isopropoxy-3-methyl-phenyl)-[cis-8-isopropoxy-10-(3-pyridyl)-11-oxa-3-azaspiro[5.5]undecan-3-yl]methanone (28.7 mg) as a clear colorless oil. $^1$H NMR (400 MHz, $CDCl_3$) δ 8.62 (s, 1H), 8.54 (d, J=3.9 Hz, 1H), 7.73 (d, J=7.8 Hz, 1H), 7.37-7.24 (m, 1H), 7.22-7.13 (m, 2H), 6.80 (d, J=8.1 Hz, 1H), 4.65-4.50 (m. 1H), 4.55 (dp, J=12.2, 6.1 Hz, 1H), 4.36 (br s, 1H), 3.85 (s, 1H), 3.76 (dt, J=12.1, 6.1 Hz, 1H), 3.70-3.01 (m, 3H), 2.25 (m, 2H), 2.19 (s, 3H), 1.95 (dd, J=12.8, 2.9 Hz, 1H), 1.84-1.37 (m, 5H), 1.34 (d, J=6.0 Hz, 6H), 1.16 (dd, J=6.0, 3.6 Hz, 6H).

ESI-MS m/z calc. 466.28, found 467.6 $(M+1)^+$; Retention time: 1.41 minutes (3 min run).

cis-8-ethoxy-10-(2-pyridyl)-11-oxa-3-azaspiro[5.5]undecan-3-yl]-(4-isopropoxy-3-methyl-phenyl)methanone

Step 1: cis-8-ethoxy-10-(2-pyridyl)-11-oxa-3-azaspiro[5.5]undecane; 2,2,2-trifluoroacetic acid

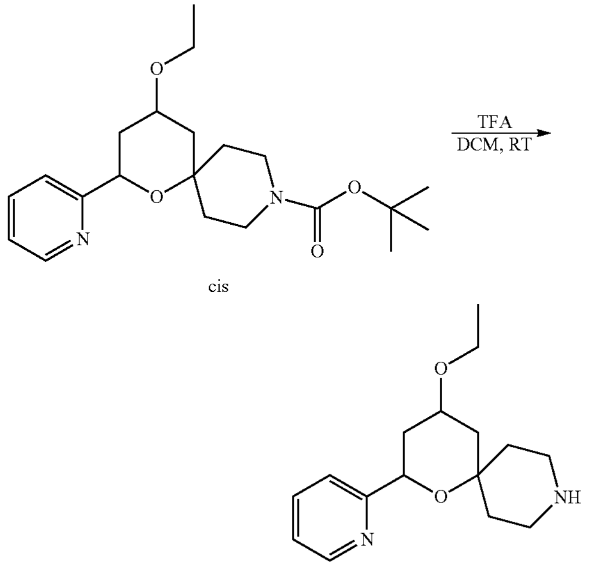

cis cis

To a solution of cis-tert-butyl 8-ethoxy-10-(2-pyridyl)-11-oxa-3-azaspiro[5.5]undecane-3-carboxylate (38 mg, 0.1 mmol) in dichloromethane (1 mL) was added TFA (400 μL, 5.2 mmol). The mixture was stirred at rt for 1 h. Solvent and excess TFA was removed. The crude cis-8-ethoxy-10-(2-pyridyl)-11-oxa-3-azaspiro[5.5]undecane; 2,2,2-trifluoroacetic acid was used directly in next step without further purification. ESI-MS m/z calc. 276.0, found 277.0 $(M+1)^+$; Retention time: 0.83 minutes. (3 min run).

The following compounds were prepared using the procedure reported above:

| Protected amine | Product |
| --- | --- |
| cis-tert-butyl 8-ethoxy-10-(3-pyridyl)-11-oxa-3-azaspiro[5.5]undecane-3-carboxylate | cis-8-ethoxy-10-(3-pyridyl)-11-oxa-3-azaspiro[5.5]undecane; 2,2,2-trifluoroacetic acid |

-continued

| Protected amine | Product |
| --- | --- |
| cis-tert-butyl 8-ethoxy-10-(4-pyridyl)-11-oxa-3-azaspiro[5.5]undecane-3-carboxylate | cis-8-ethoxy-10-(4-pyridyl)-11-oxa-3-azaspiro[5.5]undecane; 2,2,2-trifluoroacetic acid |

Step 2: cis-8-ethoxy-10-(2-pyridyl)-11-oxa-3-azaspiro[5.5]undecan-3-yl]-(4-isopropoxy-3-methyl-phenyl)methanone

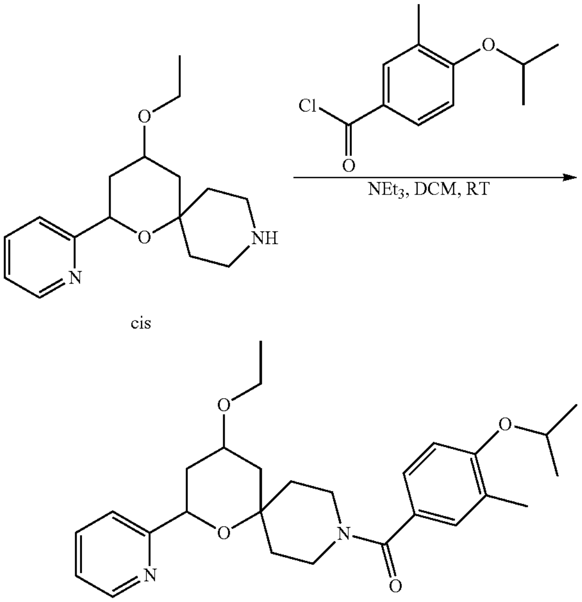

cis cis

To a solution of cis-8-ethoxy-10-(2-pyridyl)-11-oxa-3-azaspiro[5.5]undecane; 2,2,2-trifluoroacetic acid (42 mg, 0.11 mmol) in dichloromethane (1 mL) was added triethylamine (75 μL, 0.54 mmol). 4-isopropoxy-3-methyl-benzoyl chloride (46 mg, 0.21 mmol) (~50% pure) was added. The mixture was stirred at rt for 15 min. Water was added. The aqueous layer was extracted with dichloromethane (2×). The combined organic layers were washed with water, dried over $MgSO_4$, filtered and concentrated to dryness. The crude material was purified by column chromatography (40-60% ethyl acetate-hex) to provide cis-8-ethoxy-10-(2-pyridyl)-11-oxa-3-azaspiro[5.5]undecan-3-yl]-(4-isopropoxy-3-methyl-phenyl)methanone (37 mg). ESI-MS m/z calc. 452.27, found 453.3 $(M+1)^+$; Retention time: 1.38 minutes (3 min run).

The following compound was prepared using the procedure reported above:

| Amine | Acyl chloride | Product |
| --- | --- | --- |
| cis-8-ethoxy-10-(4-pyridyl)-11-oxa-3-azaspiro[5.5]undecane; 2,2,2-trifluoroacetic acid | 4-isopropoxy-3-methoxy-benzoyl chloride | cis-8-ethoxy-10-(2-pyridyl)-11-oxa-3-azaspiro[5.5]undecan-3-yl]-(4-isopropoxy-3-methoxy-phenyl)methanone |

cis-8-ethoxy-10-(2-pyridyl)-11-oxa-3-azaspiro[5.5]undecan-3-yl)(3-fluoro-2-methoxyphenyl)methanone

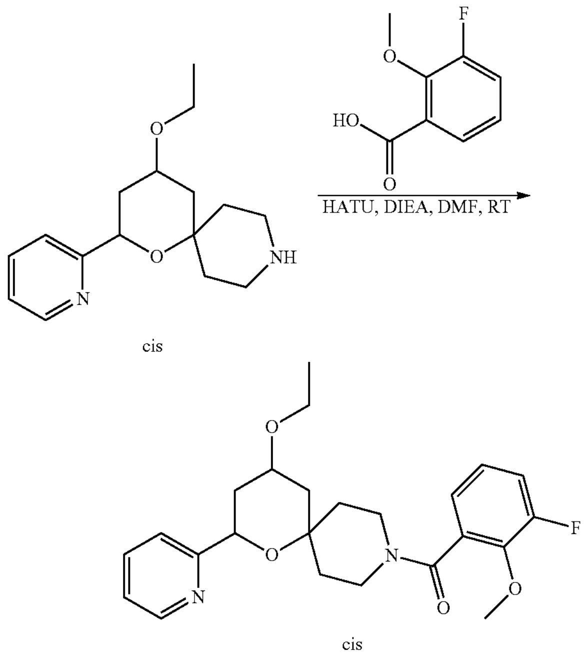

cis-8-ethoxy-10-(2-pyridyl)-11-oxa-3-azaspiro[5.5]undecane (25 mg) and the benzoic acid (1.2 eq) were combined and dissolved in DMF (300 μL). HATU (1.2 eq) was added followed by DIPEA (3.0 eq). The reaction mixtures were allowed to stir at 50° C. for 1 hour. The reaction mixtures were filtered and purified by reverse-phase HPLC: 10-99% acetonitrile/water gradient over 15 minutes. $^1H$ NMR (400 MHz, $CDCl_3$) δ 8.58-8.47 (m, 1H), 7.81-7.65 (m, 1H), 7.62-7.46 (m, 1H), 7.23-7.16 (m, 1H), 7.03 (m, 3H), 4.64 (dd, J=43.1, 11.9 Hz, 1H), 4.55-4.36 (m, 1H), 4.04-3.70 (m, 4H), 3.69-3.56 (m, 1H), 3.55-3.33 (m, 2H), 3.32-3.00 (m, 2H), 2.58 (t, J=13.8 Hz, 1H), 2.22 (dd, J=74.2, 14.3 Hz, 1H), 2.05-1.92 (m, 1H), 1.90-1.51 (m, 3H), 1.50-1.24 (m, 2H), 1.24-1.12 (m, 3H).

The following compounds were prepared using the procedure reported above:

| Amine | Acid | Product |
|---|---|---|
| cis-8-ethoxy-10-(3-pyridyl)-11-oxa-3-azaspiro[5.5]undecane | 3-fluoro-4-isopropoxy-benzoic acid | cis-8-ethoxy-10-(3-pyridyl)-11-oxa-3-azaspiro[5.5]undecan-3-yl]-(3-fluoro-4-isopropoxy-phenyl)methanone |
| cis-8-ethoxy-10-(3-pyridyl)-11-oxa-3-azaspiro[5.5]undecane | 4-(2,2,2-trifluoroethoxymethyl)benzoic acid | cis-8-ethoxy-10-(3-pyridyl)-11-oxa-3-azaspiro[5.5]undecan-3-yl]-[4-(2,2,2-trifluoroethoxymethyl)phenyl]methanone |
| cis-8-ethoxy-10-(3-pyridyl)-11-oxa-3-azaspiro[5.5]undecane | 4-(difluoromethylsulfonyl)benzoic acid | cis-[4-(difluoromethylsulfonyl)phenyl]-8-ethoxy-10-(3-pyridyl)-11-oxa-3-azaspiro[5.5]undecan-3-yl]methanone |
| cis-8-ethoxy-10-(3-pyridyl)-11-oxa-3-azaspiro[5.5]undecane | 5-isopropoxy-6-methoxy-pyridine-2-carboxylic acid | cis-8-ethoxy-10-(3-pyridyl)-11-oxa-3-azaspiro[5.5]undecan-3-yl]-(5-isopropoxy-6-methoxy-2-pyridyl)methanone |
| cis-8-ethoxy-10-(3-pyridyl)-11-oxa-3-azaspiro[5.5]undecane | 6-isopropoxy-5-methyl-pyridine-3-carboxylic acid | cis-8-ethoxy-10-(3-pyridyl)-11-oxa-3-azaspiro[5.5]undecan-3-yl]-(6-isopropoxy-5-methyl-3-pyridyl)methanone |
| cis-8-ethoxy-10-(2-pyridyl)-11-oxa-3-azaspiro[5.5]undecane | 3-fluoro-2-methoxy-benzoic acid | cis-8-ethoxy-10-(2-pyridyl)-11-oxa-3-azaspiro[5.5]undecan-3-yl]-(3-fluoro-2-methoxy-phenyl)methanone |
| cis--8-ethoxy-10-(2-pyridyl)-11-oxa-3-azaspiro[5.5]undecane | 4-(difluoromethylsulfonyl)benzoic acid | cis-[4-(difluoromethylsulfonyl)phenyl]-8-ethoxy-10-(2-pyridyl)-11-oxa-3-azaspiro[5.5]undecan-3-yl]methanone |

cis-8-ethoxy-10-(2-pyridyl)-11-oxa-3-azaspiro[5.5]undecan-3-yl)(4-isopropoxy-3-methyl-phenyl)methanone

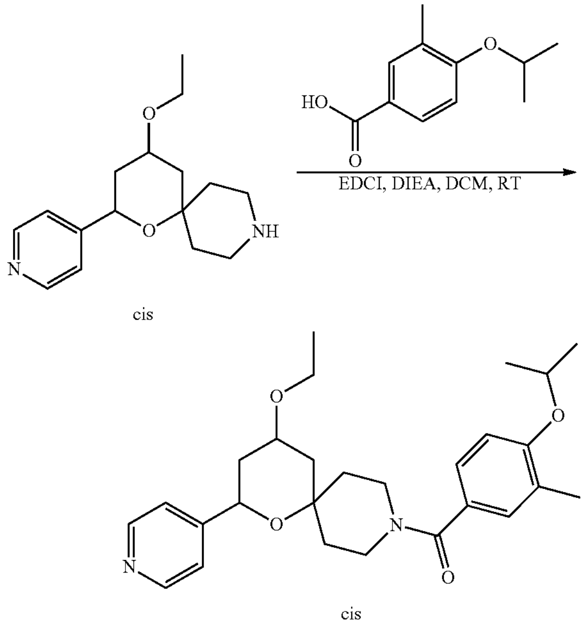

A solution of cis-8-ethoxy-10-(4-pyridyl)-11-oxa-3-azaspiro[5.5]undecane (50 mg, 0.18 mmol), EDCI (38 mg, 0.20 mmol) and 4-isopropoxy-3-methyl-benzoic acid (35 mg, 0.18 mmol) in dichloromethane (0.9 mL) was treated with DIPEA (94 μL, 0.54 mmol) and stirred for 16 h. The reaction mixture was filtered and purified by reverse phase HPLC (1-100% ACN/water) to afford cis-8-ethoxy-10-(2-pyridyl)-11-oxa-3-azaspiro[5.5]undecan-3-yl)(4-isopropoxy-3-methyl-phenyl)methanone (47 mg, 57.58%). ESI-MS m/z calc. 452.27, found 453.2 $(M+1)^+$; Retention time: 1.059 minutes (3 min run).

The following compounds were prepared using the procedure reported above:

| Amine | Acid | Product |
|---|---|---|
| cis-8-ethoxy-10-(3-fluorophenyl)-11-oxa-3-azaspiro[5.5]undecane | 4-isopropoxy-3-methoxy-benzoic acid | cis-8-ethoxy-10-(3-fluorophenyl)-11-oxa-3-azaspiro[5.5]undecan-3-yl]-(4-isopropoxy-3-methoxy-phenyl)methanone |
| cis-8-ethoxy-10-(3-fluorophenyl)-11-oxa-3-azaspiro[5.5]undecane | 4-isopropoxy-3-methyl-benzoic acid | cis-8-ethoxy-10-(3-fluorophenyl)-11-oxa-3-azaspiro[5.5]undecan-3-yl]-(4-isopropoxy-3-methyl-phenyl)methanone |
| cis-8-ethoxy-10-(4-pyridyl)-11-oxa-3-azaspiro[5.5]undecane; [cis-8-ethoxy-10-(4-pyridyl)-11-oxa-3-azaspiro[5.5]undecan-3-yl]-(4-isopropoxy-3-methyl-phenyl)methanone | 4-isopropoxy-3-methyl-benzoic acid | cis-8-ethoxy-10-(4-pyridyl)-11-oxa-3-azaspiro[5.5]undecan-3-yl]-(4-isopropoxy-3-methyl-phenyl)methanone; [cis-8-ethoxy-10-(4-pyridyl)-11-oxa-3-azaspiro[5.5]undecan-3-yl]-(4-isopropoxy-3-methyl-phenyl)methanone |
| cis--(4-tert-butyl-3-methoxy-phenyl)-8-ethoxy-10-(3-pyridyl)-11-oxa-3-azaspiro[5.5]undecan-3-yl]methanone; (8S,10S)-8-ethoxy-10-(3-pyridyl)-11-oxa-3-azaspiro[5.5]undecane | 4-tert-butyl-3-methoxy-benzoic acid | cis-(4-tert-butyl-3-methoxy-phenyl)-8-ethoxy-10-(3-pyridyl)-11-oxa-3-azaspiro[5.5]undecan-3-yl]methanone; (4-tert-butyl-3-methoxy-phenyl)-[cis-8-ethoxy-10-(3-pyridyl)-11-oxa-3-azaspiro[5.5]undecan-3-yl]methanone |
| cis-8-ethoxy-10-(3-pyridyl)-11-oxa-3-azaspiro[5.5]undecane; [cis-8-ethoxy-10-(3-pyridyl)-11-oxa-3-azaspiro[5.5]undecan-3-yl]-(5-isopropoxy-6-methyl-2-pyridyl)methanone | 5-isopropoxy-6-methyl-pyridine-2-carboxylic acid | cis-8-ethoxy-10-(3-pyridyl)-11-oxa-3-azaspiro[5.5]undecan-3-yl]-(5-isopropoxy-6-methyl-2-pyridyl)methanone; [cis-8-ethoxy-10-(3-pyridyl)-11-oxa-3-azaspiro[5.5]undecan-3-yl]-(5-isopropoxy-6-methyl-2-pyridyl)methanone |
| cis-8-ethoxy-10-(3-pyridyl)-11-oxa-3-azaspiro[5.5]undecane; [cis-8-ethoxy-10-(3-pyridyl)-11-oxa-3-azaspiro[5.5]undecan-3-yl]-(4-isopentyloxy-3-methoxy-phenyl)methanone | 4-isopentyloxy-3-methoxy-benzoic acid | cis-8-ethoxy-10-(3-pyridyl)-11-oxa-3-azaspiro[5.5]undecan-3-yl]-(4-isopentyloxy-3-methoxy-phenyl)methanone; [cis-8-ethoxy-10-(3-pyridyl)-11-oxa-3-azaspiro[5.5]undecan-3-yl]-(4-isopentyloxy-3-methoxy-phenyl)methanone |
| cis-8-ethoxy-10-(3-pyridyl)-11-oxa-3-azaspiro[5.5]undecane; [cis-8-ethoxy-10-(3-pyridyl)-11-oxa-3-azaspiro[5.5]undecan-3-yl]-(4-ethyl-3-methoxy-phenyl)methanone | 4-ethyl-3-methoxy-benzoic acid | cis-8-ethoxy-10-(3-pyridyl)-11-oxa-3-azaspiro[5.5]undecan-3-yl]-(4-ethyl-3-methoxy-phenyl)methanone; [cis-8-ethoxy-10-(3-pyridyl)-11-oxa-3-azaspiro[5.5]undecan-3-yl]-(4-ethyl-3-methoxy-phenyl)methanone |
| cis-8-ethoxy-10-(3-pyridyl)-11-oxa-3-azaspiro[5.5]undecane; [cis-8-ethoxy-10-(3-pyridyl)-11-oxa-3-azaspiro[5.5]undecan-3-yl]-(4-isopropoxy-3-methyl-phenyl)methanone | 4-isopropoxy-3-methyl-benzoic acid | cis-8-ethoxy-10-(3-pyridyl)-11-oxa-3-azaspiro[5.5]undecan-3-yl]-(4-isopropoxy-3-methyl-phenyl)methanone; [cis-8-ethoxy-10-(3-pyridyl)-11-oxa-3-azaspiro[5.5]undecan-3-yl]-(4-isopropoxy-3-methyl-phenyl)methanone |
| cis-8-ethoxy-10-(3-pyridyl)-11-oxa-3-azaspiro[5.5]undecane; [trans-8-ethoxy-10-(3-pyridyl)-11-oxa-3-azaspiro[5.5]undecan-3-yl]-(4-isopropoxy-3-methyl-phenyl)methanone | 4-isopropoxy-3-methyl-benzoic acid | cis-8-ethoxy-10-(3-pyridyl)-11-oxa-3-azaspiro[5.5]undecan-3-yl]-(4-isopropoxy-3-methyl-phenyl)methanone; [trans-8-ethoxy-10-(3-pyridyl)-11-oxa-3-azaspiro[5.5]undecan-3-yl]-(4-isopropoxy-3-methyl-phenyl)methanone |

cis-4-ethoxy-2-(5-fluoropyridin-3-yl)-1-oxa-9-aza-spiro[5.5]undecan-9-yl)(4-isopropoxy-3-methylphenyl)methanone Step 1: 1-(1-(4-isopropoxy-3-methylbenzoyl)piperidin-4-ylidene)propan-2-one

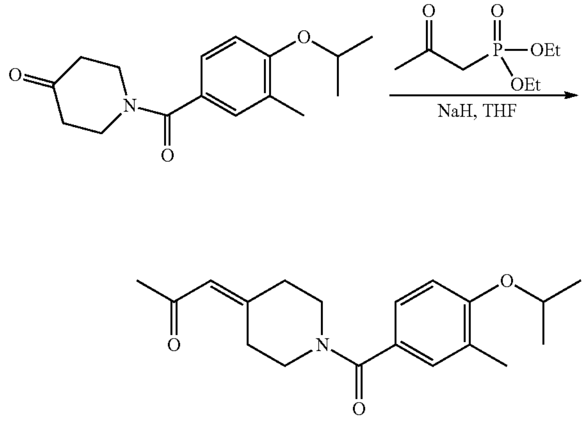

To an oven dried flask was placed 60% sodium hydride in mineral oil (1.5 g, 36 mmol). To the flask was added tetrahydrofuran (90 mL) under a nitrogen atmosphere. The mixture was cooled to 0° C. and a solution of 1-diethoxyphosphorylpropan-2-one (7.1 mL, 37 mmol) in tetrahydrofuran (20 mL) was added dropwise. The mixture was stirred at 25° C. for 30 min and treated with 1-(4-isopropoxy-3-methyl-benzoyl)piperidin-4-one (10 g, 36 mmol) in tetrahydrofuran (90 mL). The mixture was stirred at 25° C. for 24 h. The reaction was quenched with saturated aqueous sodium bicarbonate and extracted with ethyl acetate (3×200 mL). The combined organics were washed with brine, dried over magnesium sulfate and evaporated. The crude product was purified on silica gel utilizing a gradient of 0-30% ethyl acetate in hexanes to afford 1-[1-(4-isopropoxy-3-methyl-benzoyl)-4-piperidylidene]propan-2-one (10.2 g) $^{1}$H NMR (400 MHz, $CDCl_3$) δ 7.25-7.17 (m, 2H), 6.81 (d, J=8.2 Hz, 1H), 6.12 (s, 1H), 4.60-4.51 (m, 1H), 3.66 (br d, 4H), 2.95 (br s, 2H), 2.50-2.33 (m, 2H), 2.19 (s, 6H), 1.34 (d, J=6.0 Hz, 6H). ESI-MS m/z calc. 315.18, found 316.0 $(M+1)^+$; Retention time: 2.2 minutes (3 min run).

Step 2: 4-(5-fluoropyridin-3-yl)-4-hydroxy-1-(1-(4-isopropoxy-3-methylbenzoyl)piperidin-4-ylidene)butan-2-one

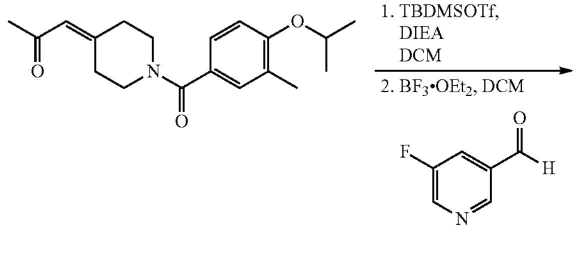

-continued

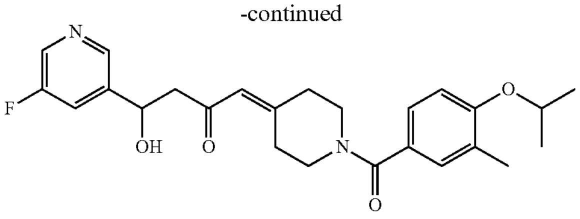

Step 1: A solution of 1-[1-(4-isopropoxy-3-methyl-benzoyl)-4-piperidylidene]propan-2-one (130 mg, 0.41 mmol) in dichloromethane (1.7 mL) was treated with diisopropylethylamine (93 μL, 0.53 mmol) at 0° C. followed by the addition of (tert-butyl(dimethyl)silyl) trifluoromethanesulfonate (114 mg, 99 μL, 0.43 mmol). The mixture was stirred at 0° C. for 30 min.

Step 2: A solution of 5-fluoronicotinaldehyde (51 mg, 0.41 mmol) in dichloromethane (1.7 mL) was cooled to −78° C. and boron trifluoride diethyl etherate (164 μL, 0.82 mmol) was added. The mixture was stirred at −78° C. for 5 min. The solution from step 1 was added. The mixture was stirred at −78° C. for 5 min, quenched with a buffer solution of pH=7. The aqueous layer was extracted with dichloromethane (3×50 mL). The combined organic layers were dried over magnesium sulfate, filtered, and concentrated to dryness. The crude product was purified on silica gel utilizing a gradient of 60-100% ethyl acetate in hexanes to afford 4-(5-fluoro-3-pyridyl)-4-hydroxy-1-[1-(4-isopropoxy-3-methyl-benzoyl)-4-piperidylidene]butan-2-one (105 mg). $^{1}$H NMR (400 MHz, $CDCl_3$) δ 8.46-8.31 (m, 2H), 7.53-7.49 (m, 1H), 7.24-7.22 (m, 2H), 6.83 (d, J=8.1 Hz, 1H), 6.09 (s, 1H), 5.26 (dd, J=8.9, 5.9 Hz, 1H), 4.62-4.53 (m, 1H), 4.13-4.12 (m, 1H), 3.69 (br d, 4H), 3.00 (br s, 2H), 2.88 (d, J=6.2 Hz, 2H), 2.37 (br s, 2H), 2.21 (s, 3H), 1.36 (d, J=6.0 Hz, 6H). ESI-MS m/z calc. 440.21, found 441.4 $(M+1)^+$; Retention time: 1.65 minutes (3 min run).

Step 3: 1-(5-fluoropyridin-3-yl)-4-(1-(4-isopropoxy-3-methylbenzoyl)piperidin-4-ylidene)butane-1,3-dione

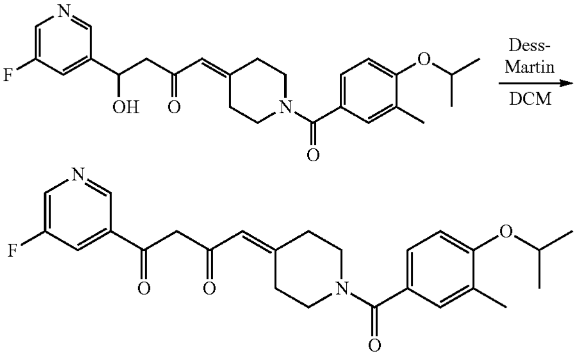

A solution of 4-(5-fluoro-3-pyridyl)-4-hydroxy-1-[1-(4-isopropoxy-3-methyl-benzoyl)-4-piperidylidene]butan-2-one (475 mg, 1.08 mmol) in dichloromethane (15 mL) was cooled to 0° C. and treated with Dess-Martin periodinane (457 mg, 1.08 mmol). The reaction mixture was stirred for 30 min and was treated with additional Dess-Martin periodinane (150 mg, 0.35 mmol). The reaction mixture was stirred for 30 min and was quenched by the addition of saturated aqueous sodium sulfite. The mixture was extracted with dichloromethane (3×50 mL) and the combined organics were washed with saturated aqueous sodium bicarbonate, dried over sodium sulfate, filtered and concentrated under reduced pressure. The crude product was purified on silica gel utilizing a gradient of 60-100% ethyl acetate in hexanes to yield 1-(5-fluoro-3-pyridyl)-4-[1-(4-isopropoxy-3-methyl-benzoyl)-4-piperidylidene]butane-1,3-dione (317 mg). $^1H$ NMR (400 MHz, $CDCl_3$) δ 16.25 (br s, OH), 8.81 (t, J=1.5 Hz, 1H), 8.52 (d, J=2.8 Hz, 1H), 7.82 (ddd, J=9.0, 2.7, 1.8 Hz, 1H), 7.18 (dd, J=11.4, 3.0 Hz, 2H), 6.76 (d, J=8.1 Hz, 1H), 6.08 (s, 1H), 5.86 (s, 1H), 4.50 (m, 1H), 3.65 (br s, 4H), 3.02 (br s, 2H), 2.36 (br s, 2H), 2.14 (s, 3H), 1.28 (d, J=6.0 Hz, 6H). ESI-MS m/z calc. 438.20, found 439.5 $(M+1)^+$; Retention time: 2.15 minutes as a colorless oil (3 min run).

Step 4: 2-(5-fluoropyridin-3-yl)-9-(4-isopropoxy-3-methylbenzoyl)-1-oxa-9-azaspiro[5.5]undec-2-en-4-one

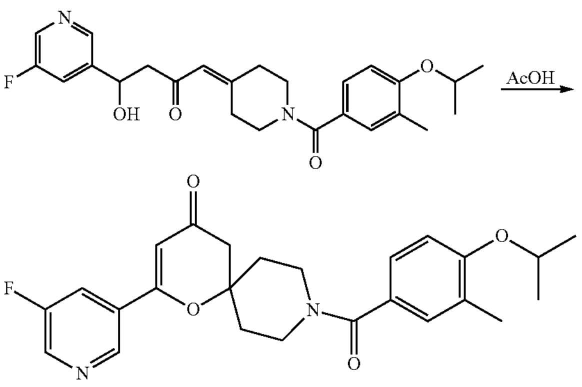

A mixture of 1-(5-fluoro-3-pyridyl)-4-[1-(4-isopropoxy-3-methyl-benzoyl)-4-piperidylidene]butane-1,3-dione (100 mg, 0.23 mmol) in acetic acid (1.7 mL, 30 mmol) was heated at 120° C. for 1 h. The reaction mixture was cooled to 25° C. and repartitioned between ethyl acetate and water. The aqueous layer was separated and extracted with ethyl acetate (3×50 mL). The combined organics were washed with brine, dried over magnesium sulfate, and concentrated to dryness. The crude product was purified on silica gel utilizing a gradient of 60-100% ethyl acetate in hexanes to yield 10-(5-fluoro-3-pyridyl)-3-(4-isopropoxy-3-methyl-benzoyl)-11-oxa-3-azaspiro[5.5]undec-9-en-8-one (92 mg). $^1H$ NMR (400 MHz, $CDCl_3$) δ 8.86 (s, 1H), 8.61 (d, J=2.7 Hz, 1H), 7.74 (ddd, J=9.0, 2.7, 1.9 Hz, 1H), 7.28-7.24 (m, 2H), 6.84 (d, J=9.0 Hz, 1H), 6.09 (s, 1H), 4.58 (dt, J=12.1, 6.1 Hz, 1H), 3.42 (br s, 2H), 2.68 (s, 2H), 2.27-2.22 (m, 6H), 1.75 (m, 3H), 1.36 (d, J=6.0 Hz, 6H). ESI-MS m/z calc. 438.20, found 439.3 $(M+1)^+$; Retention time: 1.78 minutes (3 min run).

Step 5: (2-(5-fluoropyridin-3-yl)-4-hydroxy-1-oxa-9-azaspiro[5.5]undec-2-en-9-yl)(4-isopropoxy-3-methylphenyl)methanone

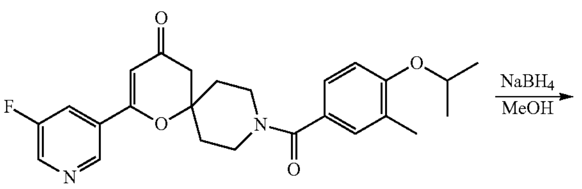

-continued

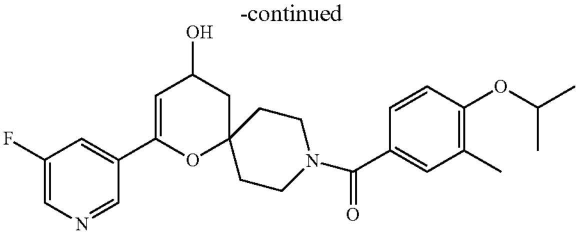

To a solution of 10-(5-fluoro-3-pyridyl)-3-(4-isopropoxy-3-methyl-benzoyl)-11-oxa-3-azaspiro[5.5]undec-9-en-8-one (273 mg, 0.62 mmol) in methanol (7.8 mL) was slowly added sodium borohydride (25 mg, 0.65 mmol) The reaction mixture was allowed to stir for 30 minutes. A solution of saturated aqueous ammonium chloride (50 mL) was added. After brief stirring, the mixture was concentrated to half volume and was extracted with dichloromethane (3×75 mL). The organic layers were combined, dried over sodium sulfate, filtered, and concentrated under reduced pressure. The crude product was purified on silica gel utilizing a gradient of 60-100% ethyl acetate in hexanes to yield [10-(5-fluoro-3-pyridyl)-8-hydroxy-11-oxa-3-azaspiro[5.5]undec-9-en-3-yl]-(4-isopropoxy-3-methyl-phenyl)methanone (256 mg) as a colorless oil. ESI-MS m/z calc. 440.2, found 441.3 $(M+1)^+$; Retention time: 1.73 minutes (3 min run).

Step 6: cis-4-ethoxy-2-(5-fluoropyridin-3-yl)-1-oxa-9-azaspiro[5.5]undecan-9-yl)(4-isopropoxy-3-methylphenyl)methanone

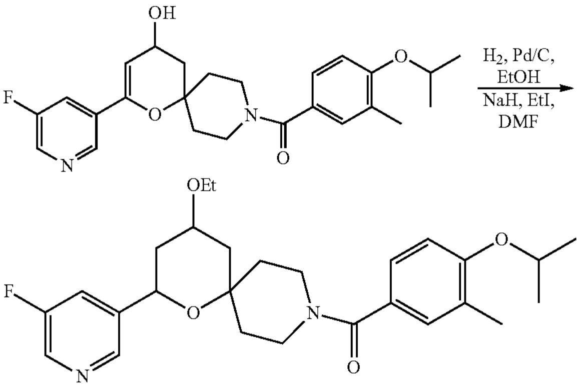

cis

A solution of [10-(5-fluoro-3-pyridyl)-8-hydroxy-11-oxa-3-azaspiro[5.5]undec-9-en-3-yl]-(4-isopropoxy-3-methyl-phenyl)methanone (56 mg, 0.13 mmol) in ethanol (4.4 mL) was purged with nitrogen for 5 min and treated with 10% palladium on carbon (13 mg, 0.012 mmol). The mixture was evacuated and put under a hydrogen atmosphere (balloon). The reaction mixture was stirred for 12 h at 25° C. The reaction mixture was evacuated and put under an inert atmosphere and re-charged with 10% palladium on carbon (54 mg, 0.05 mmol). The mixture was evacuated and put under a hydrogen atmosphere (balloon) and stirred for 4 h. The reaction mixture was evacuated and put under an inert atmosphere. The Pd-catalyst was removed via filtration and was washed with ethyl acetate. The filtrate was concentrated to dryness and dissolved in DMF (2.4 mL). The mixture was cooled to 0° C. and treated with 60% NaH (28 mg, 1.19 mmol)

and ethyl iodide (95 µL, 1.2 mmol). The reaction mixture was warmed to 25° C. and stirred for 2 h. The reaction mixture was quenched by the addition of methanol and partitioned between water and ethyl acetate. The layers were separated and the aqueous layer was extracted with ethyl acetate (3×50 mL). The combined organics were washed with saturated aqueous sodium chloride, dried over sodium sulfate, filtered, and concentrated under reduced pressure. Purification by reverse phase HPLC (1-100% acetonitrile in water, no modifier) afforded cis-4-ethoxy-2-(5-fluoropyridin-3-yl)-1-oxa-9-azaspiro[5.5]undecan-9-yl)(4-isopropoxy-3-methylphenyl)methanone (68 mg) ESI-MS m/z calc. 470.26, found 471.2 $(M+1)^+$; Retention time: 1.453 minutes (3 min run).

The following compounds were prepared using the procedure reported above:

-continued

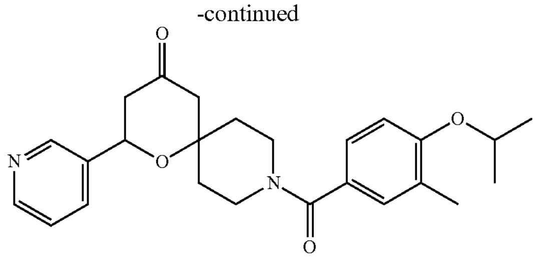

A solution of [8-hydroxy-10-(3-pyridyl)-11-oxa-3-azaspiro[5.5]undecan-3-yl]-(4-isopropoxy-3-methyl-phenyl) methanone (100 mg, 0.24 mmol) in dichloromethane (3.4 mL) was cooled to 0° C. and treated with Dess-Martin periodinane (100 mg, 0.24 mmol). The reaction mixture was

| Alcohol | Product |
|---|---|
| [cis-4-hydroxy-2-(4-methylthiazol-5-yl)-1-oxa-9-azaspiro[5.5]undecan-9-yl)(4-isopropoxy-3-methylphenyl)methanone | [cis-4-ethoxy-2-(4-methylthiazol-5-yl)-1-oxa-9-azaspiro[5.5]undecan-9-yl)(4-isopropoxy-3-methylphenyl)methanone |
| [cis-8-hydroxy-10-(2-methylthiazol-5-yl)-11-oxa-3-azaspiro[5.5]undecan-3-yl]-(4-isopropoxy-3-methyl-phenyl)methanone | [cis-8-ethoxy-10-(2-methylthiazol-5-yl)-11-oxa-3-azaspiro[5.5]undecan-3-yl]-(4-isopropoxy-3-methyl-phenyl)methanone |
| [cis-8-hydroxy-10-thiazol-5-yl-11-oxa-3-azaspiro[5.5]undecan-3-yl]-(4-isopropoxy-3-methyl-phenyl)methanone | (4-isopropoxy-3-methyl-phenyl)-[cis-8-propoxy-10-thiazol-5-yl-11-oxa-3-azaspiro[5.5]undecan-3-yl]methanone |
| [cis-8-hydroxy-10-thiazol-5-yl-11-oxa-3-azaspiro[5.5]undecan-3-yl]-(4-isopropoxy-3-methyl-phenyl)methanone | [cis-8-ethoxy-10-thiazol-5-yl-11-oxa-3-azaspiro[5.5]undecan-3-yl]-(4-isopropoxy-3-methyl-phenyl)methanone |
| [cis-8-hydroxy-10-(2-methylpyrazol-3-yl)-11-oxa-3-azaspiro[5.5]undecan-3-yl]-(4-isopropoxy-3-methyl-phenyl)methanone | [cis-8-ethoxy-10-(2-methylpyrazol-3-yl)-11-oxa-3-azaspiro[5.5]undecan-3-yl]-(4-isopropoxy-3-methyl-phenyl)methanone |
| [cis-8-hydroxy-10-(2-methylpyrazol-3-yl)-11-oxa-3-azaspiro[5.5]undecan-3-yl]-(4-isopropoxy-3-methyl-phenyl)methanone | (4-isopropoxy-3-methyl-phenyl)-[cis-10-(2-methylpyrazol-3-yl)-8-propoxy-11-oxa-3-azaspiro[5.5]undecan-3-yl]methanone; (4-isopropoxy-3-methyl-phenyl) |
| [cis-8-hydroxy-10-(3-pyridyl)-11-oxa-3-azaspiro[5.5]undecan-3-yl]-(4-isopropoxy-3-methyl-phenyl)methanone; (4-isopropoxy-3-methyl-phenyl) | (4-isopropoxy-3-methyl-phenyl)-[cis-8-(1,1,2,2,2-pentadeuterioethoxy)-10-(3-pyridyl)-11-oxa-3-azaspiro[5.5]undecan-3-yl]methanone |
| [cis-8-ehydroxy-10-(5-fluoro-3-pyridyl)-11-oxa-3-azaspiro[5.5]undecan-3-yl]-(4-isopropoxy-3-methyl-phenyl)methanone | [cis-8-ethoxy-10-(5-fluoro-3-pyridyl)-11-oxa-3-azaspiro[5.5]undecan-3-yl]-(4-isopropoxy-3-methyl-phenyl)methanone |
| [cis-8-hydroxy-10-(5-methoxy-3-pyridyl)-11-oxa-3-azaspiro[5.5]undecan-3-yl]-(4-isopropoxy-3-methyl-phenyl)methanone | [cis-8-ethoxy-10-(5-methoxy-3-pyridyl)-11-oxa-3-azaspiro[5.5]undecan-3-yl]-(4-isopropoxy-3-methyl-phenyl)methanone |
| [cis-8-hydroxy-10-(5-methoxy-3-pyridyl)-11-oxa-3-azaspiro[5.5]undecan-3-yl]-(4-isopropoxy-3-methyl-phenyl)methanone | (4-isopropoxy-3-methyl-phenyl)-cis-10-(5-methoxy-3-pyridyl)-8-propoxy-11-oxa-3-azaspiro[5.5]undecan-3-yl]methanone |

(4-hydroxy-2-(pyridin-3-yl)-1-oxa-9-azaspiro[5.5] undecan-9-yl)(4-isopropoxy-3-methylphenyl)methanone was prepared according to Scheme 3 (Steps 1-6)

Step 1: 9-(4-isopropoxy-3-methylbenzoyl)-2-(pyridin-3-yl)-1-oxa-9-azaspiro[5.5]undecan-4-one stirred for two hours and was quenched by the addition of saturated aqueous sodium sulfite. The mixture was extracted with dichloromethane (3×25 mL), and the combined organics were dried over sodium sulfate, filtered, and concentrated under reduced pressure. The crude product was purified on silica gel utilizing a gradient of 50-100% ethyl acetate in hexanes to yield 3-(4-isopropoxy-3-methyl-benzoyl)-10-(3-pyridyl)-11-oxa-3-azaspiro[5.5]undecan-8-one (84 mg) ESI-MS m/z calc. 422.22, found 423.3 $(M+1)^+$; Retention time: 1.41 minutes (3 min run).

Step 2: (4-ethyl-2-(pyridin-3-yl)-1-oxa-9-azaspiro [5.5]undec-4-en-9-yl)(4-isopropoxy-3-methylphenyl) methanone

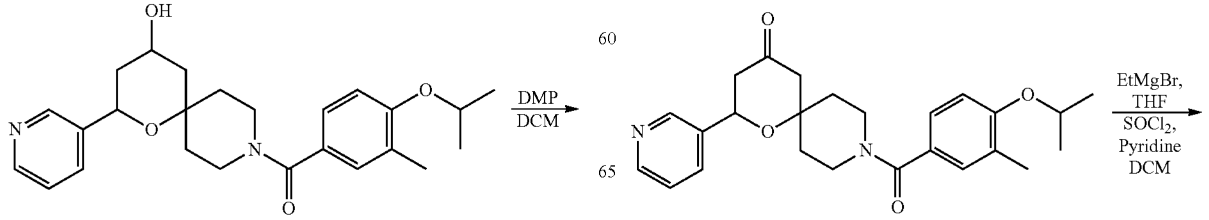

-continued

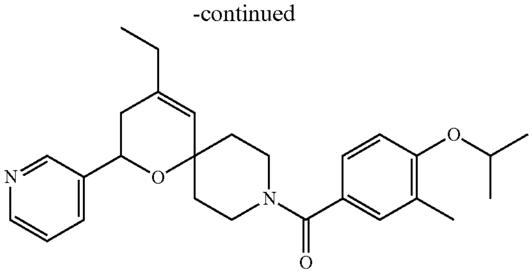

A solution of 3-(4-isopropoxy-3-methyl-benzoyl)-10-(3-pyridyl)-11-oxa-3-azaspiro[5.5]undecan-8-one (148 mg, 0.35 mmol) in THF (1.8 mL) was cooled to 0° C. and treated with ethyl-magnesium bromide (42 μL of 1 M, 0.42 mmol). The reaction mixture was stirred for 2 h and was quenched by the addition of saturated aqueous ammonium chloride. The mixture was extracted with ethyl acetate (3×100 mL) and the combined organics were washed with saturated aqueous sodium chloride, dried over sodium sulfate, filtered and concentrated under reduced pressure. The resultant oil was diluted with dichloromethane (2 mL) and treated with pyridine (34 μL, 0.42 mmol). The reaction mixture was cooled to 0° C. and treated with thionyl chloride (28 μL, 0.39 mmol) dropwise. The reaction mixture was stirred for 90 min, quenched with ice-cold water (5 mL), and diluted with $CH_2Cl_2$ (80 mL). The mixture was washed with dilute HCl (5%, 2×15 mL), water (2×20 mL), and sodium bicarbonate (5%, 15 mL). The organic layer was dried over sodium sulfate, filtered, and concentrated in vacuo. The crude product was purified on silica gel utilizing a gradient 50-100% ethyl acetate in hexanes to yield [8-ethyl-10-(3-pyridyl)-11-oxa-3-azaspiro[5.5]undec-7-en-3-yl]-(4-isopropoxy-3-methyl-phenyl)methanone (90 mg) ESI-MS m/z calc. 434.26, found 435.3 $(M+1)^+$; Retention time: 1.74 minutes (3 min run).

(cis-4-ethyl-2-(pyridin-3-yl)-1-oxa-9-azaspiro[5.5]undecan-9-yl)(4-isopropoxy-3-methylphenyl)methanone

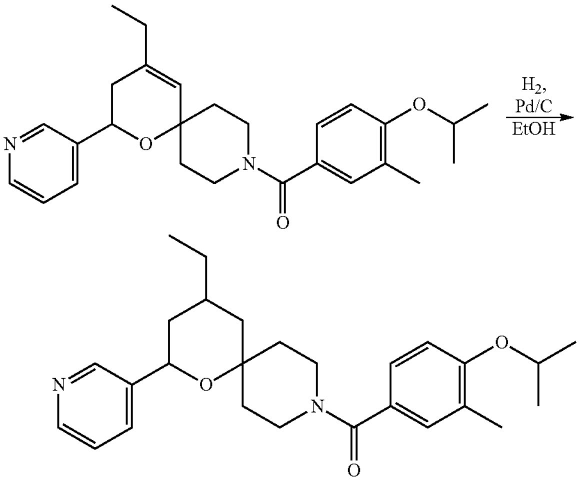

cis

A solution of [8-ethyl-10-(3-pyridyl)-11-oxa-3-azaspiro[5.5]undec-7-en-3-yl]-(4-isopropoxy-3-methyl-phenyl)methanone (90 mg, 0.21 mmol) in EtOH (14 mL) was purged with nitrogen for 5 min and then treated with 10% palladium on carbon (220 mg, 0.21 mmol). The mixture was evacuated and put under a hydrogen atmosphere (balloon). The reaction mixture was stirred for 4 h at 25° C. The reaction mixture was evacuated and put under an inert atmosphere. The Pd-catalyst was removed via filtration and was washed with ethyl acetate. The filtrate was concentrated to dryness. The crude mixture was purified on silica gel utilizing a gradient of 50-100% ethyl acetate and hexanes to yield (cis-4-ethyl-2-(pyridin-3-yl)-1-oxa-9-azaspiro[5.5]undecan-9-yl)(4-isopropoxy-3-methylphenyl)methanone (17 mg) ESI-MS m/z calc. 436.27, found 437.5 $(M+1)^+$; Retention time: 1.68 minutes (3 min run).

4-(1-Hydroxy-1-methyl-ethyl)-3-methyl-benzoic acid

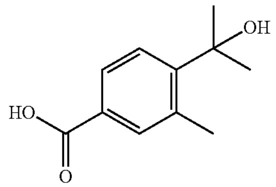

4-Bromo-3-methyl-benzoic acid (3.96 g, 18.4 mmol) was dissolved in tetrahydrofuran (100 mL) and the solution was cooled to −78° C. n-Butyllithium in hexanes (16.2 mL of 2.5 M, 41 mmol) was added dropwise over 20 minutes. The reaction mixture was allowed to stir for 30 minutes at −78° C. and then acetone (1.35 mL, 18.4 mmol) was added in a drop-wise manner. The reaction mixture was allowed to stir for 30 minutes at −78° C., and then it was allowed to warm to room temperature. The reaction mixture was then diluted with 100 mL of 1M aqueous sodium hydroxide. The organic layer was discarded and then the aqueous layer was made acidic with 4M aqueous hydrochloric acid. The aqueous layer was then extracted 3 times with ethyl acetate. The combined extracts were dried over sodium sulfate and then evaporated to dryness. The crude material was further purified on silica gel utilizing a gradient of 0-10% methanol in dichloromethane to give 4-(1-hydroxy-1-methyl-ethyl)-3-methyl-benzoic acid (1.51 g, 42%). $^1H$ NMR (400 MHz, DMSO) δ 12.74 (s, 1H), 7.68 (dd, J=3.9, 2.5 Hz, 2H), 7.55 (d, J=8.7 Hz, 1H), 5.06 (s, 1H), 2.56 (s, 3H), 1.51 (s, 6H).

5-Isopropoxy-6-methylpicolinic acid

Step 1: 4,6-dibromo-2-methylpyridin-3-ol

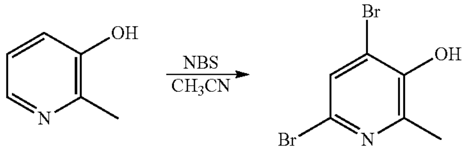

2-Methyl-3-pyridinol (8.3 g, 76.1 mmol) was suspended in acetonitrile (125 mL). A solution of NBS (27.7 g, 155.6 mmol, 2.05 equiv) in acetonitrile (275 mL) was added to the suspension drop-wise over 1 hour. The mixture was heated at reflux for 1.5 h. The mixture was concentrated and the residue was purified by column chromatography (DCM) to give 4,6-dibromo-2-methylpyridin-3-ol (15.8 g, 78%) as a yellow solid. $^1H$ NMR (300 MHz, DMSO) 2.41 (s, 3H), 7.70 (s, 1H), 9.98 (s, 1H).

Step 2: 6-bromo-2-methylpyridin-3-ol

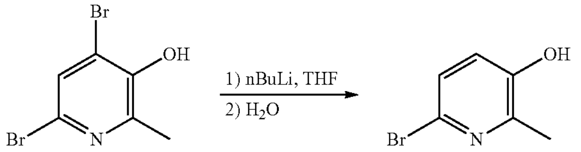

4,6-Dibromo-2-methylpyridin-3-ol (15.8 g, 59.4 mmol) was dissolved in THF (200 mL). The solution was cooled to −78° C. and n-BuLi (50 mL, 125 mmol, 2.5 M in hexane) was added drop-wise keeping the temperature below −78° C. The mixture was allowed to stir at that temperature for 2 h. The mixture was quenched with water (50 mL) and was neutralized with 2 N HCl. The aqueous mixture was extracted with dichloromethane (2×). The combined organic layers were dried ($Na_2SO_4$) and concentrated to give 6-bromo-2-methylpyridin-3-ol (10.5 g, 95%) as a yellow oil. $^1H$-NMR (300 MHz, DMSO) 2.29 (s, 3H), 7.08 (d, 1H), 7.26 (d, 1H), 10.08 (s, 1H).

Step 3: 6-bromo-3-isopropoxy-2-methylpyridine

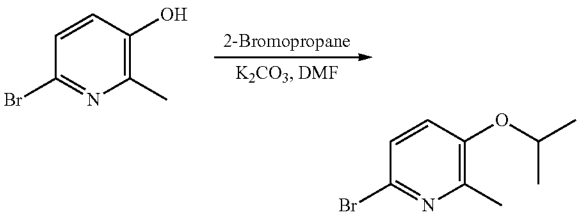

6-Bromo-2-methylpyridin-3-ol (10.5 g, 55.9 mmol) was dissolved in DMF (100 mL). $K_2CO_3$ (19.3 g, 139.6 mmol) and 2-bromopropane (13.1 ml, 139.6 mmol) were added to the solution and the mixture was heated at 100° C. overnight. The mixture was poured into a mixture of water and EtOAc (200 mL). The layers were separated and the aqueous layer was extracted with EtOAc (2×). The combined organic layers were dried ($Na_2SO_4$) and concentrated. The crude oil was purified by column chromatography (0-20% ethyl acetate/heptanes) to give 6-bromo-3-isopropoxy-2-methylpyridine (10.9 g, 85) as a yellow oil. $^1H$-NMR (300 MHz, $CDCl_3$) 1.42 (d, 6H), 2.48 (s, 3H), 4.65 (m, 1H), 7.20 (d, 1H), 8.04 (d, 1H).

Step 4: methyl 5-isopropoxy-6-methylpicolinate

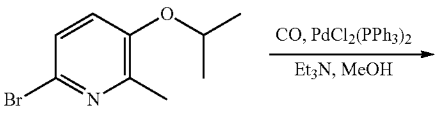

-continued

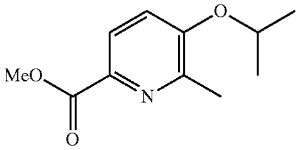

6-Bromo-3-isopropoxy-2-methylpyridine (2.00 g, 8.70 mmol), $PdCl_2(PPh_3)_2$ (0.18 g, 0.26 mmol) and $Et_3N$ (1.8 ml, 13.04 mmol) were added to MeOH (5.2 mL) and acetonitrile (20 mL) in a Berghoff reactor. The reactor was charged with 10 bar CO (g) and was heated at 60° C. overnight. The mixture was concentrated and the residue was partitioned between DCM and water. The layers were separated and the organic layer was washed with brine and dried ($Na_2SO_4$). The mixture was concentrated and purified by column chromatography to give methyl 5-isopropoxy-6-methylpicolinate (1.3 g, 71%) as a yellow oil. $^1H$-NMR (300 MHz, $CDCl_3$) 1.40 (d, 6H), 2.53 (s, 3H), 3.98 (s, 3H), 4.62 (m, 1H), 7.12 (d, 1H), 7.98 (d, 1H).

Step 5: 5-isopropoxy-6-methylpicolinic acid

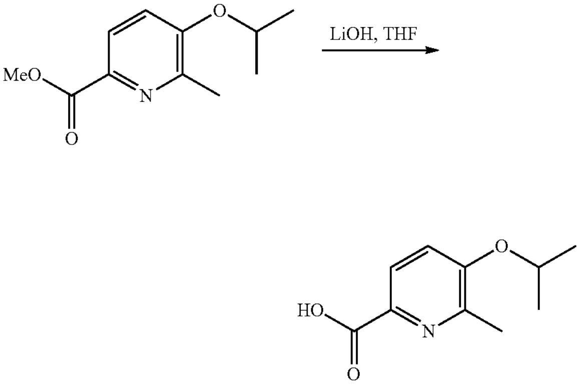

Methyl 5-isopropoxy-6-methylpicolinate (1.3 g, 6.22 mmol) was dissolved in THF/water 2:1 (9 mL). LiOH*$H_2O$ (0.26 g, 6.22 mmol) was added and the mixture was stirred at room temperature overnight. The mixture was poured into a mixture of water and EtOAc and the layers were separated. The aqueous layer was acidified to pH 4 with 2 N HCl and was extracted with EtOAc (2×). The combined organics were dried ($Na_2SO_4$) and concentrated to give 5-isopropoxy-6-methylpicolinic acid (860 mg, 74%) as a beige solid. $^1H$-NMR (300 MHz, DMSO) 1.31 (d, 6H), 4.73 (m, 1H), 7.44 (d, 1H), 7.86 (d, 1H).

4-(2-Hydroxypropan-2-yl)-3-methoxybenzoic acid

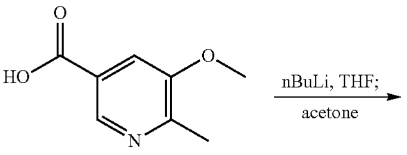

-continued

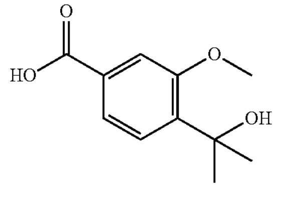

4-Bromo-3-methoxy-benzoic acid (2.00 g, 8.67 mmol) was dissolved in THF (50 mL) and the solution was cooled to −78° C. n-BuLi in hexanes (7.6 mL of 2.5 M, 19 mmol) was added dropwise over 15 minutes. The reaction mixture was allowed to stir for 30 minutes at −78° C. and then acetone (640 μL, 8.9 mmol) was added in a dropwise manner. The reaction mixture was allowed to stir for 30 minutes at −78° C., and then it was allowed to warm to room temperature. The reaction mixture was then diluted with 100 mL of 1M aqueous sodium hydroxide. The organic layer was discarded and the aqueous layer was made acidic with 4M aqueous hydrochloric acid. The aqueous layer was then extracted 3 times with ethyl acetate. The combined extracts were dried over sodium sulfate and then evaporated to dryness. The crude material was purified by column chromatography utilizing a gradient of 0-5% methanol in dichloromethane to give 4-(2-hydroxypropan-2-yl)-3-methoxybenzoic acid (618 mg, 34%). ESI-MS m/z calc. 210.1, found 209.1 $(M-1)^-$; Retention time: 0.68 minutes (3 min run).

4-(Isopropylsulfonyl)-3-methylbenzoic acid

Step 1: 4-(Isopropylthio)-3-methylbenzoic acid

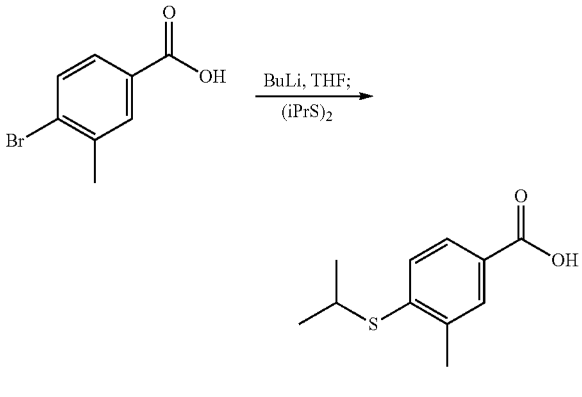

Butyllithium (16 mL of 1.6 M, 26 mmol) was added dropwise to a mixture of 4-bromo-3-methyl-benzoic acid (2.5 g, 12 mmol) and THF (63 mL) at −78° C. The mixture was allowed to stir at −78° C. for 30 minutes before a solution of 2-isopropyldisulfanylpropane (1.7 g, 12 mmol) in THF (2 mL) was added drop-wise. The mixture was allowed to stir at −78° C. for 30 min, then 30 min at rt. The reaction mixture was then diluted with 100 mL of 1M aqueous sodium hydroxide. The organic layer was discarded and the aqueous layer was made acidic with 4M aqueous hydrochloric acid. The aqueous layer was then extracted 3 times with ethyl acetate. The combined extracts were dried over sodium sulfate and then evaporated to dryness. The crude material was purified by column chromatography using a gradient of 0-5% MeOH in dichloromthane to give 4-(isopropylthio)-3-methylbenzoic acid (870 mg, 18%). MS m/z calc. 210.3, found 211.2 $(M+1)^+$. Retention time: 2.32 minutes (3 min run).

Step 2: 4-(Isopropylsulfonyl)-3-methylbenzoic acid

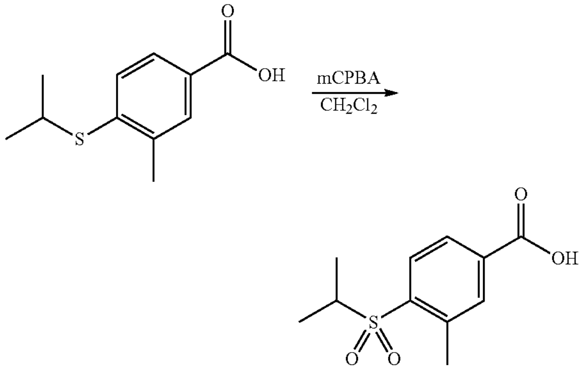

3-Chlorobenzenecarboperoxoic acid (930 mg, 4.2 mmol) was added to a mixture of 4-(isopropylthio)-3-methylbenzoic acid (250 mg, 1.2 mmol) and dichloromethane (5.0 mL) at 25° C. The mixture was allowed to stir at 25° C. for 2 h before it was concentrated in vacuo. The white solid material was taken up in dichloromethane and was subjected to column chromatography (0-2% MeOH/dichloromethane) to give 4-isopropylsulfonyl-3-methyl-benzoic acid (90 mg, 31%) as a white solid. ESI-MS m/z calc. 242.3, found 243.2 $(M+1)^+$. Retention time: 1.57 minutes (3 min run). $^1H$ NMR (400 MHz, DMSO) δ 13.50 (s, 1H), 8.50-7.66 (m, 3H), 3.50-3.47 (m, 1H), 2.67 (s, 3H), 1.19 (d, J=1.16 Hz, 6H).

3-Formyl-4-isopropoxybenzoic acid

Step 1: Methyl 3-formyl-4-isopropoxybenzoate

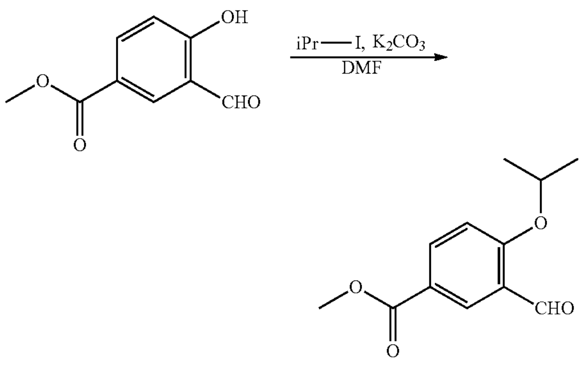

To methyl 3-formyl-4-hydroxy-benzoate (10.0 g, 55.5 mmol), potassium carbonate (30.7 g, 222 mmol) and N,N-dimethylformamide (63 mL) was added 2-iodopropane (11.1 mL, 111 mmol). The mixture was heated at 60° C. for 18 hours. The mixture was filtered using ethyl acetate (200 mL) and the solvent was evaporated under reduced pressure. The residue was dissolved in ethyl acetate (150 mL) and was washed with water (3×75 mL) and a saturated aqueous solution of sodium chloride (1×75 mL). The organic layer was dried over sodium sulfate, filtered and the solvent was evaporated under reduced pressure to yield methyl 3-formyl-4- isopropoxy-benzoate (98%) as a yellow viscous liquid. ESI-MS m/z calc. 222.2, found 223.3 (M+1)+; Retention time: 1.51 minutes (3 min run). $^1$H NMR (400 MHz, DMSO) δ 10.35 (s, 1H), 8.23 (d, J=2.3 Hz, 1H), 8.17 (dd, J=8.8, 2.3 Hz, 1H), 7.39 (d, J=8.9 Hz, 1H), 4.98-4.83 (m, 1H), 3.85 (s, 3H), 1.38 (d, J=6.0 Hz, 6H).

Step 2: 3-Formyl-4-isopropoxybenzoic acid

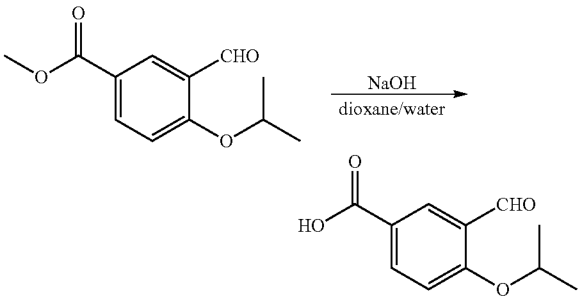

To a solution of the ester (from previous step) in dioxane (4 mL) was added 2 mL of sodium hydroxide solution (5N). The reaction mixture was heated at 65° C. for 4 hours. The reaction mixture was cooled to room temperature and was diluted with 20 mL of water. The water layer was extracted with 20 mL portion of ethyl acetate (2×). The organic extracts were discarded and the aqueous layer was made acidic with 1M HCl. The resulting product was then extracted into ethyl acetate, dried over $MgSO_4$, filtered, and evaporated to dryness to yield 3-formyl-4-isopropoxy-benzoic acid (320 mg, 55% over 2 steps) as a white solid. $^1$H NMR (400 MHz, DMSO) δ 10.36 (s, 1H), 8.23 (d, J=2.5 Hz, 1H), 8.15 (dd, J=2.5, 8.9 Hz, 1H), 7.37 (d, J=8.9 Hz, 1H), 4.96-4.87 (m, 1H), 1.37 (d, J=5.6 Hz, 6H).

3-(Hydroxymethyl)-4-isopropoxy-benzoic acid

Step 1: Methyl 3-formyl-4-isopropoxy-benzoate

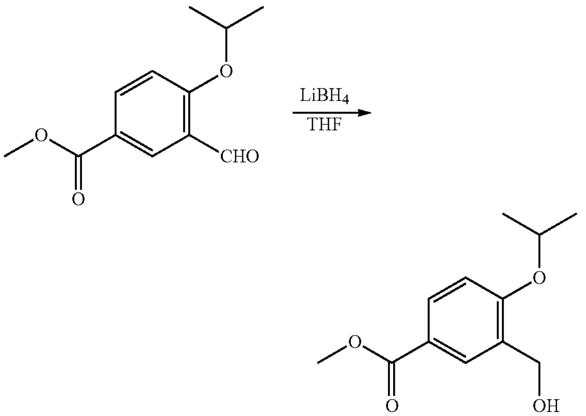

Methyl 3-formyl-4-isopropoxy-benzoate (180 mg, 0.81 mmol) was dissolved in tetrahydrofuran (4.8 mL) and $LiBH_4$ (35 mg, 1.6 mmol) was added. The reaction was stirred at room temperature for 30 minutes before it was quenched with methanol (3 mL). The reaction was neutralized by the addition of a saturated aqueous solution of sodium bicarbonate (3 mL) and was then extracted with ethyl acetate (3×10 mL). The combined organics were washed with a saturated aqueous solution of sodium chloride (1×10 mL), dried over sodium sulfate, filtered and the solvent was evaporated under reduced pressure to yield methyl 3-(hydroxymethyl)-4-isopropoxy-benzoate (99%) as a viscous liquid. ESI-MS m/z calc. 224.3, found 225.3 (M+1)+; Retention time: 1.26 minutes (3 min run). $^1$H NMR (400 MHz, DMSO) δ 8.09 (s, 1H), 7.89 (d, J=8.6 Hz, 1H), 7.13 (d, J=8.6 Hz, 1H), 5.25 (t, J=5.6 Hz, 1H), 4.86-4.68 (m, 1H), 4.54 (d, J=5.6 Hz, 2H), 3.87 (s, 3H), 1.35 (d, J=6.0 Hz, 6H).

Step 2: 3-(Hydroxymethyl)-4-isopropoxy-benzoic acid

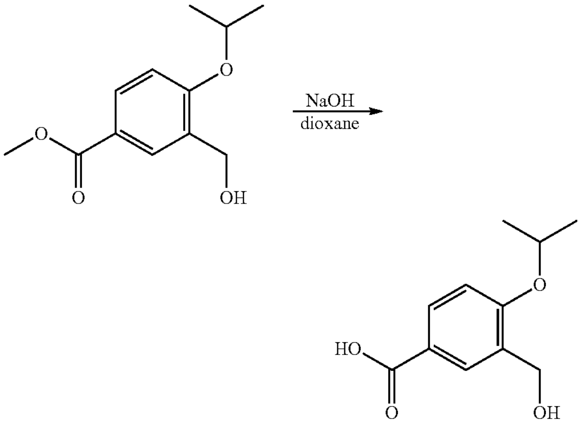

To methyl 3-(hydroxymethyl)-4-isopropoxy-benzoate (180 mg, 0.80 mmol) and 1,4-dioxane (1.895 mL) was added sodium hydroxide (2.1 mL of 1.0 M, 2.1 mmol) and the mixture was heated at 80° C. for 50 minutes. The solvent was evaporated under reduced pressure. The crude mixture was dissolved in water (10 mL) and was washed with ethyl acetate (3×10 mL) which was discarded. The aqueous layer was acidified with hydrochloric acid. The aqueous layer was extracted with ethyl acetate (3×10 mL). The combined organics were dried over sodium sulfate, filtered and the solvent was evaporated under reduced pressure to yield 3-(hydroxymethyl)-4-isopropoxy-benzoic acid (89%) as a white solid. ESI-MS m/z calc. 210.2, found 211.3 $(M+1)^+$; Retention time: 1.01 minutes (3 min run).

3-cyano-4-isopropylsulfonyl-benzoic acid

Step 1: Methyl 3-cyano-4-fluoro-benzoate

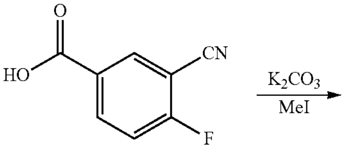

-continued

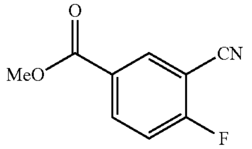

To a 100 mL rbf was added 3-cyano-4-fluoro-benzoic acid (2.6 g, 15.9 mmol), potassium carbonate (6.6 g, 47.6 mmol), and DMF (30 mL) and the reaction was allowed to stir for 10 minutes. Iodomethane (1.1 mL, 17.5 mmol) was added dropwise and the reaction was allowed to stir for 1 h. The reaction was complete by 1 cms. The reaction was quenched with brine and extracted with EtOAC. The organic layer was washed with brine 3 times and the organic layer was dried over sodium sulfate and evaporated. Methyl 3-cyano-4-fluoro-benzoate (2.5 g, 62%) was isolated as a white solid. ESI-MS m/z calc. 179.0, found 180.0 $(M+1)^+$; Retention time: 1.15 minutes (3 min run).

Step 2: 3-cyano-4-isopropylsulfonyl-benzoic acid

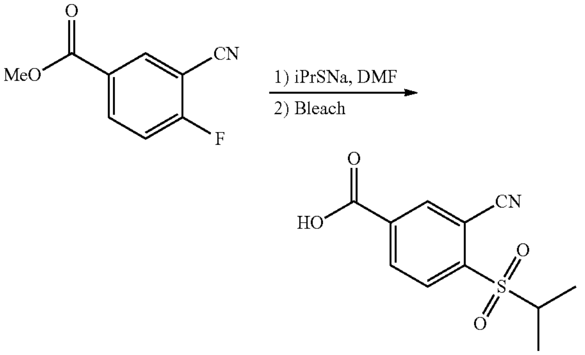

To a 100 mL rbf was added methyl 3-cyano-4-fluoro-benzoate (2.5 g, 14.0 mmol) followed by DMF (20 mL). Isopropylsulfanylsodium (3.8 g, 39.7 mmol) was added and the reaction was placed in a preheated 65° C. oil bath and allowed to stir overnight. The reaction was complete by 1 cms. The reaction was quenched with brine and extracted 3 times with EtOAc. The aqueous layer was then treated with bleach (100 mL) and the reaction was allowed to stir for 10 minutes. 1N HCl was then added until pH 1. The reaction was then extracted with EtOAc and the organic layer was further washed with brine 3 times. The organic layer was then dried over sodium sulfate and the solvent was removed. 3-cyano-4-isopropylsulfonyl-benzoic acid (2.24 g) was isolated as a white solid. $^1H$ NMR (400 MHz, $CDCl_3$) δ 8.59 (d, J=1.4 Hz, 1H), 8.47 (dd, J=8.2, 1.7 Hz, 1H), 8.28 (d, J=8.2 Hz, 1H), 3.64 (s, 1H), 1.39 (d, J=6.8 Hz, 6H).

Preparation of 3-Fluoro-4-isopropoxy-benzoic acid

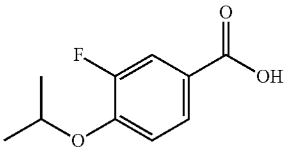

Step 1:

To methyl 3-fluoro-4-hydroxy-benzoate (2.0 g, 11.8 mmol) in DMF (12 mL) was added $K_2CO_3$ (6.50 g, 47.04 mmol) followed by 2-iodopropane (2.35 mL, 23.5 mmol). The reaction mixture was heated at 60° C. for 1.5 hours. The reaction mixture was cooled and diluted with EtOAc, filtered and the solvent was evaporated in vacuo. The resulting residue was dissolved in EtOAc and washed sequentially with water (3×10 mL) and brine solution (1×10 mL). The organics were separated and dried over $Na_2SO_4$, filtered and concentrated in vacuo to give the desired ester. ESI-MS m/z calc. 212.2, found 213.3 $(M+1)^+$; Retention time: 1.7 minutes (3 min run). $^1H$ NMR (400 MHz, DMSO) δ 7.76 (ddd, J=8.6, 2.1, 1.2 Hz, 1H), 7.69 (dd, J=11.9, 2.1 Hz, 1H), 7.31 (t, J=8.6 Hz, 1H), 4.79 (dt, J=12.1, 6.0 Hz, 1H), 3.82 (s, 3H), 1.32 (d, J=6.5 Hz, 6H).

Step 2:

To the ester from above was added dioxane (31 mL) and NaOH solution (31.2 mL of 1 M, 31.2 mmol) and the reaction was heated at 80° C. for 20 minutes, then concentrated in vacuo. The crude mixture was dissolved in water and washed with EtOAc (3×10 mL). The layers were separated and the aqueous layer was acidified using 1 M HCl solution. The aqueous layer was extracted with EtOAc (3×10 mL). The organic layer was dried over $Na_2SO_4$, filtered and concentrated in vacuo to yield 3-fluoro-4-isopropoxy-benzoic acid (1.7 g, 72%) as a white solid. ESI-MS m/z calc. 198.1, found 199.1 $(M+1)^+$; Retention time: 1.7 minutes (3 min run). $^1H$ NMR (400 MHz, DMSO) δ 12.90 (br s, 1H), 7.73 (ddd, J=8.6, 2.0, 1.1 Hz, 1H), 7.65 (dd, J=11.9, 2.1 Hz, 1H), 7.28 (t, J=8.6 Hz, 1H), 4.77 (hept, J=6.1 Hz, 1H), 1.32 (d, J=6.0 Hz, 6H).

The following compound was also prepared by the procedures described above:

4-isopropoxy-3-methylbenzoic acid

Preparation of 4-Isopropoxy-3-methoxy-benzoic acid

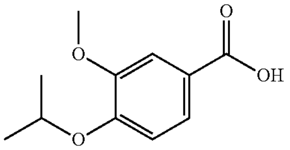

Step 1:

2-Bromopropane (3.39 mL, 36.2 mmol) was added to a suspension of 4-bromo-2-methoxy-phenol (5 g, 24.1 mmol), $K_2CO_3$ (6.67 g, 48.3 mmol) and DMSO (71 mL) at room temperature. The heterogeneous mixture was stirred at 55° C. for 2 hours, then cooled to room temperature and diluted with water. The reaction mixture was extracted with $Et_2O$ and the extract was washed successively with 10% aq. NaOH solution, water, then brine solution. The organics were separated and dried over sodium sulfate, filtered and concentrated in vacuo to give 4-bromo-1-isopropoxy-2-methoxy-benzene (5.83 g, 94%) as a pale yellow oil. ESI-MS m/z calc. 244.0, found 245.0 $(M+1)^+$; Retention time: 1.93 minutes (3 min run). $^1H$ NMR (400 MHz, $CDCl_3$) δ 7.03-6.95 (m, 2H), 6.76 (dd, J=7.7, 1.1 Hz, 1H), 4.47 (dt, J=12.2, 6.1 Hz, 1H), 3.84 (s, 3H), 1.35 (d, J=6.1 Hz, 6H).

Step 2:

Under an atmosphere of nitrogen, tert-butyllithium (2.14 mL of 1.6 M in toluene, 3.42 mmol) was added dropwise to a solution of 4-bromo-1-isopropoxy-2-methoxy-benzene (400 mg, 1.63 mmol) in THF (6 mL) at −78° C. The reaction mixture was allowed to stir for 1 hour at −78° C., then added dropwise to a flask containing $CO_2$ (1.8 g, 40.8 mmol) (solid, dry ice) in THF (2 mL). The reaction mixture was allowed to stir for 30 minutes warming to room temperature. Water (20 mL) was added to the reaction mixture and the volatiles were removed in vacuo. The resultant aqueous layer was acidified with 1N HCl solution to pH 1 and was extracted with ethyl acetate (3×15 mL). The organics were separated and the combined organics were washed with brine solution, dried over sodium sulfate, filtered and concentrated in vacuo to give 4-isopropoxy-3-methoxy-benzoic acid (310 mg, 85%) as a white solid. ESI-MS m/z calc. 210.1, found 211.1 $(M+1)^+$; Retention time: 1.23 minutes (3 min run). $^1H$ NMR (400 MHz, DMSO) δ 12.63 (s, 1H), 7.53 (dd, J=8.4, 2.0 Hz, 1H), 7.44 (d, J=2.0 Hz, 1H), 7.04 (d, J=8.7 Hz, 1H), 4.67 (dt, J=12.1, 6.0 Hz, 1H), 3.78 (s, 3H), 1.28 (d, J=6.0 Hz, 6H).

Preparation of 4-(2-Hydroxy-2-methyl-propoxy)benzoic acid

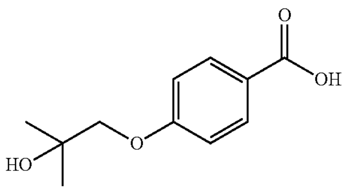

Step 1:

A mixture of 1-chloro-2-methyl-propan-2-ol (10 mL), 4-hydroxybenzonitrile (2 g, 16.8 mmol), $K_2CO_3$ (9.3 g, 67.3 mmol) in water (6 mL) and ethanol (60 mL) was heated at 80° C. for 16 hours. The reaction mixture was cooled and the solvent was concentrated in vacuo. The residue was diluted with ether (200 mL) and filtered and the filtrate was washed sequentially with water (50 mL) and brine solution (50 mL). The organics were separated and dried over $MgSO_4$ and solvent was removed in vacuo to give a residue which was purified by silica gel column chromatography using (0-100%) EtOAc/DCM as eluent to give 4-(2-hydroxy-2-methyl-propoxy)benzonitrile (3.0 g, 94%) as a yellow solid. ESI-MS m/z calc. 191.1, found 192.3 $(M+1)^+$; Retention time: 1.05 minutes (3 min run).

Step 2:

To 4-(2-hydroxy-2-methyl-propoxy)benzonitrile (1.0 g, 5.2 mmol) in ethanol (15 mL) was added NaOH solution (5 mL of 5 M, 25 mmol) and the reaction mixture was heated at 85° C. for 1 hour, concentrated in vacuo and diluted with ethyl acetate (50 mL). To the organic layer was added a mixture of brine solution (10 mL) and 6N HCl (3 mL, to adjust to pH 6). The organic layer was separated, dried over $MgSO_4$ and concentrated in vacuo to give a yellow solid, which was triturated twice with diethyl ether to give 4-(2-hydroxy-2-methyl-propoxy)benzoic acid (0.8 g, 76%) as a white solid. ESI-MS m/z calc. 195.1, found 196.1 $(M+1)^+$; Retention time: 0.62 minutes (3 min run). $^1H$ NMR (400 MHz, DMSO) δ 12.59 (s, 1H), 7.98-7.66 (m, 2H), 7.09-6.81 (m, 2H), 4.66 (d, J=9.3 Hz, 1H), 3.77 (d, J=7.9 Hz, 2H), 1.30-1.00 (s, 6H).

Preparation of 4-(1-hydroxycyclopentyl)benzoic acid

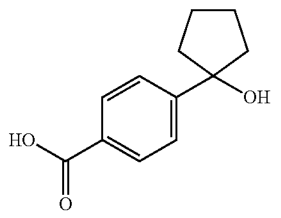 [SMILES: O=C(O)c1ccc(C2(O)CCCC2)cc1]

A solution of 4-bromobenzoic acid (4.02 g, 20.0 mmol) in tetrahydrofuran (100 mL) was purged with argon for 5 min. n-Butyllithium (16.0 mL of 2.5 M in hexanes, 40 mmol) was added dropwise at −78° C., resulting in a yellow thick syrup. The mixture was stirred at −78° C. for 30 min. Cyclopentanone (3.89 mL, 44.0 mmol) was added dropwise. The reaction was quenched immediately with saturated $NH_4Cl$ and allowed to warm to room temperature. The mixture was acidified with 1 N HCl to pH ~3 and extracted with ethyl acetate (3×50 mL). The combined organic layers were washed with brine, dried over $MgSO_4$ and concentrated in vacuo. The solid residue was suspended in hexanes, filtered, and the solid washed with additional hexanes. The solid was re-suspended in dichloromethane followed by hexanes. The resulting precipitate was filtered, washed with hexane and air dried to yield 4-(1-hydroxycyclopentyl)benzoic acid (1.25 g, 30%) as a white solid. $^1H$ NMR (400 MHz, DMSO) δ 12.78 (s, 1H), 7.88 (d, J=8.5 Hz, 2H), 7.58 (d, J=8.5 Hz, 2H), 4.93 (s, 1H), 1.93-1.71 (m, 8H).

The following compounds were prepared by the general procedure above:

4-(1-hydroxycyclobutyl)benzoic acid
4-(2-hydroxybutan-2-yl)benzoic acid
3-fluoro-4-(2-hydroxypropan-2-yl)benzoic acid 4-tert-Butoxy-3-methoxybenzoic acid Step 1: 4-tert-Butoxy-3-methoxybenzaldehyde

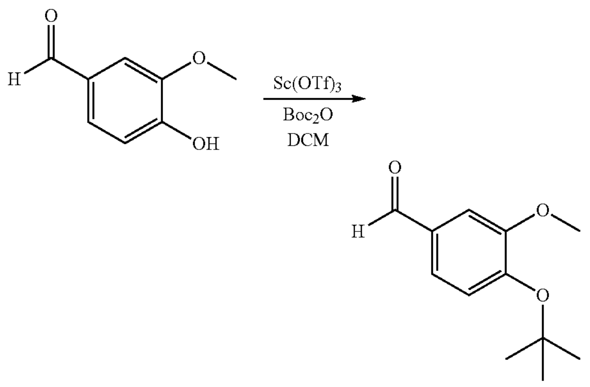

4-Hydroxy-3-methoxy-benzaldehyde (500 mg, 3.29 mmol), $Boc_2O$ (1.74 g, 7.97 mmol), and $Sc(OTf)_3$ (0.080 g, 0.16 mmol) were combined in dichloromethane (5 mL). The reaction mixture was allowed to stir at room temperature for 24 h. Water (5 mL) and dichloromethane (5 mL) were added and the two phases were separated. The aqueous layer was extracted with dichloromethane (3×5 mL) and the combined organics were stirred with 10% aqueous potassium hydroxide until all remaining starting material was not observed in the organic phase (TLC, 40% ethyl acetate in hexanes). The two phases were separated and the dichloromethane layer was then washed twice with a saturated aqueous solution of sodium chloride, dried over sodium sulfate, filtered, and evaporated to dryness to give 4-tert-butoxy-3-methoxybenzaldehyde (130 mg, 19%) as a yellow oil. Rf=0.66 ($SiO_2$, 40% ethyl acetate in hexanes); ESI-MS m/z calc. 208.1, found 209.2 $(M+1)^+$. Retention time: 0.96 minutes (6 min run).

Step 2: 4-tert-Butoxy-3-methoxybenzoic acid

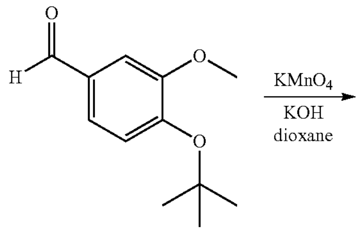

-continued

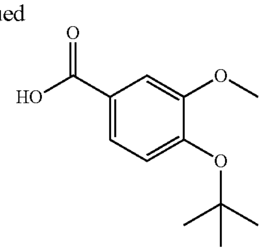

4-tert-Butoxy-3-methoxybenzaldehyde (130 mg, 0.62 mmol) was suspended in a mixture of dioxane (520 μL) and potassium hydroxide (6.5 mL of 0.20 M, 1.3 mmol). $KMnO_4$ (150 mg, 0.93 mmol) was added and the reaction was stirred vigorously for 16 h. The reaction mixture was filtered and then concentrated to 3 mL. Hydrochloric acid (1M, 4 mL) was added and the resulting precipitate was filtered (after standing for 15 minutes) and washed with 1M HCl and a small amount of water to yield 4-tert-butoxy-3-methoxy-benzoic acid (68 mg, 49%) as a white solid. Rf=0.23 ($SiO_2$, 40% ethyl acetate in hexanes); ESI-MS m/z calc. 224.1, found 225.2 $(M+1)^+$. Retention time: 1.66 minutes (3 min run). $^1H$ NMR (400 MHz, DMSO) δ 12.80 (s, 1H), 7.66-7.41 (m, 2H), 7.09 (d, J=8.8 Hz, 1H), 3.78 (s, 3H), 1.32 (s, 9H).

Table 2 below recites the analytical data for the compounds of Table 1.

TABLE 2

| Cmpd. No. | LC/MS M + 1 | LC/RT min | NMR |
|---|---|---|---|
| 1 | 473.50 | 1.51 | |
| 2 | 497.60 | 1.71 | |
| 3 | 483.70 | 1.60 | 1H NMR (400 MHz, CDCl3) δ 8.24 (s, 2H), 7.36 (s, 1H), 7.19 (d, J = 8.6 Hz, 2H), 6.80 (d, J = 8.2 Hz, 1H), 4.55 (dt, J = 12.2, 6.0 Hz, 2H), 4.34 (s, 1H), 4.12 (q, J = 7.1 Hz, 1H), 3.91 (s, 3H), 3.78 (s, 1H), 3.54 (d, J = 7.1 Hz, 3H), 3.32-2.98 (m, 1H), 2.32 (d, J = 11.2 Hz, 1H), 2.20 (s, 4H), 2.05 (s, 2H), 1.70 (s, 6H), 1.40 (d, J = 11.5 Hz, 2H), 1.34 (d, J = 6.0 Hz, 6H), 1.26 (t, J = 7.1 Hz, 1H), 1.21 (t, J = 7.0 Hz, 3H). |
| 4 | 473.50 | 1.56 | |
| 5 | 470.30 | 1.83 | 1H NMR (400 MHz, CDCl3) δ 7.54 (s, 1H), 7.20 (d, J = 8.7 Hz, 2H), 6.81 (d, J = 8.2 Hz, 1H), 6.31 (s, 1H), 4.73 (d, J = 10.5 Hz, 1H), 4.56 (dt, J = 12.0, 6.0 Hz, 1H), 4.07 (s, 3H), 3.73 (br s, 1H), 3.51-3.38 (m, 3H), 3.30 ( br s, 1H), 2.33 (d, J = 12.6 Hz, 1H), 2.20 (s, 3H), 2.15 (br s, 1H), 2.07 (dd, J = 12.8, 3.1 Hz, 1H), 1.73-1.54 (m, 6H), 1.42-1.37 (m, 1H), 1.35 (d, J = 6.0 Hz, 6H), 0.93 (t, J = 7.4 Hz, 3H). |
| 6 | 456.50 | 1.67 | 1H NMR (400 MHz, CDCl3) δ 7.72 (d, J = 2.1 Hz, 1H), 7.20 (d, J = 8.3 Hz, 2H), 6.81 (d, J = 8.1 Hz, 1H), 6.43 (d, J = 1.9 Hz, 1H), 4.78 (d, J = 10.8 Hz, 1H), 4.56 (dt, J = 12.1, 6.0 Hz, 1H), 4.22 (s, 3H), 3.76 (s, 1H), 3.61-3.50 (m, 2H), 3.44 (s, 1H), 3.27 (d, J = 10.1 Hz, 1H), 2.34 (d, J = 12.9 Hz, 1H), 2.20 (s, 3H), 2.19-2.07 (m, 2H), 1.65 (dd, J = 22.9, 11.0 Hz, 4H), 1.44-1.36 (m, 1H), 1.35 (d, J = 6.0 Hz, 6H), 1.23 (t, J = 7.0 Hz, 3H). |
| 7 | 437.50 | 1.68 | |
| 8 | 473.50 | 1.73 | |
| 9 | 458.40 | 0.93 | |
| 10 | 495.50 | 1.32 | 1H NMR (400 MHz, CDCl3) δ 8.53 (dd, J = 10.2, 4.5 Hz, 1H), 8.10-7.97 (m, 2H), 7.73 (q, J = 8.0 Hz, 1H), 7.68-7.60 (m, 2H), 7.54 (dd, J = 22.1, 7.8 Hz, 1H), 7.22 (ddd, J = 7.5, 4.9, 1.1 Hz, 1H), 6.21 (t, J = 53.3 Hz, 1H), 4.77-4.35 (m, 2H), 3.94-3.70 (m, 1H), 3.70-3.01 (m, 5H), 2.59 (t, J = 11.2 Hz, 1H), 2.28 (dd, J = 65.0, 13.5 Hz, 1H), 2.04-1.37 (m, 7H), 1.30 (q, J = 11.8 Hz, 1H), 1.19 (dd, J = 12.6, 6.6 Hz, 3H). |

TABLE 2-continued

| Cmpd. No. | LC/MS M + 1 | LC/RT min | NMR |
|---|---|---|---|
| 11 | 429.40 | 1.29 | 1H NMR (400 MHz, CDCl3) δ 8.58-8.47 (m, 1H), 7.78-7.65 (m, 1H), 7.61-7.48 (m, 1H), 7.25-7.16 (m, 1H), 7.15-6.87 (m, 3H), 4.64 (dd, J = 43.1, 11.9 Hz, 1H), 4.55-4.39 (m, 1H), 3.96 (t, J = 5.4 Hz, 2H), 3.94-3.87 (m, 2H), 3.87-3.71 (m, 1H), 3.71-3.56 (m, 1H), 3.42 (dddd, J = 24.9, 16.4, 12.3, 5.5 Hz, 2H), 3.29-3.00 (m, 2H), 2.58 (t, J = 13.8 Hz, 1H), 2.31 (d, J = 14.5 Hz, 1H), 2.13 (d, J = 14.2 Hz, 1H), 2.08-1.92 (m, 1H), 1.92-1.73 (m, 2H), 1.68 (d, J = 12.8 Hz, 1H), 1.64-1.49 (m, 1H), 1.49-1.24 (m, 2H), 1.24-1.12 (m, 3H). |
| 12 | 453.80 | 1.34 | |
| 13 | 470.10 | 1.17 | |
| 14 | 495.40 | 1.12 | |
| 15 | 492.70 | 1.29 | |
| 16 | 457.70 | 1.29 | |
| 17 | 471.20 | 1.45 | |
| 18 | 459.70 | 1.60 | 1H NMR (400 MHz, CDCl3) δ 8.77 (s, 1H), 7.77 (s, 1H), 7.26-7.12 (m, 2H), 6.81 (d, J = 8.1 Hz, 1H), 4.89 (s, 1H), 4.68-4.48 (m, 1H), 3.76 (s, 1H), 3.65-3.46 (m, 2H), 3.76-3.24 (m, 4H), 2.42 (t, J = 22.9 Hz, 1H), 2.19 (d, J = 11.0 Hz, 4H), 2.09-1.80 (m, 2H), 1.84-1.45 (m, 4H), 1.34 (d, J = 6.0 Hz, 6H), 1.29-1.12 (m, 3H). |
| 19 | 445.90 | 1.83 | |
| 20 | 471.00 | 1.37 | 1H NMR (400 MHz, CDCl3) δ 8.62 (s, 1H), 8.55 (dd, J = 4.8, 1.6 Hz, 1H), 7.74 (d, J = 7.8 Hz, 1H), 7.31 (dd, J = 7.9, 4.8 Hz, 1H), 7.24-7.15 (m, 2H), 6.80 (d, J = 8.1 Hz, 1H), 4.58 (ddd, J = 18.2, 10.2, 5.1 Hz, 3H), 4.49 (t, J = 4.2 Hz, 1H), 4.36 (s, 1H), 3.87 (s, 1H), 3.75 (ddd, J = 29.2, 9.6, 5.9 Hz, 3H), 3.30 (d, J = 157.2 Hz, 2H), 2.34 (d, J = 12.1 Hz, 1H), 2.19 (s, 4H), 2.05 (dd, J = 12.8, 2.7 Hz, 1H), 1.76 (s, 6H), 1.55-1.37 (m, 3H), 1.34 (d, J = 6.0 Hz, 6H). |
| 21 | 454.70 | 2.01 | 1H NMR (400 MHz, CDCl3) δ 7.43-7.25 (m, 5H), 6.54 (s, 2H), 4.57 (s, 1H), 4.38 (s, 1H), 3.80 (d, J = 14.0 Hz, 7H), 3.66-3.44 (m, 4H), 3.17 (s, 1H), 2.31 (d, J = 12.3 Hz, 1H), 2.09 (s, 3H), 2.03-1.97 (m, 1H), 1.95-1.48 (m, 3H), 1.42 (dt, J = 21.7, 10.9 Hz, 2H), 1.20 (t, J = 7.0 Hz, 3H). |
| 22 | 437.80 | 2.03 | |
| 23 | 453.40 | 2.11 | 1H NMR (400 MHz, CDCl3) δ 8.05 (s, 1H), 7.47 (s, 1H), 7.42-7.32 (m, 4H), 7.29 (ddd, J = 6.6, 3.9, 1.8 Hz, 1H), 5.43-5.30 (m, 1H), 4.56 (s, 1H), 4.38 (s, 1H), 3.78 (s, 1H), 3.69-3.47 (m, 4H), 3.36 (s, 1H), 3.12 (s, 1H), 2.32 (d, J = 10.4 Hz, 2H), 2.17 (s, 7H), 2.01 (s, 2H), 1.68 (s, 6H), 1.49-1.38 (m, 3H), 1.36 (d, J = 6.1 Hz, 6H), 1.21 (t, J = 7.0 Hz, 3H). |
| 24 | 424.50 | 1.96 | 1H NMR (400 MHz, CDCl3) δ 7.43-7.18 (m, 7H), 6.80 (d, J = 8.2 Hz, 1H), 4.56 (s, 1H), 4.36 (s, 1H), 3.84 (s, 3H), 3.79 (d, J = 8.1 Hz, 1H), 3.68-3.45 (m, 3H), 2.32 (d, J = 10.8 Hz, 1H), 2.21 (s, 3H), 2.17 (s, 1H), 2.00 (d, J = 1.9 Hz, 1H), 1.99-1.95 (m, 1H), 1.62 (s, 4H), 1.41 (dt, J = 23.3, 11.6 Hz, 2H), 1.21 (t, J = 7.0 Hz, 3H). |
| 25 | 394.19 | 1.83 | |
| 26 | 436.19 | 1.84 | |
| 27 | 410.19 | 1.77 | |
| 28 | 438.22 | 1.93 | |
| 29 | 466.25 | 2.12 | |
| 30 | 422.19 | 1.78 | |
| 31 | 440.22 | 1.78 | |
| 32 | 435.18 | 1.77 | 1H NMR (400 MHz, CDCl3) δ 7.66-7.59 (m, 2H), 7.42-7.27 (m, 5H), 7.02-6.97 (m, 1H), 4.57 (s, 1H), 4.37 (s, 1H), 3.97 (s, 3H), 3.78 (s, 1H), 3.67-3.42 (m, 4H), 3.38 (s, 1H), 3.12 (s, 1H), 2.32 (d, J = 9.9 Hz, 2H), 2.17 (s, 2H), 2.03-1.95 (m, 2H), 1.61 (s, 6H), 1.53-1.32 (m, 3H), 1.21 (t, J = 7.0 Hz, 3H). |
| 33 | 483.40 | 1.29 | 1H NMR (400 MHz, CDCl3) δ 8.62 (s, 1H), 8.55 (s, 1H), 7.73 (d, J = 7.8 Hz, 1H), 7.35-7.27 (m, 1H), 7.22-7.15 (m, 2H), 6.80 (d, J = 8.2 Hz, 1H), 4.56 (td, J = 12.1, 6.1 Hz, 2H), 4.36 (s, 1H), 3.84 (s, 1H), 3.75-3.59 (m, 3H), 3.54 (t, J = 4.6 Hz, 3H), 3.38 (s, 4H), 2.33 (d, J = 12.8 Hz, 1H), 2.19 (s, 4H), 2.05 (dd, J = 12.8, 2.8 Hz, 1H), 1.79 (s, 5H), 1.53-1.37 (m, 3H), 1.34 (d, J = 6.0 Hz, 7H). |

TABLE 2-continued

| Cmpd. No. | LC/MS M + 1 | LC/RT min | NMR |
|---|---|---|---|
| 34 | 479.60 | 1.46 | 1H NMR (400 MHz, CDCl3) δ 8.62 (s, 1H), 8.55 (d, J = 3.9 Hz, 1H), 7.74 (d, J = 7.8 Hz, 1H), 7.30 (dd, J = 7.8, 4.8 Hz, 1H), 7.23-7.15 (m, 2H), 6.80 (d, J = 8.2 Hz, 1H), 4.56 (td, J = 12.1, 6.1 Hz, 2H), 4.37 (s, 1H), 3.94-3.40 (m, 3H), 3.34 (d, J = 6.8 Hz, 2H), 3.29-2.98 (m, 1H), 2.29 (t, J = 15.8 Hz, 1H), 2.19 (s, 4H), 2.07-1.97 (m, 1H), 1.70 (s, 4H), 1.44 (dd, J = 23.6, 12.0 Hz, 3H), 1.34 (d, J = 6.0 Hz, 6H), 1.05 (s, 1H), 0.55 (dt, J = 5.2, 2.6 Hz, 2H), 0.20 (q, J = 4.8 Hz, 2H). |
| 35 | 467.60 | 1.41 | 1H NMR (400 MHz, CDCl3) δ 8.62 (s, 1H), 8.54 (d, J = 3.9 Hz, 1H), 7.73 (d, J = 7.7 Hz, 1H), 7.30 (dd, J = 7.8, 4.8 Hz, 1H), 7.23-7.15 (m, 2H), 6.80 (d, J = 8.2 Hz, 1H), 4.56 (dq, J = 12.1, 6.1 Hz, 2H), 4.36 (s, 1H), 3.95-3.02 (m, 5H), 2.22 (d, J = 21.1 Hz, 5H), 1.95 (dd, J = 12.8, 2.9 Hz, 1H), 1.72 (s, 5H), 1.44 (dd, J = 23.5, 12.0 Hz, 3H), 1.34 (d, J = 6.0 Hz, 6H), 1.16 (dd, J = 6.0, 3.6 Hz, 6H). |
| 36 | 453.20 | 1.06 | |
| 37 | 467.40 | 1.17 | |
| 38 | 454.20 | 0.88 | |
| 39 | 497.10 | 1.10 | |
| 40 | 439.20 | 1.00 | |
| 41 | 467.40 | 1.16 | |
| 42 | 500.35 | 1.89 | |
| 43 | 468.32 | 1.24 | |
| 44 | 536.34 | 2.01 | |
| 45 | 506.30 | 1.95 | |
| 46 | 492.26 | 1.94 | |
| 47 | 466.32 | 1.35 | |
| 48 | 450.33 | 1.44 | |
| 49 | 446.26 | 1.86 | |
| 50 | 420.29 | 1.66 | |
| 51 | 492.19 | 1.68 | |
| 52 | 454.25 | 1.49 | |
| 53 | 461.28 | 2.09 | |
| 54 | 437.23 | 1.41 | |
| 55 | 432.23 | 1.88 | |
| 56 | 431.27 | 1.36 | |
| 57 | 441.28 | 1.89 | |
| 58 | 431.27 | 1.65 | |
| 59 | 479.31 | 1.34 | |
| 60 | 479.31 | 1.85 | |
| 61 | 479.24 | 1.93 | |
| 62 | 476.22 | 1.93 | |
| 63 | 466.34 | 2.15 | |
| 64 | 464.32 | 1.46 | |
| 65 | 464.32 | 1.42 | |
| 66 | 461.30 | 1.57 | |
| 67 | 424.29 | 1.29 | |
| 68 | 459.22 | 2.02 | |
| 69 | 452.30 | 1.48 | |
| 70 | 450.19 | 1.30 | |
| 71 | 450.19 | 1.33 | |
| 72 | 449.14 | 1.86 | |
| 73 | 446.13 | 1.88 | |
| 74 | 446.13 | 1.91 | |
| 75 | 438.19 | 1.37 | |
| 76 | 437.17 | 1.48 | |
| 77 | 434.16 | 1.33 | |
| 78 | 434.16 | 1.30 | |
| 79 | 425.17 | 1.72 | |
| 80 | 425.13 | 1.77 | |
| 81 | 424.15 | 1.30 | |
| 82 | 424.15 | 1.26 | |
| 83 | 412.27 | 1.97 | |
| 84 | 424.29 | 1.83 | |
| 85 | 424.29 | 1.95 | |
| 86 | 465.33 | 1.81 | |
| 87 | 444.24 | 1.95 | |
| 88 | 412.27 | 1.95 | |
| 89 | 420.26 | 1.44 | |
| 90 | 428.25 | 1.89 | 1H NMR (400 MHz, CDCl3) δ 7.43-7.25 (m, 5H), 7.05 (dt, J = 40.6, 21.9 Hz, 3H), 4.53 (dd, J = 51.1, 11.7 Hz, 2H), 4.01-3.86 (m, 3H), 3.86-3.64 (m, 1H), 3.64-3.46 (m, 3H), 3.46-3.05 (m, 3H), 1.99 (dd, J = 19.7, 7.3 Hz, 1H), 1.61 (dddd, J = 49.6, 37.9, 25.1, 13.4 Hz, 6H), 1.29-1.14 (m, 3H). |

TABLE 2-continued

| Cmpd. No. | LC/MS M + 1 | LC/RT min | NMR |
|---|---|---|---|
| 91 | 432.22 | 2.05 | |
| 92 | 432.28 | 1.61 | |
| 93 | 465.33 | 1.75 | |
| 94 | 424.29 | 1.89 | |
| 95 | 431.27 | 1.60 | |
| 96 | 430.27 | 1.93 | |
| 97 | 412.27 | 1.97 | |
| 98 | 446.17 | 1.87 | |
| 99 | 446.17 | 1.90 | |
| 100 | 478.23 | 1.81 | |
| 101 | 478.23 | 1.99 | |
| 102 | 478.24 | 2.03 | |
| 103 | 460.29 | 1.95 | |
| 104 | 460.29 | 1.83 | |
| 105 | 479.24 | 2.03 | |
| 106 | 478.24 | 2.03 | |
| 107 | 464.32 | 1.42 | |
| 108 | 460.29 | 2.01 | |
| 109 | 433.29 | 1.91 | |
| 110 | 431.27 | 1.85 | |
| 111 | 431.27 | 1.73 | |
| 112 | 428.25 | 1.89 | |
| 113 | 428.25 | 1.91 | |
| 114 | 428.25 | 1.89 | |
| 115 | 424.29 | 1.97 | |
| 116 | 424.29 | 1.95 | |
| 117 | 424.29 | 1.93 | |
| 118 | 424.29 | 1.93 | |
| 119 | 420.26 | 2.05 | |
| 120 | 411.26 | 1.69 | |
| 121 | 411.26 | 1.83 | |
| 122 | 395.27 | 1.56 | |
| 123 | 440.30 | 1.09 | 1H NMR (400 MHz, CDCl3) δ 8.63 (d, J = 19.2 Hz, 1H), 8.55 (d, J = 4.8 Hz, 1H), 7.76 (t, J = 9.3 Hz, 1H), 7.46 (t, J = 9.4 Hz, 1 H), 7.37-7.28 (m, 1H), 7.11 (d, J = 8.5 Hz, 1H), 4.71-4.37 (m, 3H), 3.88 (d, J = 17.0 Hz, 1H), 3.79-3.51 (m, 2H), 3.49 (s, 1H), 3.37 (dd, J = 15.1, 13.3 Hz, 4H), 3.10 (s, 1H), 2.44 (s, 3H), 2.32 (dd, J = 35.7, 15.0 Hz, 2H), 2.23-2.08 (m, 1H), 2.04 (dd, J = 12.7, 2.9 Hz, 1H), 1.90-1.58 (m, 5H), 1.43-1.31 (m, 8H). |
| 124 | 439.50 | 1.32 | 1H NMR (400 MHz, CDCl3) δ 8.63 (s, 1H), 8.55 (dd, J = 4.8, 1.4 Hz, 1H), 7.74 (d, J = 7.8 Hz, 1H), 7.31 (dd, J = 7.8, 4.8 Hz, 1H), 7.23-7.15 (m, 2H), 6.80 (d, J = 8.1 Hz, 1H), 4.56 (td, J = 12.2, 6.1 Hz, 2H), 4.36 (s, 1H), 3.68 (s, 2H), 3.49 (s, 2H), 3.38 (s, 3H), 3.16 (d, J = 33.5 Hz, 1H), 2.34 (d, J = 12.6 Hz, 1H), 2.21 (d, J = 11.5 Hz, 4H), 2.03 (dd, J = 12.7, 2.8 Hz, 1H), 1.70 (s, 3H), 1.58-1.42 (m, 1H), 1.40-1.22 (m, 9H). |
| 125 | 420.21 | 3.87 | |
| 126 | 438.20 | 4.03 | |
| 127 | 463.18 | 3.75 | |
| 128 | 439.17 | 3.67 | |
| 129 | 500.14 | 3.43 | |
| 130 | 473.12 | 3.03 | |
| 131 | 453.00 | 3.50 | |
| 132 | 470.18 | 2.77 | |
| 133 | 478.13 | 3.87 | |
| 134 | 468.19 | 3.23 | 1H NMR (400 MHz, CDCl3) δ 7.44-7.32 (m, 4H), 7.32-7.25 (m, 1H), 7.24-7.18 (m, 2H), 6.86-6.78 (m, 1H), 4.56 (d, J = 11.8 Hz, 1H), 4.14 (t, J = 5.9 Hz, 2H), 3.88 (t, J = 5.9 Hz, 2H), 3.85-3.72 (m, 1H), 3.66-3.41 (m, 3H), 3.21 (d, J = 11.8 Hz, 1H), 2.38-2.28 (m, 1H), 2.21 (s, 4H), 2.08 (p, J = 5.9 Hz, 2H), 2.03-1.88 (m, 3H), 1.71 (s, 2H), 1.44 (dq, J = 35.2, 11.7 Hz, 3H), 1.21 (t, J = 7.0 Hz, 3H). |
| 135 | 476.13 | 3.68 | |
| 136 | 482.22 | 4.01 | |
| 137 | 482.22 | 3.85 | 1H NMR (400 MHz, CDCl3) δ 7.42-7.32 (m, 4H), 7.29 (ddd, J = 6.7, 3.9, 1.7 Hz, 1H), 6.99 (d, J = 8.1 Hz, 1H), 6.95 (d, J = 1.9 Hz, 1H), 6.86 (dd, J = 8.1, 1.9 Hz, 1H), 4.56 (d, J = 11.2 Hz, 1H), 3.88-3.71 (m, 4H), 3.66-3.37 (m, 3H), 3.21 (s, 1H), 2.36-2.28 (m, 1H), 2.24 (d, J = 13.1 Hz, 1H), 2.06-1.96 (m, 1H), 1.68 (d, J = 41.2 Hz, 2H), 1.59-1.38 (m, 3H), 1.35 (s, 9H), 1.20 (t, J = 7.0 Hz, 3H). |
| 138 | 484.18 | 3.20 | |
| 139 | 482.22 | 3.88 | |

TABLE 2-continued

| Cmpd. No. | LC/MS M + 1 | LC/RT min | NMR |
|---|---|---|---|
| 140 | 468.19 | 3.72 | |
| 141 | 482.22 | 3.42 | |
| 142 | 452.19 | 3.40 | |
| 143 | 454.19 | 3.28 | |
| 144 | 438.20 | 3.94 | |
| 145 | 453.30 | 1.38 | |
| 146 | 453.50 | 1.57 | |
| 147 | 453.50 | 1.64 | |
| 148 | 469.40 | 1.13 | |
| 149 | 474.50 | 1.66 | 1H NMR (400 MHz, CDCl3) δ 7.60 (t, J = 8.1 Hz, 1H), 7.31 (td, J = 8.1, 5.9 Hz, 1H), 7.16-7.04 (m, 4H), 7.01-6.93 (m, 1H), 4.65-4.33 (m, 2H), 3.80 (s, 1H), 3.53 (d, J = 5.8 Hz, 4H), 3.19 (dd, J = 98.9, 20.9 Hz, 2H), 2.21 (d, J = 75.3 Hz, 3H), 2.03-1.94 (m, 1H), 1.90-1.71 (m, 1H), 1.64 (s, 7H), 1.59 (s, 2H), 1.41 (dq, J = 23.7, 11.6 Hz, 3H), 1.21 (t, J = 7.0 Hz, 3H), 1.02 (s, 1H). |
| 150 | 470.50 | 1.97 | 1H NMR (400 MHz, CDCl3) δ 7.35-7.27 (m, 1H), 7.22-7.16 (m, 2H), 7.12 (dd, J = 6.9, 5.4 Hz, 2H), 7.01-6.93 (m, 1H), 6.80 (d, J = 8.1 Hz, 1H), 4.55 (dt, J = 12.1, 6.0 Hz, 2H), 3.76 (t, J = 11.1 Hz, 1H), 3.55 (ddq, J = 14.0, 8.9, 7.0 Hz, 3H), 3.17 (s, 1H), 2.31 (dd, J = 10.4, 2.1 Hz, 1H), 2.19 (s, 4H), 2.04-1.94 (m, 1H), 1.71 (s, 3H), 1.50 (d, J = 6.0 Hz, 1H), 1.40 (dd, J = 12.0, 5.3 Hz, 2H), 1.34 (d, J = 6.0 Hz, 7H), 1.20 (t, J = 7.0 Hz, 3H). |
| 151 | 486.50 | 1.76 | 1H NMR (400 MHz, CDCl3) δ 7.31 (td, J = 8.0, 6.0 Hz, 1H), 7.16-7.09 (m, 2H), 7.00-6.90 (m, 3H), 6.86 (d, J = 8.2 Hz, 1H), 4.56 (dt, J = 12.2, 6.1 Hz, 2H), 3.86 (s, 3H), 3.77 (s, 1H), 3.63-3.42 (m, 3H), 3.18 (s, 1H), 2.31 (d, J = 12.3 Hz, 1H), 2.20 (d, J = 15.9 Hz, 1H), 1.99 (dd, J = 12.7, 2.7 Hz, 1H), 1.72 (s, 2H), 1.61 (s, 2H), 1.53 (d, J = 11.0 Hz, 1H), 1.44-1.32 (m, 8H), 1.26-1.16 (m, 3H). |
| 152 | 482.20 | 2.13 | |
| 153 | 529.08 | 3.64 | |
| 154 | 460.13 | 3.86 | |
| 155 | 481.10 | 3.92 | |
| 156 | 472.16 | 3.60 | |
| 157 | 517.12 | 3.44 | |
| 158 | 470.14 | 4.38 | |
| 159 | 474.11 | 4.04 | |
| 160 | 488.15 | 3.49 | |
| 161 | 512.08 | 3.74 | 1H NMR (400 MHz, CDCl3) δ 8.03 (d, J = 8.3 Hz, 2H), 7.67-7.60 (m, 2H), 7.33 (d, J = 4.8 Hz, 2H), 7.09-7.00 (m, 2H), 6.20 (t, J = 53.3 Hz, 1H), 4.51 (dd, J = 49.8, 11.6 Hz, 2H), 3.90-3.04 (m, 7H), 2.44-2.09 (m, 2H), 2.03-1.95 (m, 1H), 1.70 (ddt, J = 36.4, 24.7, 12.2 Hz, 4H), 1.40 (dd, J = 23.7, 11.9 Hz, 2H), 1.22 (dd, J = 14.4, 7.6 Hz, 3H). |
| 162 | 474.11 | 3.44 | 1H NMR (400 MHz, CDCl3) δ 7.60 (t, J = 8.0 Hz, 1H), 7.34 (dd, J = 8.6, 5.5 Hz, 2H), 7.13 (dd, J = 7.9, 1.4 Hz, 1H), 7.09-6.99 (m, 3H), 4.46 (d, J = 60.1 Hz, 2H), 3.76 (s, 1H), 3.62-3.41 (m, 4H), 3.12 (s, 2H), 2.25 (t, J = 24.6 Hz, 2H), 2.00 (d, J = 5.2 Hz, 2H), 1.97 (dd, J = 12.4, 9.5 Hz, 3H), 1.63 (s, 7H), 1.48-1.32 (m, 3H), 1.21 (t, J = 7.0 Hz, 3H). |
| 163 | 486.14 | 3.82 | |
| 164 | 470.40 | 1.87 | 1H NMR (400 MHz, CDCl3) δ 7.40 (d, J = 7.1 Hz, 2H), 7.35 (t, J = 7.5 Hz, 2H), 7.32-7.24 (m, 3H), 7.11 (dd, J = 12.5, 5.2 Hz, 2H), 4.86 (s, 1H), 4.39 (s, 1H), 3.83 (s, 1H), 3.63-3.17 (m, 5H), 2.84 (s, 2H), 2.62 (s, 1H), 2.08 (d, J = 13.4 Hz, 1H), 1.89 (d, J = 14.6 Hz, 1H), 1.61 (dd, J = 41.8, 30.5 Hz, 8H), 1.24 (d, J = 14.5 Hz, 10H). |
| 165 | 456.40 | 2.16 | 1H NMR (400 MHz, CDCl3) δ 7.43-7.38 (m, 2H), 7.38-7.32 (m, 2H), 7.27 (tdd, J = 4.3, 2.9, 1.4 Hz, 1H), 7.17-7.08 (m, 2H), 6.96 (t, J = 8.2 Hz, 1H), 4.87 (d, J = 11.1 Hz, 1H), 4.57 (dt, J = 12.2, 6.1 Hz, 1H), 3.86-3.79 (m, 1H), 3.59-3.35 (m, 3H), 3.21 (s, 1H), 2.75 (s, 1H), 2.08 (dd, J = 13.8, 2.5 Hz, 1H), 1.88 (d, J = 14.3 Hz, 1H), 1.75-1.56 (m, 4H), 1.50 (t, J = 12.6 Hz, 2H), 1.37 (d, J = 6.1 Hz, 6H), 1.22 (t, J = 7.0 Hz, 3H). |
| 166 | 468.20 | 2.03 | 1H NMR (400 MHz, CDCl3) δ 7.45-7.38 (m, 2H), 7.38-7.32 (m, 2H), 7.31-7.23 (m, 1H), 6.98-6.88 (m, 2H), 6.86 (d, J = 8.3 Hz, 1H), 4.88 (d, J = 10.5 Hz, 1H), 4.55 (dt, J = 12.2, 6.1 Hz, 1H), 3.91-3.78 (m, 4H), 3.57-3.39 (m, 3H), 3.22 (s, 1H), 2.76 (s, 1H), 2.12-1.82 (m, 2H), 1.72-1.55 (m, 4H), 1.48 (d, J = 11.4 Hz, 2H), 1.37 (d, J = 6.1 Hz, 6H), 1.22 (t, J = 7.0 Hz, 3H). |

TABLE 2-continued

| Cmpd. No. | LC/MS M + 1 | LC/RT min | NMR |
|---|---|---|---|
| 167 | 494.20 | 1.82 | 1H NMR (400 MHz, CDCl3) δ 8.03 (d, J = 8.3 Hz, 2H), 7.68-7.58 (m, 2H), 7.35 (dd, J = 9.8, 3.8 Hz, 4H), 7.29 (ddd, J = 12.7, 6.1, 3.3 Hz, 1H), 6.21 (t, J = 53.3 Hz, 1H), 4.67-4.35 (m, 2H), 3.78 (ddd, J = 36.5, 16.9, 9.1 Hz, 1H), 3.65-3.06 (m, 5H), 2.29 (dt, J = 42.8, 14.1 Hz, 2H), 2.08-1.93 (m, 1H), 1.71 (dddd, J = 42.9, 30.9, 23.5, 8.2 Hz, 3H), 1.42 (dt, J = 21.5, 10.8 Hz, 3H), 1.32-1.12 (m, 3H). |
| 168 | 438.40 | 1.98 | 1H NMR (400 MHz, CDCl3) δ 7.42-7.24 (m, 7H), 6.90-6.83 (m, 2H), 4.57 (dp, J = 12.0, 6.0 Hz, 2H), 4.36 (s, 1H), 3.78 (s, 1H), 3.67-3.05 (m, 5H), 2.37-2.07 (m, 2H), 1.99 (ddd, J = 12.6, 4.3, 1.6 Hz, 1H), 1.62 (d, J = 62.5 Hz, 3H), 1.54-1.37 (m, 3H), 1.34 (d, J = 6.1 Hz, 7H), 1.20 (q, J = 6.6 Hz, 3H). |
| 169 | 438.00 | 1.98 | 1H NMR (400 MHz, CDCl3) δ 7.46-7.32 (m, 4H), 7.28 (ddd, J = 11.7, 5.7, 3.5 Hz, 2H), 6.97-6.85 (m, 3H), 4.64-4.31 (m, 3H), 3.77 (d, J = 31.0 Hz, 1H), 3.52 (s, 4H), 3.43-2.97 (m, 1H), 2.31 (s, 2H), 2.13 (d, J = 13.3 Hz, 1H), 2.06-1.90 (m, 1H), 1.90-1.50 (m, 3H), 1.50-1.34 (m, 3H), 1.33 (d, J = 6.1 Hz, 6H), 1.21 (t, J = 6.9 Hz, 3H). |
| 170 | 438.40 | 1.95 | 1H NMR (400 MHz, CDCl3) δ 7.48-7.33 (m, 4H), 7.33-7.21 (m, 3H), 7.16 (d, J = 7.4 Hz, 1H), 6.93 (ddt, J = 23.5, 19.8, 7.4 Hz, 2H), 4.65-4.54 (m, 1H), 4.54-4.38 (m, 2H), 3.90-3.66 (m, 1H), 3.66-3.44 (m, 2H), 3.44-3.02 (m, 3H), 2.40-2.24 (m, 2H), 2.06-1.10 (m, 18H). |
| 171 | 472.14 | 4.10 | |
| 172 | 499.12 | 3.25 | |
| 173 | 470.18 | 3.27 | |
| 174 | 452.19 | 3.25 | |
| 175 | 464.20 | 3.37 | |
| 176 | 450.16 | 3.18 | |
| 177 | 456.18 | 3.23 | |
| 178 | 468.19 | 3.23 | |
| 179 | 452.19 | 3.23 | |
| 180 | 438.20 | 3.03 | |
| 181 | 512.07 | 3.90 | |
| 182 | 486.14 | 3.25 | |
| 183 | 472.11 | 3.10 | |
| 184 | 468.19 | 3.33 | |
| 185 | 456.70 | 1.87 | 1H NMR (400 MHz, CDCl3) δ 7.46-7.33 (m, 4H), 7.32-7.24 (m, 1H), 7.14 (dd, J = 16.1, 5.3 Hz, 2H), 6.96 (t, J = 8.2 Hz, 1H), 4.58 (dt, J = 12.2, 6.1 Hz, 2H), 4.47-4.16 (m, 1H), 3.77 (s, 2H), 3.65-3.36 (m, 3H), 3.20 (s, 1H), 2.28 (dd, J = 27.2, 12.2 Hz, 2H), 1.98 (dd, J = 12.7, 2.8 Hz, 1H), 1.67 (d, J = 39.5 Hz, 3H), 1.55-1.42 (m, 2H), 1.39 (dd, J = 13.6, 7.4 Hz, 6H), 1.21 (t, J = 7.0 Hz, 3H). |
| 186 | 454.50 | 1.66 | 1H NMR (400 MHz, CDCl3) δ 7.48-7.33 (m, 4H), 7.33-7.28 (m, 1H), 7.01-6.90 (m, 2H), 6.86 (d, J = 8.2 Hz, 1H), 4.66-4.46 (m, 2H), 4.12-3.90 (m, 2H), 3.86 (s, 3H), 3.76-3.61 (m, 1H), 3.48 (s, 1H), 3.37 (d, J = 4.5 Hz, 3H), 3.21 (t, J = 11.8 Hz, 1H), 2.28 (dd, J = 39.8, 13.2 Hz, 2H), 2.00 (dd, J = 12.6, 2.7 Hz, 1H), 1.85-1.62 (m, 3H), 1.59-1.44 (m, 1H), 1.42-1.33 (m, 7H). |
| 187 | 468.70 | 1.91 | |
| 188 | 482.70 | 2.02 | |
| 189 | 498.18 | 1.75 | |
| 190 | 452.30 | 2.18 | 1H NMR (400 MHz, CDCl3) δ 7.43-7.32 (m, 4H), 7.32-7.25 (m, 1H), 7.22-7.15 (m, 2H), 6.80 (d, J = 8.1 Hz, 1H), 4.55 (dt, J = 12.1, 6.0 Hz, 2H), 4.26 (d, J = 36.7 Hz, 1H), 3.78 (s, 1H), 3.68-3.33 (m, 4H), 3.19 (s, 1H), 2.32 (d, J = 12.4 Hz, 1H), 2.19 (s, 4H), 2.12-1.92 (m, 1H), 1.67 (d, J = 21.8 Hz, 3H), 1.55-1.36 (m, 2H), 1.34 (d, J = 6.0 Hz, 6H), 1.21 (q, J = 7.1 Hz, 3H). |
| 191 | 466.50 | 2.18 | |
| 192 | 452.30 | 2.38 | |
| 193 | 416.70 | 2.00 | |
| 194 | 404.50 | 2.04 | |

Assays for Detecting and Measuring NaV Inhibition Properties of Compound

E-VIPR Optical Membrane Potential Assay Method with Electrical Stimulation

Sodium channels are voltage-dependent proteins that can be activated by inducing membrane voltage changes by applying electric fields. The electrical stimulation instrument and methods of use are described in Ion Channel Assay Methods PCT/US01/21652, herein incorporated by reference and are referred to as E-VIPR. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

24 hours before the assay on E-VIPR, HEK cells expressing human NaV subtype, like NaV 1.7, are seeded in 384-well poly-lysine coated plates at 15,000-20,000 cells per well. Other subtypes are performed in an analogous mode in a cell line expressing the NaV of interest. HEK cells are grown in media (exact composition is specific to each cell type and NaV subtype) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% $CO_2$, to 100% confluence. They are usually split by trypsinization 1:10 or 1:20, depending on scheduling needs, and grown for 2-3 days before the next split.

Reagents and Solutions 100 mg/mL Pluronic F-127 (Sigma #P2443), in dry DMSO

Compound Plates: 384-well round bottom plate, e.g. Corning 384-well Polypropylene Round Bottom #3656

Cell Plates: 384-well tissue culture treated plate, e.g. Greiner #781091-1B 10 mM $DiSBAC_6(3)$ (Aurora #00-100-010) in dry DMSO 10 mM CC2-DMPE (Aurora #00-100-008) in dry DMSO 200 mM ABSC1 in $H_2O$ Bath1 buffer. Glucose 10 mM (1.8 g/L), Magnesium Chloride (Anhydrous), 1 mM (0.095 g/L), Calcium Chloride, 2 mM (0.222 g/L), HEPES 10 mM (2.38 g/L), Potassium Chloride, 4.5 mM (0.335 g/L), Sodium Chloride 160 mM (9.35 g/L).

Hexyl Dye Solution: Bath1 Buffer+0.5% β-cyclodextrin (make this prior to use, Sigma #C4767), 8 μM CC2-DMPE+2.5 μM $DiSBAC_6(3)$. To make the solution Add volume of 10% Pluronic F127 stock equal to volumes of CC2-DMPE+$DiSBAC_6(3)$. The order of preparation is first mix Pluronic and CC2-DMPE, then add $DiSBAC_6(3)$ while vortexing, then add Bath1+β-Cyclodextrin.

Assay Protocol

1) Pre-spot compounds (in neat DMSO) into compound plates. Vehicle control (neat DMSO), the positive control (20 mM DMSO stock tetracaine, 125 μM final in assay) and test compounds are added to each well at 160× desired final concentration in neat DMSO. Final compound plate volume will be 80 μL (80-fold intermediate dilution from 1 μL DMSO spot; 160-fold final dilution after transfer to cell plate). Final DMSO concentration for all wells in assay is 0.625%.

2) Prepare Hexyl Dye Solution.

3) Prepare cell plates. On the day of the assay, medium is aspirated and cells are washed three times with 100 μL of Bath1 Solution, maintaining 25 μL residual volume in each well.

4) Dispense 25 μL per well of Hexyl Dye Solution into cell plates. Incubate for 20-35 minutes at room temp or ambient conditions.

5) Dispense 80 μL per well of Bath1 into compound plates. Acid Yellow-17 (1 mM) is added and Potassium Chloride can be altered from 4.5 to 20 mM depending on the NaV subtype and assay sensitivity.

6) Wash cell plates three times with 100 μL per well of Bath1, leaving 25 of residual volume. Then transfer 25 uL per well from Compound Plates to Cell Plates. Incubate for 20-35 minutes at room temp/ambient condition 7) Read Plate on E-VIPR. Use the current-controlled amplifier to deliver stimulation wave pulses for typically 9 seconds and a scan rate of 400 Hz. A pre-stimulus recording is performed for 0.5 seconds to obtain the un-stimulated intensities baseline. The stimulatory waveform is applied for 9 seconds followed by 0.5 seconds of post-stimulation recording to examine the relaxation to the resting state. The stimulatory waveform of the electrical stimulation is specific for each cell type and can vary the magnitude, duration and frequency of the applied current to provide an optimal assay signal.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\ nm} - background_{460\ nm})}{(intensity_{580\ nm} - background_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated and reported as a function of time.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

IonWorks Assays.

Sodium currents were recorded using the automated patch clamp system, IonWorks (Molecular Devices Corporation, Inc.). Cells expressing Nav subtypes are harvested from tissue culture and placed in suspension at 0.5-4 million cells per mL Bath1. The IonWorks instrument measures changes in sodium currents in response to applied voltage clamp similarly to the traditional patch clamp assay, except in a 384-well format. Using the IonWorks, dose-response relationships were determined in voltage clamp mode by depolarizing the cell from the experiment specific holding potential to a test potential of about 0 mV before and following addition of the test compound. The influence of the compound on currents are measured at the test potential.

1-Benzazepin-2-one binding assay

The sodium channel inhibiting properties of the compounds of the invention can also be determined by assay methods described in Williams, B. S. et al., "Characterization of a New Class of Potent Inhibitors of the Voltage-Gated Sodium Channel NaV 1.7," *Biochemistry,* 2007, 46, 14693-14703, the entire contents of which are incorporated herein by reference.

The exemplified compounds of Table 1 herein are active against one or more sodium channels as measured using the assays described herein above as presented in Table 3.

TABLE 3

IC50: +++ <= 2.0 μM < ++ <= 5.0 μM < +

| Cmpd. No. | Binned Activity Data |
|---|---|
| 1 | +++ |
| 2 | +++ |
| 3 | +++ |
| 4 | +++ |
| 5 | +++ |
| 6 | ++ |
| 7 | +++ |
| 8 | +++ |
| 9 | +++ |
| 10 | ++ |
| 11 | + |
| 12 | + |
| 13 | ++ |
| 14 | + |
| 15 | ++ |
| 16 | ++ |
| 17 | +++ |
| 18 | +++ |
| 19 | +++ |
| 20 | +++ |
| 21 | + |
| 22 | +++ |
| 23 | +++ |
| 24 | +++ |
| 25 | + |
| 26 | +++ |
| 27 | +++ |
| 28 | +++ |
| 29 | +++ |
| 30 | +++ |
| 31 | +++ |
| 32 | ++ |
| 33 | ++ |
| 34 | +++ |
| 35 | +++ |
| 36 | +++ |
| 37 | +++ |
| 38 | ++ |
| 39 | +++ |
| 40 | + |
| 41 | +++ |

TABLE 3-continued

IC50: +++ <= 2.0 μM < ++ <= 5.0 μM < +

| Cmpd. No. | Binned Activity Data |
|---|---|
| 42 | +++ |
| 43 | +++ |
| 44 | +++ |
| 45 | +++ |
| 46 | +++ |
| 47 | + |
| 48 | +++ |
| 49 | +++ |
| 50 | + |
| 51 | ++ |
| 52 | ++ |
| 53 | ++ |
| 54 | ++ |
| 55 | ++ |
| 56 | + |
| 57 | +++ |
| 58 | ++ |
| 59 | ++ |
| 60 | +++ |
| 61 | +++ |
| 62 | +++ |
| 63 | ++ |
| 64 | +++ |
| 65 | +++ |
| 66 | +++ |
| 67 | + |
| 68 | ++ |
| 69 | +++ |
| 70 | ++ |
| 71 | + |
| 72 | ++ |
| 73 | +++ |
| 74 | ++ |
| 75 | +++ |
| 76 | ++ |
| 77 | ++ |
| 78 | +++ |
| 79 | +++ |
| 80 | +++ |
| 81 | ++ |
| 82 | ++ |
| 83 | + |
| 84 | ++ |
| 85 | +++ |
| 86 | + |
| 87 | +++ |
| 88 | + |
| 89 | +++ |
| 90 | +++ |
| 91 | ++ |
| 92 | +++ |
| 93 | +++ |
| 94 | +++ |
| 95 | + |
| 96 | + |
| 97 | +++ |
| 98 | + |
| 99 | + |
| 100 | +++ |
| 101 | +++ |
| 102 | ++ |
| 103 | +++ |
| 104 | +++ |
| 105 | +++ |
| 106 | +++ |
| 107 | +++ |
| 108 | ++ |
| 109 | +++ |
| 110 | +++ |
| 111 | ++ |
| 112 | +++ |
| 113 | + |
| 114 | ++ |
| 115 | +++ |
| 116 | +++ |
| 117 | + |

TABLE 3-continued

| IC50: +++ <= 2.0 μM < ++ <= 5.0 μM < + | |
|---|---|
| Cmpd. No. | Binned Activity Data |
| 118 | +++ |
| 119 | ++ |
| 120 | ++ |
| 121 | ++ |
| 122 | + |
| 123 | + |
| 124 | ++ |
| 125 | +++ |
| 126 | +++ |
| 127 | +++ |
| 128 | +++ |
| 129 | +++ |
| 130 | ++ |
| 131 | +++ |
| 132 | + |
| 133 | +++ |
| 134 | +++ |
| 135 | +++ |
| 136 | +++ |
| 137 | +++ |
| 138 | +++ |
| 139 | +++ |
| 140 | +++ |
| 141 | +++ |
| 142 | +++ |
| 143 | +++ |
| 144 | +++ |
| 145 | +++ |
| 146 | +++ |
| 147 | + |
| 148 | + |
| 149 | +++ |
| 150 | +++ |
| 151 | +++ |
| 152 | + |
| 153 | + |
| 154 | ++ |
| 155 | +++ |
| 156 | +++ |
| 157 | +++ |
| 158 | +++ |
| 159 | +++ |
| 160 | +++ |
| 161 | ++ |
| 162 | +++ |
| 163 | +++ |
| 164 | + |
| 165 | + |
| 166 | + |
| 167 | +++ |
| 168 | +++ |
| 169 | ++ |
| 170 | +++ |
| 171 | +++ |
| 172 | +++ |
| 173 | +++ |
| 174 | +++ |
| 175 | +++ |
| 176 | +++ |
| 177 | +++ |
| 178 | +++ |
| 179 | +++ |
| 180 | ++ |
| 181 | +++ |
| 182 | ++ |
| 183 | +++ |
| 184 | ++ |
| 185 | +++ |
| 186 | +++ |
| 187 | +++ |
| 188 | +++ |
| 189 | +++ |
| 190 | +++ |
| 191 | +++ |
| 192 | +++ |
| 193 | ++ |
| 194 | ++ |

Many modifications and variations of the embodiments described herein may be made without departing from the scope, as is apparent to those skilled in the art. The specific embodiments described herein are offered by way of example only.

We claim:

1. A compound of formula I:

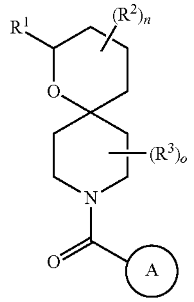

I or a pharmaceutically acceptable salt thereof, wherein, independently for each occurrence:

$R^1$ is an optionally substituted phenyl, pyridyl, thiazole, or pyrazole,

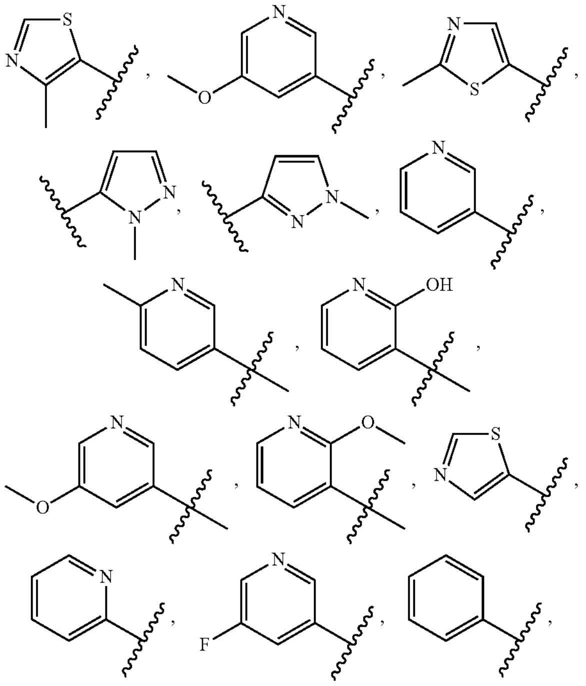

-continued

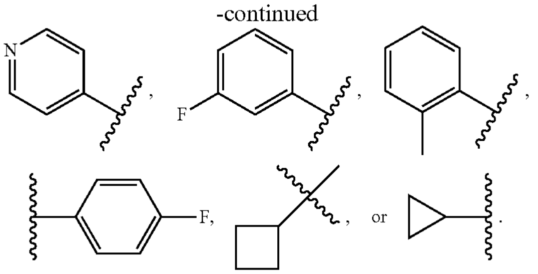

, , , , or .

$R^2$ is C1-C6 alkyl, deuterated C1-C6 alkyl, C1-C6 alkoxy, C1-C6 fluoroalkyl, $CF_3$, $CHF_2$, or a straight chain, branched, or cyclic (C1-C8)-$R^9$ wherein up to two $CH_2$ units may be replaced with O, CO, S, SO, $SO_2$, N, $CF_2$, or $NR^8$;

$R^3$ is C1-C6 alkyl or halo;

$R^8$ is H, C1-C6 alkyl, C3-C8 cycloalkyl, $CF_3$, or a straight chain, branched, or cyclic (C1-C8)-$R^9$ wherein up to two $CH_2$ units may be replaced with O, CO, S, SO, $SO_2$, N, $CF_2$, or NR, or 2 $R^8$ taken together with the atoms to which they are attached form a ring;

$R^9$ is H, $CF_3$, $CHF_2$, $CH_2F$, $CO_2R$, halo, OH, optionally substituted aryl, heteroaryl, C3-C8 cycloalkyl, heterocycloalkyl, $N(R)_2$, NRCOR, $CON(R)_2$, CN, or $SO_2R$;

R is H, C1-C6 alkyl, optionally substituted aryl, heteroaryl, C3-C8 cycloalkyl, or heterocycloalkyl;

ring A is

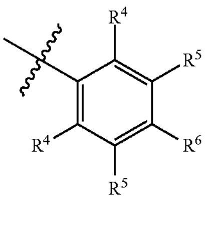

wherein:

$R^4$ is H, C1-C6 alkyl, C1-C6 alkoxy, C3-C8 cycloalkyl halo, CN, $OR^8$ $SO_2R^8$ $SO_7N(R^8)_2$, $CHF_2$ $CF_3$ $OCF_3$ $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$ N, $CF_2$, or $NR^8$;

$R^5$ is H, C1-C6 alkyl, C1-C6 alkoxy, C3-C8 cycloalkyl, halo, CN, $OR^8$, $SO_2R^8$ $SO_7N(R^8)_2$, $CHF_2$ $CF_3$ $OCF_3$ $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$ N, $CF_2$, or $NR^8$;

$R^6$ is H, C1-C6 alkyl, C1-C6 alkoxy, C3-C8 cycloalkyl, halo, CN, $OR^8$, $SO_2R^8$, $SO,N(R^8)_2$, $CHF_2$ $CF_3$ $OCF_3$ $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$ N, $CF_2$, or $NR^8$; or two occurrences of $R^4$ and $R^5$, or $R^5$ and $R^6$ together with the carbons to which they are attached form an optionally substituted ring comprising up to 2 heteroatoms; or

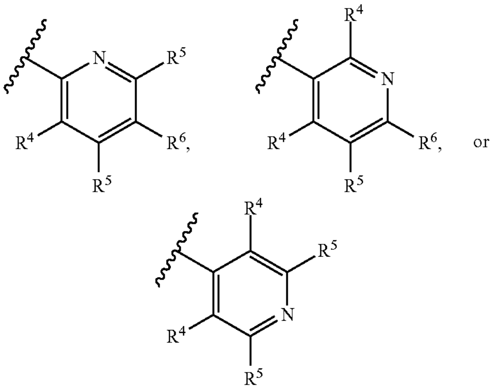

, , or wherein:

$R^4$ is H, C1-C6 alkyl, C3-C8 cycloalkyl, C1-C6 alkoxy, C1-C6 fluoroalkoxy, halo, CN, OH, $OR^8$, $N(R^8)_2$, $SO_2R^8$, $SO_2N(R^8)_2$, $CHF_2$, $CF_3$, $R^9$, heterocycloalkyl, or a straight chain, branched, or cyclic (C1-C8)-$R^9$ wherein up to three $CH_2$ units may be replaced with O, CO, S, SO, $SO_2$ N, $CF_2$, or $NR^8$;

$R^5$ is H, C1-C6 alkyl, C3-C8 cycloalkyl, C1-C6 alkoxy, C1-C6 fluoroalkoxy, halo, CN, OH, $OR^8$, $N(R^8)_2$, $SO_2R^8$, $SO_2N(R^8)_2$ $CHF_2$, $CF_3$, $R^9$, heterocycloalkyl, or a straight chain, branched, or cyclic (C1-C8)-$R^9$ wherein up to three $CH_2$ units may be replaced with O, CO, S, SO, $SO_2$ N, $CF_2$, or $NR^8$;

$R^6$ is H, C1-C6 alkyl, C3-C8 cycloalkyl, C1-C6 alkoxy, C1-C6 fluoroalkoxy, halo, CN, OH, $OR^8$, $N(R^8)_2$, $SO_2R^8$ $SO_2N(R^8)_2$ $CHF_2$ $CF_3$, $R^9$, heterocycloalkyl, or a straight chain, branched, or cyclic (C1-C8)-$R^9$ wherein up to three $CH_2$ units may be replaced with O, CO, S, SO, $SO_2$ N, $CF_2$, or $NR^8$; or two occurrences of $R^4$ and $R^5$, or $R^5$ and $R^6$ together with the carbons to which they are attached form an optionally substituted ring comprising up to 2 heteroatoms;

n is 1 or 2; and o is 0 or 1.

2. The compound of claim 1, wherein $R^2$ is $CH_2CH_3$, $OCH_3$, $OCH_2CH_3$, $OCH_2CH_2CH_3$, $OCH_2CH_2F$, $OCH_2CH_2OCH_3$, or $OCH(CH_3)_2$.

3. The compound of claim 1, wherein A is

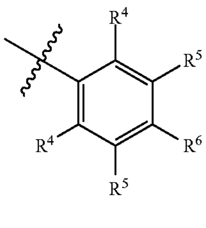

wherein:

$R^4$ is H, C1-C6 alkyl, C1-C6 alkoxy, C3-C8 cycloalkyl, halo, CN, $OR^8$, $SO_2R^8$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$;

$R^5$ is H, C1-C6 alkyl, C1-C6 alkoxy, C3-C8 cycloalkyl, halo, CN, $OR^8$, $SO_2R^8$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-

C8)-$R^9$ wherein up to three $CH_2$ units may be replaced with O, CO, S, SO, $SO_2$, N, $CF_2$, or $NR^8$;

$R^6$ is H, C1-C6 alkyl, C1-C6 alkoxy, C3-C8 cycloalkyl, halo, CN, $OR^8$, $SO_2R^8$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$; or two occurrences of $R^4$ and $R^5$, or $R^5$ and $R^6$ together with the carbons to which they are attached form an optionally substituted ring comprising up to 2 heteroatoms.

4. The compound of claim 3, wherein $R^4$ is H, $CH_3$, $OCH_3$, $OCH_2CH_3$, F, Cl, $OCHF_2$, $CHF_2$, $CF_3$, $CH_2OCH_3$, $OCH(CH_3)_2$, $CH_2OCH_3$, or

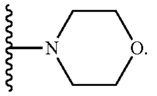

5. The compound of claim 3, wherein $R^5$ is H, $CH_3$, $OCH_3$, $OCH(CH_3)_2$, F, Cl, $CF_3$, CN, or $CH_2OH$.

6. The compound of claim 3, wherein $R^6$ is H, F, Cl, $CH_3$, $CF_3$, $CH_2CH_3$, $OCH_3$, $OCH_2CF_3$, $OCH_2CH_3$, $OCH_2CH_2CH_3$, $OCH_2CH_2CH(CH_3)_2$, OtBu, tBu, $OCH(CH_3)_2$, $OCH_2CH(CH_3)_2$, $OCH(CH_3)CH_2CH_3$, $CH(OH)CH(CH_3)_2$, $C(OH)(CH_3)CH_2CH_3$, $OCH_2C(CH_3)_2OH$, $C(CH_3)_2OH$, $CH_2C(CH_3)_2OH$ $OCH_2CH_2OCH_3$, $OCH_2CH_2OH$, $OCH_2CH_2CH_2OH$, $SO_2CH_3$, $SO_2CF_3$, $SO_2CH(CH_3)_2$, $SO_2CH_2CH_3$, $CH_2OCH_2CF_3$, $CH_2OCH_2CH_2CF_3$, $OCHF_2$, $OCH_2CF(CH_3)_2$,

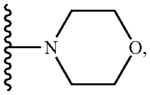 [SMILES: *N1CCOCC1] 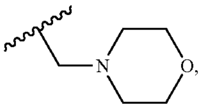 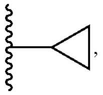

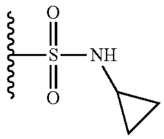 , 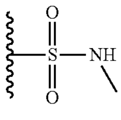 , 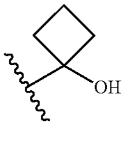 ,

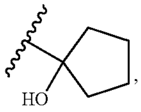 , 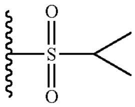 , 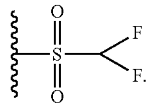

7. The compound of claim 3, wherein

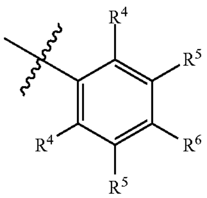

is selected from:

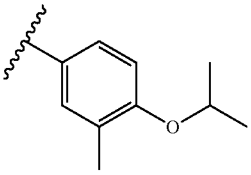 , 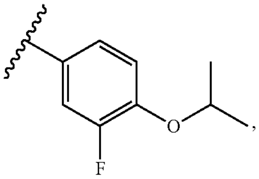 ,

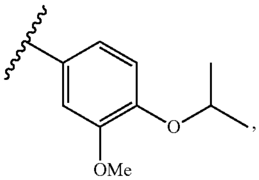 , 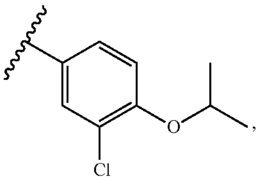 ,

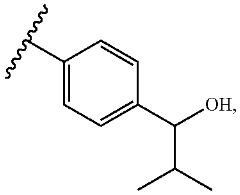 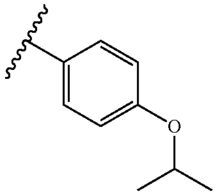 ,

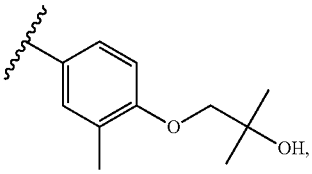

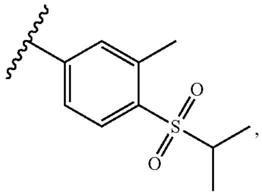 ,

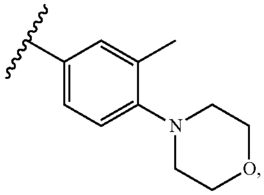 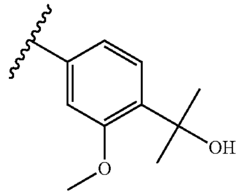 ,

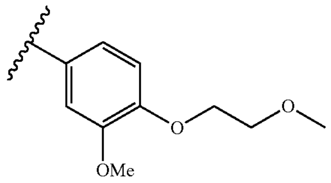 , 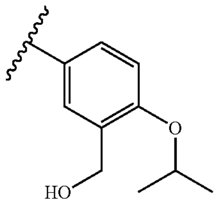 ,

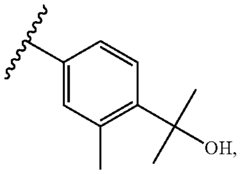 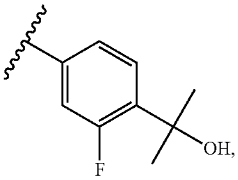

-continued
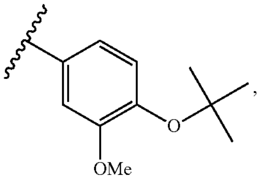, 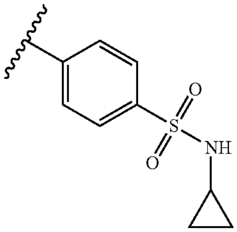,
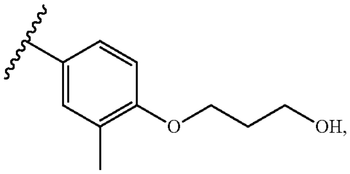
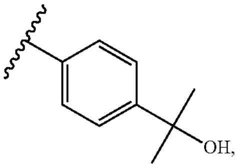 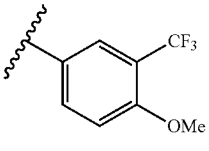,
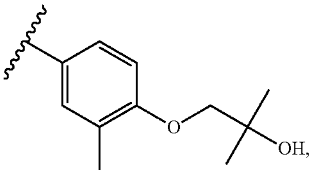 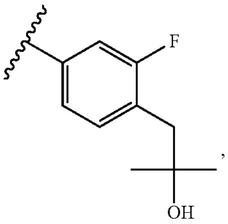,
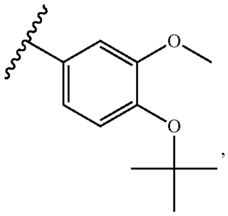, 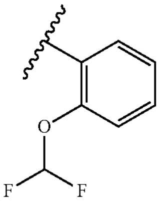,
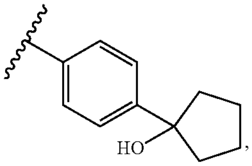, 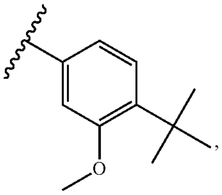,
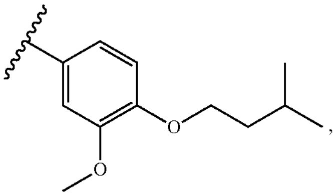,
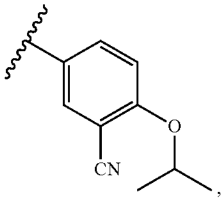, 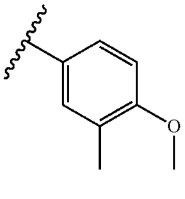,
-continued
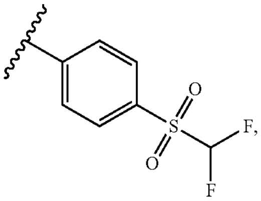 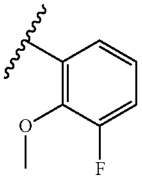,
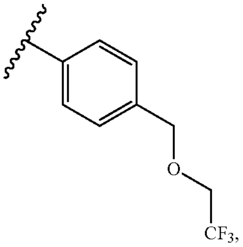
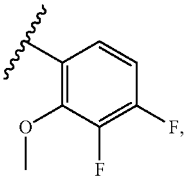 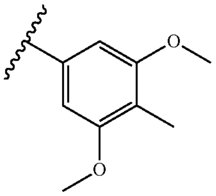,
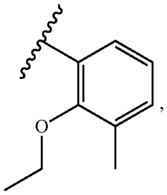, 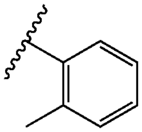, 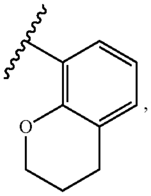,
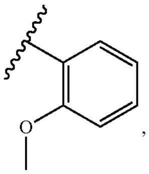, 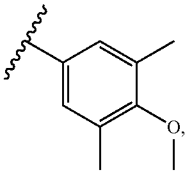 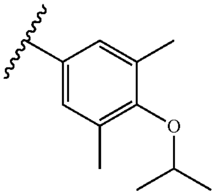,
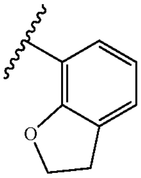, 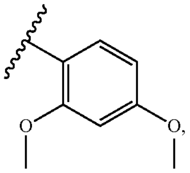
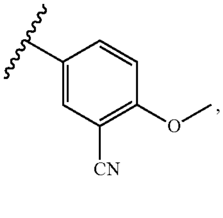, 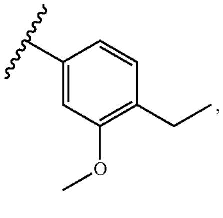,
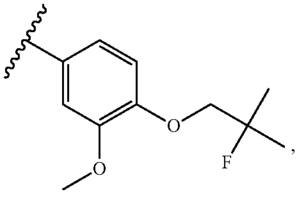, -continued
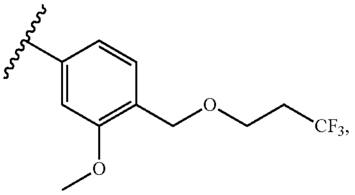
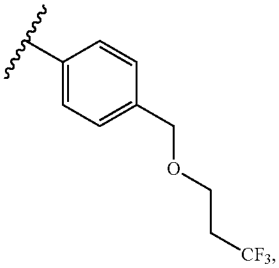 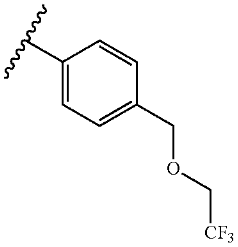,
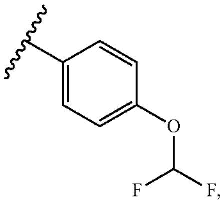 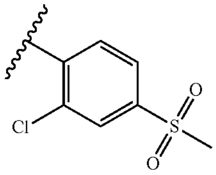,
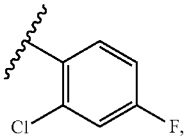 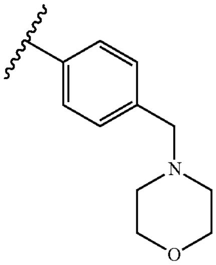,
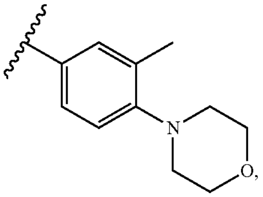 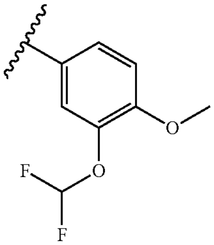,
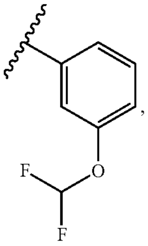 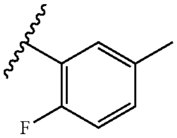, 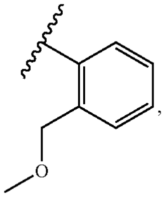
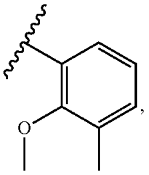 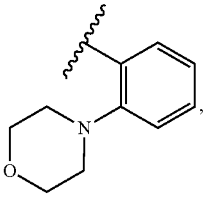
-continued
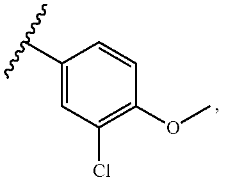 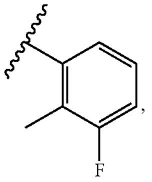
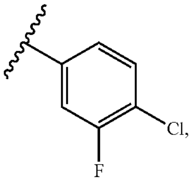 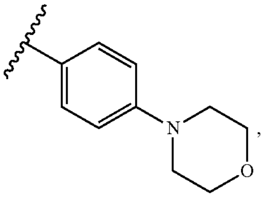
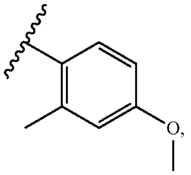 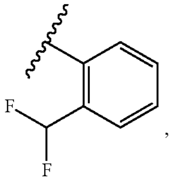
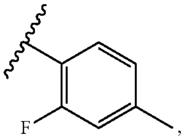 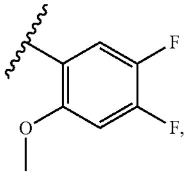
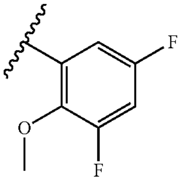, 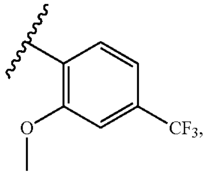
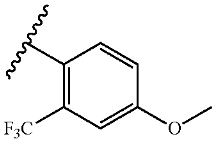, 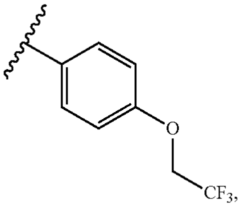
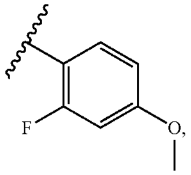
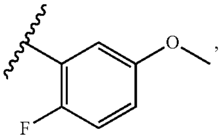 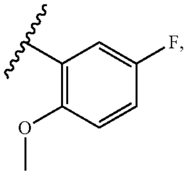
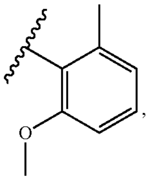 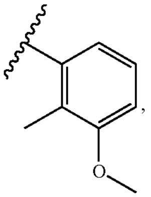 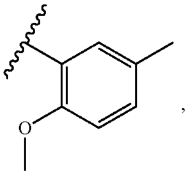

-continued
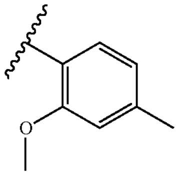, 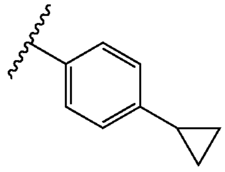,
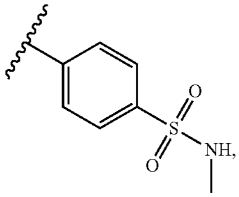
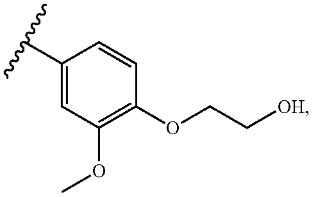
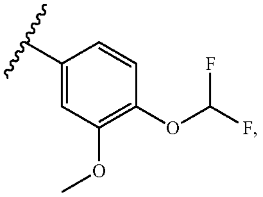 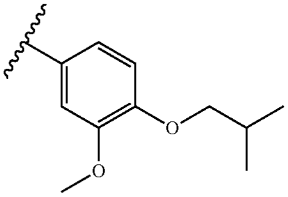,
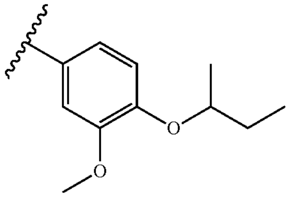,
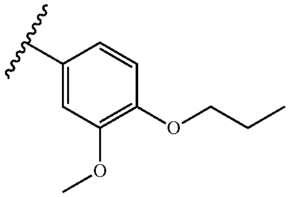,
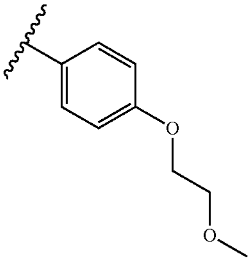, 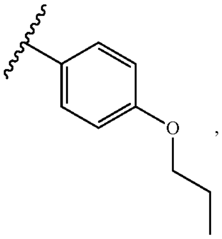,
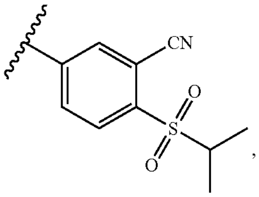, 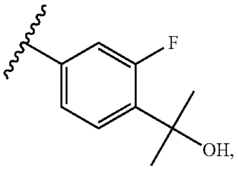
-continued
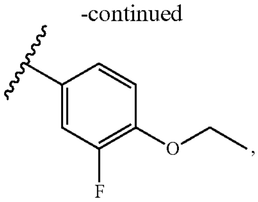
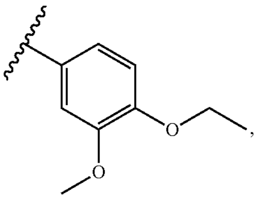, 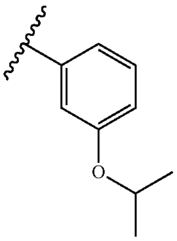,
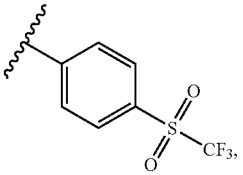 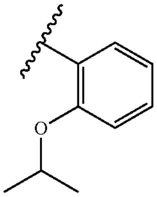,
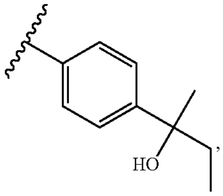, 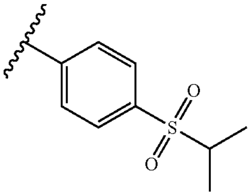,
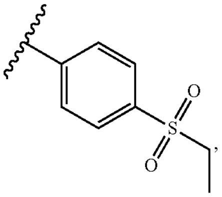, or 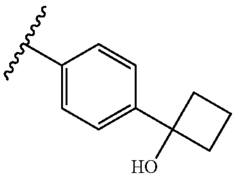.
8. The compound of claim 1, wherein A is
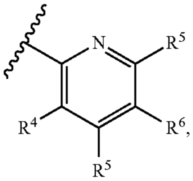 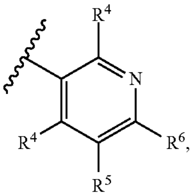 or
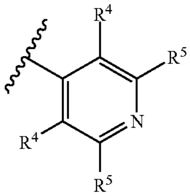
wherein:
$R^4$ is H, C1-C6 alkyl, C3-C8 cycloalkyl, C1-C6 alkoxy, C1-C6 fluoroalkoxy, halo, CN, OH, $OR^8$, $N(R^8)_2$, $SO_2R^8$, $SO_2N(R^8)_2$, $CHF_2$, $CF_3$, $R^9$, heterocycloalkyl, or a straight chain, branched, or cyclic (C1-C8)-$R^9$ wherein up to three $CH_2$ units may be replaced with O, CO, S, SO, $SO_2$, N, $CF_2$, or $NR^8$;

$R^5$ is H, C1-C6 alkyl, C3-C8 cycloalkyl, C1-C6 alkoxy, C1-C6 fluoroalkoxy, halo, CN, OH, $OR^8$, $N(R^8)_2$, $SO_2R^8$, $SO_2N(R^8)_2$, $CHF_2$, $CF_3$, $R^9$, heterocycloalkyl, or a straight chain, branched, or cyclic (C1-C8)-$R^9$ wherein up to three $CH_2$ units may be replaced with 0, CO, S, SO, $SO_2$, N, $CF_2$, or $NR^8$;

$R^6$ is H, C1-C6 alkyl, C3-C8 cycloalkyl, C1-C6 alkoxy, C1-C6 fluoroalkoxy, halo, CN, OH, $OR^8$, $N(R^8)_2$, $SO_2R^8$, $SO_2N(R^8)_2$, $CHF_2$, $CF_3$, $R^9$, heterocycloalkyl, or a straight chain, branched, or cyclic (C1-C8)-$R^9$ wherein up to three $CH_2$ units may be replaced with 0, CO, S, SO, $SO_2$, N, $CF_2$, or $NR^8$; or two occurrences of $R^4$ and $R^5$, or $R^5$ and $R^6$ together with the carbons to which they are attached form an optionally substituted ring comprising up to 2 heteroatoms.

9. The compound of claim 8, wherein $R^4$ is H, $OCH_3$, $OCH_2CH_3$, $OCH_2CF_3$, $N(CH_3)_2$, $NH(CH_2CH(CH_3)_2)$, or

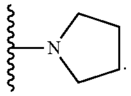

10. The compound of claim 8, wherein $R^5$ is H, $CH_3$, $OCH_3$, Cl, tBu, $N(CH_3)_2$, or

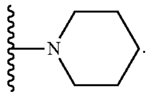

11. The compound of claim 8, wherein $R^6$ is H, CN, $OCH_3$, $OCH_2CH_3$, $OCH(CH_3)_2$, $CF_3$, $OCH_2CF_3$,

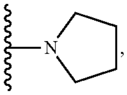, 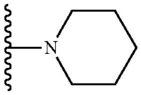, or 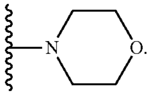

12. The compound of claim 8, wherein A is selected from the following:

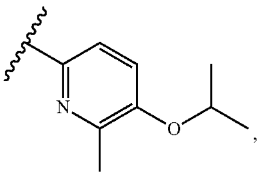, 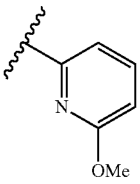,

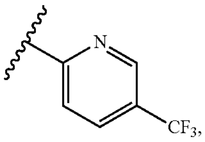 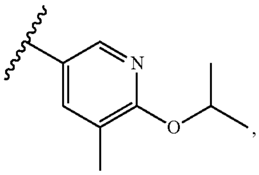,

-continued

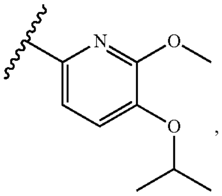, 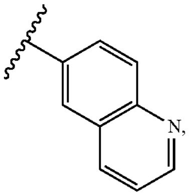

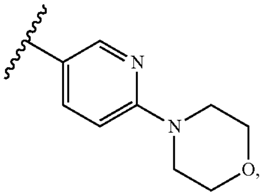

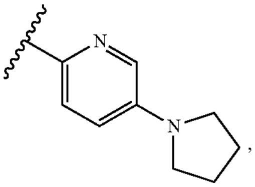

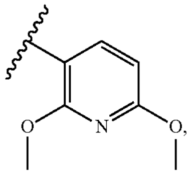

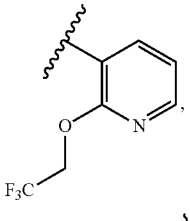, 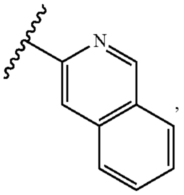,

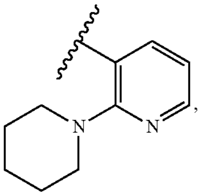

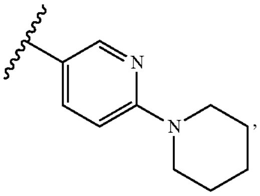, 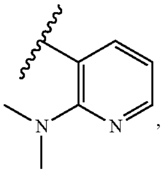,

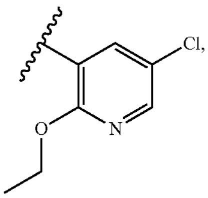 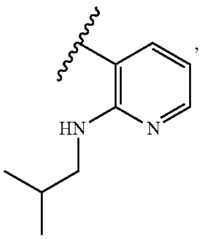

-continued

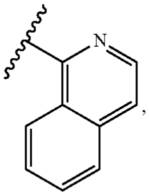,
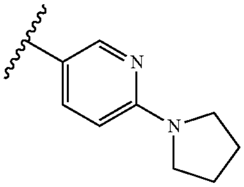,
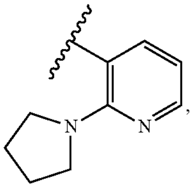,
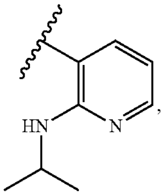,
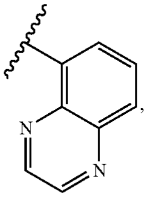,
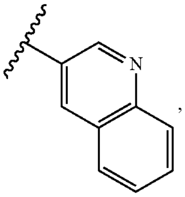,
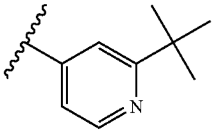,
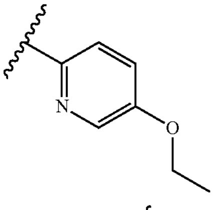,
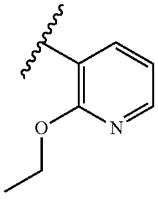,
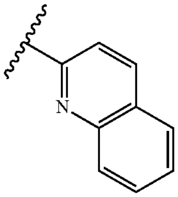,
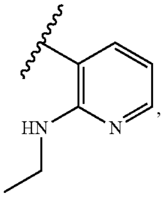,
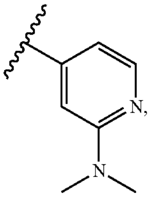
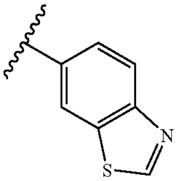,
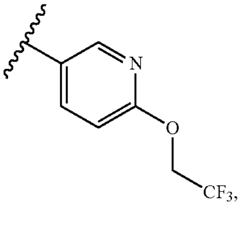
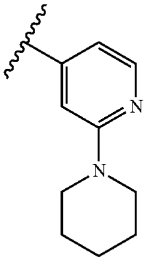, -continued

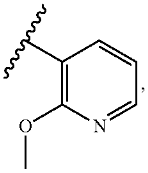,
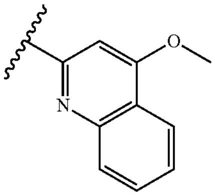,
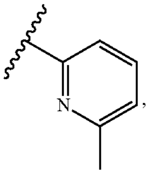,
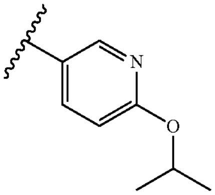, or
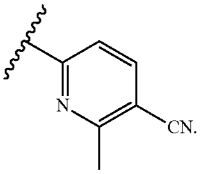

13. The compound of claim 1, wherein the compound has formula IA:

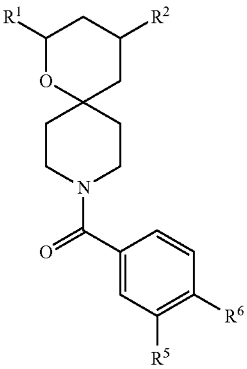
IA wherein:

$R^1$ is as defined in claim 1;

$R^2$ is C1-C6 alkoxy or C1-C6 fluoroalkoxy;

$R^5$ is H, C1-C6 alkyl, C1-C6 alkoxy, C3-C8 cycloalkyl, halo, CN, $OR^8$, $SO_2R^8$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$;

$R^6$ is H, C1-C6 alkyl, C1-C6 alkoxy, C3-C8 cycloalkyl, halo, CN, $OR^8$, $SO_2R^8$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$; and $R^8$ is H, C1-C6 alkyl, C3-C8 cycloalkyl, $CF_3$, or a straight chain, branched, or cyclic (C1-C8)-$R^9$ wherein up to two $CH_2$ units may be replaced with O, CO, S, SO, $SO_2$, N, $CF_2$, or NR, or 2 $R^8$ taken together with the atoms to which they are attached form a ring.

14. The compound of claim 13, wherein $R^1$ is

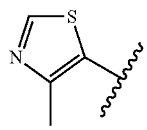, 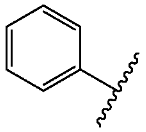, 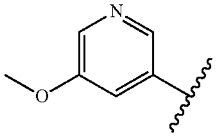, 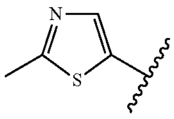, 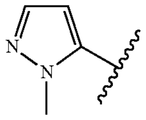, 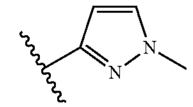, 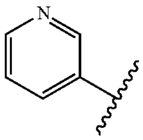, 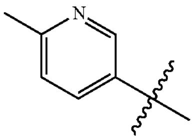, 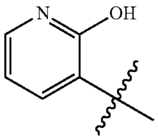, 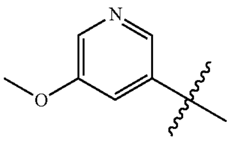, 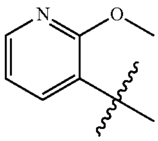, 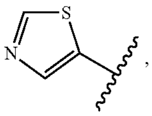, 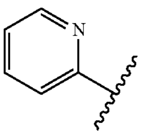, 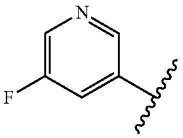, 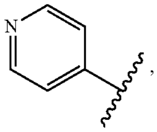, 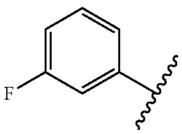, 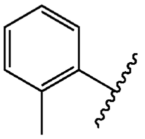, 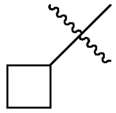, or 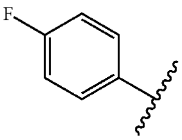.

15. The compound of claim 13, wherein $R^2$ is selected from $OCH_3$, $OCH_2CH_3$, $OCH_2CH_2CH_3$, $OCH_2CH_2F$, $OCH_2CH_2OCH_3$, or $OCH(CH_3)_2$.

16. The compound of claim 13, wherein $R^5$ is H, $CH_3$, $OCH_3$, $CF_3$, $OCHF_2$, F, Cl, CN, or $CH_2OH$.

17. The compound of claim 13, wherein $R^6$ is H, Cl $CH_2CH_3$, tBu, OtBu, $OCH_3$, $OCH(CH_3)_2$, $OCH_2CH_2(CH_3)_2$, $OCH_2CH_3$, $OCH_2CH_2CH_3$, $OCH_2CH_2CH(CH_3)_2$, $OCH_2CF(CH_3)_2$, $CH_2OCH_2CH_2CF_3$, $OCH_2CH_2OH$, $CH_2CH_2CH_2OH$, $OCHF_2$, $OCH_2CH_2OCH_3$, $OCH(CH_3)CH_2CH_3$, $OCH_2C(CH_3)_2OH$, $C(CH_3)_2OH$, $CH_2C(CH_3)_2OH$,

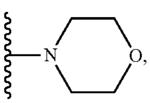, or 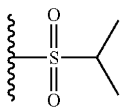.

18. The compound of claim 13, wherein the

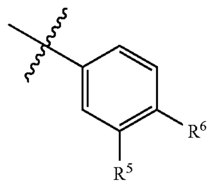

moiety is selected from:

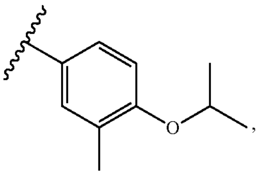, 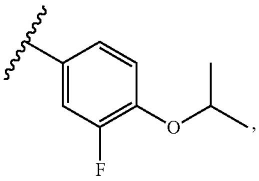, 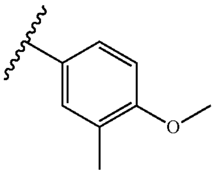, 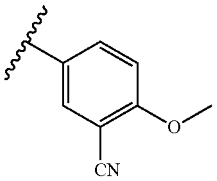, 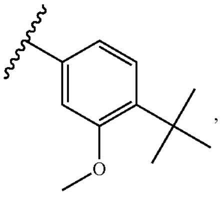, 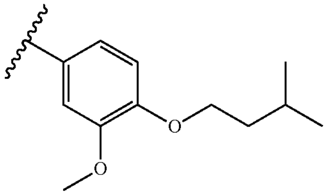, 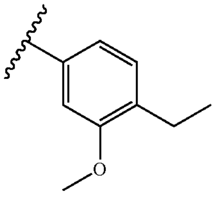, 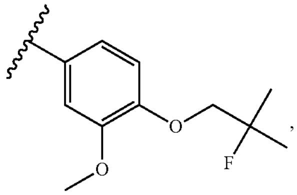, 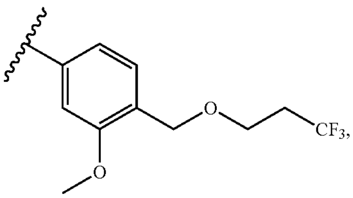, 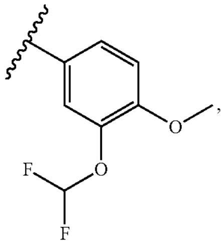, 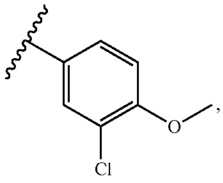, 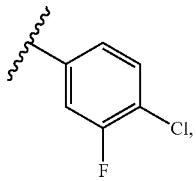, 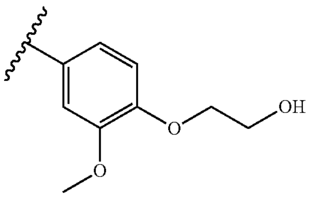, -continued
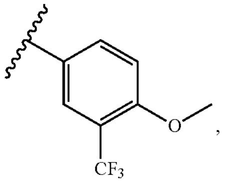
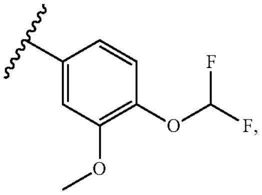
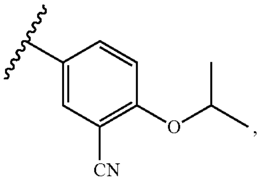
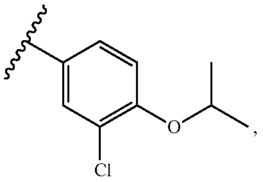
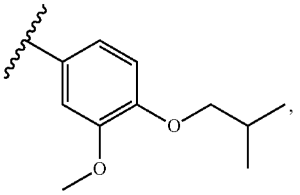
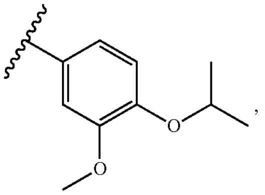
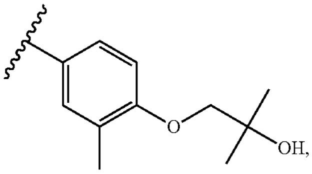
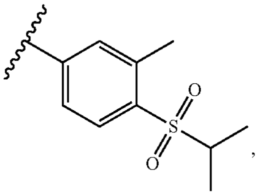
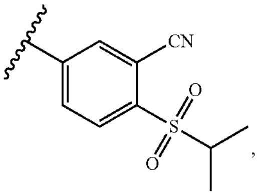
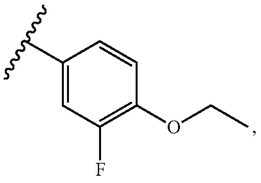
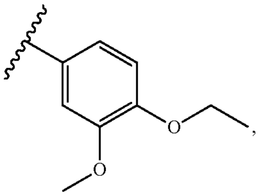
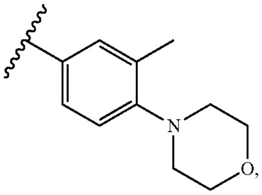
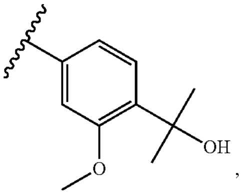
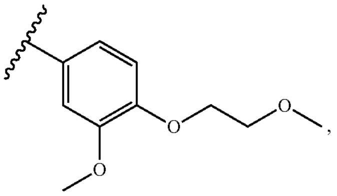
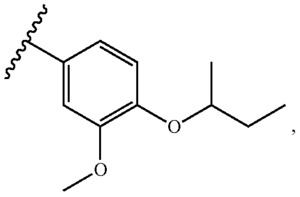
-continued
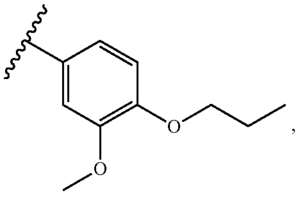
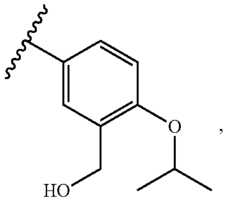
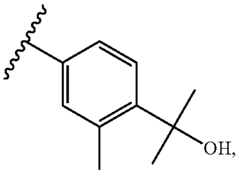
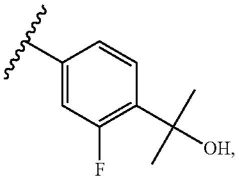
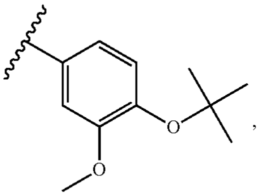
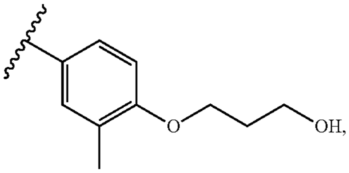
or
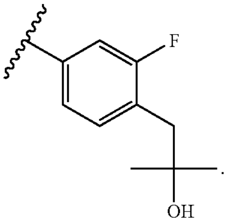
19. A compound selected from the following table:
1 cis
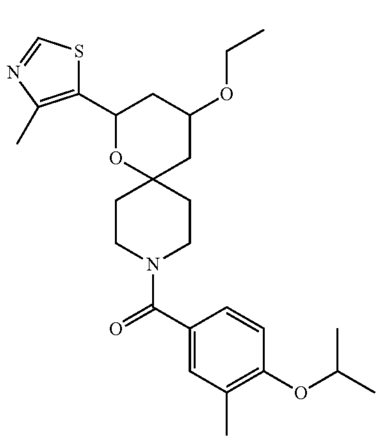

2 cis
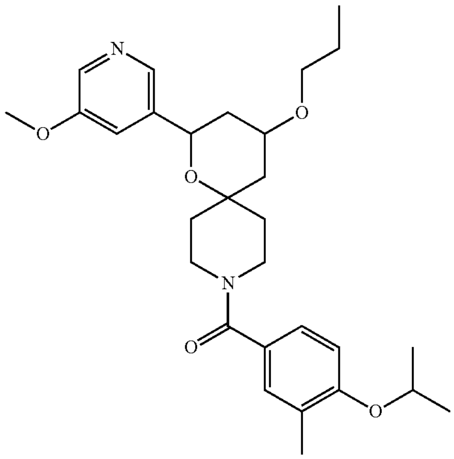
3 cis
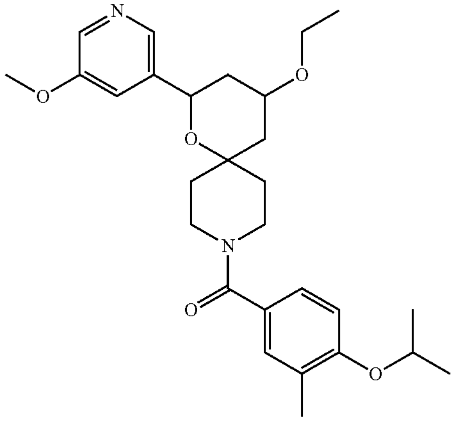
4 cis
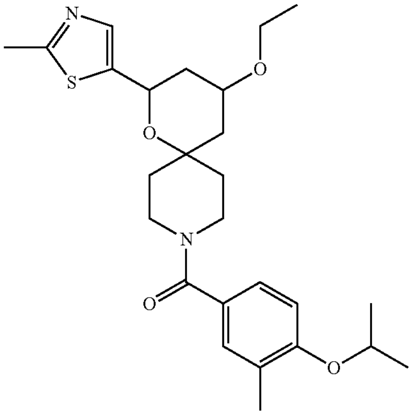
5 cis
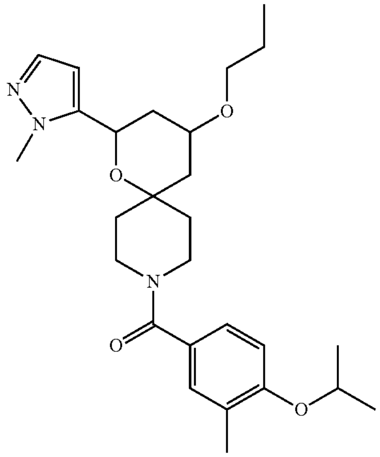
6 cis
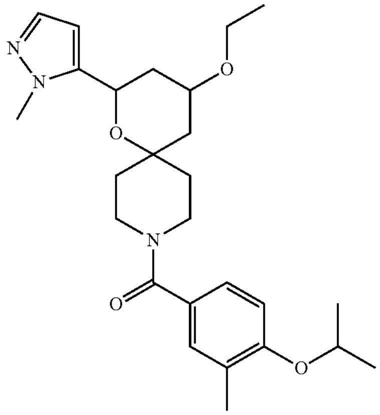
7 cis
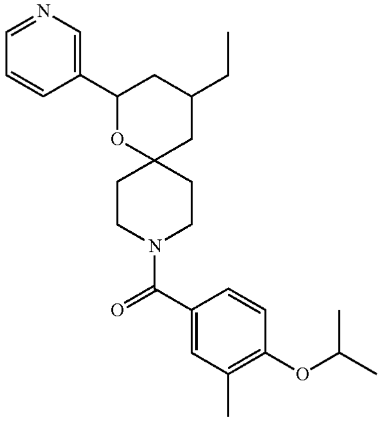

-continued
8 cis
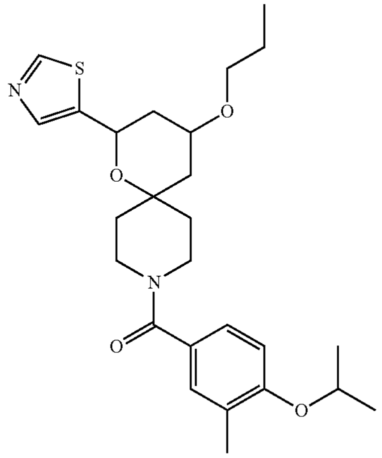
9 cis
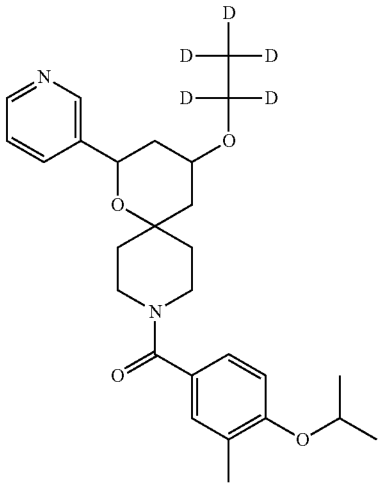
10 cis
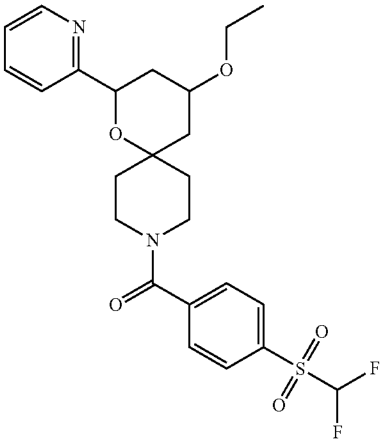
-continued
11 cis
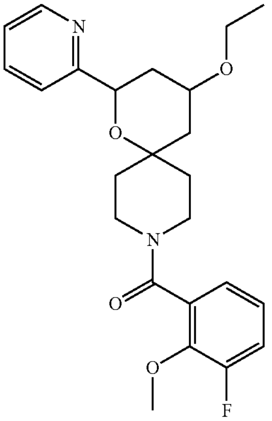
12 cis
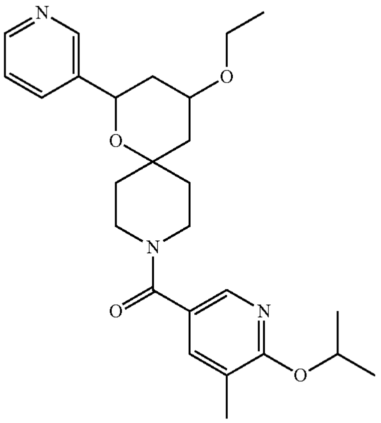
13 cis
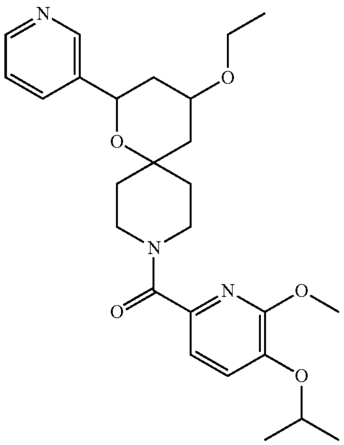

-continued
14 cis
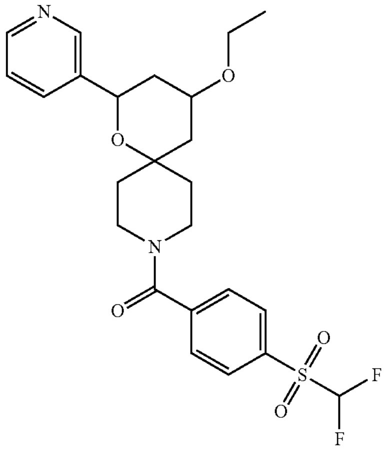
15 cis
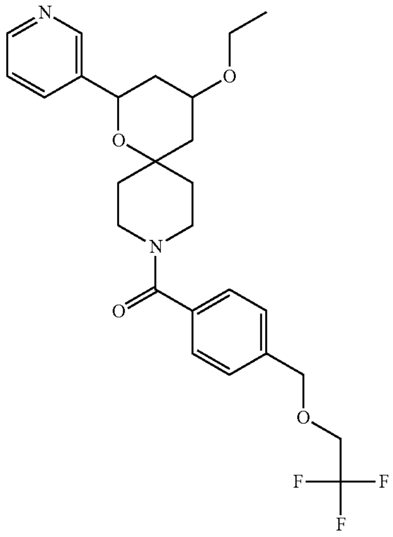
16 cis
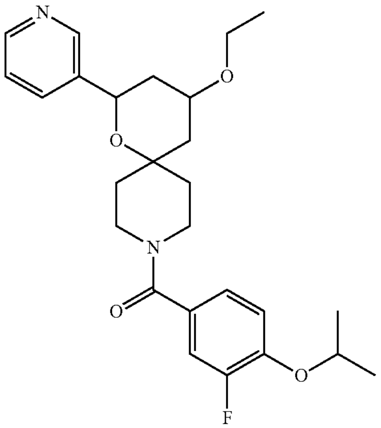
-continued
17 cis
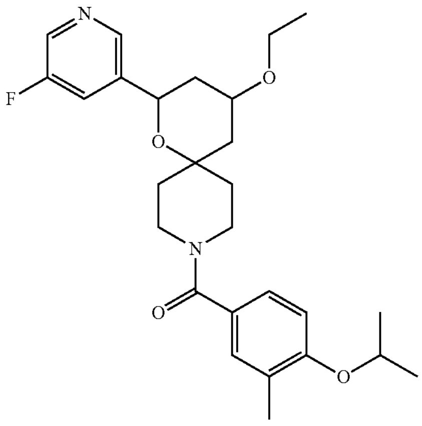
18 cis
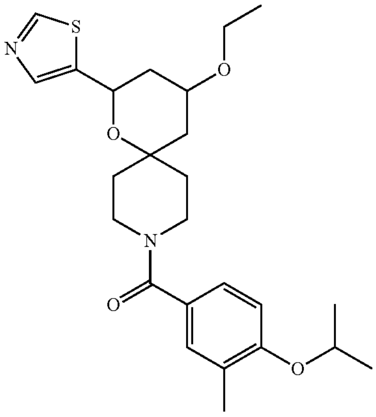
19 cis
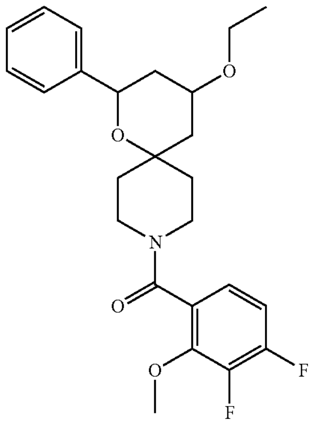

20 cis
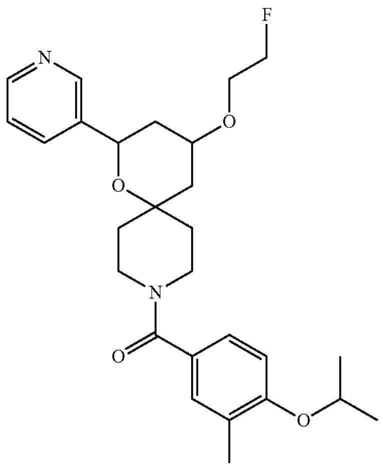
21 cis
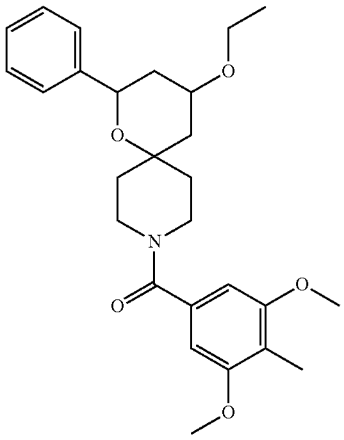
22 cis
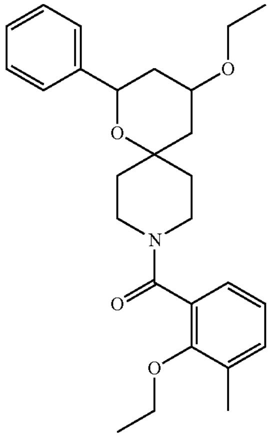
23 cis
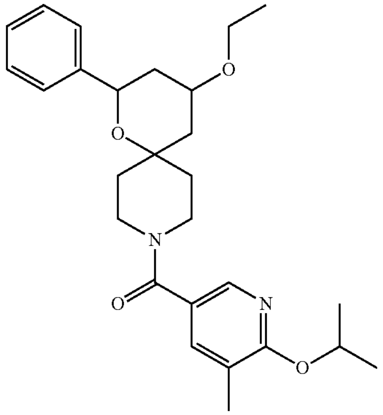
24 cis
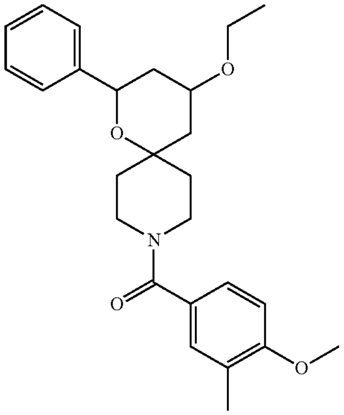
25 cis
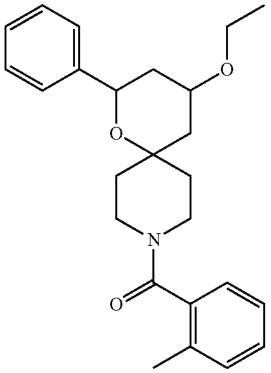
26 cis
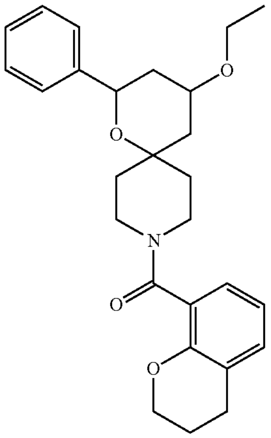

27 cis
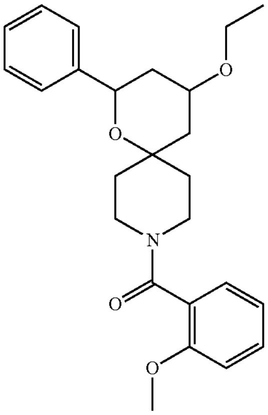
28 cis
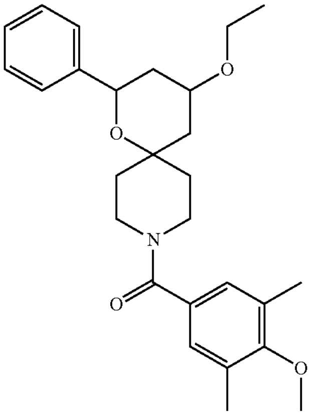
29 cis
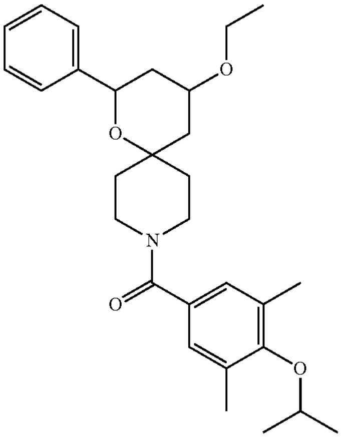
30 cis
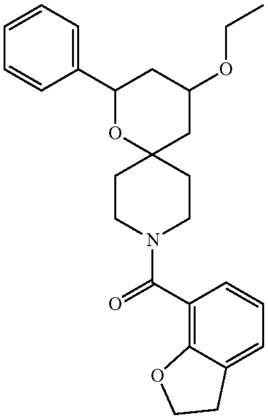
31 cis
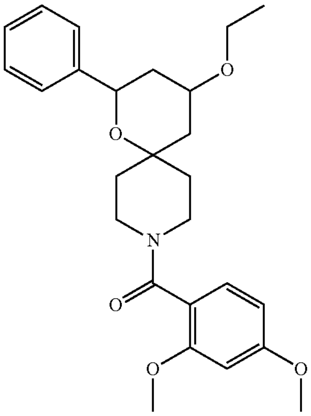
32 cis
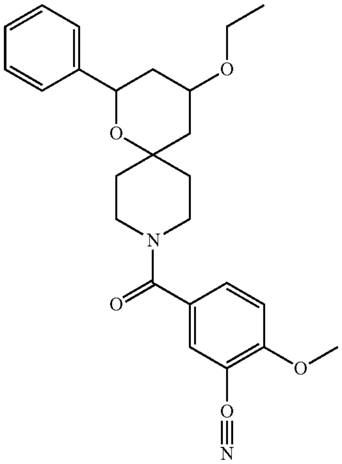

-continued
33 cis
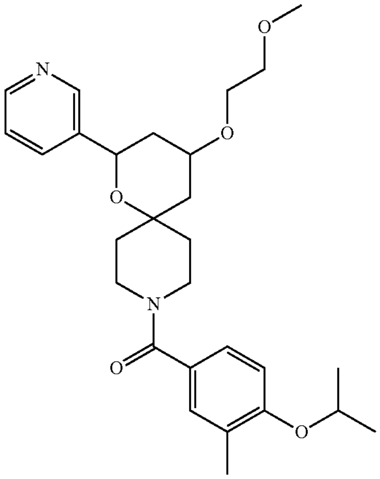
34 cis
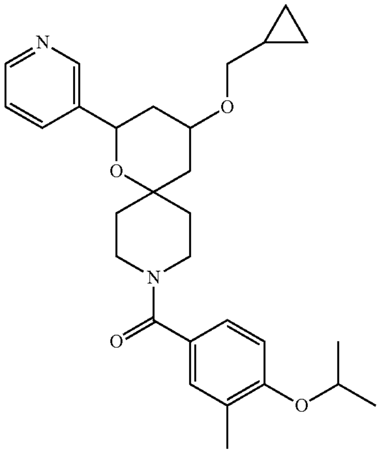
35 cis
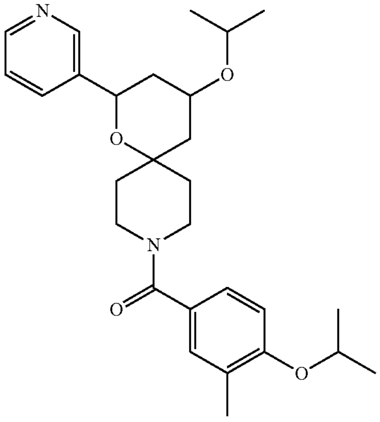
-continued
36 cis
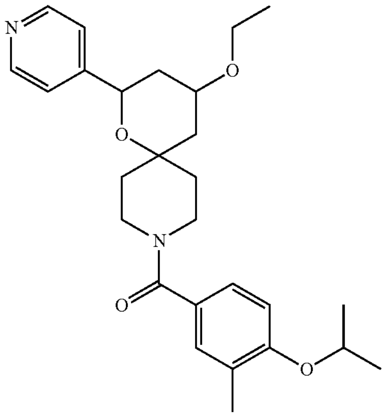
37 cis
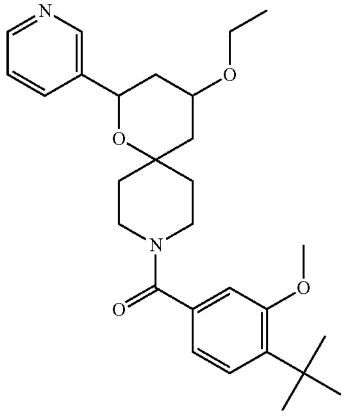
38 cis
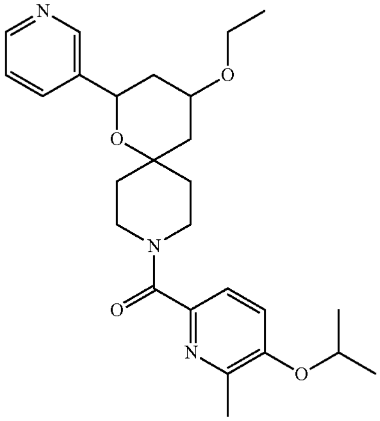

-continued
39 cis
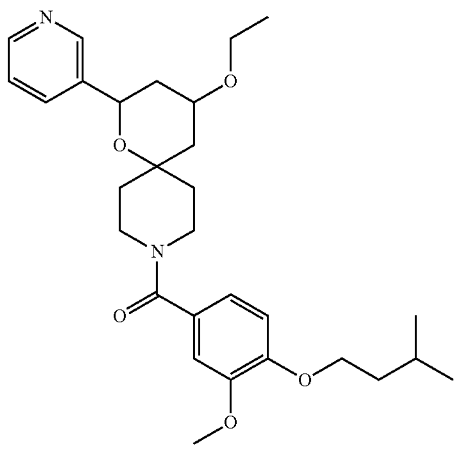
40 cis
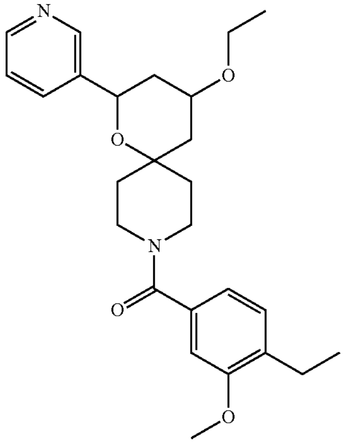
41 cis
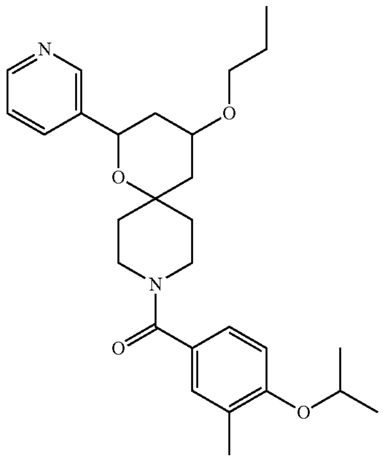
-continued
42 cis
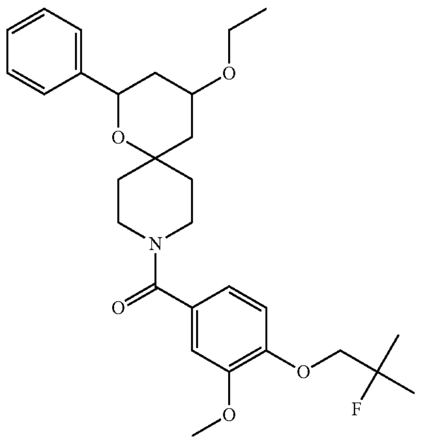
43 cis
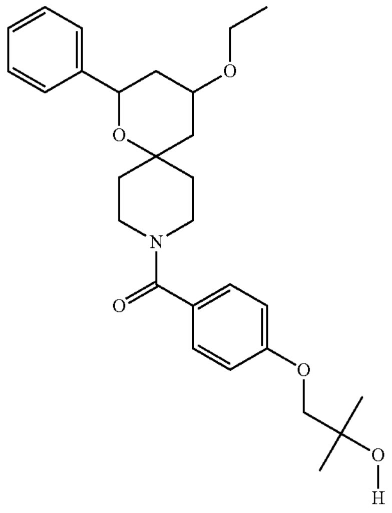
44 cis
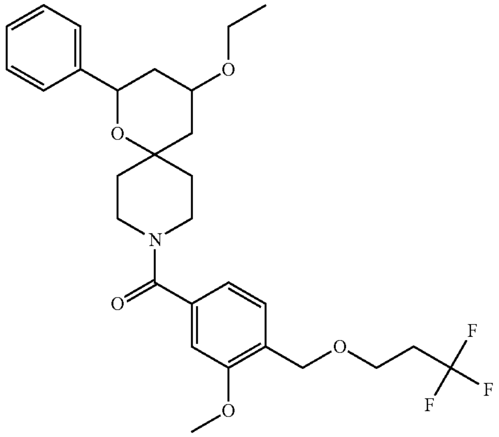

-continued
45 cis
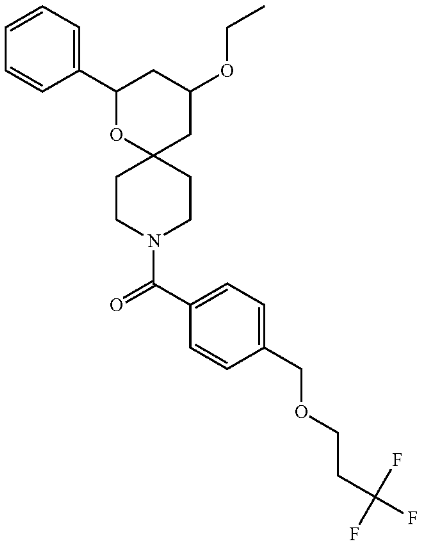
46 cis
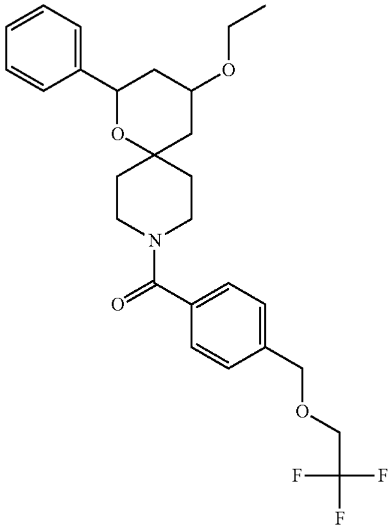
47 cis
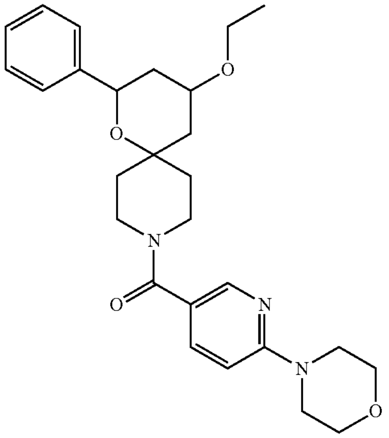
-continued
48 cis
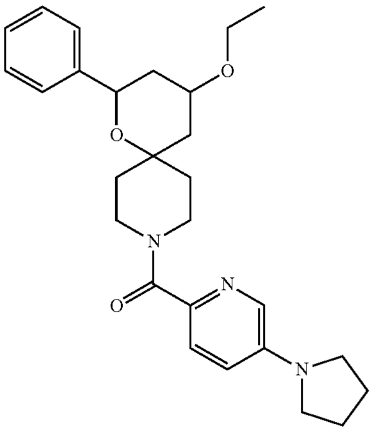
49 cis
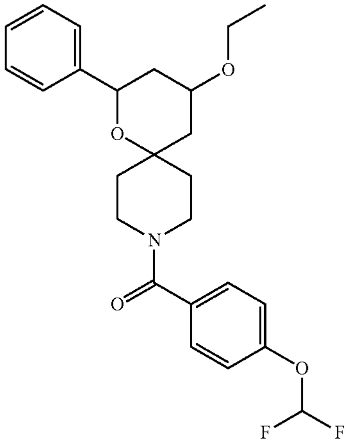
50 cis
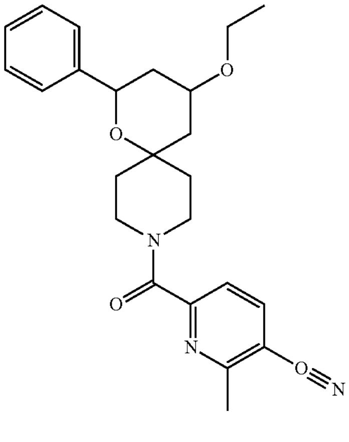

-continued
51 cis
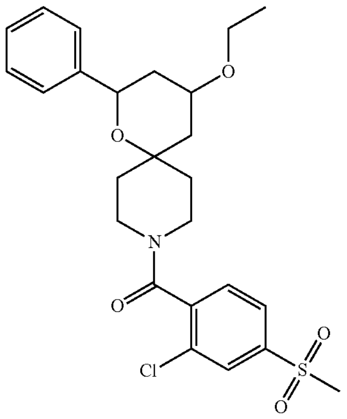
52 cis
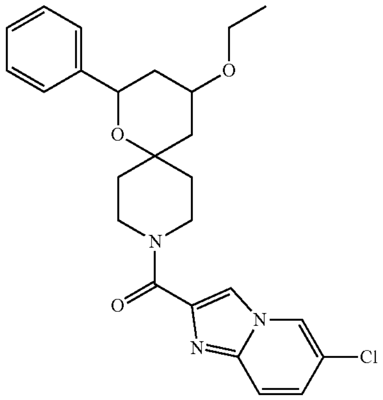
53 cis
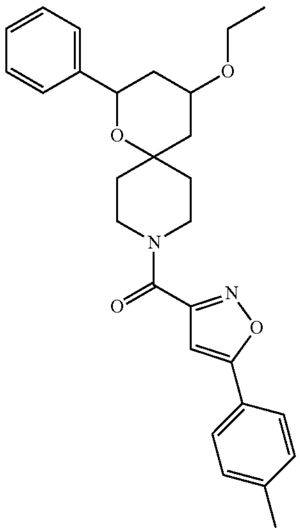
-continued
54 cis
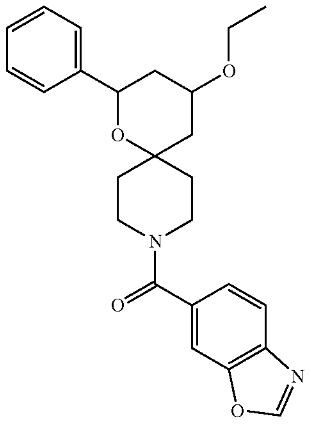
55 cis
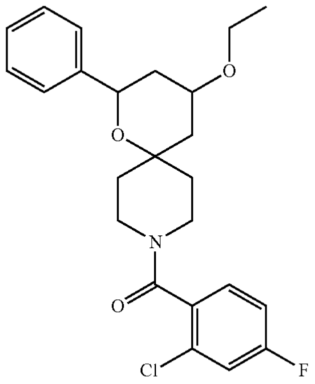
56 cis
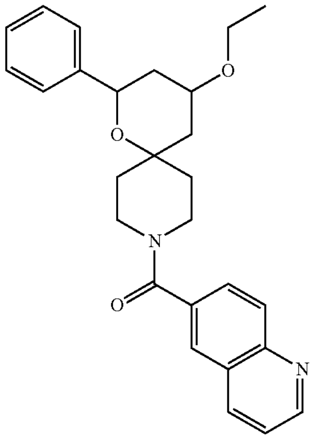

-continued
57 cis
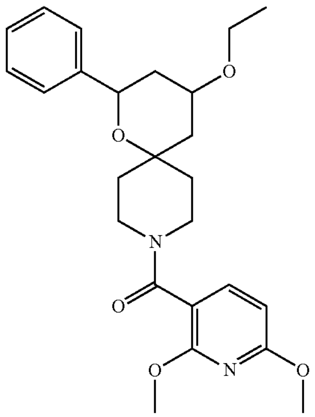
58 cis
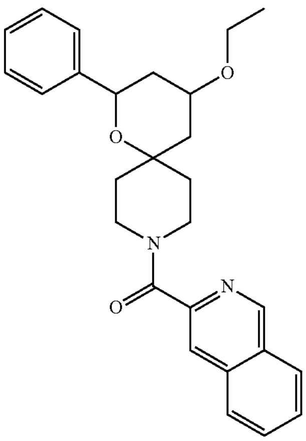
59 cis
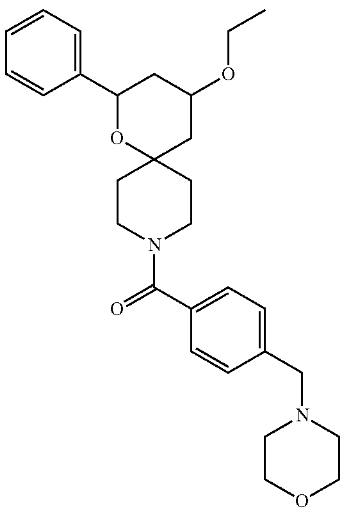
-continued
60 cis
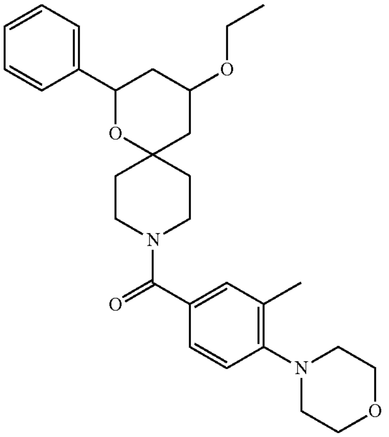
61 cis
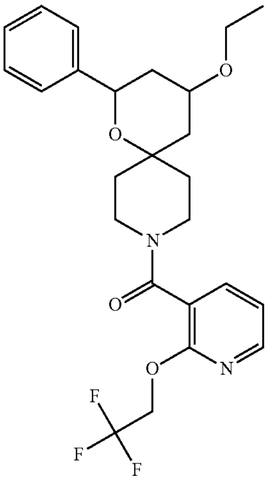
62 cis
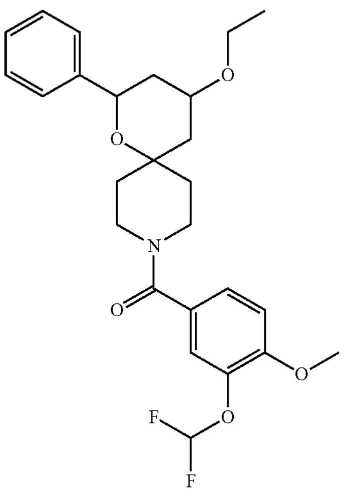

-continued
63 cis
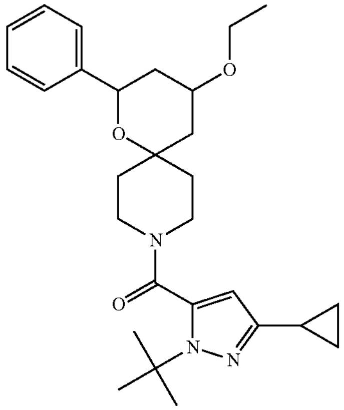
66 cis
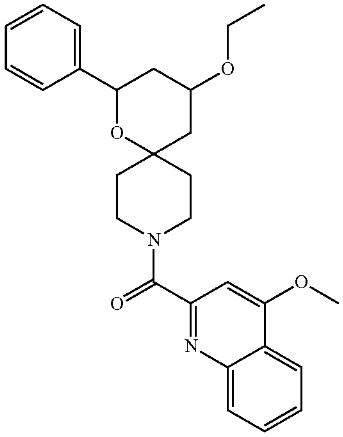
64 cis
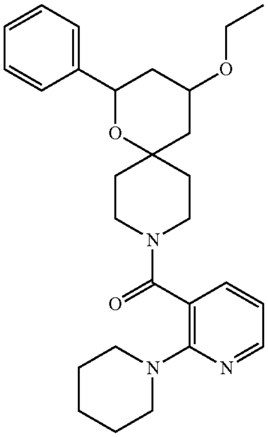
67 cis
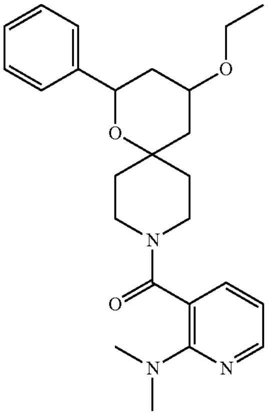
65 cis
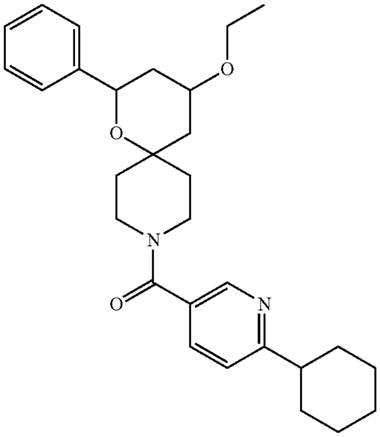
68 cis
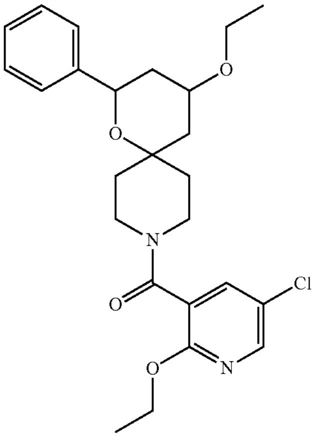

-continued
69 cis
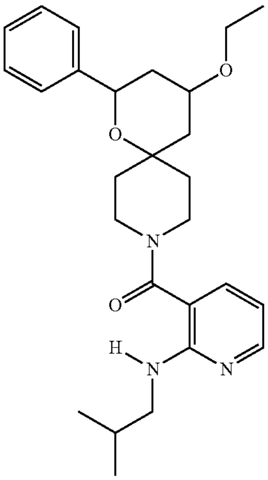
70 cis
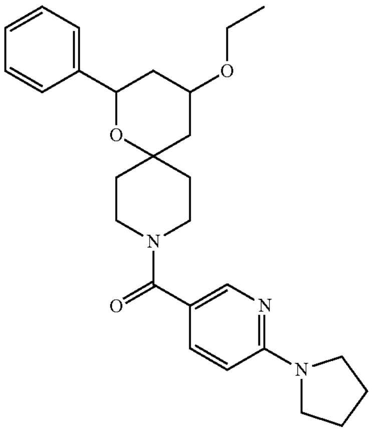
71 cis
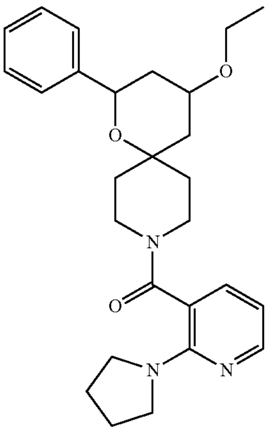
-continued
72 cis
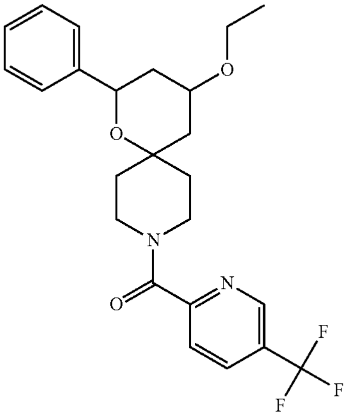
73 cis
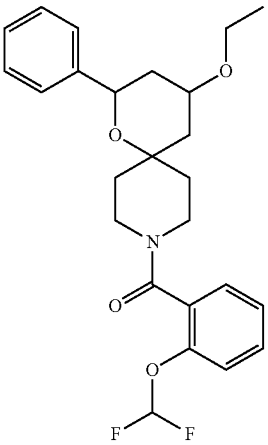
74 cis
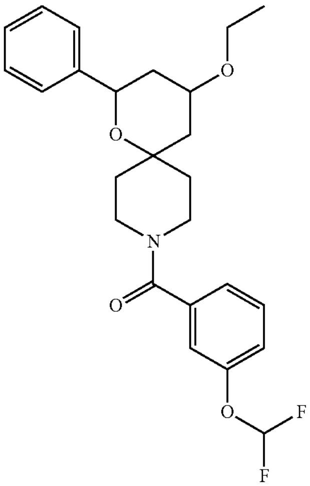

-continued
75 cis
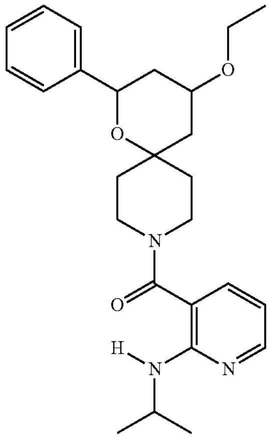
76 cis
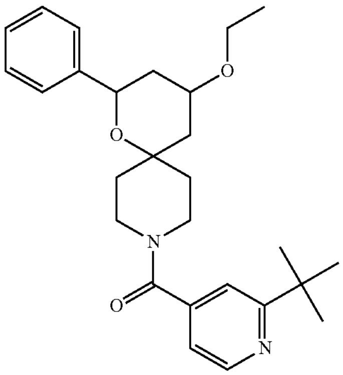
77 cis
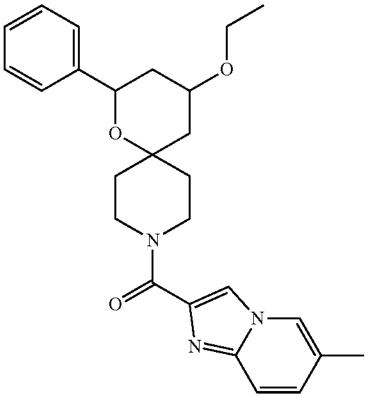
78 cis
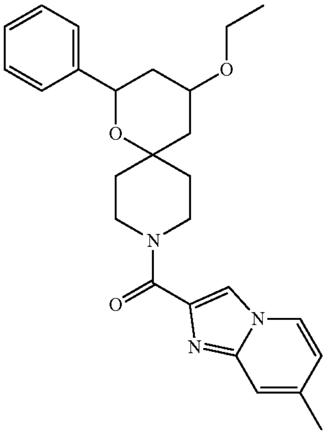
-continued
79 cis
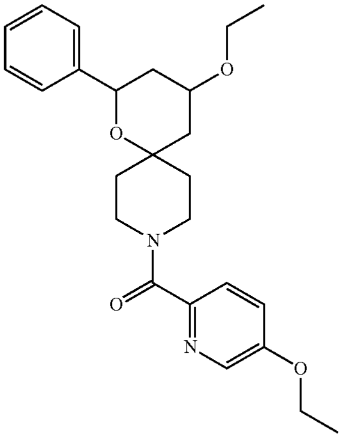
80 cis
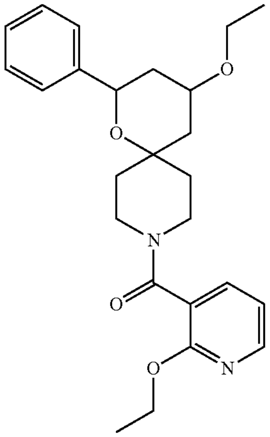
81 cis
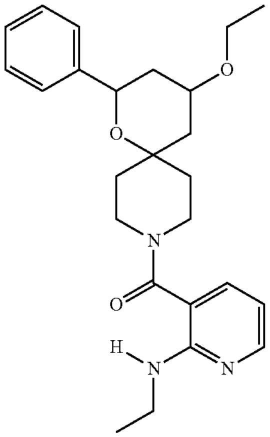

-continued
82 cis
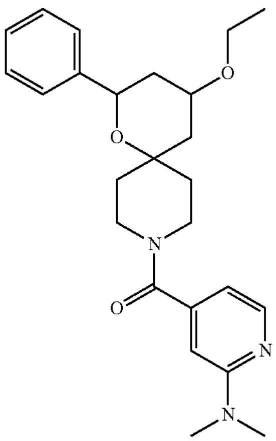
83 cis
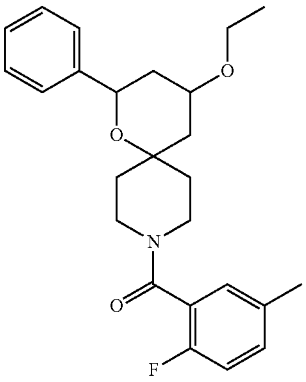
84 cis
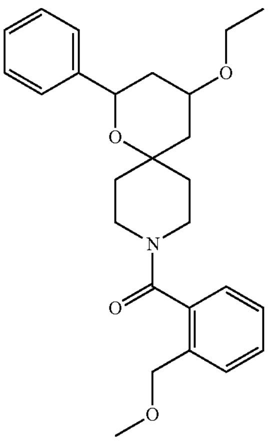
-continued
85 cis
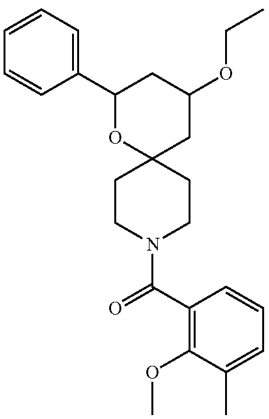
86 cis
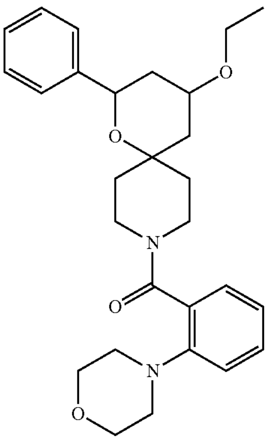
87 cis
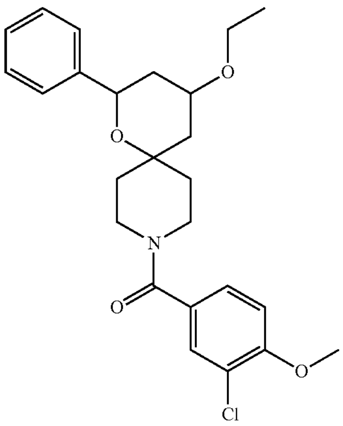

-continued
88 cis
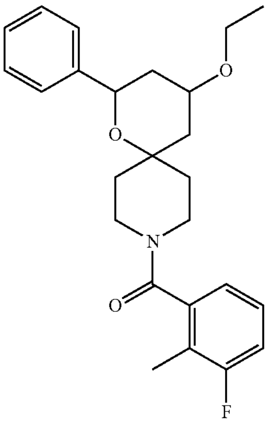
89 cis
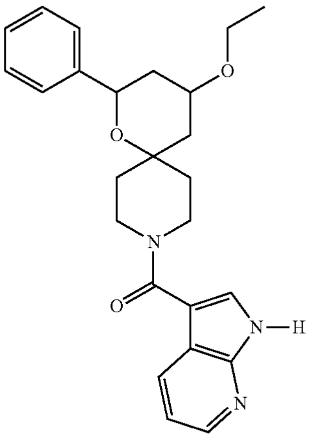
90 cis
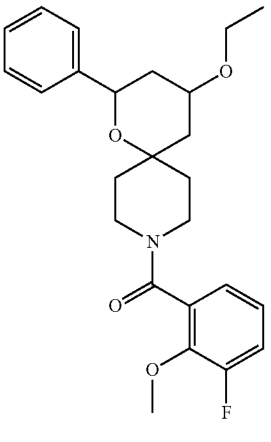
-continued
91 cis
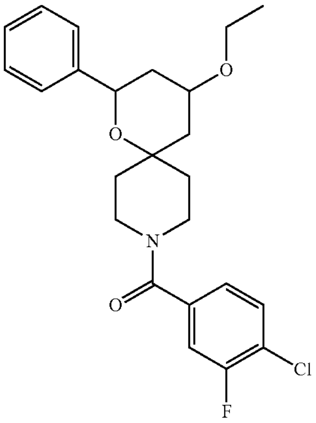
92 cis
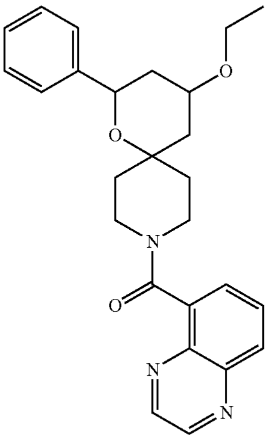
93 cis
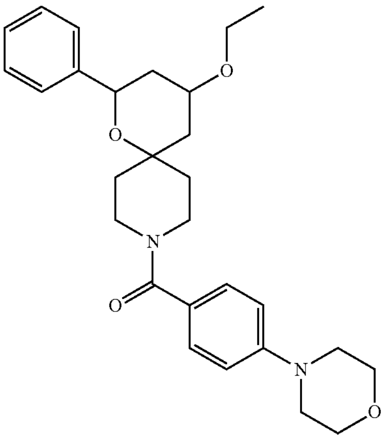

-continued
94 cis
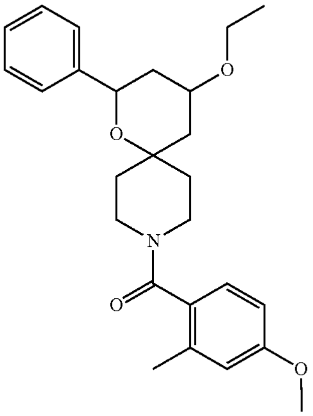
95 cis
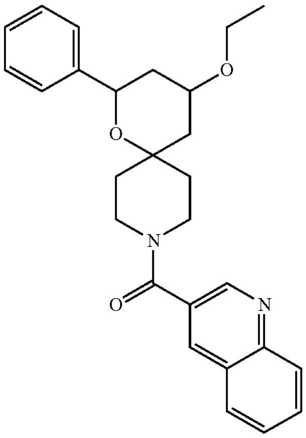
96 cis
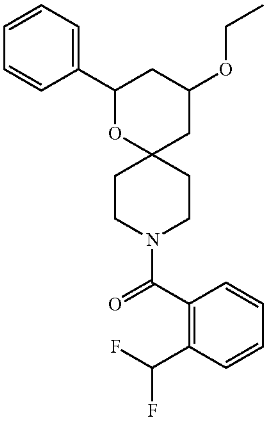
-continued
97 cis
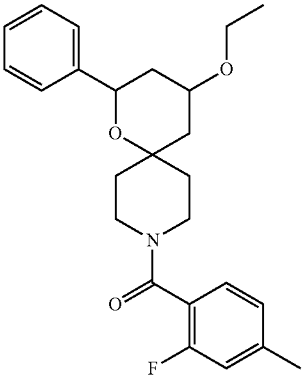
98 cis
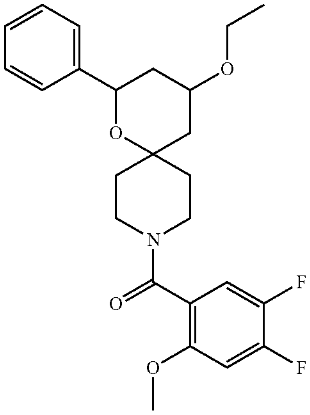
99 cis
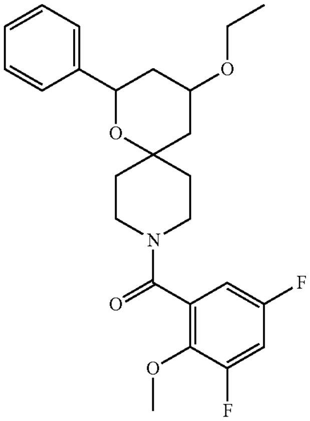
100 cis
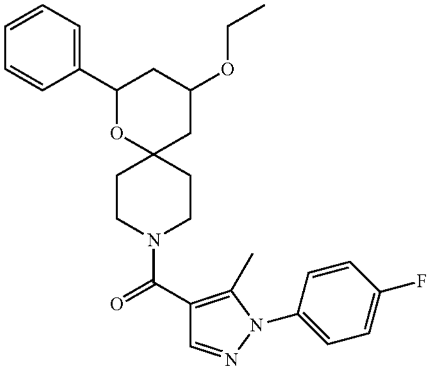

-continued
101 cis
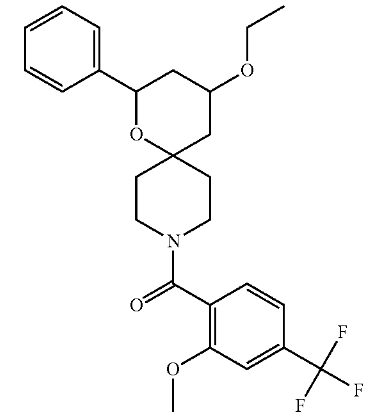
102 cis
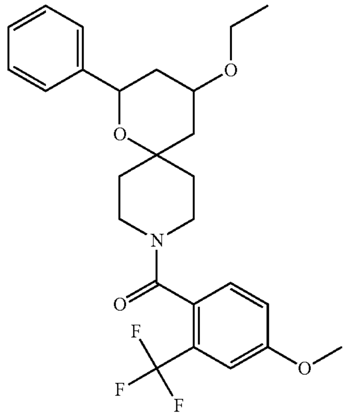
103 cis
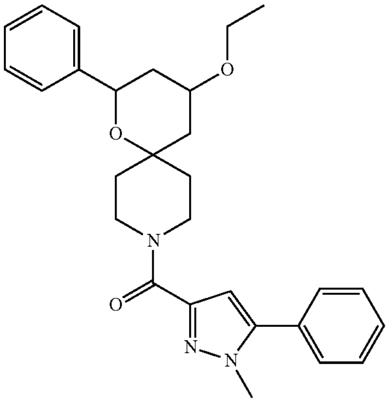
104 cis
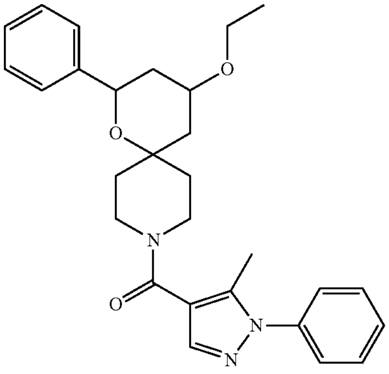
-continued
105 cis
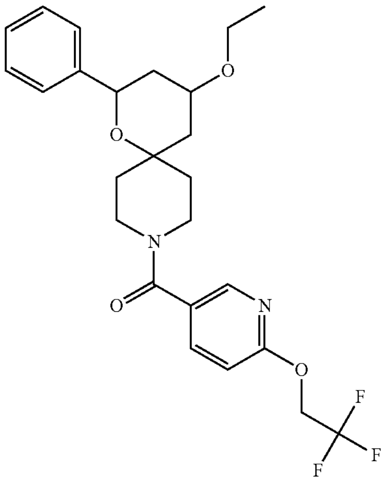
106 cis
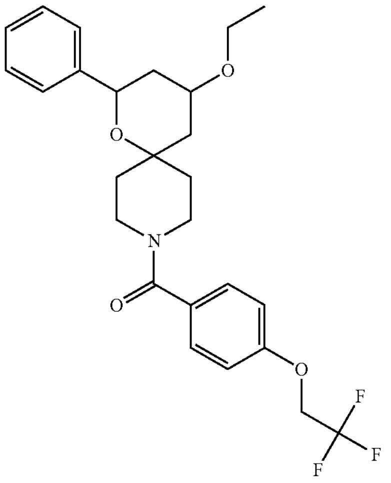
107 cis
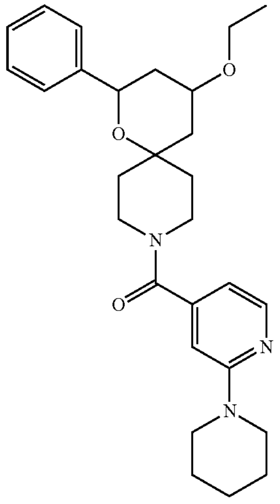

-continued
108 cis
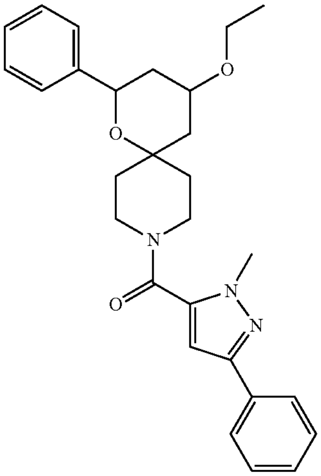
109 cis
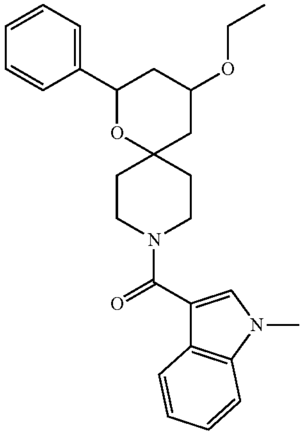
110 cis
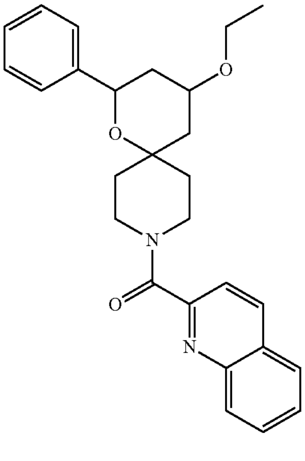
-continued
111 cis
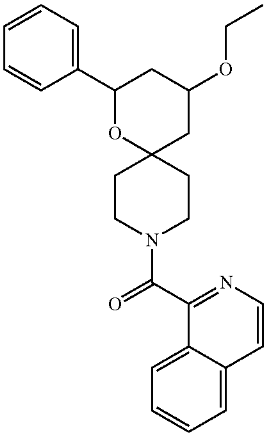
112 cis
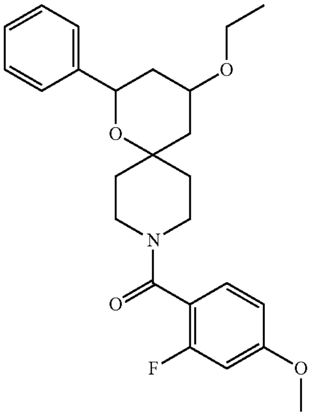
113 cis
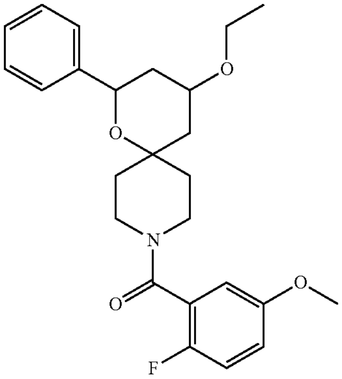
114 cis
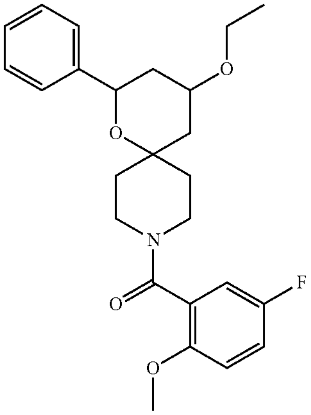

-continued
115 cis
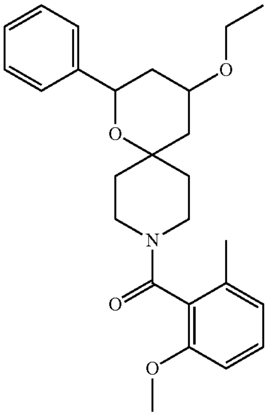
116 cis
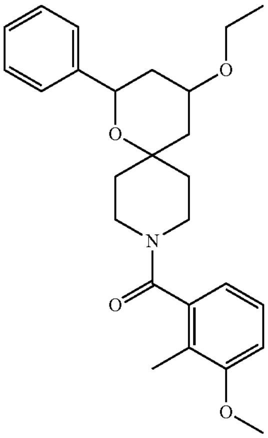
117 cis
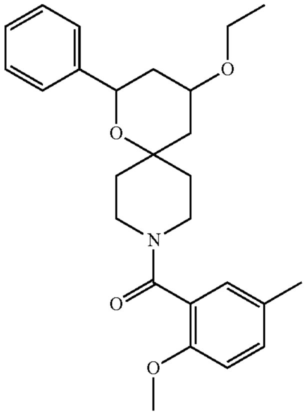
-continued
118 cis
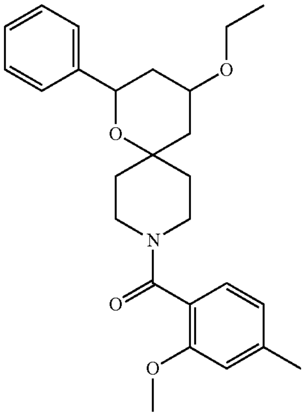
119 cis
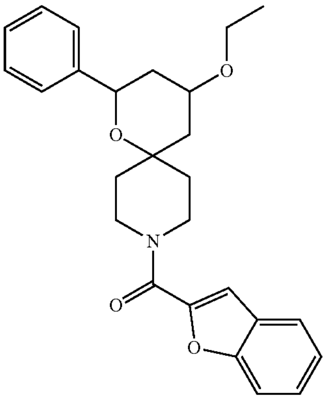
120 cis
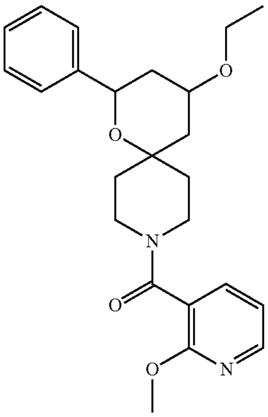

121 cis
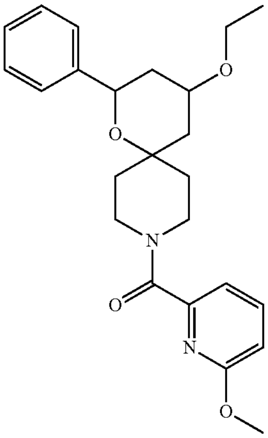
122 cis
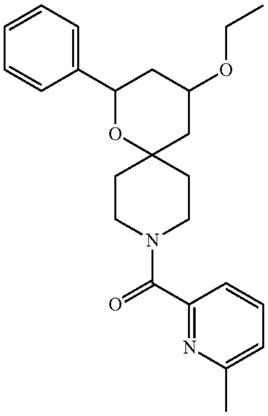
123 cis
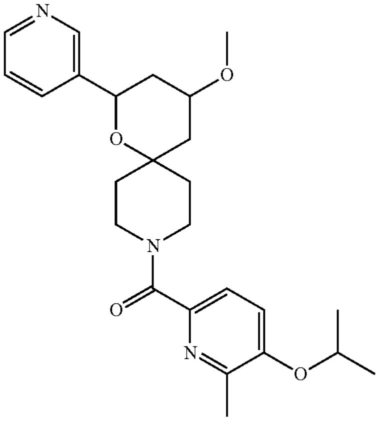
124 cis
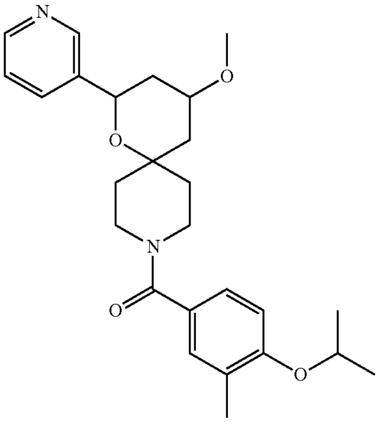
125 cis
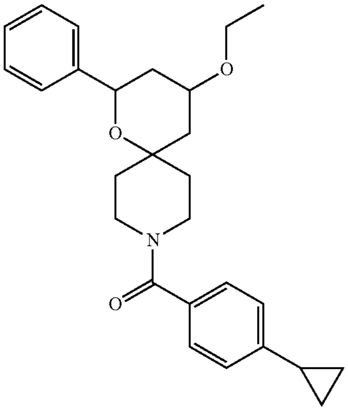
126 cis
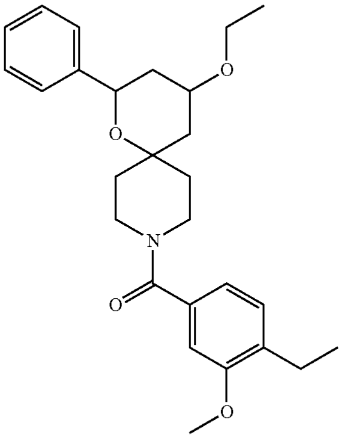

-continued
127 cis
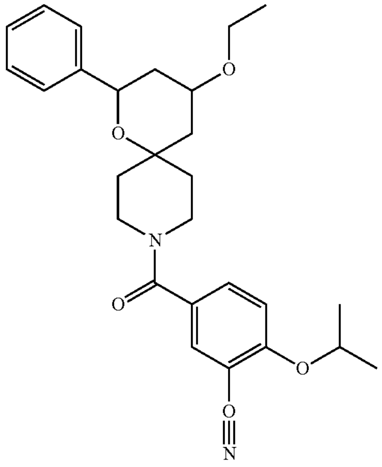
128 cis
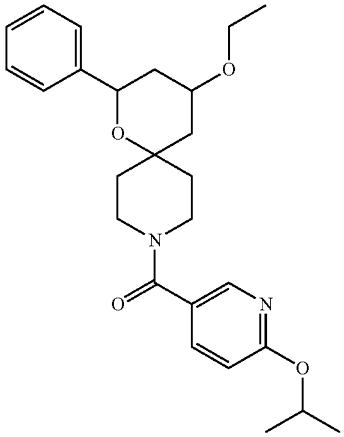
129 cis
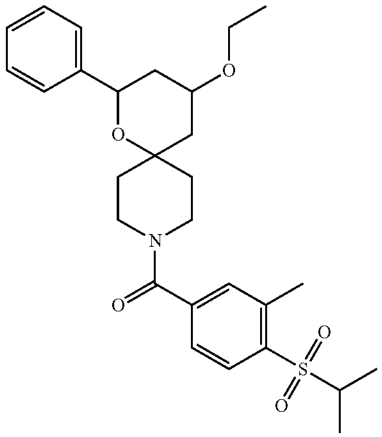
-continued
130 cis
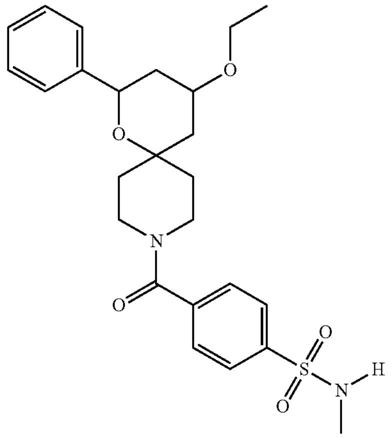
131 cis
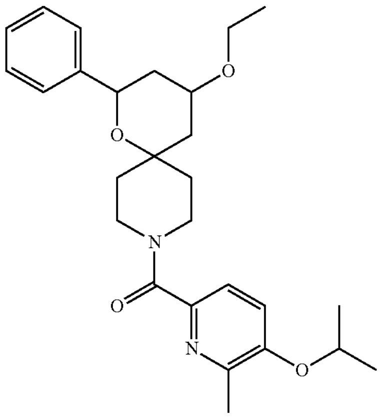
132 cis
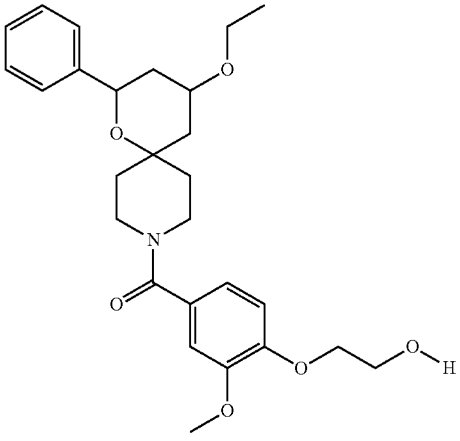

-continued
133 cis
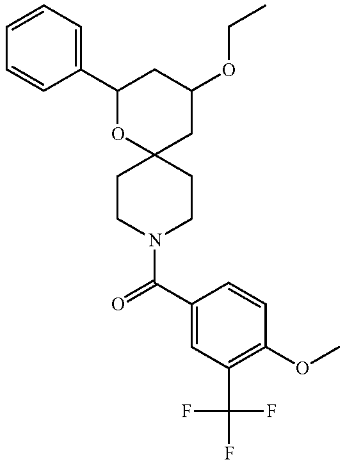
134 cis
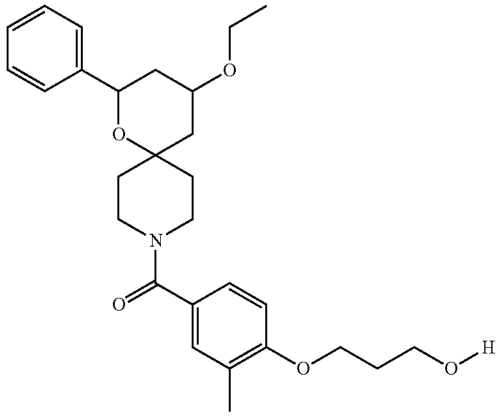
135 cis
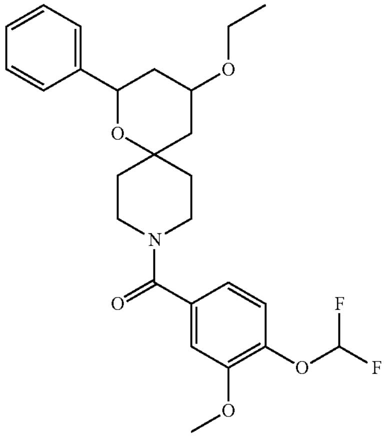
-continued
136 cis
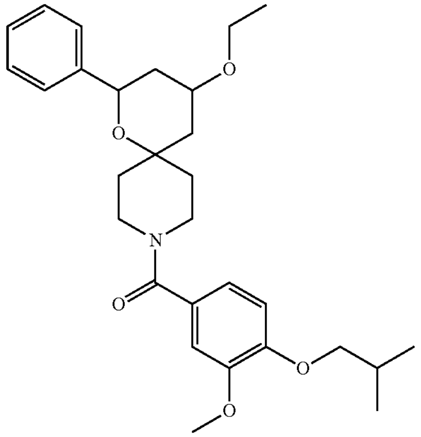
137 cis
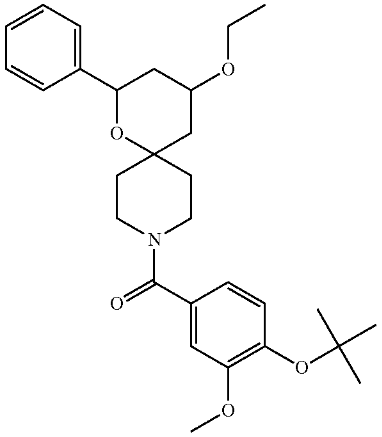
138 cis
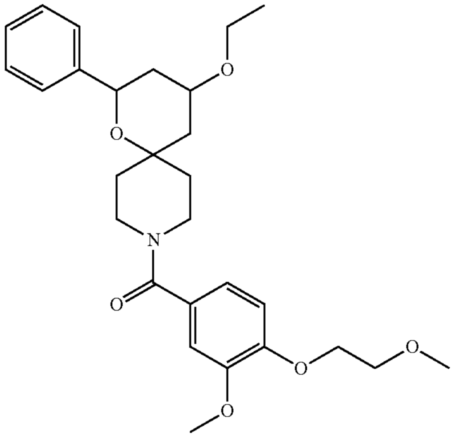

-continued
139 cis
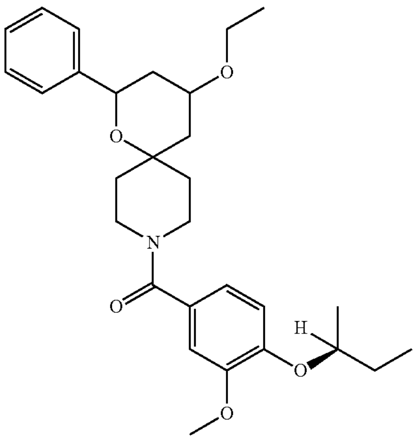
140 cis
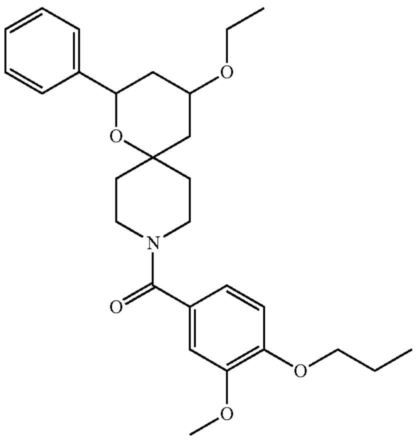
141 cis
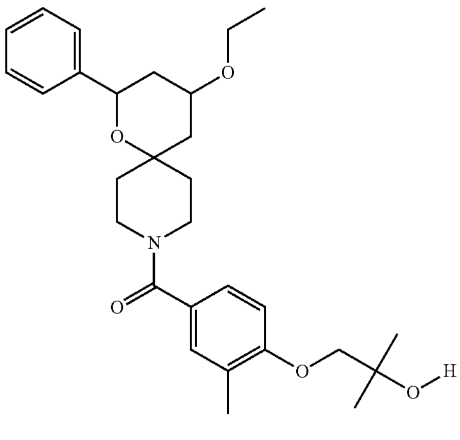
-continued
142 cis
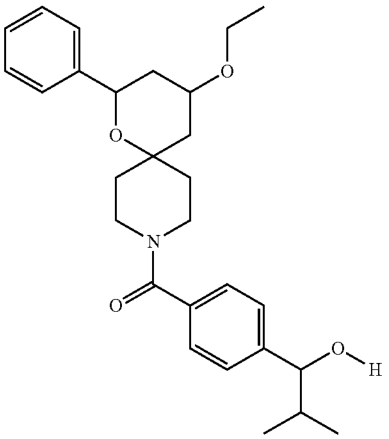
143 cis
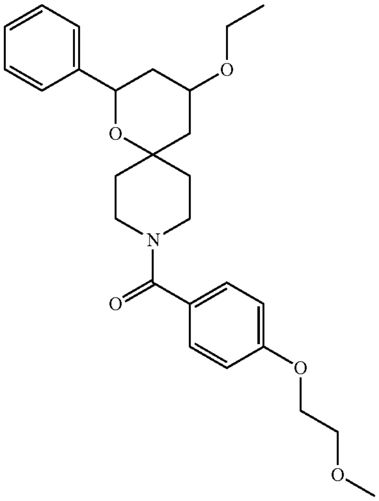
144 cis
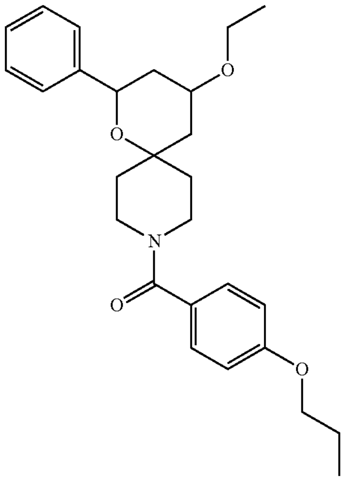

145 cis
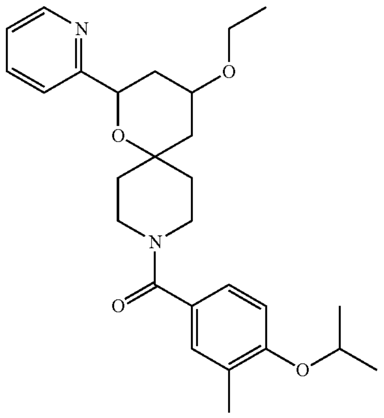
146 cis
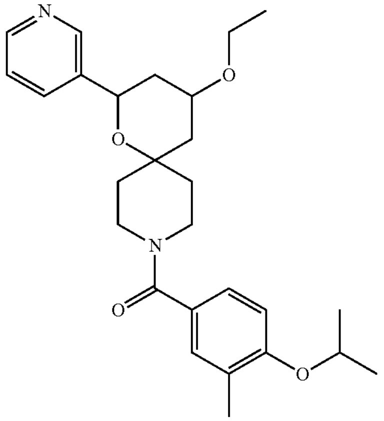
147 trans
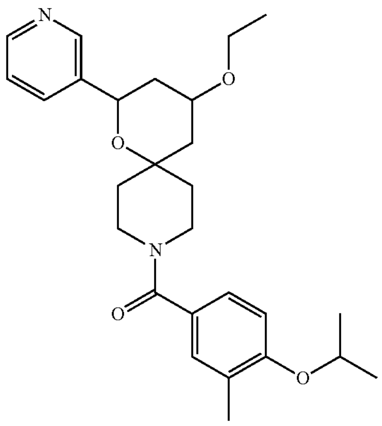
148 trans
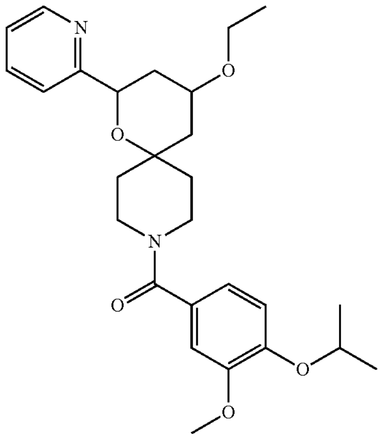
149 cis
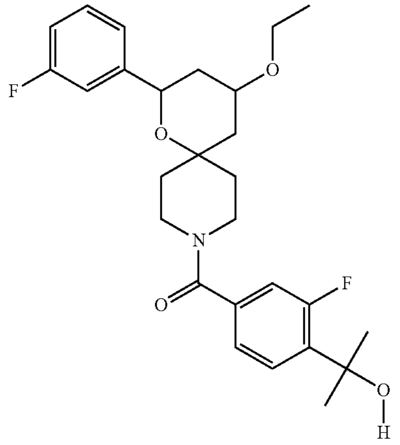
150 cis
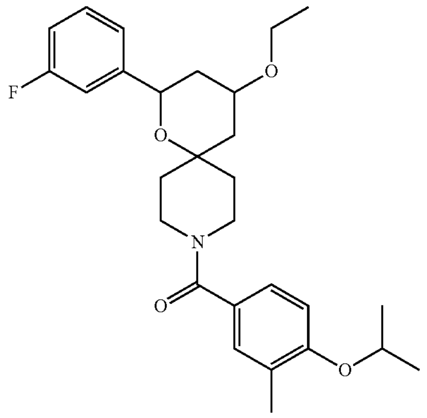

151 cis
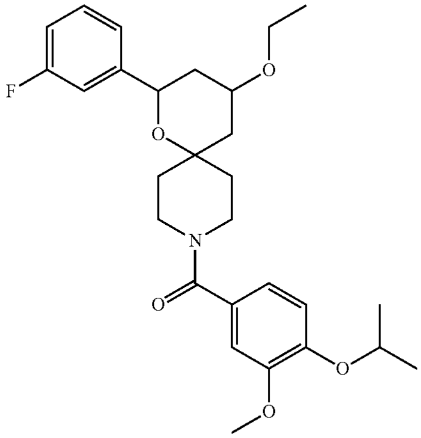
152 trans
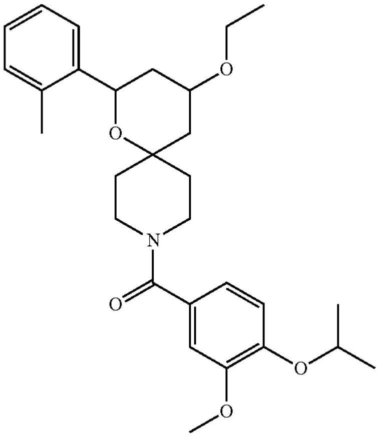
153 cis
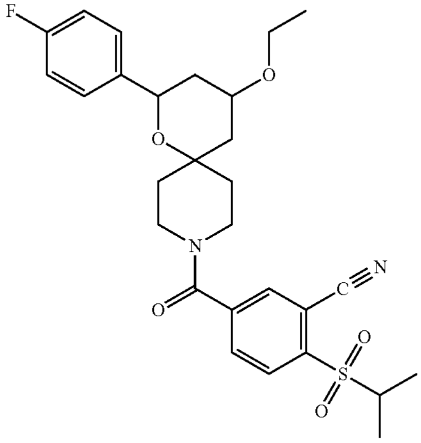
154 cis
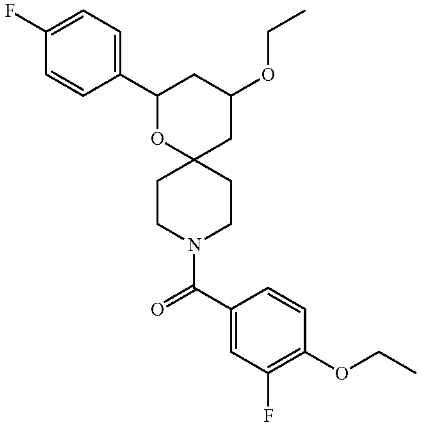
155 cis
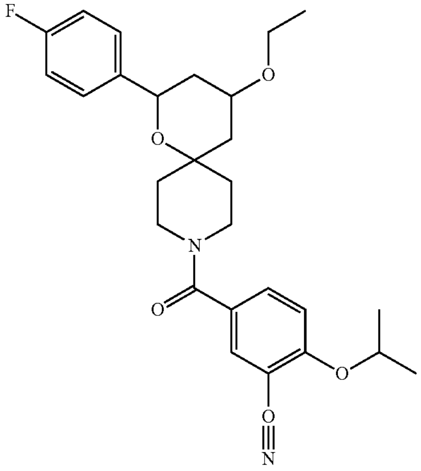
156 cis
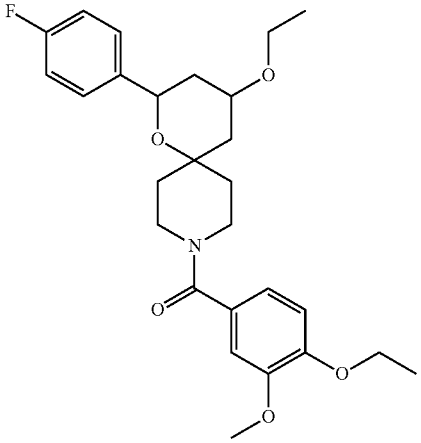

-continued
157 cis
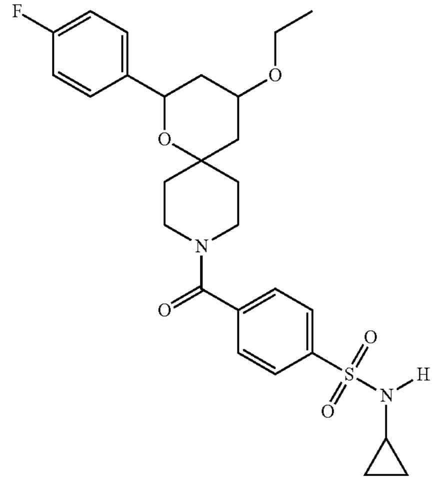
158 cis
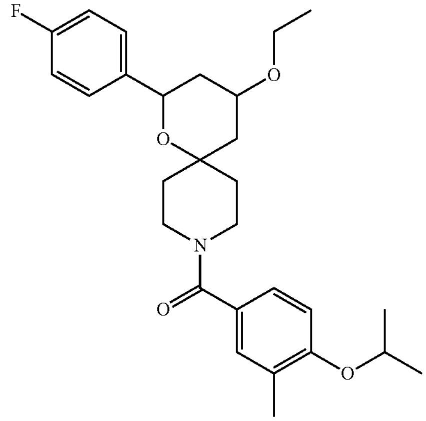
159 cis
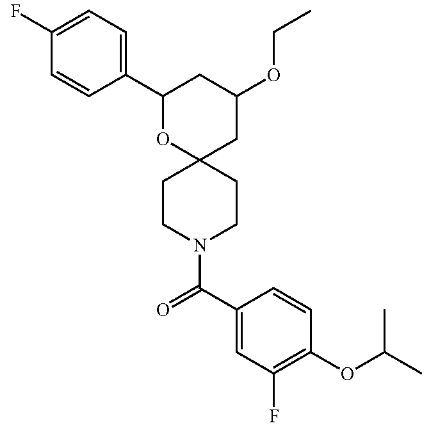
-continued
160 cis
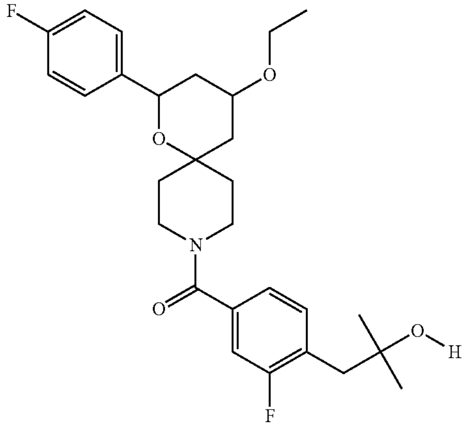
161 cis
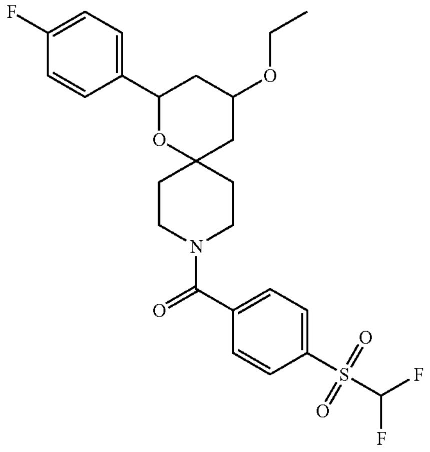
162 cis
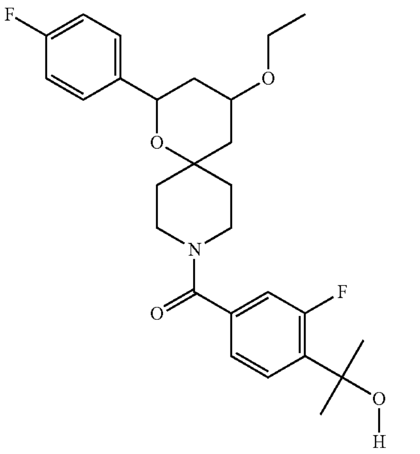

163 cis
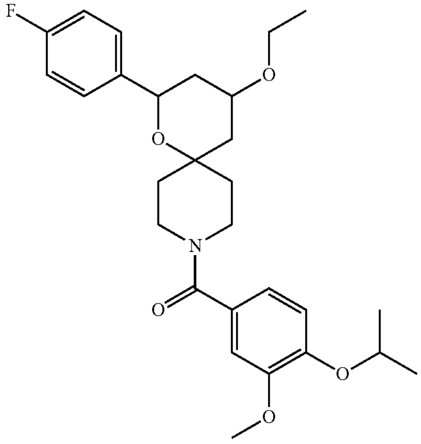
164 trans
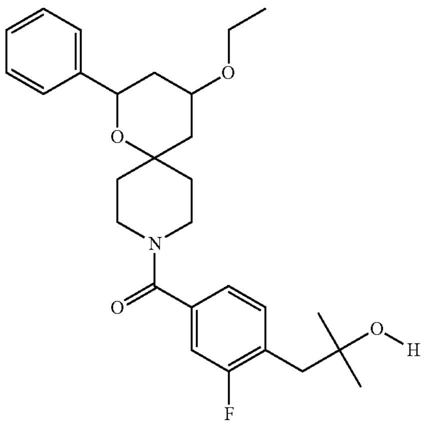
165 trans
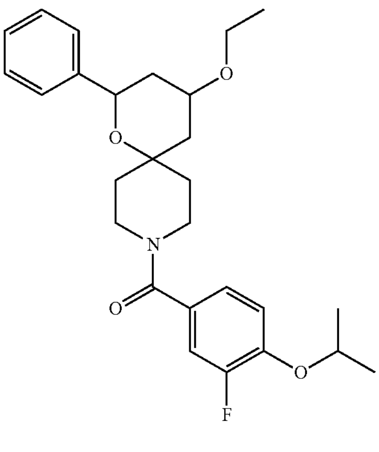
166 trans
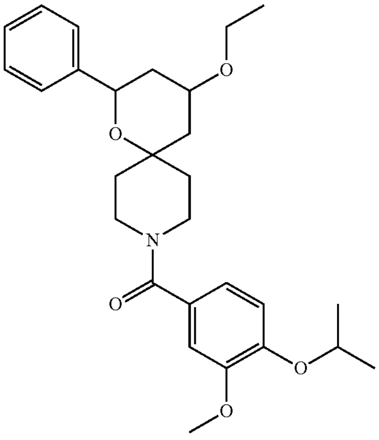
167 cis
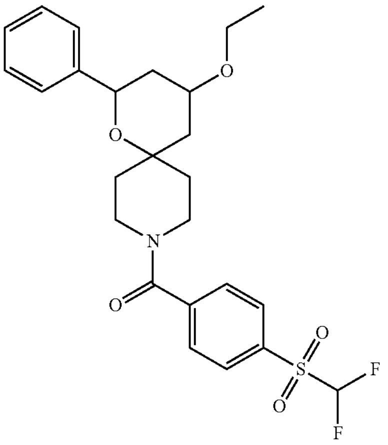
168 cis
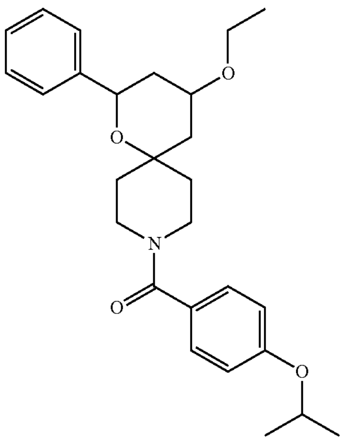

169 cis
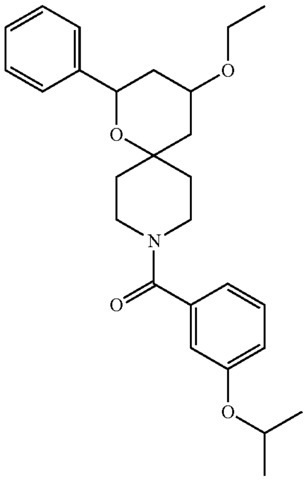
170 cis
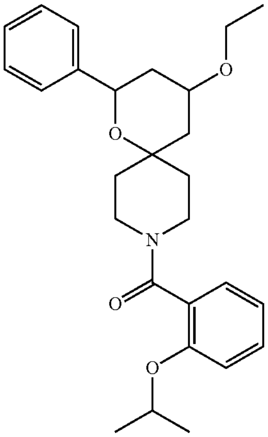
171 cis
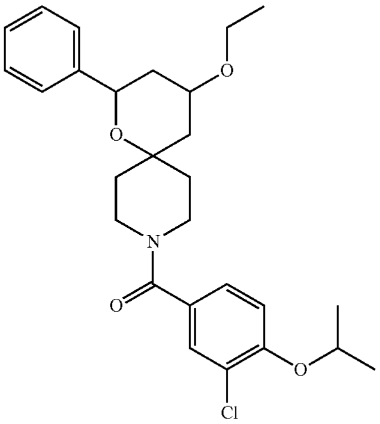
172 cis
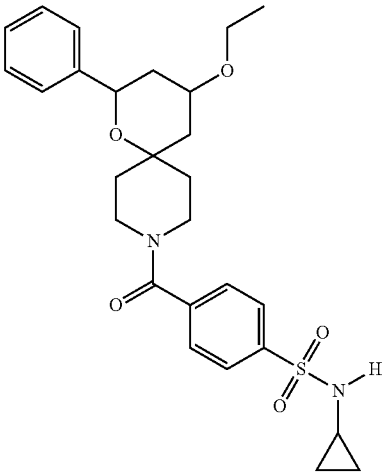
173 cis
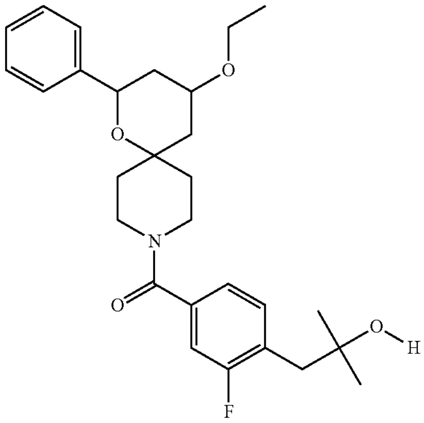
174 cis
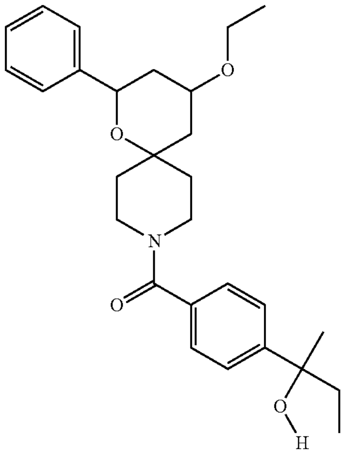

-continued
175 cis
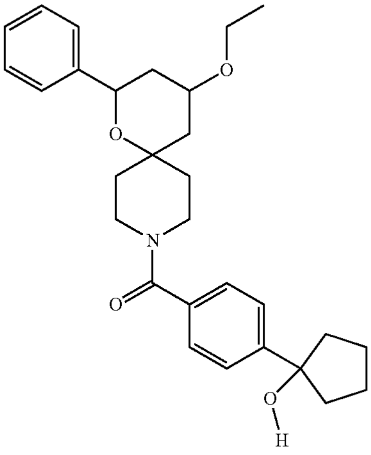
176 cis
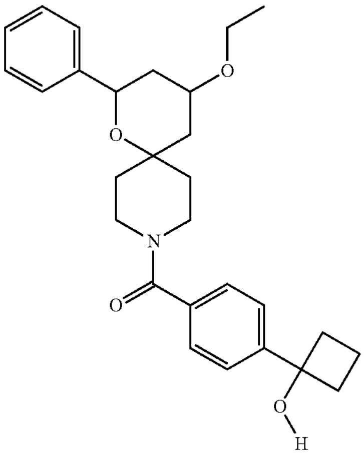
177 cis
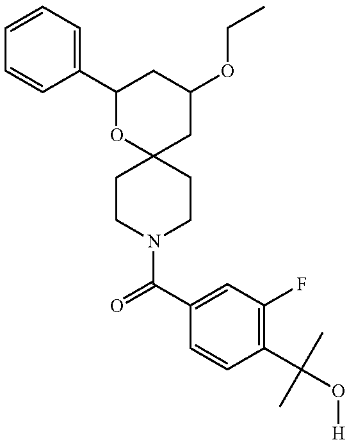
-continued
178 cis
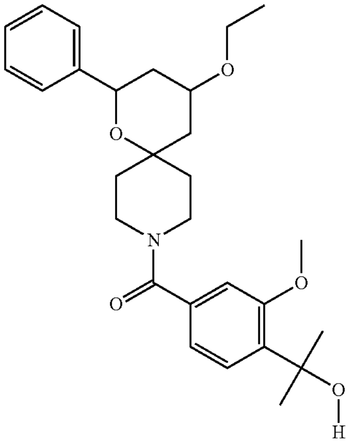
179 cis
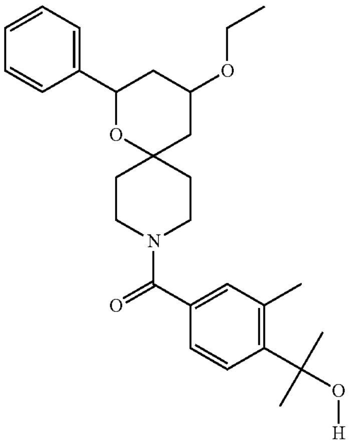
180 cis
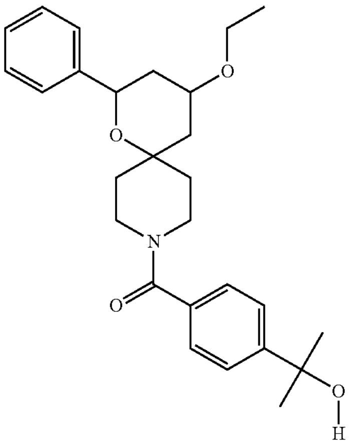

-continued
181 cis
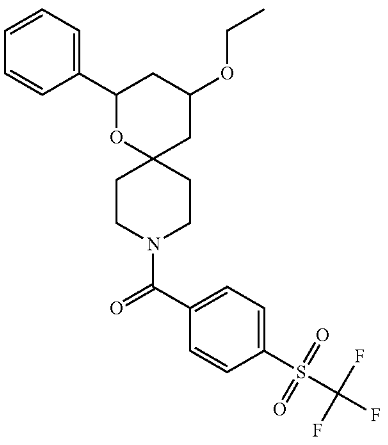
182 cis
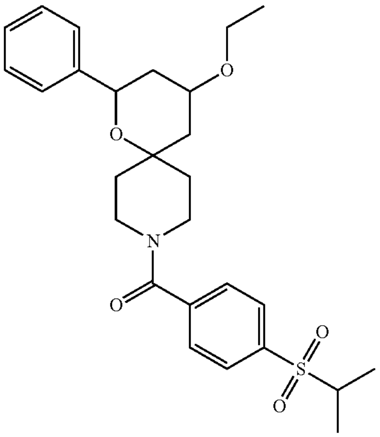
183 cis
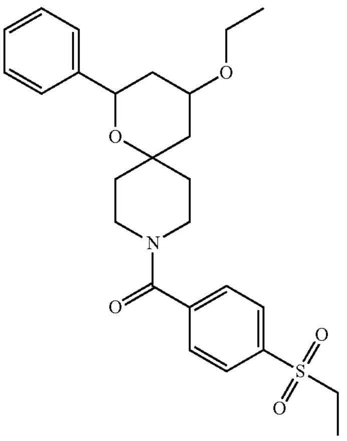
-continued
184 cis
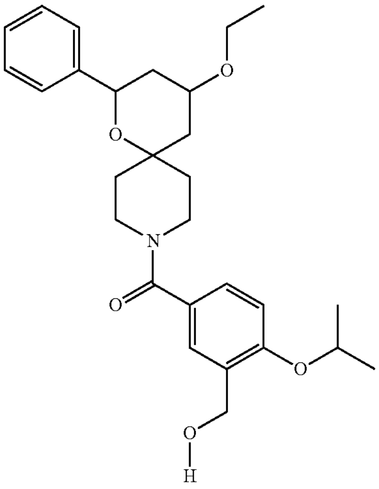
185 cis
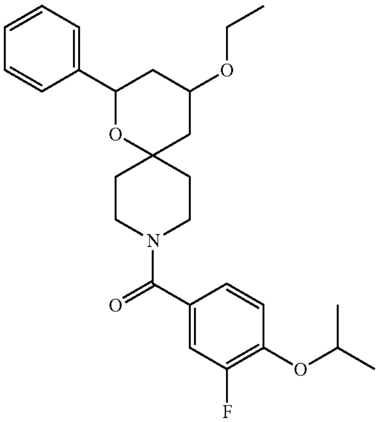
186 cis
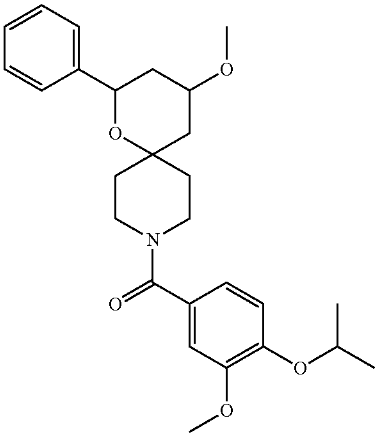

-continued
187 cis
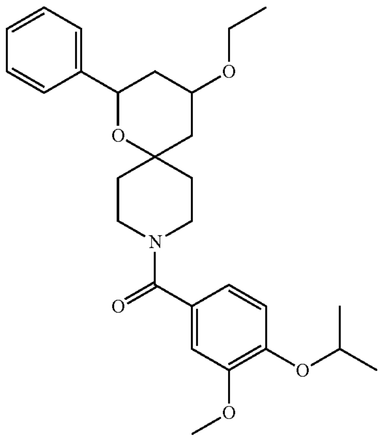
188 cis
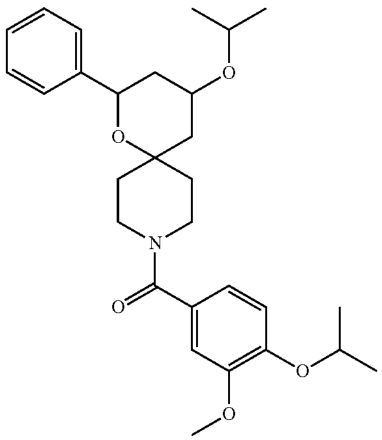
189 cis
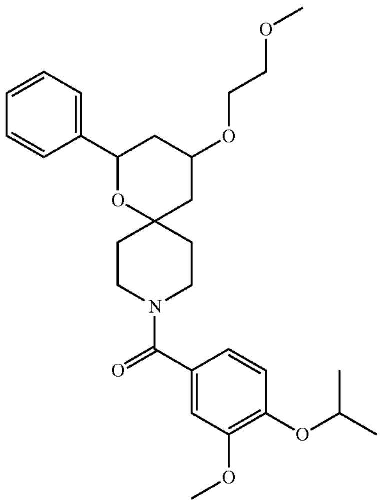
-continued
190 cis
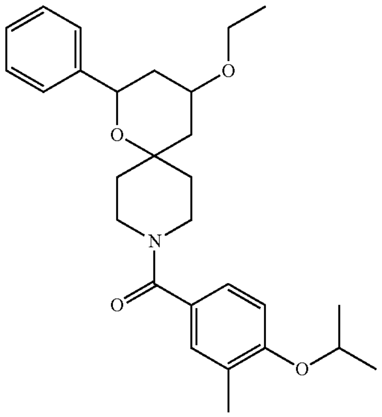
191 cis
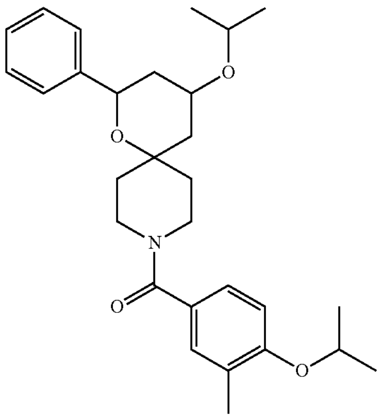
192 trans
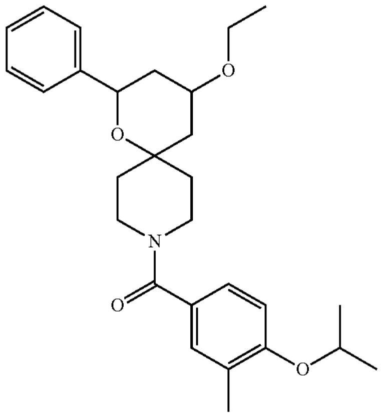

-continued 193 cis

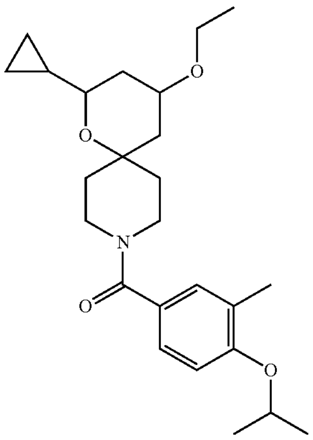

-continued 194 cis

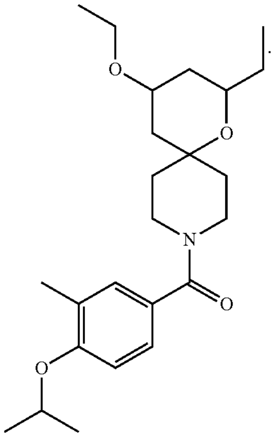

20. A pharmaceutical composition comprising the compound of claim 1 and a pharmaceutically acceptable carrier.

21. A method of inhibiting a voltage-gated sodium ion channel in:

a patient; or a biological sample;

comprising administering to the patient, or contacting the biological sample, with the compound of claim 1.

22. The method of claim 21, wherein the voltage-gated sodium ion channel is NaV 1.7.

23. A method of treating or lessening the severity in a subject of acute, chronic, neuropathic, or inflammatory pain, visceral pain, osteoarthritis pain, radicular pain, sciatica, back pain, head or neck pain, severe or intractable pain, nociceptive pain, breakthrough pain, postsurgical pain, or cancer pain, comprising administering an effective amount of a compound of claim 1.

* * * * *